(12) United States Patent
Wu et al.

(10) Patent No.: US 8,945,862 B2
(45) Date of Patent: Feb. 3, 2015

(54) TRIPLE-FUSION CONSTRUCTS AND METHODS OF MONITORING HUMAN EMBRYONIC STEM CELLS

(75) Inventors: Joseph Ching-Ming Wu, Palo Alto, CA (US); Feng Cao, San Jose, CA (US); Sanjiv Sam Gambhir, Porollo Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 173 days.

(21) Appl. No.: 13/358,838

(22) Filed: Jan. 26, 2012

(65) Prior Publication Data

US 2012/0144506 A1    Jun. 7, 2012

Related U.S. Application Data

(62) Division of application No. 12/315,873, filed on Dec. 4, 2008, now abandoned.

(60) Provisional application No. 60/992,136, filed on Dec. 4, 2007.

(51) Int. Cl.
| | |
|---|---|
| *C12Q 1/66* | (2006.01) |
| *C12N 5/0735* | (2010.01) |
| *C12N 5/073* | (2010.01) |
| *C12N 5/077* | (2010.01) |
| *C12N 5/071* | (2010.01) |
| *A61K 35/12* | (2006.01) |

(52) U.S. Cl.
CPC ............ *C12N 5/0606* (2013.01); *C12N 5/0603* (2013.01); *C12N 5/0657* (2013.01); *C12N 5/069* (2013.01); *A61K 35/12* (2013.01); *C12N 2506/02* (2013.01); *C12N 2510/00* (2013.01)
USPC .................................. 435/8; 435/6; 435/69.1

(58) Field of Classification Search
None
See application file for complete search history.

(56) References Cited

U.S. PATENT DOCUMENTS

| | | | | |
|---|---|---|---|---|
| 7,005,511 | B2 * | 2/2006 | Tsien et al. .................. | 536/23.1 |
| 7,910,093 | B2 * | 3/2011 | Meruelo et al. ............... | 424/93.2 |
| 8,586,022 | B2 * | 11/2013 | Szalay et al. ................. | 424/93.2 |

OTHER PUBLICATIONS

Wang et al. (Circulation Res., 2012, vol. 111, pp. 1494-1503).*
Szalay et al.*
Ponomarev et al. (European J. of Nuclear Medicine and Molecular Imaging, vol. 31, No. 5, May 2004).
Cowan et al. (Sci. vol. 309, pp. 1369-1373, 2005).

* cited by examiner

*Primary Examiner* — Hope Robinson
(74) *Attorney, Agent, or Firm* — Thomas|Horstemeyer, LLP

(57) ABSTRACT

Embodiments of the present disclosure include triple-fusion human embryonic stem cells, methods of imaging triple-fusion human embryonic stem cells, triple-fusion polynucleotides, triple-fusion proteins, methods of monitoring the progression of human embryonic stem cells, methods of making isolated triple-fusion human embryonic stem cells, and the like.

14 Claims, 40 Drawing Sheets

(33 of 40 Drawing Sheet(s) Filed in Color)

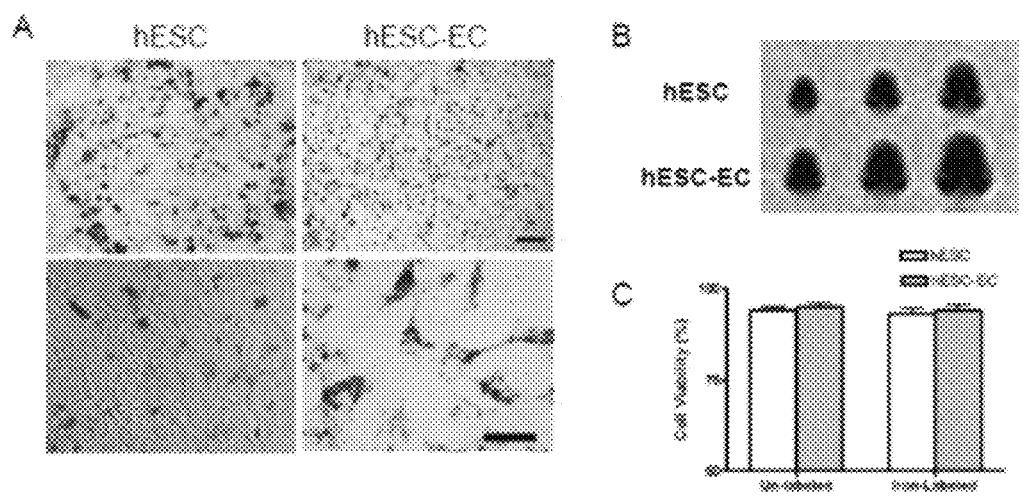
FIG. 3
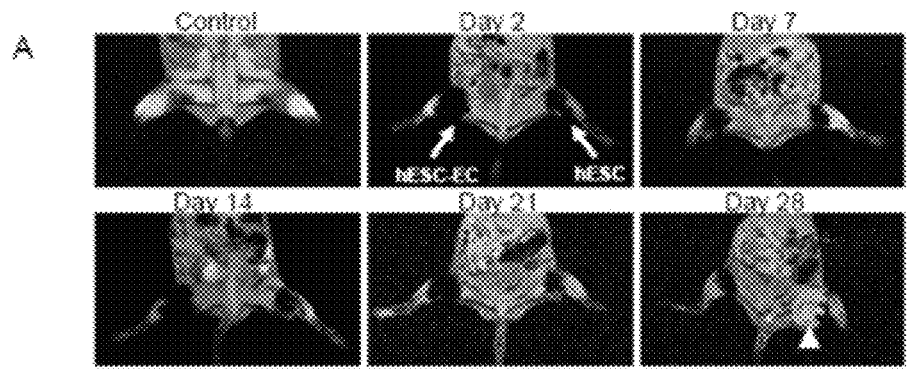
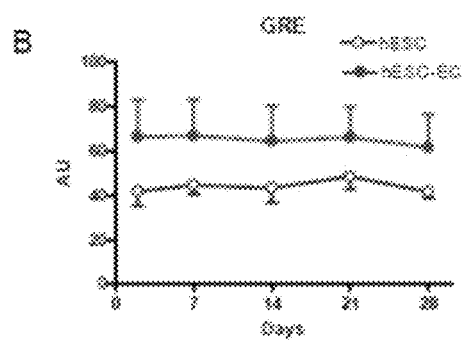
FIG. 4

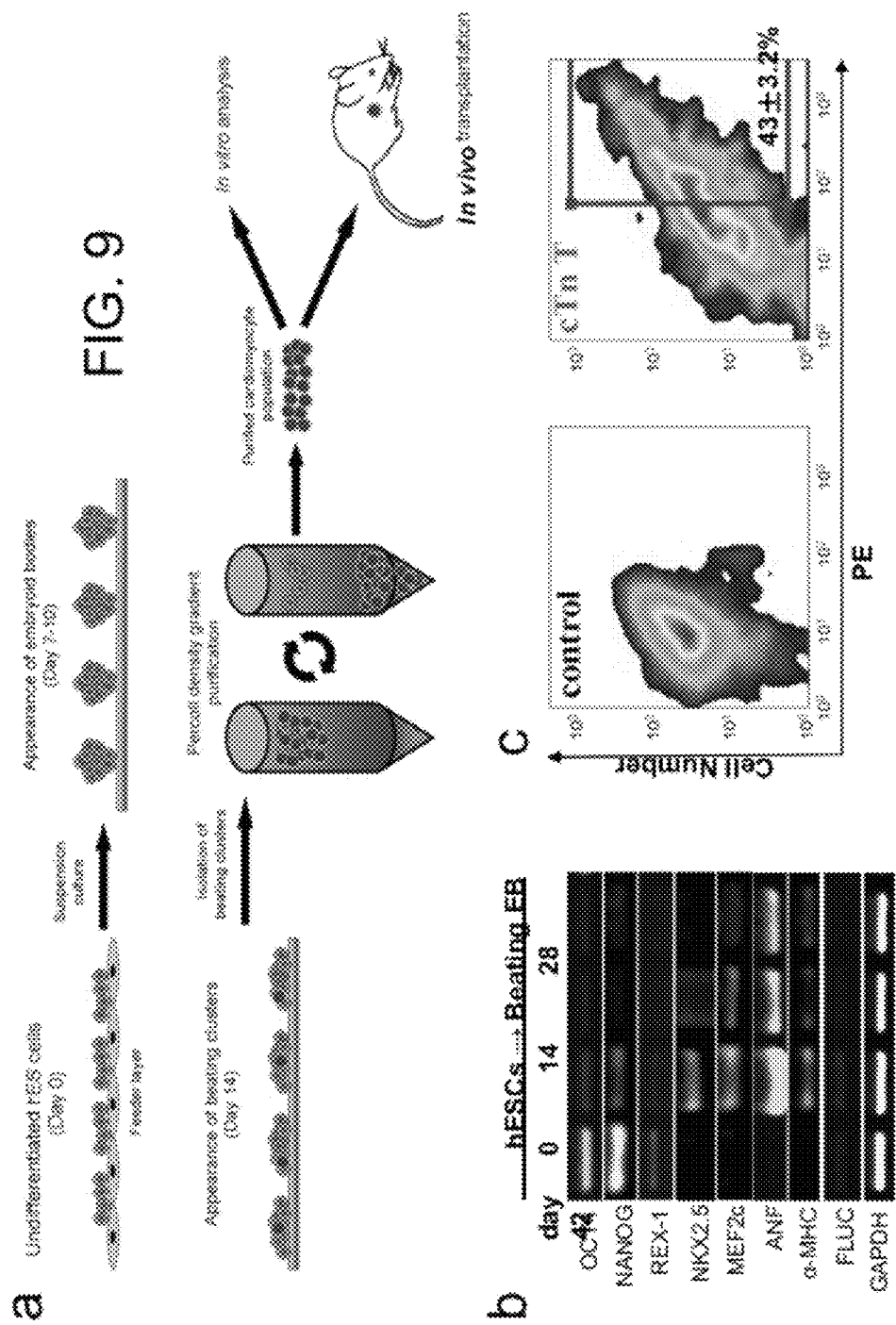

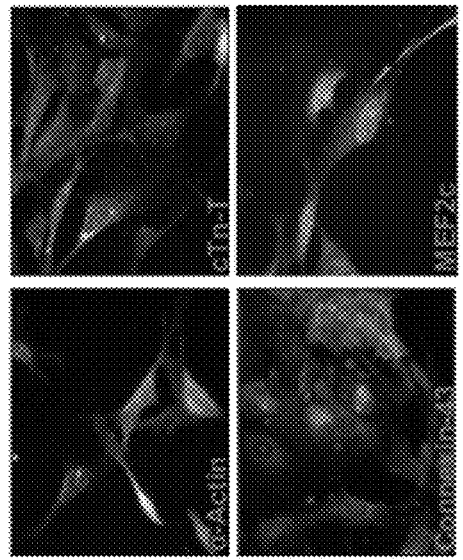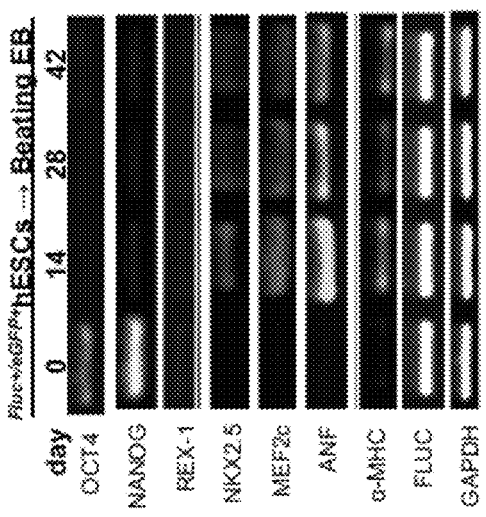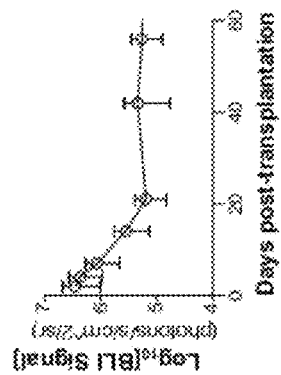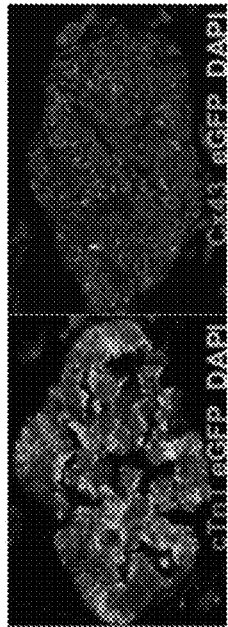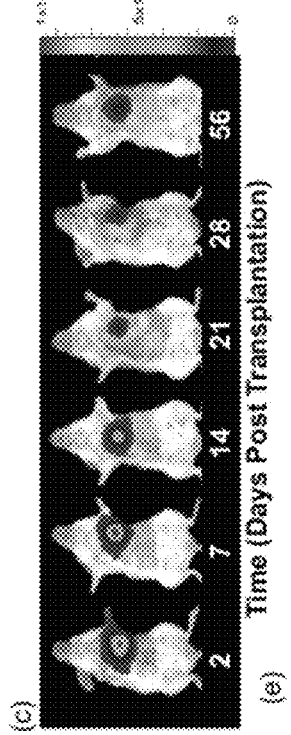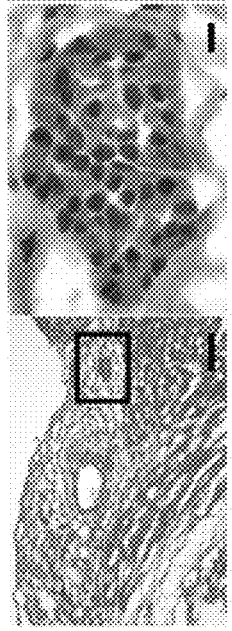
FIG. 13

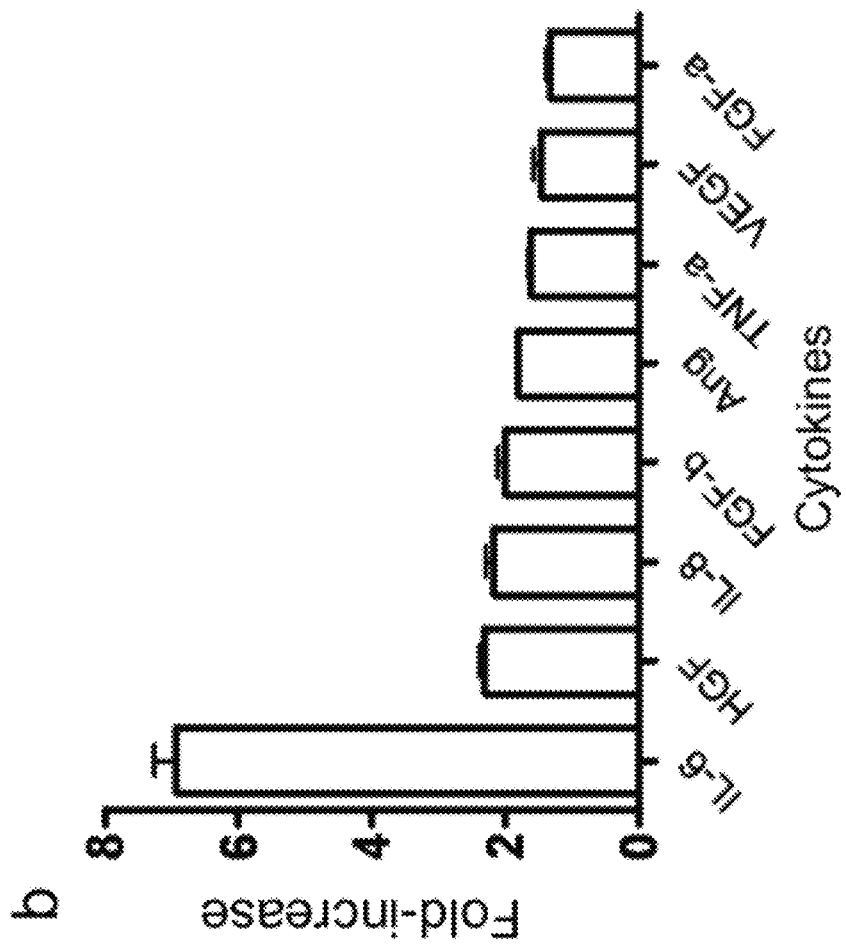
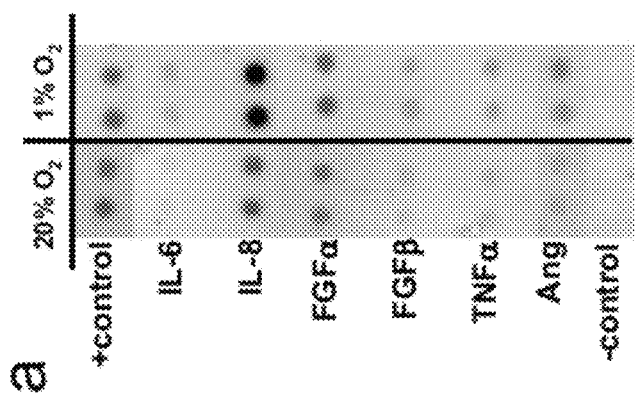
FIG. 20

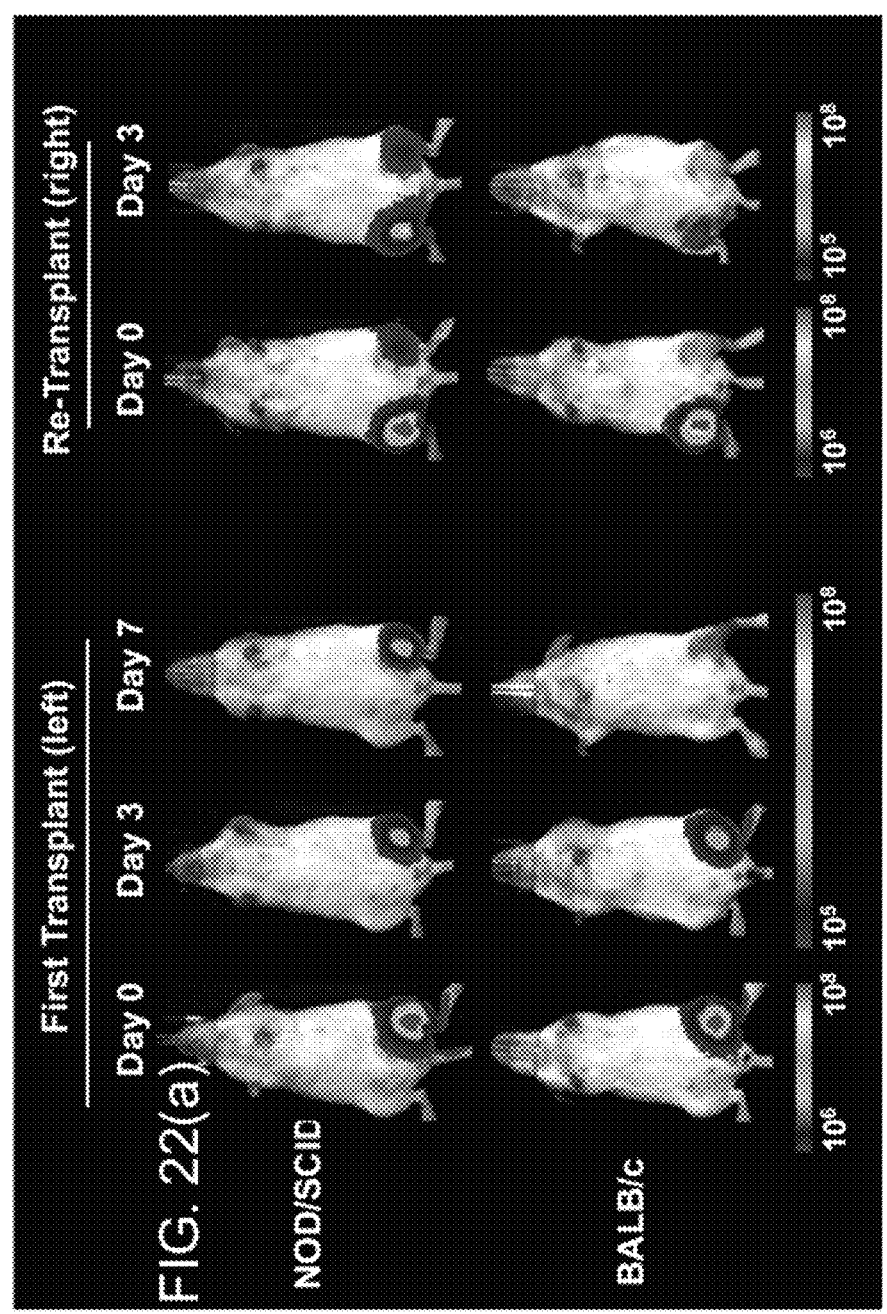

(a)

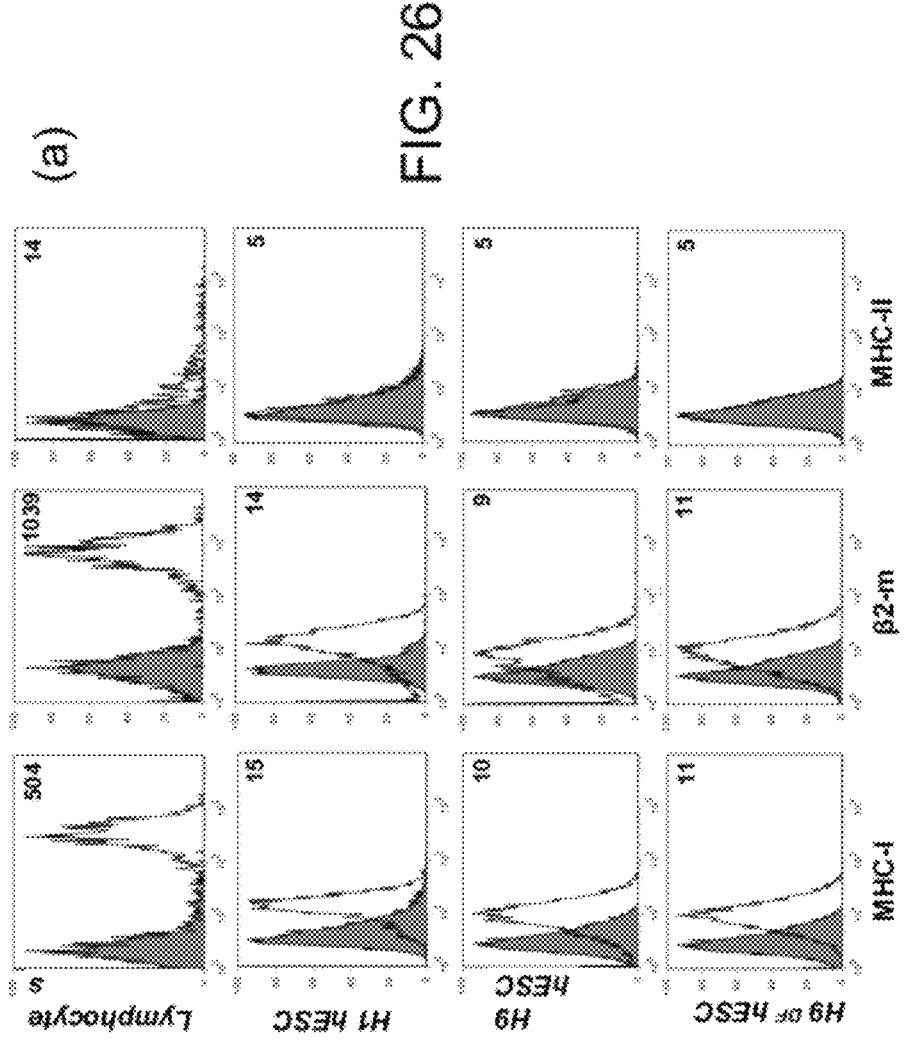

FIG. 32 Immunostaining of Triple/Double Fusion Human Embryonic Stem Cells Derived Teratoma H&E (at 8 weeks after injection)

I: squamous cell differentiation with keratin pearl, II: respiratory epithelium with ciliated columnar and mucin producing goblet cells, III: osteoid (non-mineralized bone) formation ; IV: cartilage formation; V: osteoid formation ; VI: rosette consistent with neuroectodermal (400X)

TRIPLE-FUSION CONSTRUCTS AND METHODS OF MONITORING HUMAN EMBRYONIC STEM CELLS

CROSS-REFERENCE TO RELATED APPLICATION

This application is a divisional application of copending U.S. Utility Application entitled "DOUBLE-FUSION HUMAN EMBRYONIC STEM CELLS, METHODS OF MAKING DOUBLE-FUSION HUMAN EMBRYONIC STEM CELLS, TRIPLE-FUSION HUMAN EMBRYONIC STEM CELLS, METHODS OF MAKING TRIPLE-FUSION HUMAN EMBRYONIC STEM CELLS, AND METHODS OF MONITORING DOUBLE-FUSION HUMAN EMBRYONIC STEM CELLS AND TRIPLE-FUSION HUMAN EMBRYONIC STEM CELLS" having Ser. No. 12/315,873, filed Dec. 4, 2008, which claims priority to U.S. provisional application entitled, "DOUBLE-FUSION HUMAN EMBRYONIC STEM CELLS, METHOD OF MAKING DOUBLE-FUSION HUMAN EMBRYONIC STEM CELLS, AND METHODS OF MONITORING DOUBLE-FUSION HUMAN EMBRYONIC STEM CELLS," having Ser. No. 60/992,136, filed on Dec. 4, 2007, which are entirely incorporated herein by reference.

STATEMENT REGARDING FEDERALLY SPONSORED RESEARCH OR DEVELOPMENT

This invention was made with Government support under contract HL089027 awarded by the National Institutes of Health. The Government has certain rights in this invention. This invention also had support under grant#RS1-00322 from the California Institute of Regenerative Medicine.

BACKGROUND

Human embryonic stem (hES) cells are derived from the inner cell mass of pre-implanted blastocysts. They have been shown to differentiate into a variety of cell types that represent endoderm, ectoderm, and mesoderm origins via three-dimensional structures called embryoid bodies (EBs), which at least partially mimic the spatial organization of the embryo. Various lineages have been derived from hES cells, including neurons, cardiomyocytes, hematopoietic cells, osteogenic cells, hepatocytes, insulin-producing cells, keratinocytes, and endothelial cells. Furthermore, these cells appear to be weakly immunogenic, with absent MHC-II and only low levels of MHC-I molecules. Given their unlimited self-renewal and pluripotency capacity, hES cells represent a new and exciting avenue for stem cell therapy. In cell culture, hES cells can differentiate into endothelial cells through successive maturation steps. Therefore, the isolation and use of hES-derived endothelial cells (hESC-ECs) have potential therapeutic applications, including cell transplantation for repair of ischemic tissues and tissue-engineered vascular grafts.

Stem cell therapy is an exciting area of research that promises future treatment of many diseases. However, to fully understand the beneficial effects of stem cell therapy, investigators must be able to track the biology and physiology of transplanted cells in living subjects over time. At present, most cell therapy protocols require histological analysis to determine viable engraftment of the transplanted cells. The development of sensitive, noninvasive technologies to monitor this fundamental engraftment parameter will greatly aid clinical implementation of cell therapy.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. The patent or application file contains at least one drawing executed in color. Copies of this patent or patent application publication with color drawing(s) will be provided by the Office upon request and payment of the necessary fee.

FIG. 1(A) is a schematic outline of the differentiation procedures. Undifferentiated hES cells were grown to 60%-70% confluence on mouse embryonic fibroblasts (MEFs) or on Matrigel in MEF conditioned medium, dated as day 0. At day 12, hEBs were collected and digested by Liberase Blendzyme IV and CD31$^+$ cells were isolated by FACS and sub-cultured in EGM-2 medium to expand and induce endothelial maturation. Scale bar=20 µm (upper and lower) and 100 µm (middle). FIG. 1(B) is a whole-mount immunochemistry of day-12 hEB. Areas of CD31 cells (red) within hEBs are organized in elongated clusters (I) and channels (II, arrowhead). Cell nuclei stained with DAPI (blue). Scale bar=50 µm (I) and 10 µm (II). FIG. 1(C) illustrates a flow cytometric analysis of endothelial cell markers (CD31, VE-cadherin, and KDR). Percent positive cells are shown. hESC-ECs were isolated from day-12 hEB by FACSan and subcultured. HUVECs were used as positive control. Isotype-matched antibodies were used in flow cytometry for background fluorescence. FIG. 1(D) illustrates a comparison of mRNA expression levels of hESC, hEB and hESC-EC between HUVEC. The quantification was performed by real-time RT-PCR. Experiments were performed in triplicates. $^\#$P>0.05, *P<0.05 compared to HUVEC. FIG. 1(E) illustrates an endothelial tube formation by hESC-ECs and HUVECs after 12 hours of plating on Matrigel in 24-well plates. Scale bar=20 µm. Abbreviations: hEB, human embryoid body; hESC, human ES cell; FACS, fluorescence activated cell sorting; HUVEC, human umbilical vein endothelial cell.

FIG. 2(A) illustrates schema of the double fusion reporter gene containing fusion of Fluc-eGFP. The double fusion reporter gene was cloned into a self-inactivating lentiviral vector downstream from the constitutive ubiquitin promoter. FIG. 2(B) illustrates the control nontransduced hES cells and transduced hES cells showed similar expression pattern of Oct-4 under fluorescence microscopy. DAPI staining is used as a nuclear marker. Scale bar=10 µm. FIG. 2(C) illustrates ex vivo imaging analysis of stably transduced hES cells show increasing bioluminescence signals with cell numbers of hES cells ($r^2$=0.99) and with hESC-ECs ($r^2$=0.99). Compared to hES cells, hESC-ECs expressed higher bioluminescence activity. Data are representative of three independent experiments. FIG. 2(D) illustrates a flow cytometric analysis of double fusion hESC-ECs. Percent positive cells are shown in the upper right hand corner. Double fusion hESC-ECs were isolated from day-12 hEB by FACSan and subcultured. Normal hESC-ECs were used as control. Isotype-matched antibodies were used in flow cytometry for background fluorescence. FIG. 2(E) illustrates the uptake of Dil-ac-LDL (red) by double fusion hESC-ECs.

Nuclei were stained with DAPI (blue). Data are representative of three independent experiments. Scale bar=50 μm. Abbreviations: DAPI, 4′, 6-diamidino-2-phenylindole; EC, endothelial cell; LDL, low density lipoprotein.

FIGS. 3(A)-3(C) illustrate iron particle labeling of hES cells and hESC-ECs. FIG. 3(A) illustrates prussian blue staining for iron shows cytosolic deposition of blue crystals. Upper panel is 100× and lower panel is 1000× magnification. Scale bar=100 μm (upper) and 10 μm (lower). FIG. 3(B) illustrates representative in vitro cellular MR images. Iron-labeled hESC-ECs demonstrated larger area of signal dephasing. The cell suspensions in 96-well plates each contain $1\times10^4$, $5\times10^4$, $1\times10^5$ iron-labeled cells (from left to right). FIG. 3(C) illustrates trypan blue cell viability assay show no significant difference between control unlabeled cells and iron labeled cells for both cell populations (hESC and hESC-EC).

Figure 4:
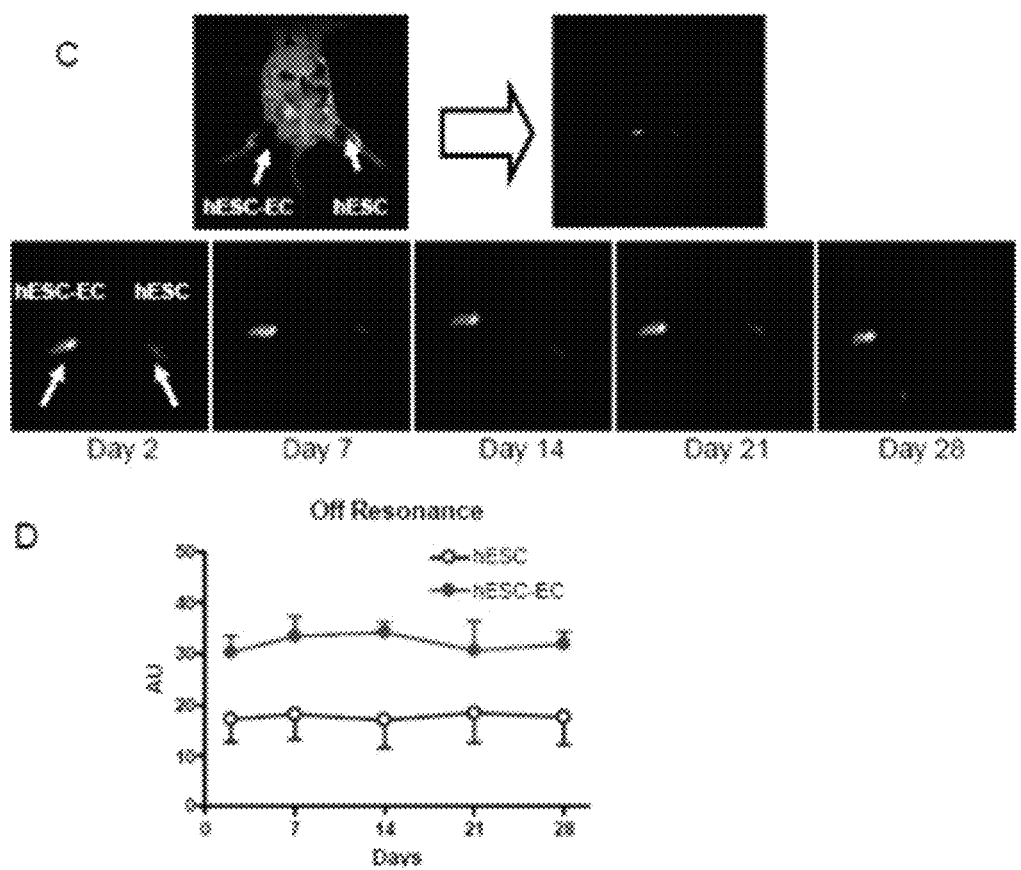

FIGS. 4(A)-4(D) illustrate serial in vivo MR imaging of iron-labeled cells from day 2 to week 4. FIG. 4(A) illustrates representative in vivo gradient-recalled echo (GRE) imaging. No hypointense signal is found in the MR image of control mouse injected with unlabeled cells. MR signals showed no significant difference from day 2 to day 28. MR image by GRE at day 28 shows bulking expansion of the left hind limb injected with hES cells due to teratoma formation (arrow head). FIG. 4(B) illustrates detailed quantitative analysis of GRE signals from all animals transplanted with hES cells and hESC-ECs (signal activity is expressed as authority unit (AU)). FIG. 4(C) illustrates representative in vivo Off-Resonance (OR) imaging. FIG. 4(D) illustrates the analysis of quantitative OR signal from all animals transplanted with iron-labeled cells. No significant differences in the OR signal analysis was observed from day 2 to day 28. Abbreviations: GRE, gradient-recalled echo; OR, off-resonance.

Figure 5:
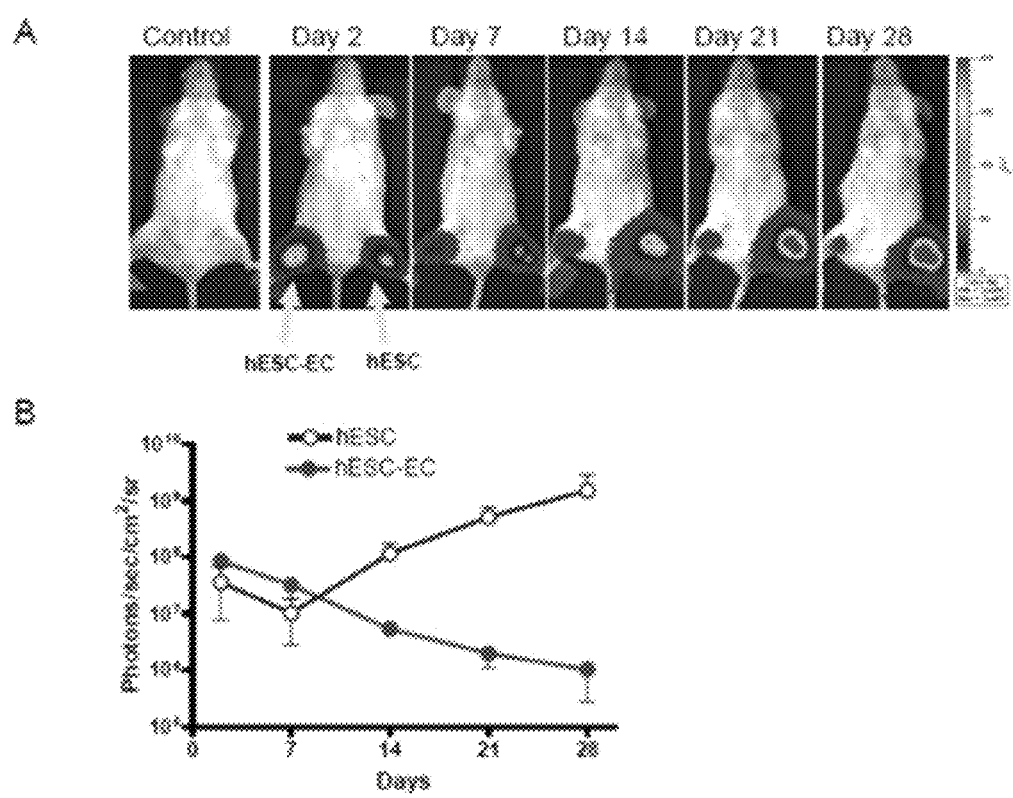

FIGS. 5(A)-5(B) illustrate reporter gene imaging of hES cell and hESC-EC fate after transplantation. FIG. 5(A) illustrates a representative animal injected with $1\times10^6$ hESC-ECs (right hind limb) shows significant bioluminescence activity at day 2, which decreases progressively over the following 4 weeks. In contrast, undifferentiated hES cells (left hind limb) show the lowest bioluminescence signals at day 7, which increases dramatically during week 2 and week 4. FIG. 5(B) illustrates a detailed quantitative analysis of signals from all animals transplanted with hES cells versus hESC-ECs. Signal activity is expressed as photons/sec/cm²/sr. Note the Y-axis is shown as log 10 scale.

Figure 6:
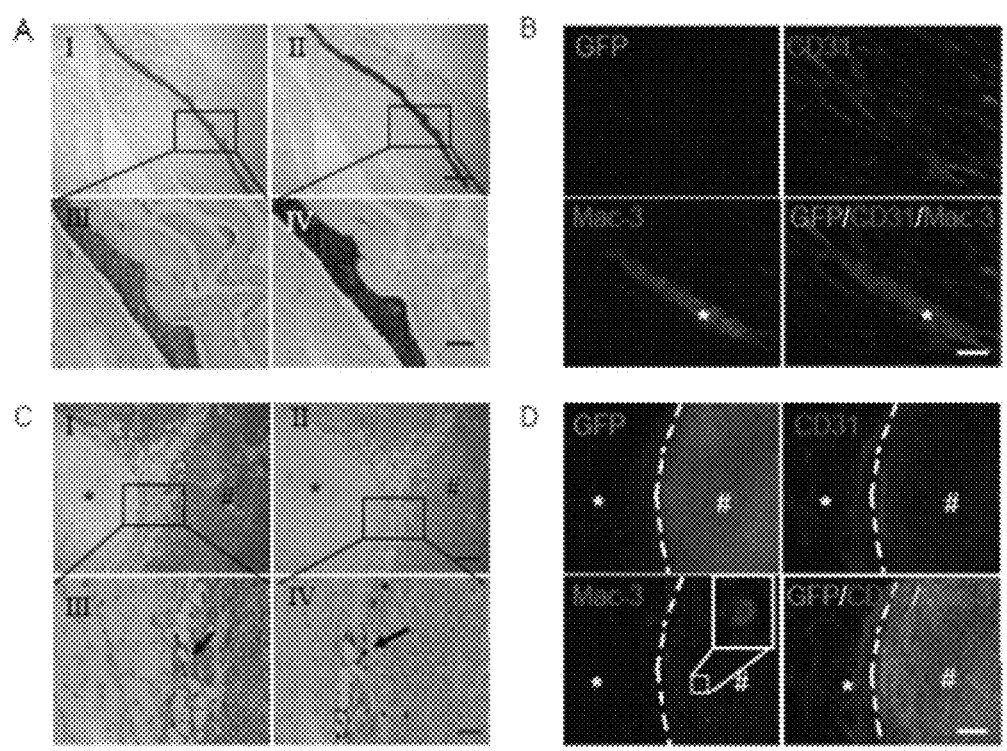

FIGS. 6(A)-6(D) illustrate the histologic analysis of double labeled hES cells and hESC-ECs. FIG. 6(A) illustrates staining for macrophages and iron 4 weeks after transplantation of hESC-ECs. Immunostaining of Mac-3 for macrophages (I, III) and Prussian blue for iron (II, IV) were counterstained with hematoxylin and nuclear fast red, respectively. Note macrophages loaded with iron particles can be found in between muscle bundles. Scale bar=100 μm (I, III) and 20 μm (II, IV). FIG. 6(B) illustrates immunofluorescence staining of GFP for transplanted double fusion hESC-ECs, CD31 for microvasculature of hindlimb, and Mac-3 for macrophages at 4 weeks after transplantation. There were no transplanted GFP⁺ hESC-ECs found nearby macrophages. Nuclei were stained with DAPI (blue). Scale bar=20 μm. FIG. 6(C) illustrates the staining for macrophages and iron 4 weeks after implantation of undifferentiated hES cells. Prussian blue positive cells are distributed between normal skeletal muscles (*) and teratoma (#). Scale bar=100 μm (I, III) and 20 μm (II, IV). FIG. 6(D) illustrates immunofluorescence staining for GFP, CD31, and macrophages 4 weeks after transplantation of hESCs. GFP staining showed teratoma formation (#) and clear edge (dashed line) separating from the normal muscle fibers (*). Nuclei were stained with DAPI (blue). Scale bar=20 μm.

Figure 7:
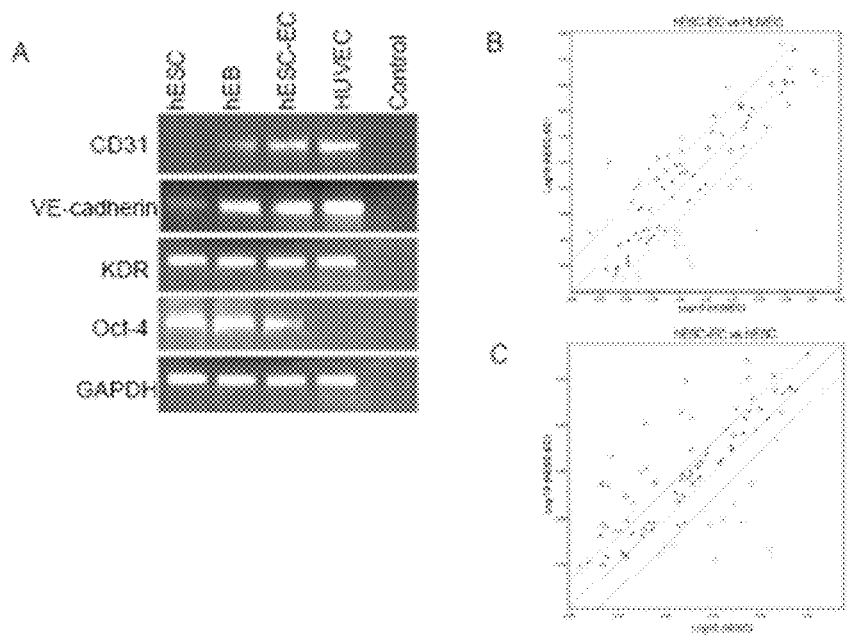

FIGS. 7(A)-7(C) illustrate the analysis of endothelial related gene expression. FIG. 7(A) illustrates a RT-PCR analysis from undifferentiated hES cells, hEBs, and hESC-ECs. The negative control (no template) and the positive control (HUVEC) are shown to the right. Amplification of the housekeeping gene GAPDH is included to demonstrate equivalent amounts of RNA among samples. The endothelial related gene expression patterns were compared between (FIG. 7(B)) hESC-ECs and HUVECs and (FIG. 7(C)) between hESC-ECs and hESCs using the Human Endothelial Cell Biology RT2 Profiler PCR Array. The array includes 84 genes related to endothelial cell biology. The lines indicate the diagonal and 4-fold changes between the two samples. Note the close similarity between hESC-ECs vs. HUVECs and the wide disparity between hESC-ECs and hESCs.

Figure 8:
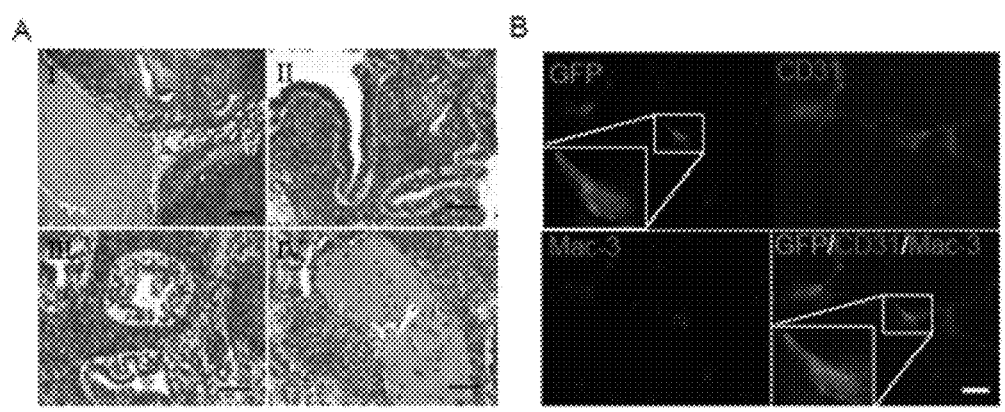

FIGS. 8(A)-8(B) illustrate the histologic analysis of double labeled hES cells and hESC-ECs. FIG. 8(A) illustrates H&E staining of teratoma formation (I) after hES cell implantation identifies various cell types, including gut epithelium (II, Ill) and osteoid formation (IV). Scale bar=100 um (I) and 20 μm (II, III, IV). FIG. 8(B) illustrates the immunofluorescence staining for GFP expression in transplanted hESC-ECs, CD31 for microvasculature of hindlimb, and Mac-3 for macrophages. Few transplanted GFP positive hESC-ECs were found to integrate into the host vasculatures. Nuclei were stained with DAPI (blue). Scale bar=20 μm.

FIGS. 9(a)-9(c) illustrate the differentiation of hESCs to cardiomyocytes that express lineage-specific genes. FIG. 9(a) is a schematic highlighting the experimental design. hESCs are maintained in an undifferentiated state on mouse embryonic fibroblasts (MEFs), then transferred to suspension culture and allowed to form embryoid bodies for 7 to 10 days. Upon appearance of beating clusters, the whole embryoid bodies are dissociated and separated by Percoll density gradient enrichment to obtain cardiomyocytes (hESC-CMs). The hESC-CMs are then used for either in vitro analysis or in vivo transplantation into the heart. FIG. 9(b) illustrates the RT-PCR analysis of embryoid bodies over the course of 6 weeks shows expression of endodermal, (AFP), mesodermal (aMHC), and endodermal (NeuroD) germ layer markers. GAPDH is used as loading control. FIG. 9(c) illustrates FACS analysis shows approximately 43.0±3.2% cells isolated by Percoll density gradient separation are positive for cardiac troponin-T. Control population is cells prior to Percoll separation.

Figure 10A:
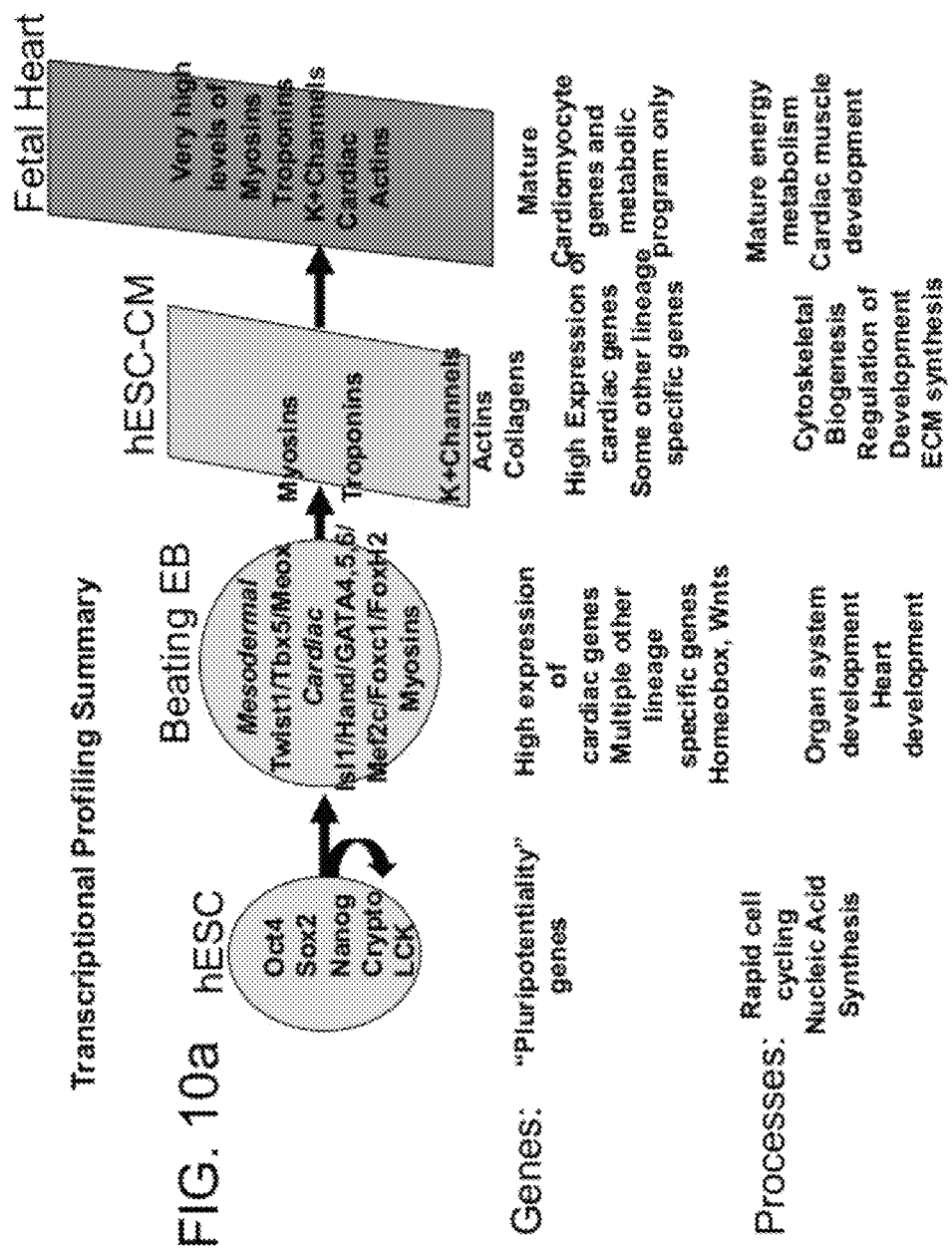
Figure 10:
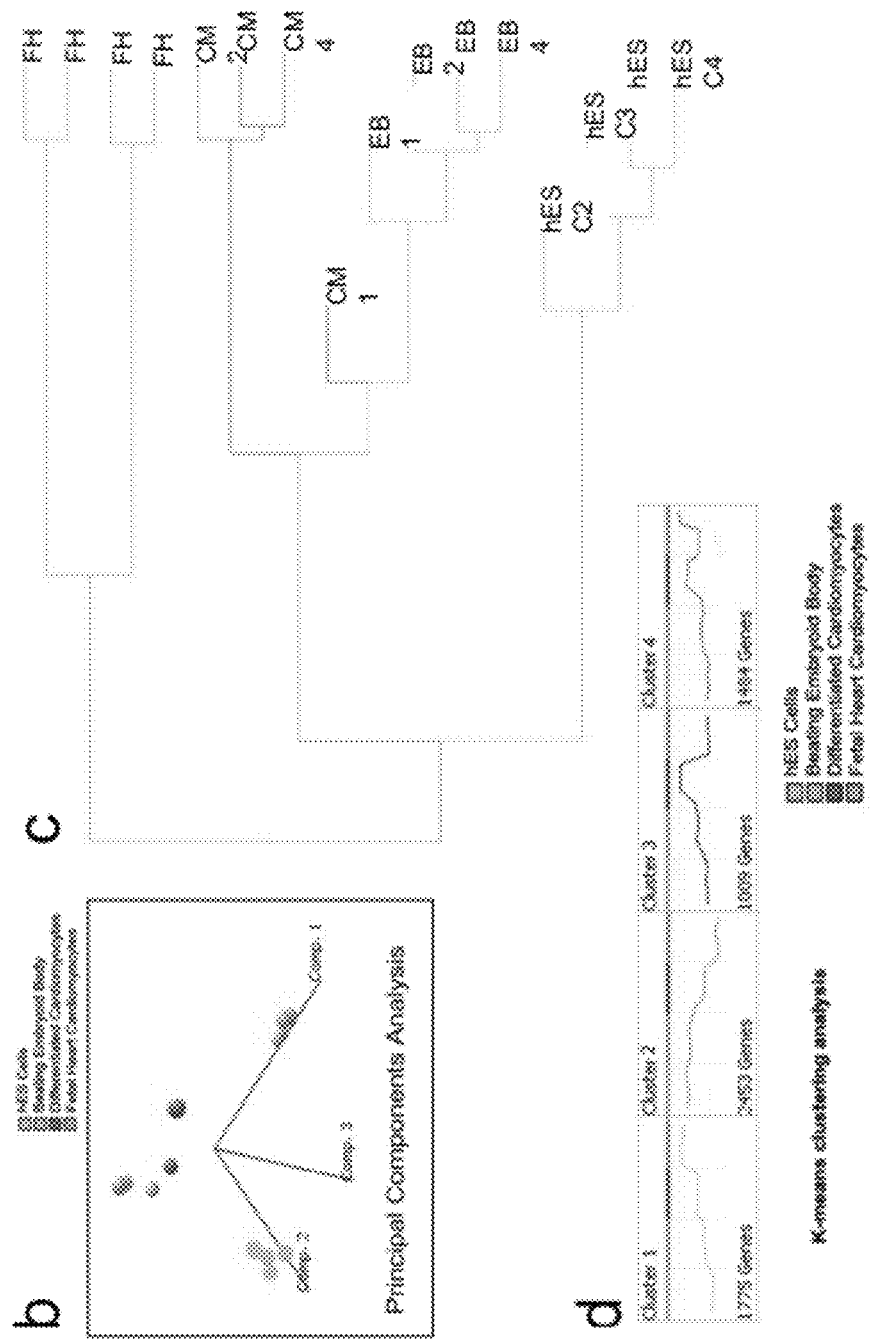

FIGS. 10(a)-10(d) illustrate the major themes in gene expression profiles at each stage of differentiation. FIG. 10(a) illustrates that hESCs express high levels of pluripotency-associated genes including Oct4, Sox2, NANOG, Crypto, and LCK. At the beating EB stage, the cells express high levels of mesodermal master regulators such as Twist1, Tbx5, and Meox as well as very enriched levels of cardiogenic specific master regulators including IsI1, Hand, GATA4, 5, 6, and Mef2C, along with high levels of cardiac specific myosins. This population also expresses genes from other cell layers, and many developmental genes from Wnt and homeobox families. Cardiomyocytes downregulate early mesodermal genes and express more cardiac specific and structural genes, while fetal heart cells have the highest levels of mature cardiac gene expression with very few other developmental lineages represented. FIG. 10(b) illustrates that the Principal Components Analysis (PCA) shows that replicate experiments of each cell type are very similar while differentiation groups separate significantly along components 1 and 2. FIG. 10(c) shows the Hierarchical Clustering Analysis—Cells from each developmental stage cluster relatively close to each other, with the most distance between hESCs and fetal heart cardiomyocytes. FIG. 10(d) shows the K-means clustering analysis identifies major trends in gene expression across the timecourse.

FIGS. 11(a) and 11(b) illustrate the electrophysiological recordings of hESC-CMs. Action potential (AP) recordings from single cells were done using the whole-cell patch-clamp technique. hESC-CMs were categorized into pacemaker-, atrial-, or ventricular-like phenotypes, based on such common electrophysiological characteristics as the AP amplitude (mV), upstroke velocity (mV/ms), APD50 and APD90 (ms), as well as the resting membrane potential (RMP, mV). FIG. 11(a) illustrates representative ventricular-, atrial-, and pacemaker-like action potentials, demonstrating electrophysiological heterogeneity in our hESC-CM population, and FIG. 11(b) illustrates $Ca^{2+}$ transients recorded from hESC-derived cardiomyocytes, confirming calcium influx of these cells. See Materials and Methods for description of experimental parameters.

Figure 12:
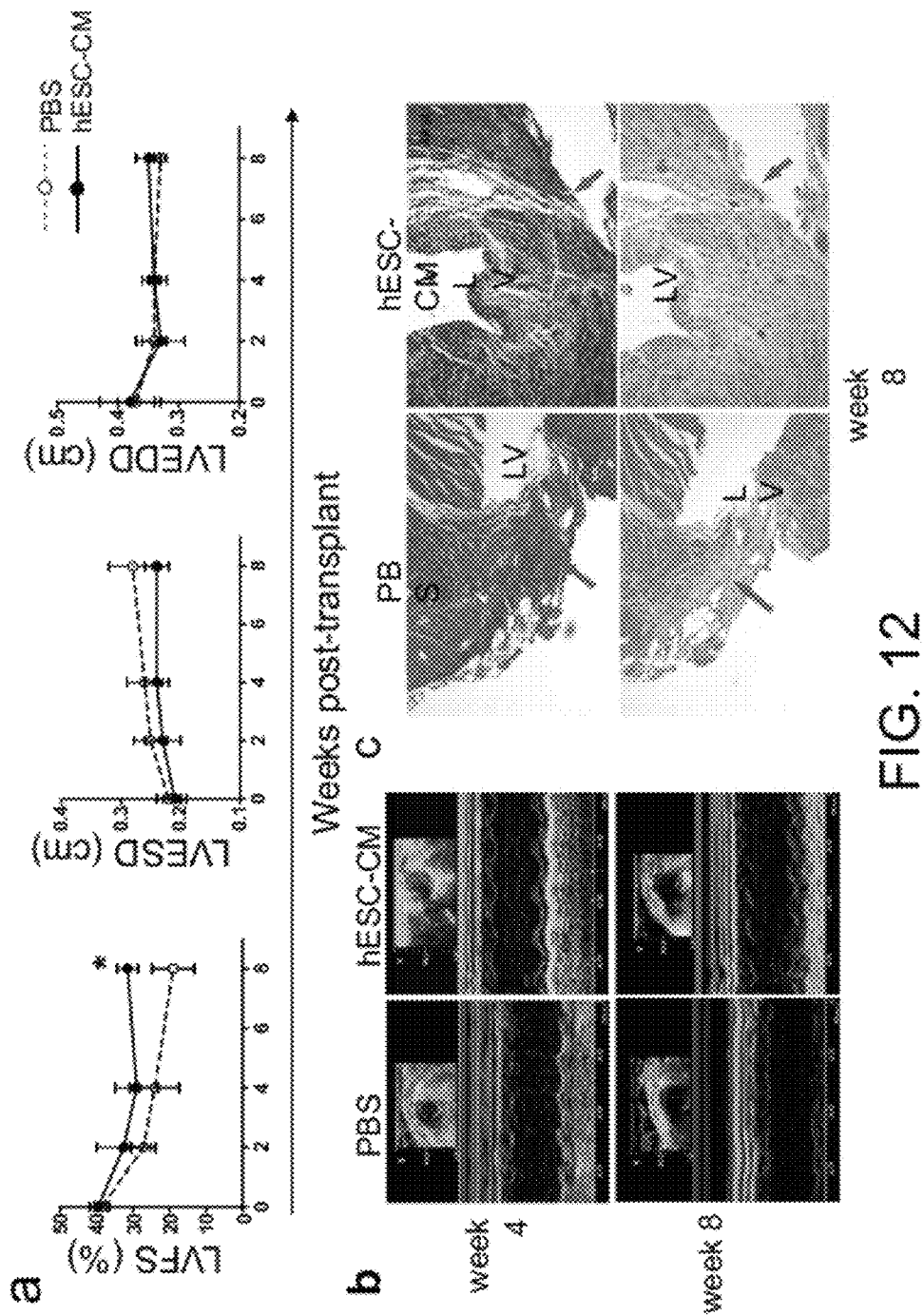

FIGS. 12(a)-12(c) illustrate the assessment of myocardial function after ischemic injury and hESC-CM transplantation. FIG. 12(a) illustrates the echocardiography demonstrates improved cardiac contractility (left ventricular fractional shortening, LVFS) following delivery of one million hESC-CMs compared to PBS injection alone at eight weeks post-transplant (P=0.03). This was primarily due to improvement in left ventricular end systolic dimension (LVESD, middle) without significant changes in left ventricular end diastolic dimension (LVEDD, right). FIG. 12(b) illustrates the representative M-mode echocardiographic images from a mouse receiving hESC-CM transplantation (right panels) versus a mouse receiving a control PBS injection (left panels) at 4 (top panels) and 8 weeks (bottom panels). FIG. 12(c) illustrates histological evaluation of infarct fibrosis reveals attenuation of scar in a representative animal treated with hESC-CMs (right panels) as compared with a representative animal receiving PBS alone (left panels) at 8 weeks post-transplantation. Masson's Trichrome stain (top panels) produces blue connective tissue and red muscle fibers to allow easy identification of the fibrotic scar resulting from ischemia reperfusion injury. Scale bars=10 µm.

FIGS. 13(a)-13(e) illustrate the survival and fate of $^{Fluc+/eGFP+}$hESC-CMs in vivo. FIG. 13(a) illustrates RT-PCR analysis of various hESC and cardiac specific markers revealed no significant differences between $^{Fluc+/eGFP+}$hESCs and control non-transduced hESCs (see FIG. 9b for comparison), other than the presence of Fluc. FIG. 13(b) illustrates $^{Fluc+/eGFP+}$hESC-CMs express cardiac specific markers such as α-actin, troponin-T, connexin-43, and MEF2C (all in red) and GFP (green, scale bars=50 µm). FIG. 13(c) illustrates a representative animal imaged for 2 months following transplantation of 1 million $^{Fluc+/eGFP+}$hESC-CMs into the heart. FIG. 13(d) illustrates in vivo bioluminescence imaging (BLI) signal measured from animals in which $^{Fluc+/eGFP+}$hESC-CMs were transplanted into the ischemic hearts (n=15). Signal activity falls drastically within the first 3 weeks of transplantation and remains stable thereafter, with no evidence of tumorigenesis (left). From 21 days post-transplantation onwards, BLI signal is reduced to <10% of the signal obtained at two days post-transplantation. FIG. 13(e) illustrates the histopathological evaluation of hearts following $^{Fluc+/eGFP+}$hESC-CM delivery. H&E staining (left panels) demonstrates cluster of cells within the infarcted region of the heart (scale bars=200, 20 µm for low and high magnification images, respectively). GFP positive cells within this cluster also express cardiac troponin-T (red, near right panel) and connexin-43 (red, far right panel). Scale bars=20 µm.

Figure 14:
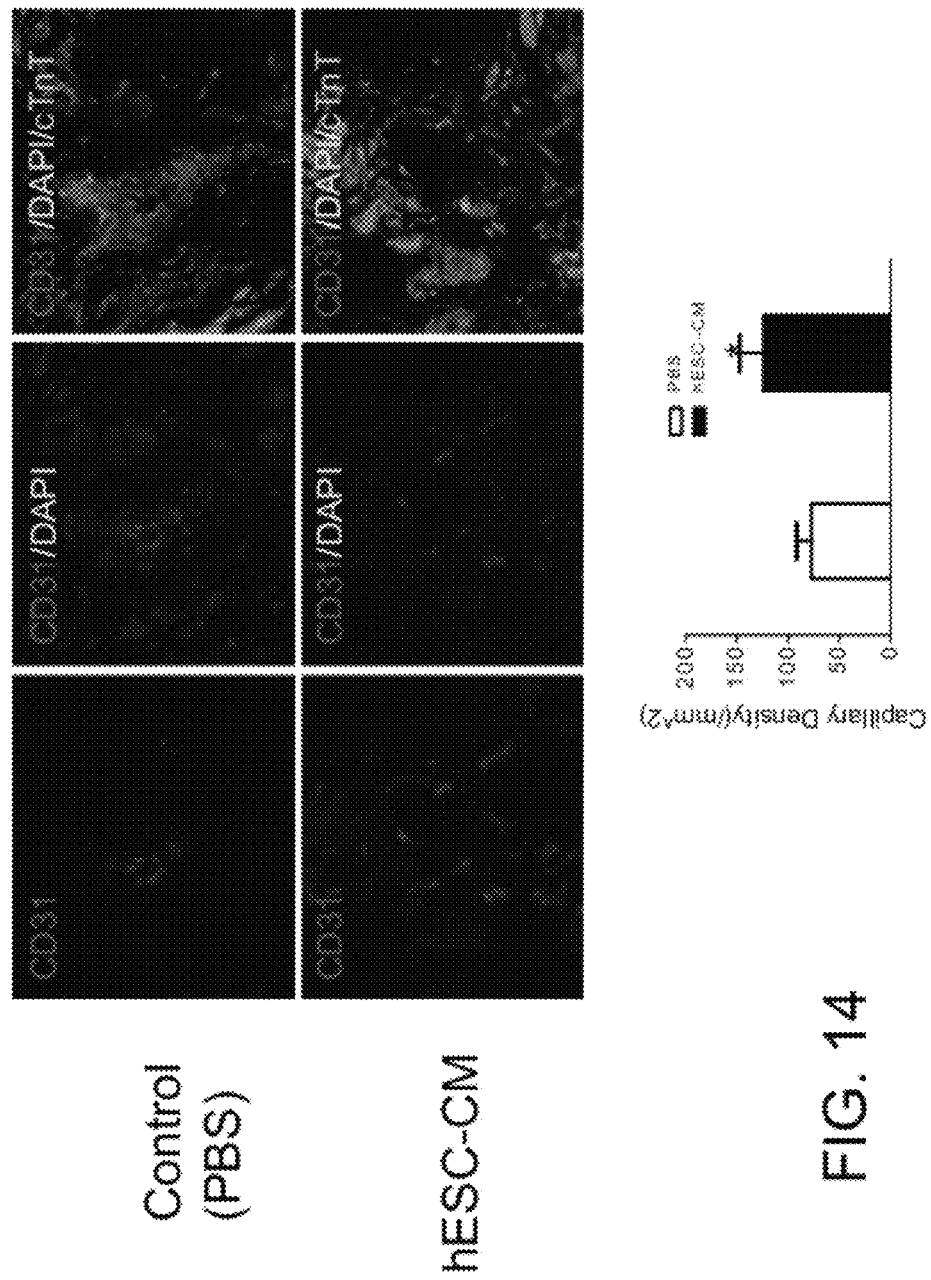

FIG. 14 illustrates the quantitative analysis of the endothelial cell marker CD31 (mouse) shows upregulation of capillary density in ischemic hearts at week 8. The hESC-CM-treated group showed significant augmentation of CD31 positive capillary density (P<0.05). Capillary densities were examined by counting the number of capillaries stained with anti-CD31 in five random fields on two different sections (approximately 3 mm apart) from each mouse. Images were analyzed using Image J software.

Figure 15A:
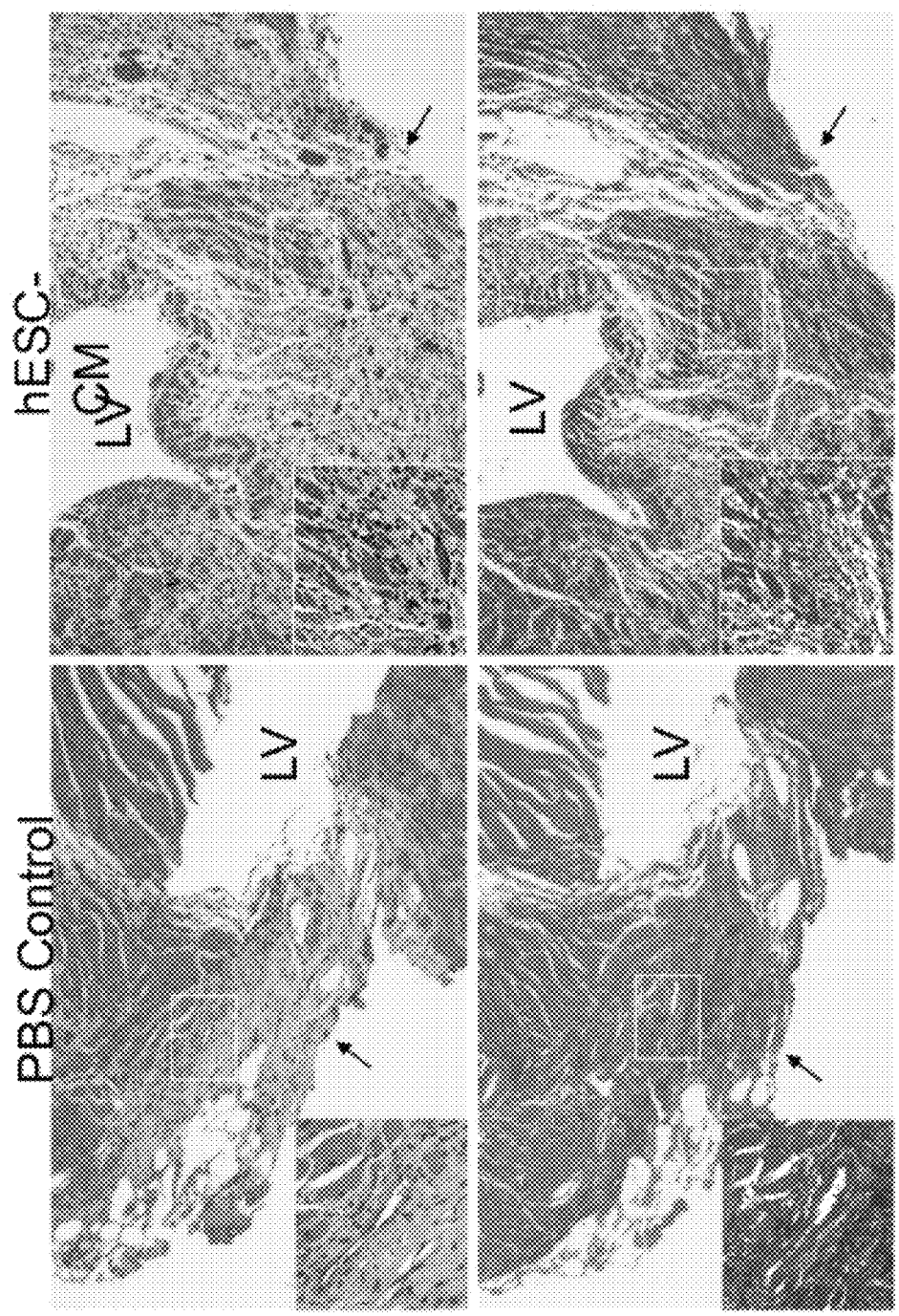
Figure 15B:
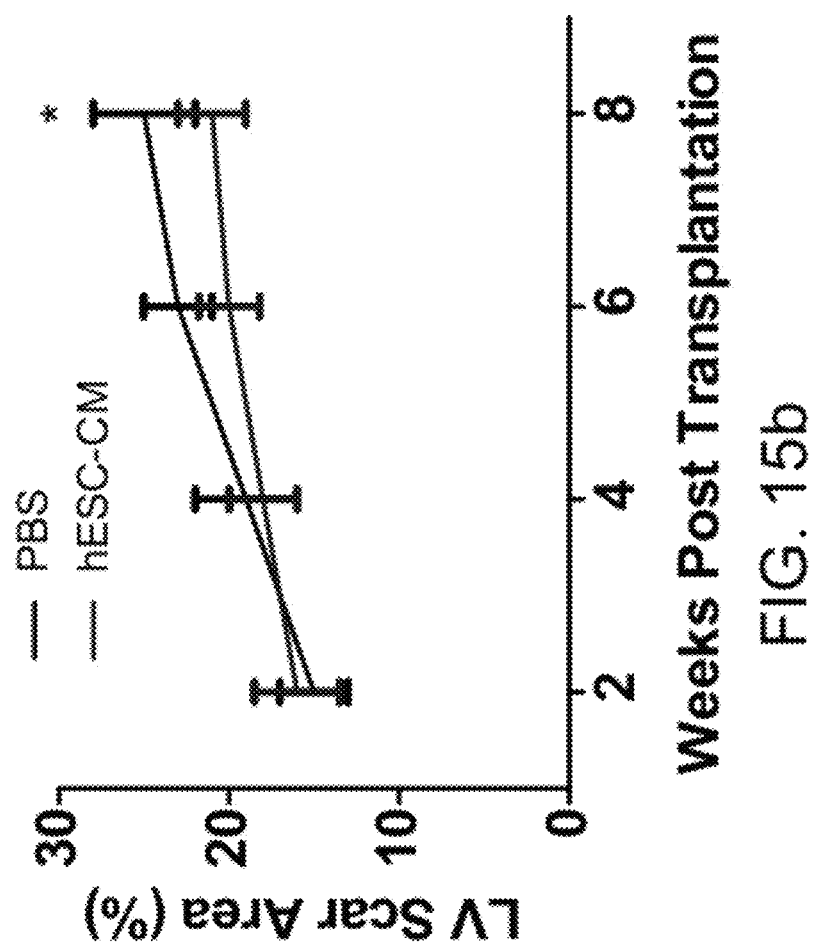

FIGS. 15(a) and 15(b) illustrate ventricular scar formation after hESC-CM transplantation. FIG. 15(a) illustrates histological evaluation of infarct fibrosis reveals attenuation of scar in a representative animal treated with hESC-CMs (right panels) as compared with a representative animal receiving PBS alone (left panels) at 8 weeks post-transplantation. Masson's Trichrome stain (bottom panels) produces blue connective tissue and red muscle fibers to allow easy identification of the fibrotic scar resulting from ischemia reperfusion injury. FIG. 15(b) illustrates the quantified infarct sizes (percent of LV) in hESC-CM-treated mice and PBS controls were 21%±3% (n=6) and 25%±2% (n=6) (P=0.041), respectively. Scale bars=10 µm.

FIGS. 16(a)-16(e) illustrate the stable lentiviral transduction of hESCs with double fusion (DF) reporter gene. FIG. 16(a) illustrates a schema of the DF reporter gene containing Fluc and eGFP with brightfield (left) and fluorescent (right) images of $^{Fluc+/eGFP+}$hESCs (scale bars=200 µm). FIG. 16(b) illustrates the stably transduced $^{Fluc+/eGFP+}$hESCs (collected by FACS) show robust correlation between cell number and reporter gene activity. Raw bioluminescence images of increasing numbers of $^{Fluc+/eGFP+}$hESCs in vitro are shown below graph. FIG. 16(c) illustrates that $^{Fluc+/eGFP+}$hESCs maintain firefly luciferase activity over successive passages. FIG. 16(d) illustrates that $^{Fluc+/eGFP+}$hESCs maintain pluripotent stem cell markers such as SSEA-4, Oct-4, and AKP, but remain negative for differentiation marker SSEA-1. Scale bars=50 µm. FIG. 16(e) illustrates the RT-PCR analysis of embryoid bodies over the course of 7 weeks shows expression of endodermal (AFP), mesodermal (aMHC), and ectodermal (NeuroD) germ layer markers for both control non-transduced hESCs and $^{Fluc+/eGFP+}$hESCs. GAPDH is used as loading control.

Figure 17:
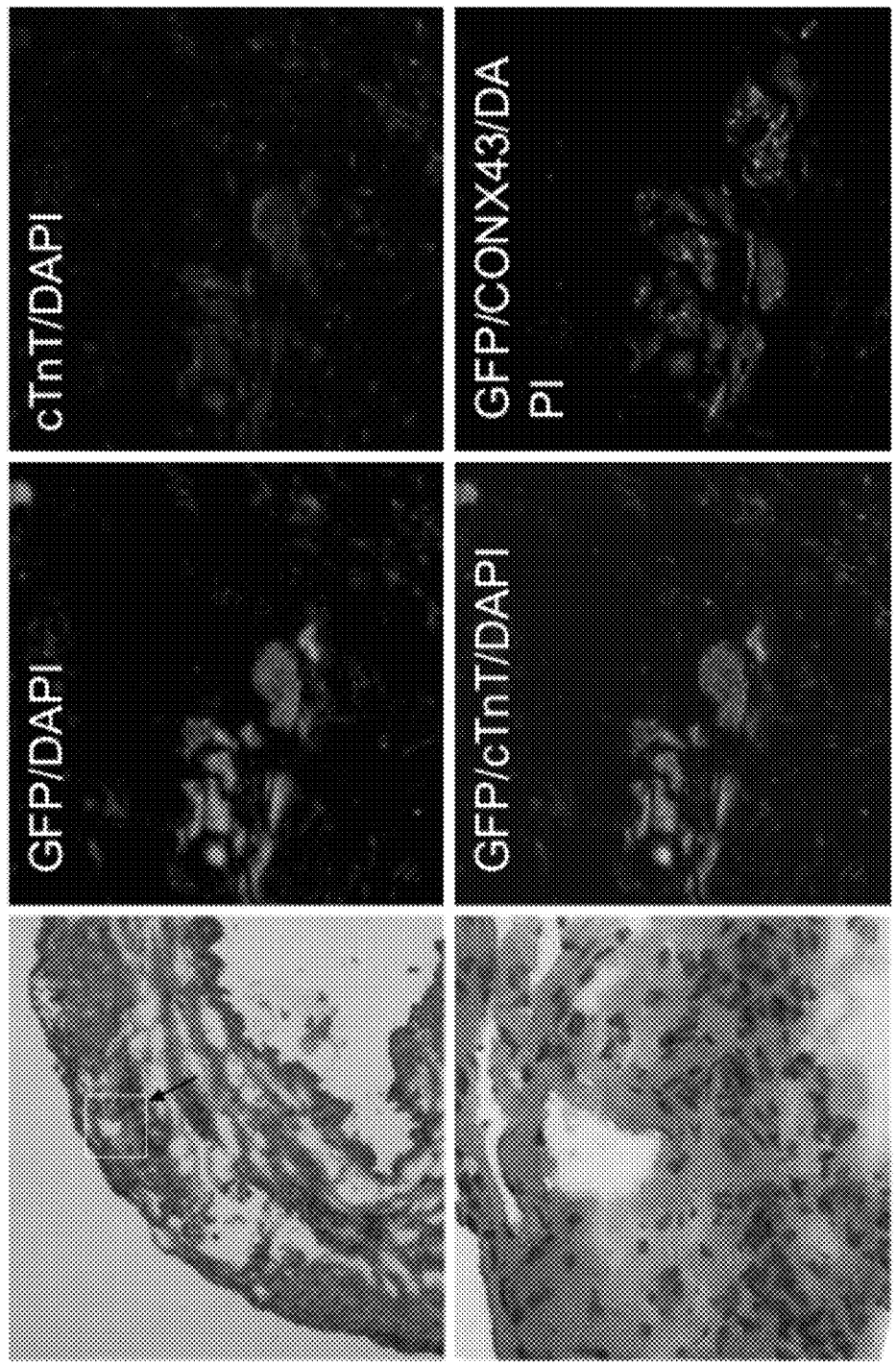

FIG. 17 illustrates the histopathological evaluation demonstrates that hESC-CMs do not integrate into host myocardium but continue to express cardiac markers. Representative histopathological images of explanted hearts taken two months after $^{Fluc+/eGFP+}$hESC-CM delivery. GFP positive cells (transplanted $^{Fluc+/eGFP+}$hESC-CMs) express cardiac troponin-T and connexin-43, but do not appear to be well integrated with the surrounding host myocardium.

FIGS. 18(a)-18(c) illustrate bioluminescence imaging and histological fate of undifferentiated $^{Fluc+/eGFP+}$hES cells transplanted into the heart. FIG. 18(a) illustrates representative images from a single animal receiving one million undifferentiated $^{Fluc+/eGFP+}$hES cells. Undifferentiated hES cells rapidly form teratomas with extra-cardiac spread within 3 to 4 weeks of transplantation. FIG. 18(b) illustrates quantification of imaging signals from animals receiving undifferentiated $^{Fluc+/eGFP+}$hESCs (n=6) or $^{Fluc+/eGFP+}$hESC-CMs (n=15) shows logarithmic increases in BLI signals in the undifferentiated group (*P<0.001) vs. the hESC-CM group due to teratoma formation. FIG. 18(c) illustrates histology demonstrating typical teratoma formation in the heart following transplantation of undifferentiated $^{Fluc+/eGFP+}$hES cells.

Histological features of low-power field of teratoma (I), respiratory epithelium (II), and cartilage formation (III) can be identified (scale bars=50 μm). The border of the graft area shows that only host myocardium stains positive for cardiac markers such as cardiac troponin-T (cTnT), while cardiac markers are absent from the eGFP+region (IV).

Figure 19:
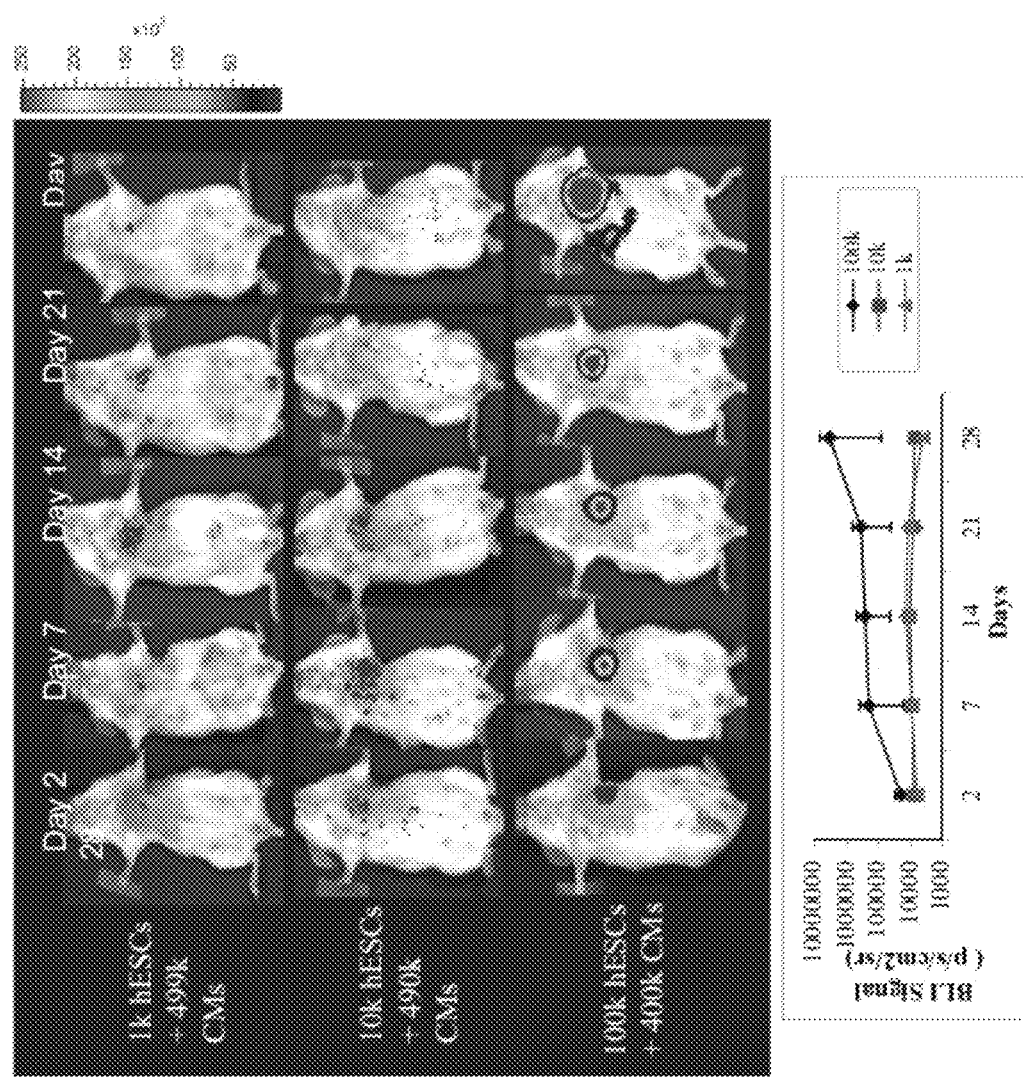

FIG. 19 illustrate bioluminescence imaging of undifferentiated $^{Fluc+/eGFP+}$hESCs mixed with non-transduced hESC-derived cardiomyocytes after transplantation to SCID mouse heart. This study represents a clinically relevant scenario in which undifferentiated hESC contaminants are mixed in with the hESC-CM population. We observed teratoma formation in the 100 k hESC contaminant group, but not in the 10 k or 1 k hESC groups. Data presented as mean±SEM.

FIGS. 20(a)-20(b) illustrate that $^{Fluc+/eGFP+}$hESC-CMs upregulate secretion of angiogenic growth factors under hypoxic conditions. FIG. 20(a) illustrates culture media from hESC-CMs under hypoxia (1% $O_2$/5% $CO_2$/94% $N_2$) or normoxia (20% $O_2$/5% $CO_2$) was washed over an antibody array to assess angiogenic protein secretion levels. FIG. 20(b) illustrates hypoxia induces significant up-regulation of multiple cytokines by $^{Fluc+/eGFP+}$hESC-CMs. Following 12 hours of hypoxia in vitro, media from $^{Fluc+/eGFP+}$hESC-CMs had increased levels of FGF, IL-6, IL-8, and VEGF as compared to cells maintained in normoxic conditions.

Figure 21:
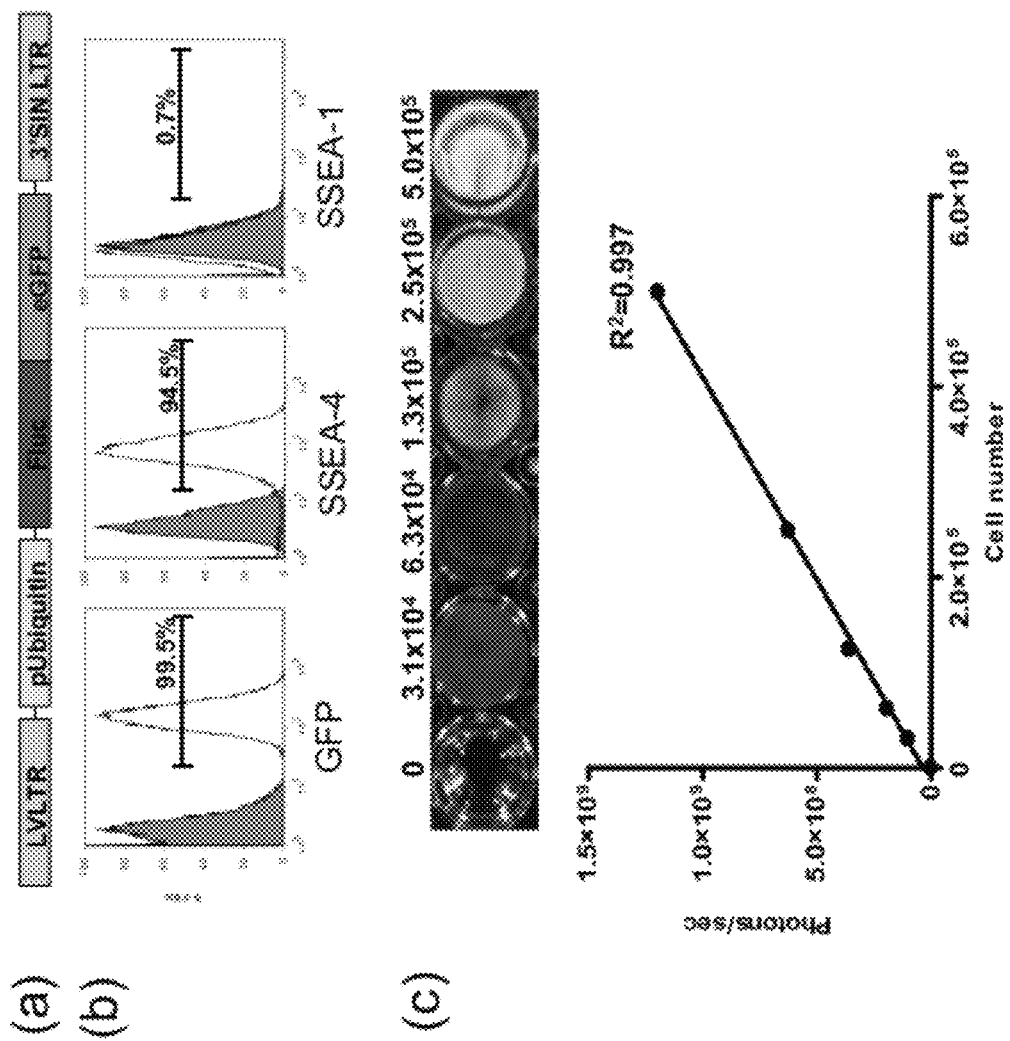
Figure 22:
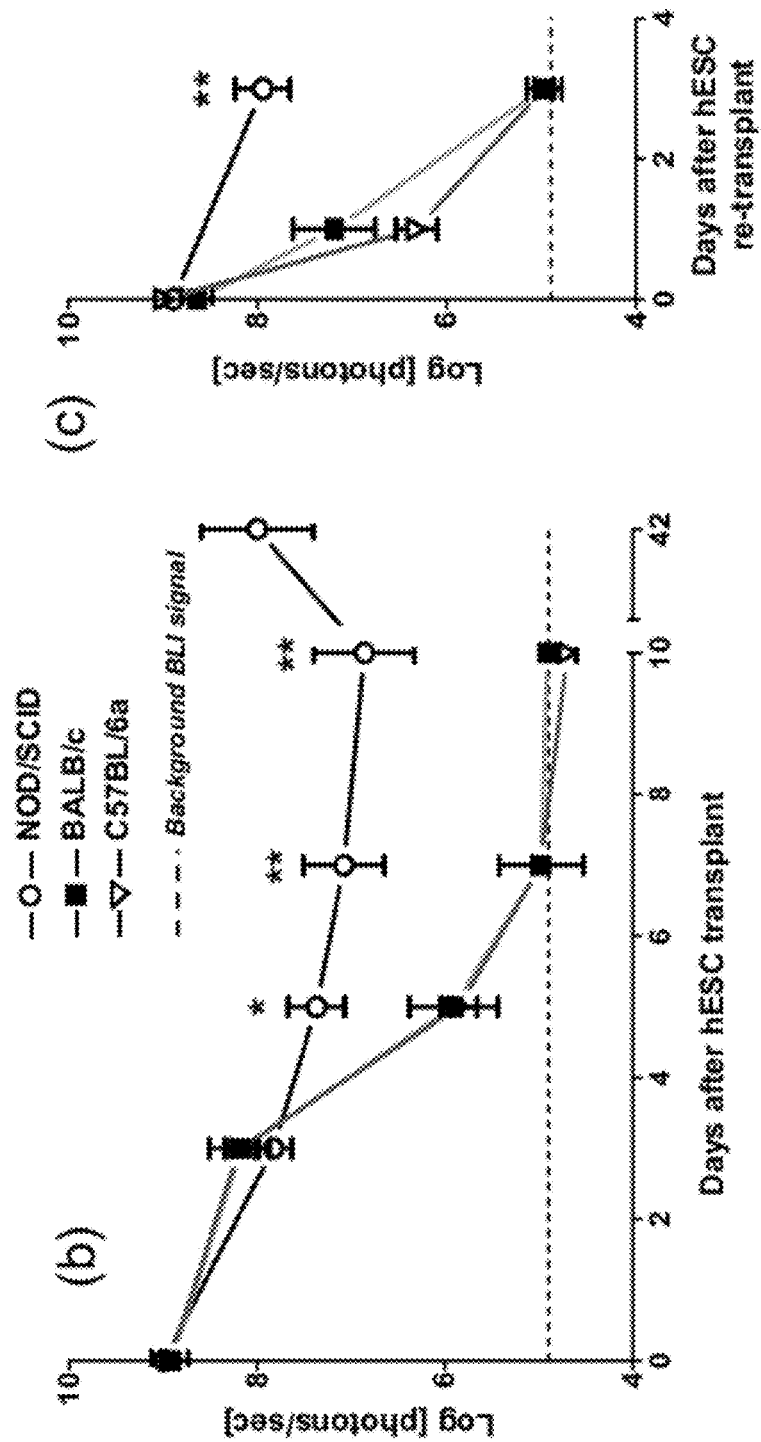
Figure 23:
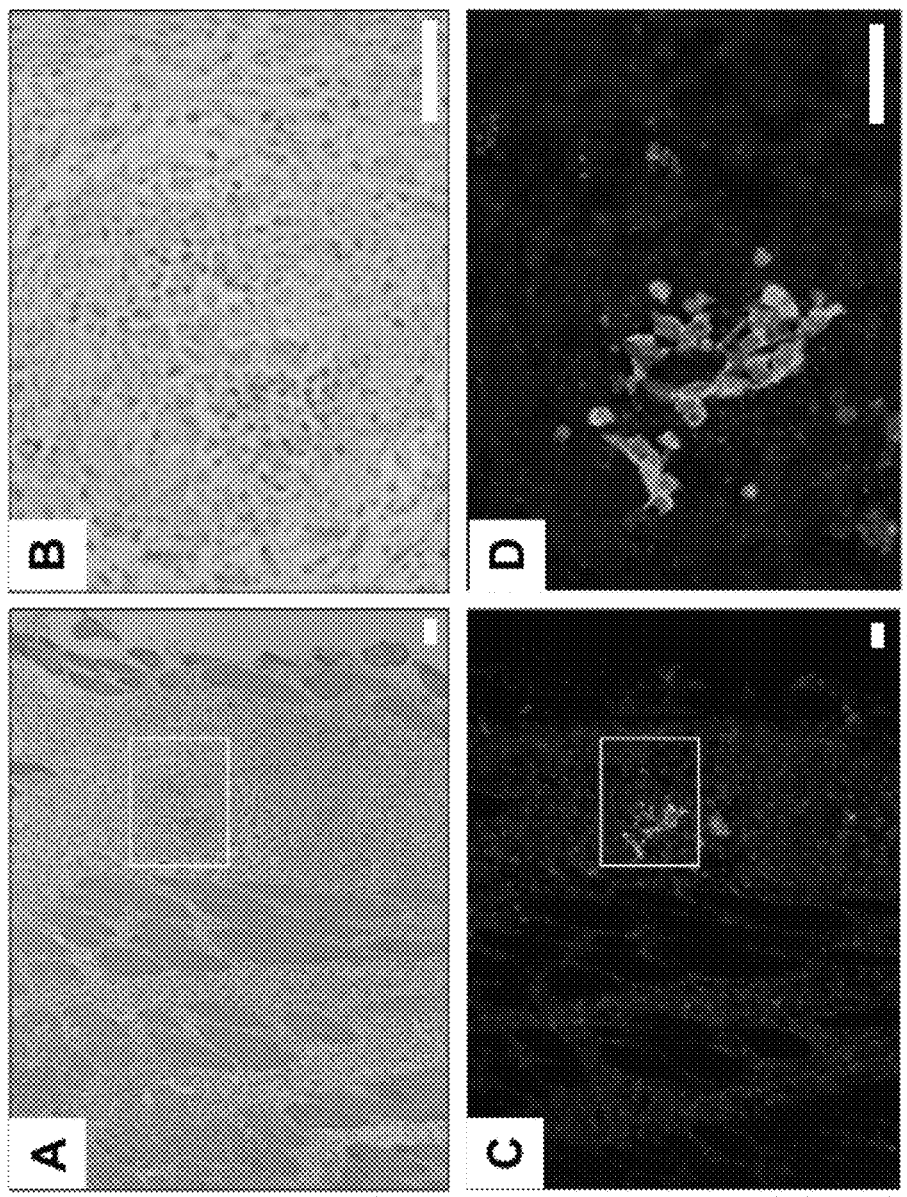
Figure 23:
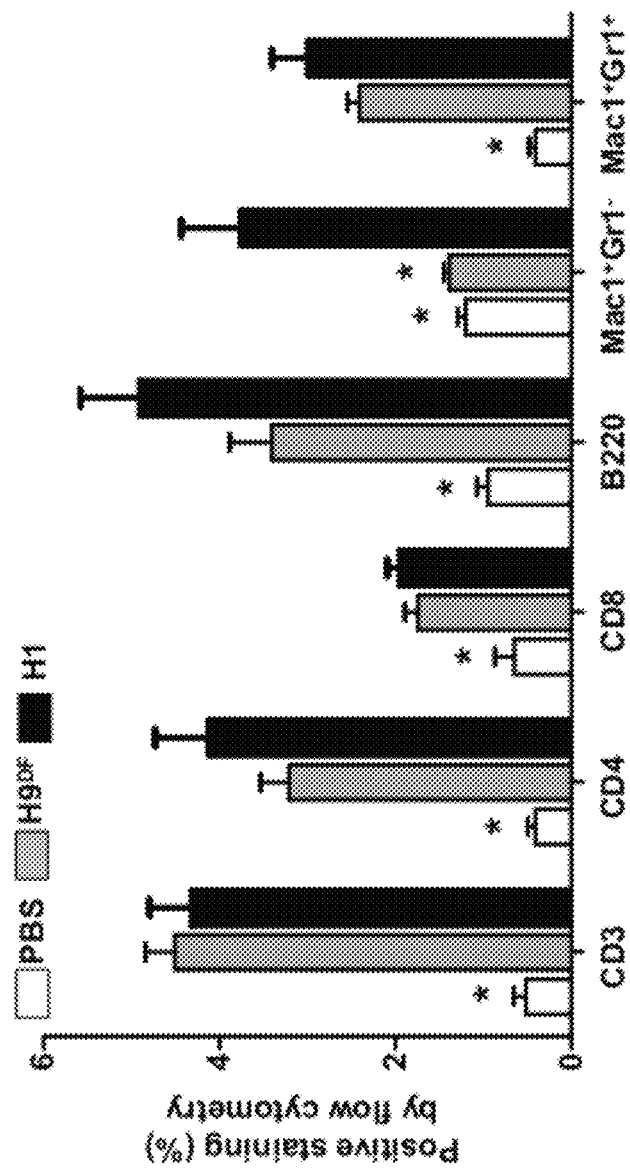

FIGS. 21(a)-21(c) illustrate the characterization of the double fusion (DF) firefly luciferase (fLuc) and enhanced green fluorescent protein (eGFP) transduced hESCs. FIG. 21(a) shows schema of the DF reporter gene containing fLuc and eGFP driven by a human ubiquitin promoter. FIG. 22(b) illustrates a flow cytometric analysis of $H9^{DF}$ hESCs shows robust expression of eGFP. Transduced hESCs are largely positive for SSEA-4, and negative for SSEA-1, confirming their pluripotent state. FIG. 23(c) illustrates the stably transduced hESCs show robust correlation between cell number and reporter gene activity. BLI of a 24-well plate containing increasing numbers of $H9^{DF}$ hESCs are shown above the corresponding graph depicting correlation between cell number and fLuc activity.

FIGS. 22(a) to 22(c) illustrate the in vivo visualization of hESC survival. FIG. 22(a) illustrates representative BLI images of $H9^{DF}$ hESC transplanted animals show a rapid decrease in BLI signal in immunocompetent animals (BALB/c), as opposed to immunodeficient (NOD/SCID) mice, reaching background levels at post-transplant day 7. Accelerated BLI signal loss in BALB/c animals was seen following repeated hESC transplantation into the contralateral gastrocnemius muscle. Color scale bar values are in photons/s/cm²/sr. Graphical representation of longitudinal BLI after FIG. 22(b) primary and FIG. 22(c) secondary hESC transplantation into immunodeficient (NOD/SCID, n=5) and two immunocompetent (BALB/c and C57BI/6a, n=5 per group) mouse strains. Note that in NOD/SCID animals, starting at post-transplant day 10, BLI intensity increases progressively, suggesting hESC proliferation. *P<0.05, **P<0.01.

FIGS. 23(a) to 23(e) illustrate the robust inflammatory cell infiltration following intramuscular hESC transplantation. Histopathological evaluation by H&E staining of muscle sections of BALB/c animals, obtained at 5 days following $H9^{DF}$ hESC transplantation, demonstrates robust intramuscular inflammatory cell infiltration at FIG. 23(a) low power and FIG. 23(b) high power view. (FIGS. 23c and 23d) Immunofluorescent staining on corresponding sections reveals abundant presence of CD3$^+$T-cells (red) surrounding eGFP$^+$ hESCs (green). Counterstaining was performed with 4,6-diamidino-2-phenylindole (DAPI, blue). Scale bars: 50 μm. FIG. 23(e) illustrates the FACS analysis of enzymatically digested muscles revealed intra-$H9^{DF}$ and H1 hESC graft infiltration of CD3$^+$T-cells, CD4$^+$T-helper cells, CD8$^+$Cytotoxic T-cells, B220$^+$B-cells, and Mac-1$^+$Gr-1$^+$ neutrophils at significantly higher intensities, compared to PBS injections. Mac-1$^+$Gr-1$^+$(macrophages) cells had a significantly higher presence only in the H1 group. *P<0.05.

Figure 24:
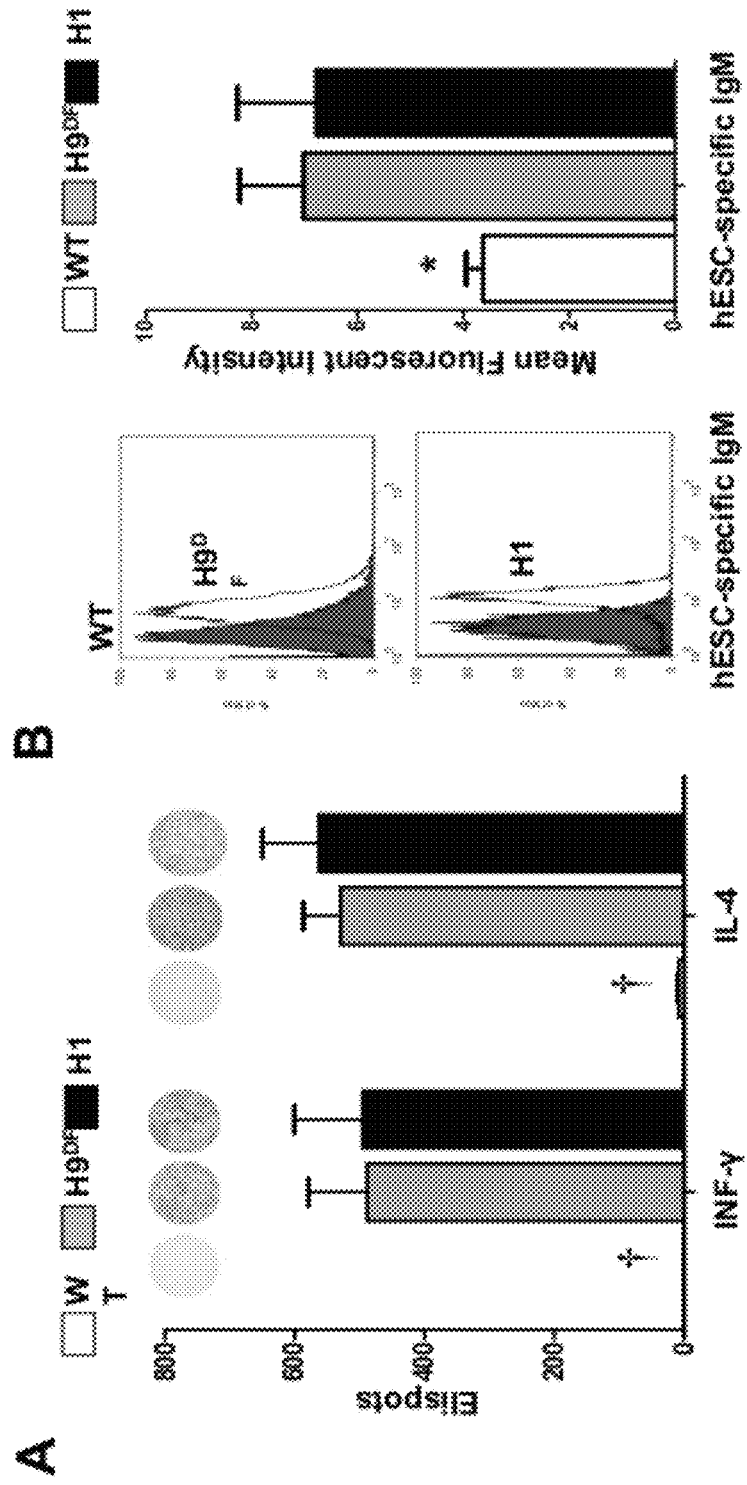

FIGS. 24(a) to 24(b) illustrate hESC transplantation triggers cellular and humoral murine immune responses. FIG. 24(a) shows that the ELISPOT assay revealed significantly higher production of both INF-γ and IL-4 by both H1 and $H9^{DF}$ hESC recipient BALB/c splenocytes (n=6), compared to wild type (WT) animals (n=3). Representative images of ELISPOT wells are shown above the corresponding bars. †P<0.001. FIG. 24(b) illustrates representative flow cytometry histograms (left panels) and graphical representation of hESC-specific xeno-reactive IgM antibodies detected at significantly higher rate in H1 and $H9^{DF}$ hESC recipient BALB/c sera (n=6), as compared to WT animals (n=3). *P<0.05.

FIGS. 25(a) to 25(f) illustrate that the immunosuppressive drug treatment prolongs survival of transplanted hESCs and mitigates adaptive immune response. Representative BLI images of $H9^{DF}$ hESCs transplanted mice receiving no treatment compared to those receiving (FIG. 25(a)) immunosuppressive monotherapy (MMF, TAC or SIR) or (FIG. 25(b)) combined therapy (TAC+MMF, SIR+MMF, TAC+SIR). Although SIR as monotherapy extended hESC survival significantly, TAC+SIR combination therapy proved to be optimal and extended survival of the cells up to post-transplant day 28. Color scale bar values are in photons/s/cm²/sr. Graphical representation of FIG. 25(c) single or FIG. 25(d) combined drug treatment efficacy on post-transplant hESC survival (n=5 per group). *P<0.05, P<0.01. Combined TAC+SIR treatment effectively suppressed (FIG. 25(e)) INF-γ and IL-4 production by hESC recipient splenocytes (P<0.01) and (FIG. 25(f)) reduced production of donor-specific xeno-reactive antibodies (P=0.14; n.s.=not significant).

Figure 26:
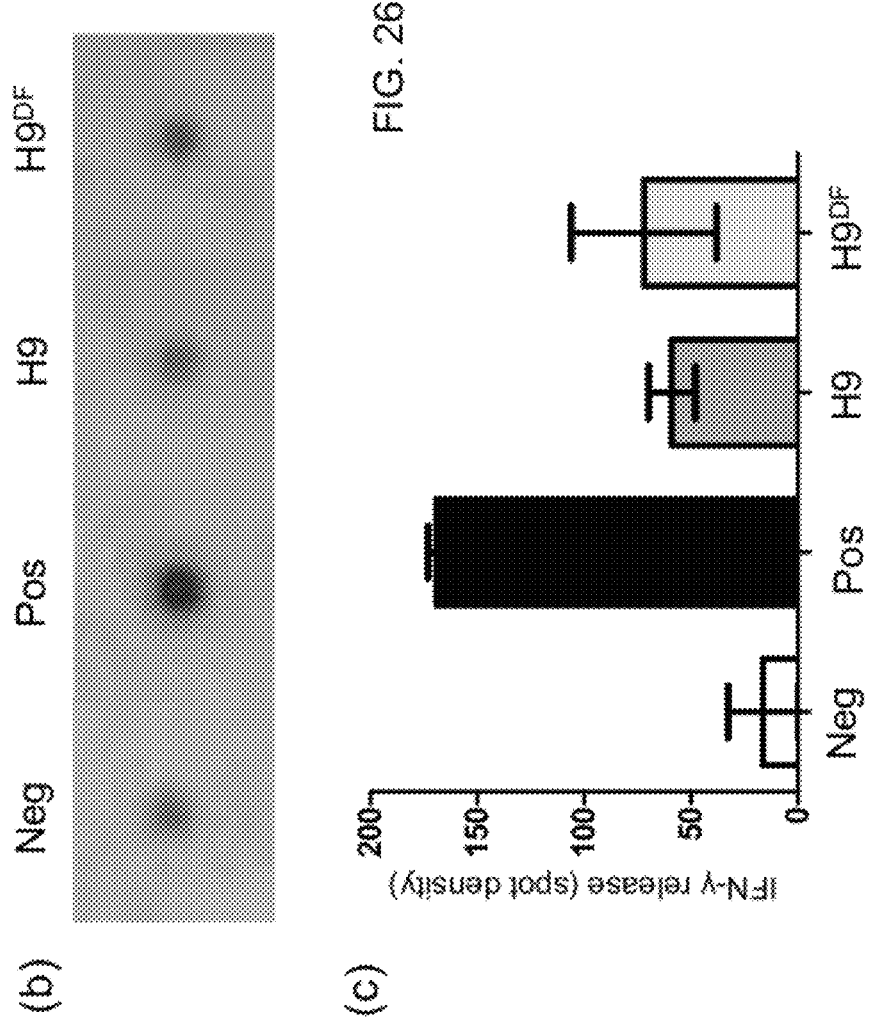

FIGS. 26(a) to 26(c) illustrate the immunological characterization of $H9^{DF}$ hESCs compared to non-transduced controls. FIG. 26(a) illustrates the comparison of human lymphocytes as a positive control to both H1 and H9 hESCs as well as transduced $H9^{DF}$ hESCs which express low amounts of MHC-1 and β2-microglobulin, and remain negative for MHC-II. Mean fluorescent intensity (MFI) is shown in the upper right corner of each panel. Results are representative of three independent experiments. FIG. 26(b) illustrates representative images and FIG. 26(c) illustrates the graphical representation of the cytokine antibody array show no difference in IFN-γ secretion by H9 or $H9^{DF}$ hESC. (neg=negative control, hESC medium; pos=positive control, medium containing recombinant human IFN-γ at 25 ng/ml).

Figure 27:
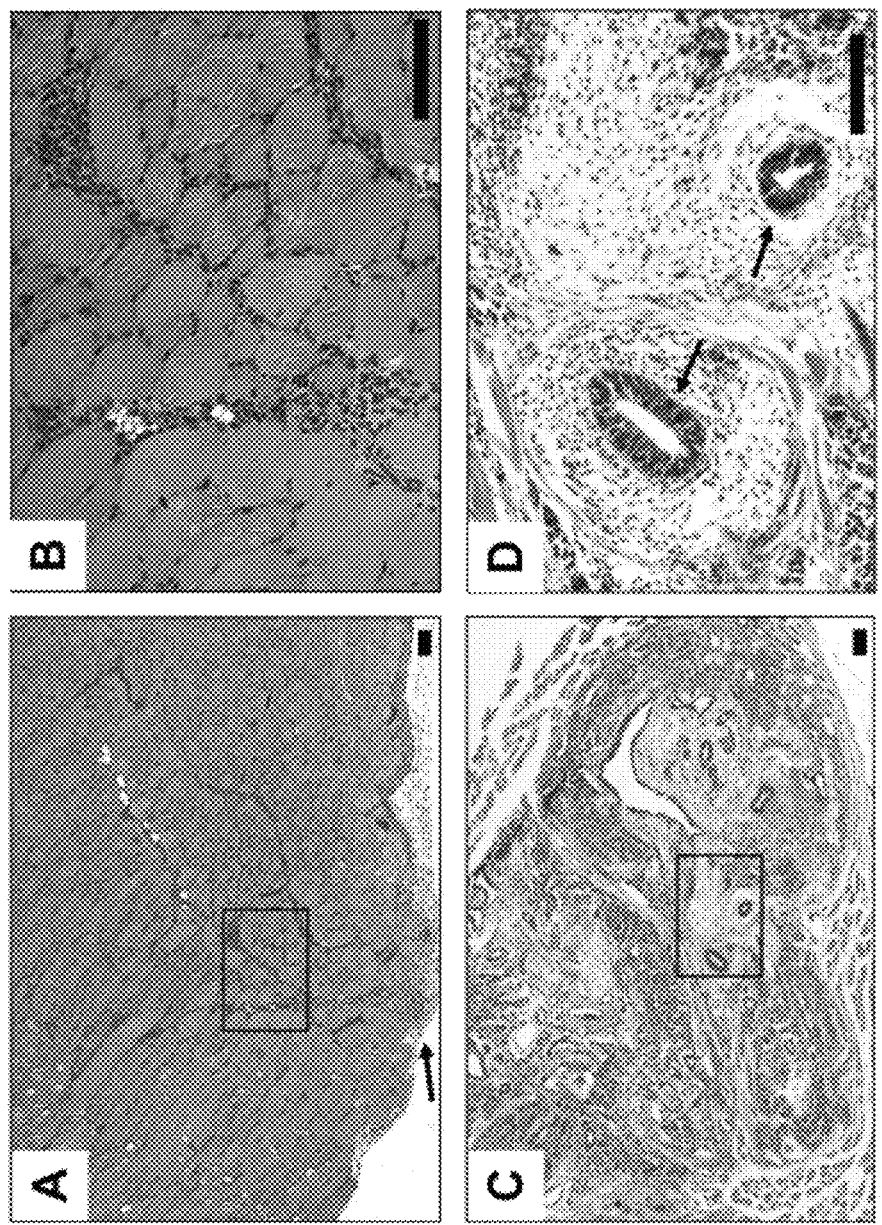

FIGS. 27(a) to 27(d) illustrate the histopathological evaluation of hESC survival. FIG. 27(a) illustrates tissue sections of BALB/c recipient muscles show endomysial mixed inflammatory infiltrated, sometimes involving the perimysium and adjacent soft tissue, representing the injection track (black arrow). FIG. 27(b) illustrates, on higher magnification, infiltrates consisting of mixed mononuclear and granulocyte infiltrates can be observed. No hESCs or cells with morphology that would suggest anything other then inflammatory could be detected. FIG. 27(c) illustrates explanted muscles of NOD/SCID animals at 42 days after transplantation demonstrates formation of intramuscular hESC-derived teratomas, composed out of tissue representing the three germ layers. FIG. 27(d) illustrates, on higher magnification, endodermal derivatived glandular epithelium (black arrows) surrounded by mesodermal derived mesenchyme can be detected. Scale bars: 50 µm.

Figure 28:
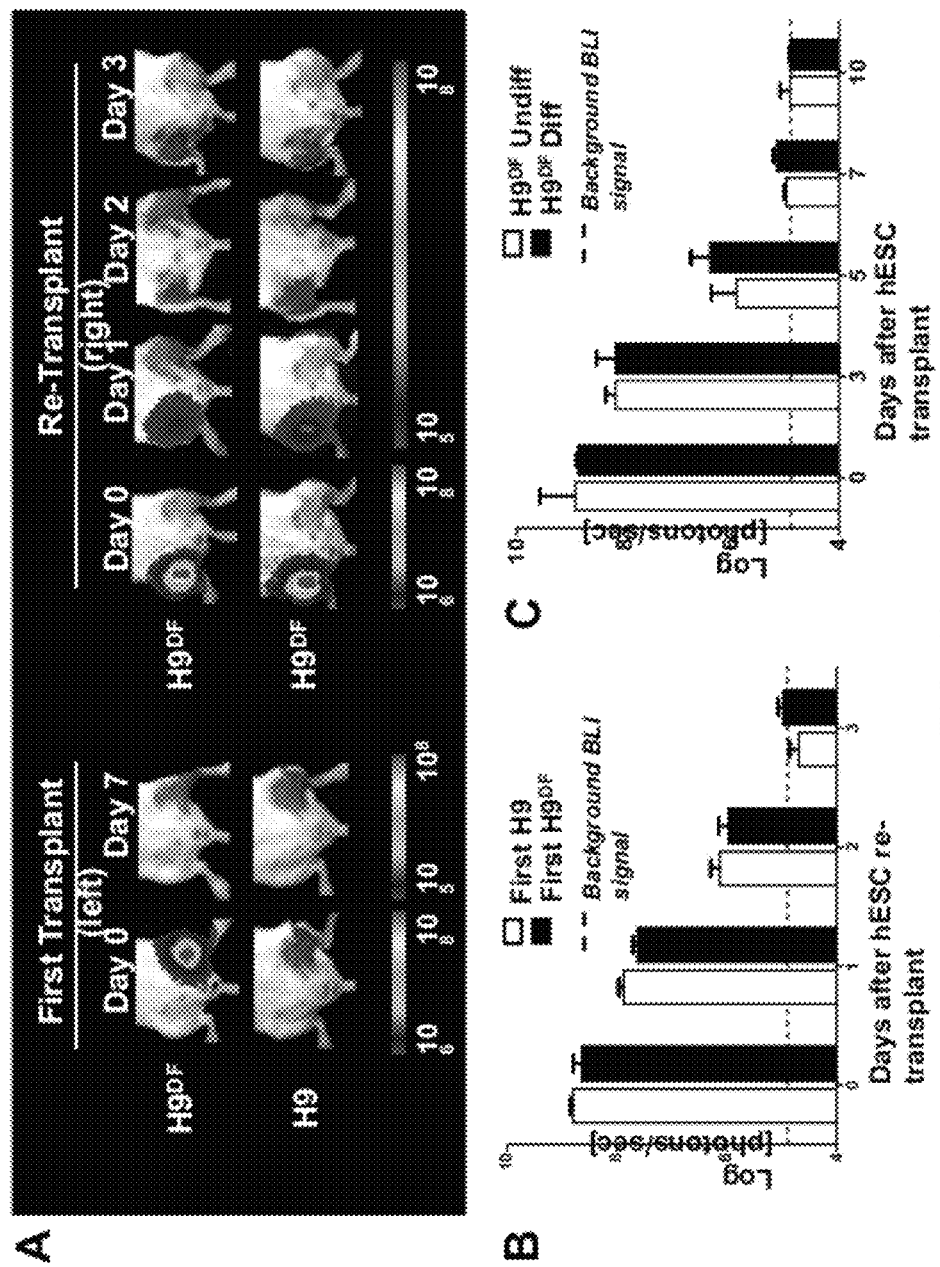

FIGS. 28(a) to 28(c) illustrate the similar hESC death after re-transplantation following primary stimulation with either transduced hESCs or non-transduced hESCs. FIG. 28(a) illustrate representative BLI images (color scale bar values are in photons/s/cm$^2$/sr) and FIG. 28(b) illustrates the graphical representation shows a similar trend in BLI signal loss in the 3 days following secondary transplantation of H9$^{DF}$ hESCs in BALB/c animals, after primary stimulation with either non-transduced H9 hESCs (n=3) or transduced hESCs (n=6) two weeks earlier. FIG. 28(c) illustrates the graphical representation of BLI signals comparing survival of undifferentiated H9$^{DF}$ hESC(H9$^{DF}$ undiff) versus 14 day differentiated H9$^{DF}$ hESC(H9$^{DF}$ diff) following transplantation. No significant difference in cell survival was found.

Figure 29:
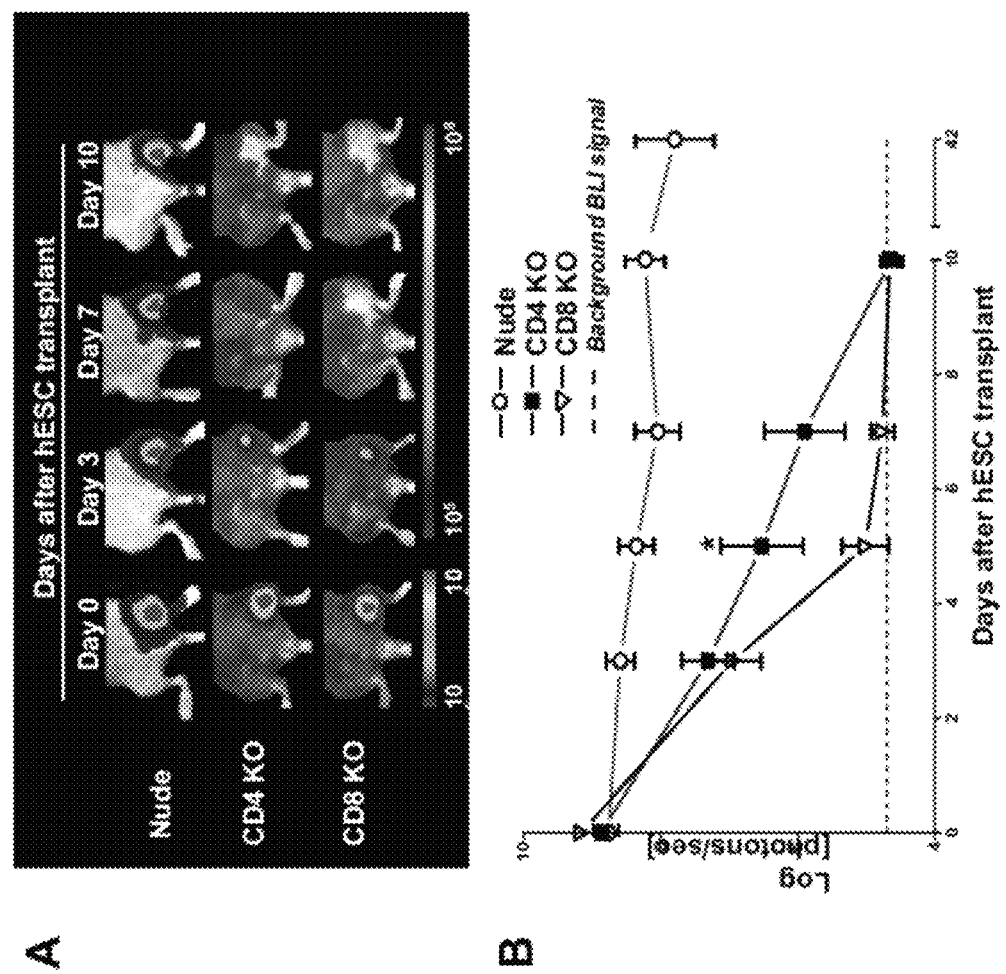

FIGS. 29(a) and 29(b) illustrate the role of T-cell subsets in mouse anti-hESC immune rejection. FIG. 29(a) illustrates the representative BLI images of H9$^{DF}$ hESCs transplanted into different immunodeficient mouse strains show survival of the donor cells in Nude mice up to 42 days following transplantation, suggesting an important role for T-cells in mouse anti-hESC rejection. Although hESCs are eventually rejected in both CD4 knockout (CD4-KO) and CD8 knockout (CD8-KO) mice, there is significantly longer survival of hESC in CD4-KO animals. Color scale bar values are in photons/s/cm$^2$/sr. FIG. 29(b) illustrates the graphical representation of BLI of hESC survival in the three groups (n=4 or 5 per group). *P<0.05.

FIGS. 30(a) to 30(c) illustrate that the stable lentiviral transduction of hESCs with the triple fusion (TF) reporter gene can be done. FIG. 30(a) is an achema of the TF reporter gene containing fusion of Fluc-RFP-HSVttk. The TF reporter gene was cloned into a SIN lentiviral vector downstream from the ubiquitin promoter. The three fusion proteins are joined by a 14-(LENSHASAGYQAST, SEQ ID NO: 22) and 8-amino acid (TAGPGSAT, SEQ ID NO: 22) linker, respectively. FIG. 30(b) illustrates FACS histograms of hESCss 48 hours after transduction with lentivirus carrying the TF reporter gene shows ~12.5% RFP+ cells. FIG. 30(c) illustrates brightfiled and fluorescence images of stably transduced cells.

FIGS. 31(a) to 31(b) show imaging of hESCs stably transduced with double or triple fusion reporter gene. FIG. 31(a) illustrates that 1×10$^6$ hESCs were transplanted into the shoulders of animals. Bioluminescence imaging at day 2 and 4 show robust signals in both shoulders. FIG. 31(b) illustrates a PET image at day 14 in coronal, horizontal, and sagittal views show signals in the right shoulder (triple fusion cells) but not left shoulder (double fusion cells lacking HSVttk).

Figure 32:
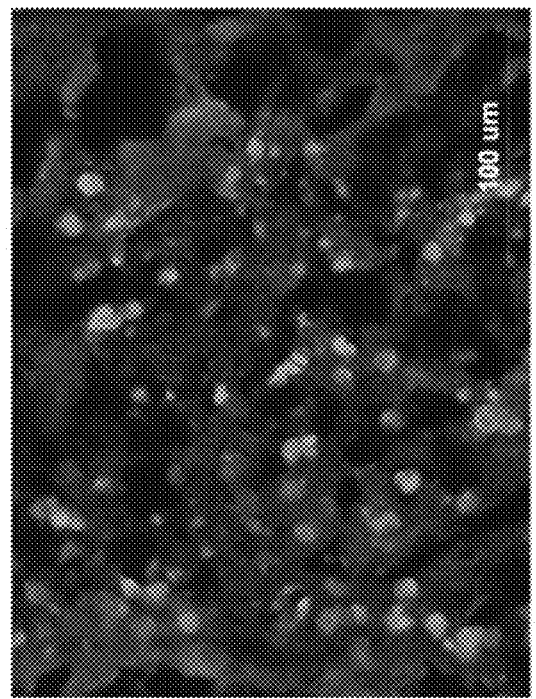

FIG. 32 illustrates immunostaining of triple (Fluc-RFP-HSVttk) and double (Fluc-GFP) fusion hESCs confirms red fluorescence (left) and green fluorescence (right).

Figure 33:
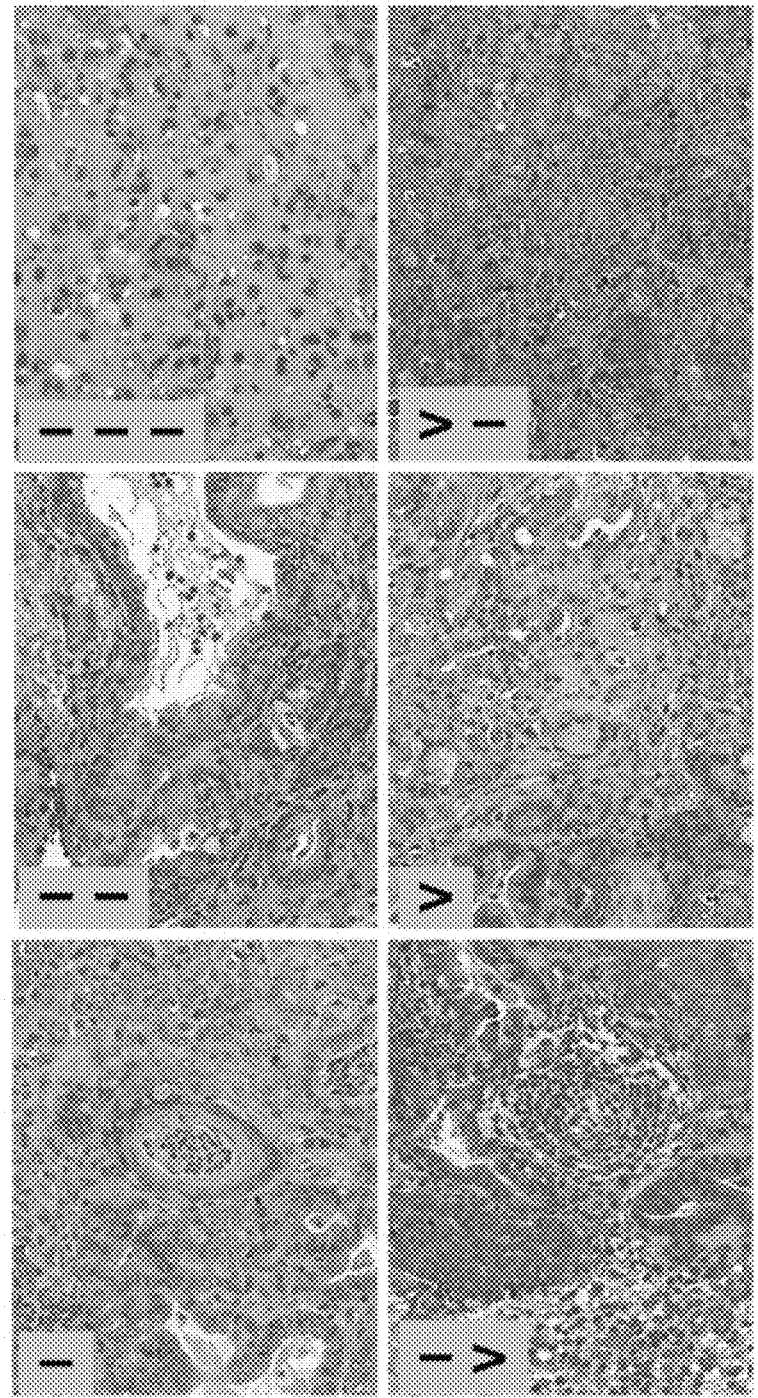

FIG. 33 illustrates the histology of explanted teratomas at 8 weeks show (I):squamous cell differentiation with keratin pearl; (II) respiratory epithelium with ciliated columnar and mucin producing goblet cells; (III):osteoid (non-mineralized bonn formation; (IV) cartilage formation; V:osteoid formation; and (VI): rosette consistent with neuroectodermal (400×).

SUMMARY

Embodiments of the present disclosure include double-fusion human embryonic stem cells, methods of imaging double-fusion human embryonic stem cells, double-fusion polynucleotides, double-fusion proteins, triple-fusion human embryonic stem cells, methods of imaging triple-fusion human embryonic stem cells, triple-fusion polynucleotides, triple-fusion proteins, methods of monitoring the progression of human embryonic stem cells, methods of making isolated double-fusion human embryonic stem cells, methods of making isolated triple-fusion human embryonic stem cells, and the like.

In particular, embodiments of the present disclosure provide for: isolated double-fusion human embryonic stem cell (hESC), methods of preparing isolated double-fusion hESC, methods of monitoring double-fusion human embryonic stem cell, isolated double-fusion hESC, isolated triple-fusion hESC, methods of preparing isolated double-fusion hESC, methods of preparing isolated triple-fusion hESC, and the like.

Embodiments of the isolated double-fusion hESC, among others, include: hESC that: expresses a firefly luciferase reporter gene encoding a firefly luciferase protein; and expresses an enhanced green fluorescent reporter gene encoding an enhanced green fluorescent protein.

Embodiments of the method of preparing isolated double-fusion, among others, include: providing a human embryonic stem cell; transducing the human embryonic stem cell with an expression vector including Fluc and eGFP, Fluc is a firefly luciferase reporter gene, and eGFP is enhanced green fluorescent reporter gene.

Embodiments of the method of monitoring double-fusion human embryonic stem cell, among others, include: providing an isolated double-fusion human embryonic stem cell (hESC) as described herein; and detecting fluorescence, bioluminescence, or both fluorescence and bioluminescence emitted from the double-fusion hESC and progeny thereof.

Embodiments of the isolated double-fusion hESC, among others, include: an hESC that includes a double-fusion gene that includes a firefly luciferase reporter gene encoding a firefly luciferase protein and an enhanced green fluorescent reporter gene encoding an enhanced green fluorescent protein.

Embodiments of the isolated triple-fusion hESC, among others, include: an hESC that expresses a firefly luciferase reporter gene encoding a firefly luciferase protein, expresses a red fluorescent reporter gene encoding a red fluorescent protein, and expresses a Herpes Simplex Virus 1 thymidine kinase (HSV1-tk) positron emission tomography (PET) reporter gene encoding a enzyme protein (HSV1-TK).

Embodiments of the method of preparing isolated double-fusion hESC, among others, include: providing a human embryonic stem cell; transducing the human embryonic stem cell with an expression vector including Fluc, RFP, and tTK, Fluc is a firefly luciferase reporter gene, mRFP is the red fluorescent reporter gene, and tTK is the truncated HSV1-tk PET reporter gene.

Embodiments of the method of monitoring triple-fusion human embryonic stem cells, among others, include: providing an isolated triple-fusion human embryonic stem cells (hESC) as described herein; and detecting fluorescence, bioluminescence, or both fluorescence, and bioluminescence emitted from the triple-fusion hESC and progeny thereof.

These embodiments, uses of these embodiments, and other uses, features and advantages of the present disclosure, will become more apparent to those of ordinary skill in the relevant art when the following detailed description of the preferred embodiments is read in conjunction with the appended figures.

DETAILED DESCRIPTION

Before the present disclosure is described in greater detail, it is to be understood that this disclosure is not limited to particular embodiments described, and that the various embodiments of the invention may, of course, vary. It is also to be understood that the terminology used herein is for the purpose of describing particular embodiments only, and is not intended to be limiting, because the scope of the present disclosure is to be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biology, molecular biology, synthetic organic chemistry, biochemistry, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

"Stem cells", as used herein, refers to cells which under suitable conditions are capable of differentiating into other cell types having a particular, specialized function (i.e., "fully differentiated" cells) and while under other suitable conditions are capable of self renewing and remaining in an undifferentiated pluripotential state as detailed below. The stem cells are preferably embryonic stem (ES) cells obtained from the embryonic tissue formed after gestation (e.g., blastocyst).

A "cell" as used herein refers to a single cell as well as to a population of (i.e., more than one) cells. The population may be a pure population comprising one cell type. Alternatively, the population may comprise more than one cell type.

"Embryonic stem cell" and "Pluripotent embryonic stem cell", as used herein, refer to a cell that can give rise to many differentiated cell types in an embryo or an adult, including the germ cells (sperm and eggs). This cell type is also referred to as an "ES" cell.

"Cell culture" or "Cultured cell", as used herein, refer to cells or tissues that are maintained, cultured, cultivated or grown in an artificial, in vitro environment. Included within this term are continuous cell lines (e.g., with an immortal phenotype), primary cell cultures, finite cell lines (e.g., non-transformed cells), and any other cell population maintained in vitro. In this connection, a primary cell is a cell that is directly obtained from a tissue or organ of an animal, including a human, in the absence of culture. Typically, though not necessarily, a primary cell is capable of undergoing ten or fewer passages in vitro before senescence and/or cessation of proliferation.

"Undifferentiated", as used herein, refers to cultured cells when a substantial proportion (at least 20%, and possibly over 50% or 80%) of the cells and their derivatives in the population display morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

"Undifferentiated pluripotential ES cells", "Pluripotent SC", and "ESC", as used herein, refer to precursor cells that have the ability to form any adult cell. Such cells are true cell lines in that they: (i) are capable of indefinite proliferation in vitro in an undifferentiated state; and (ii) are capable of differentiation to derivatives of all three embryonic germ layers (endoderm, mesoderm, and ectoderm) even after prolonged culture. Human ES cells (hES cells) are derived from fertilized embryos that are less than one week old (in the cleavage or blastocyte stage) or produced by artificial means (such as by nuclear transfer) that have equivalent characteristics. Human ES cells are capable of proliferating in vitro in an undifferentiated state, maintaining a normal karyotype through prolonged culture, and maintaining the potential to differentiate into derivatives of all three embryonic germ layers (i.e., mesoderm, ectoderm and endoderm). Cells and tissues that are derived from endoderm cells include: thymus, thyroid, parathyroid glands, larynx, trachea, lung, urinary bladder, vagina, urethra, gastrointestinal (GI) organs (liver, pancreas), lining of the GI tract, lining of the respiratory tract. Cells and tissues that are derived from mesoderm cells include: bone marrow (blood), adrenal cortex, lymphatic tissue, skeletal, smooth, and cardiac muscle, connective tissues (including bone, cartilage), urogenital system, heart and blood vessels (vascular system). Cells and tissues derived from the ectoderm include: central nervous system, retina and lens, cranial and sensory, ganglia and nerves, pigment cells, head connective tissue, epidermis, hair, and mammary glands.

"Maintenance" means continued survival of a cell or population of cells, at times, with an increase in numbers of cells.

"Proliferation", "propagation", "expansion" and "growth", which may be used interchangeably with each other, refer to such an increase in cell number.

"Cell suspension" as used herein, refers to a culture of cells in which the majority of the cells freely float in the medium, typically a culture medium (system), and the cells floating as single cells, as cell clusters and/or as cell aggregates. In other words, the cells survive and propagate in the medium without being attached to a substrate.

"Culture system", as used herein, refers to a culture system suitable for the propagation of SCs. The term denotes a combination of elements, at minimum including a basic medium (a cell culture medium usually comprising a defined base solution, which includes salts, sugars and amino acids) and the serum replacement supplement. The culture system in accordance with the present disclosure may further comprise other elements such as, without being limited thereto, an extracellular matrix (ECM) component, a serum or serum replacement, a culture (nutrient) medium and other exogenously added factors, which together provide suitable conditions that support SC growth. The conditions are such that SC can proceed through the cell cycle, grow, and divide. Preferably, the conditions are such which enable growth of human stem cells, preferably, human embryonic stem cells (hESC).

In some instances, the embodiments of the present embodiment provide the hESC lines in an isolated form. As used herein, the term "isolated" means that the cells are physically separated from their naturally occurring environment such as a blastocyst, an ICM, and components thereof. The lines are generally provided as a clonal population. In an embodiment, the human embryonic stem cell population is embryonic stem cell line H9 line from Wicell, passages 35 to 45, and progeny thereof. The progeny may be undifferentiated or differentiated progeny including, but not limited to, cardiac, neural, muscular, hematopoietic differentiated progeny, and the like.

The terms "polypeptide," "peptide," and "protein" are used interchangeably herein to refer to a polymeric form of amino acid residues. The terms apply to amino acid polymers in which three or more amino acid residue is chemically or biochemically modified or derivatized amino acids of a corresponding naturally occurring amino acid, as well as to naturally occurring amino acid polymers and non-naturally occurring amino acid polymer. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

"Peptide" refers to a polymer in which the monomers are amino acid residues, which are joined together through amide bonds, alternatively referred to as a polypeptide. A "single polypeptide" is a continuous peptide that constitutes the protein. When the amino acids are alpha-amino acids, either the L-optical isomer or the D-optical isomer can be used, the L-isomers being preferred. Additionally, unnatural amino acids such as beta-alanine, phenylglycine, and homo-arginine are meant to be included. Commonly encountered amino acids, which are not gene-encoded can also be used herein, although preferred amino acids are those that are encodable. For a general review, see, for example, Spatola, A. F., in Chemistry and Biochemistry of Amino Acids, Peptides and Proteins, B. Weinstein, ed., Marcel Dekker, N.Y., p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but functions in a manner similar to a naturally occurring amino acid.

"Amino acids" may be referred to herein by either their commonly known three letter symbols or by the one-letter symbols recommended by the IUPAC-IUB Biochemical Nomenclature Commission as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Nucleotides, likewise, may be referred to by their commonly accepted single-letter codes as indicated as follows: Adenine (A), Guanine (G), Cytosine (C), Thymidine (T), and Uracil (U).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides used herein.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in Xenopus oocytes by microinjection of mutated mRNA and chemically aminoacylated suppressor tRNAs (Turcatti, et al., J. Biol. Chem., 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

As used herein, DNA may be obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

The DNA encoding the protein disclosed herein can be prepared by the usual methods: cloning cDNA from mRNA encoding the protein, isolating genomic DNA and splicing it, chemical synthesis, and so on.

cDNA can be cloned from mRNA encoding the protein by, for example, the method described below:

First, the mRNA encoding the protein is prepared from the above-mentioned tissues or cells expressing and producing the protein. mRNA can be prepared by isolating total RNA by a known method such as guanidine-thiocyanate method (Chirgwin et al., Biochemistry, 18:5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase, such as the method of Okayama et al (Mol. Cell. Biol. 2:161 (1982); Mol. Cell. Biol. 3:280 (1983)) or the method of Hoffman et al. (Gene 25:263 (1983)), and converted into double-stranded cDNA. A cDNA library is prepared by transforming E. coli with plasmid vectors, phage vectors, or cosmid vectors having this cDNA or by transfecting E. coli after in vitro packaging.

The plasmid vectors used herein are not limited as long as they are replicated and maintained in hosts. Any phage vector that can be replicated in hosts can also be used. Examples of usually used cloning vectors are pUC19, gt10, gt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p. 1.53, 1989). cDNA can be inserted into a phage vector by, for example, the method of Hyunh et al. (DNA cloning, a practical approach, 1, p. 49 (1985)). These methods can be simply performed by using a commercially available cloning kit (for example, a product from Takara Shuzo). The recombinant plasmid or phage vector thus obtained is introduced into an appropriate host cell such as a prokaryote (for example, E. coli: HB101, DH5a, MC1061/P3, etc).

Examples of a method for introducing a plasmid into a host (e.g., cell) are, calcium chloride method, calcium chloride/rubidium chloride method and electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham). Genes can also be introduced into a host using viral and non-viral vectors.

The identification of cDNA encoding protein, its expression being augmented depending on the stimulation of cytokines like AID protein disclosed herein, can be carried out by for example suppression subtract hybridization (SSH) (Proc. Natl. Acad. Sci. USA, 93:6025-6030, 1996; Anal. Biochem., 240:90-97, 1996) taking advantage of suppressive PCR effect (Nucleic Acids Res., 23:1087-1088, 1995), using two cDNA libraries, namely, cDNA library constructed from mRNA derived from stimulated cells (tester cDNA library) and that constructed from mRNA derived from unstimulated cells (driver cDNA library).

Specific examples of the vectors for recombination used are E. coli-derived plasmids such as pBR322, pBR325, pUC12, pUC13, and pUC19, yeast-derived plasmids such as pSH19 and pSH15, and Bacillus subtilis-derived plasmids such as pUB110, pTP5, and pC194. Examples of phages are a bacteriophage such as phage, and an animal or insect virus (pVL1393, Invitrogen) such as a retrovirus, vaccinia virus, and nuclear polyhedrosis virus.

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS (Nucleic Acids Res. 18:5322 (1990) and so on), pME18S (Experimental Medicine: SUPPLEMENT, "Handbook of Genetic Engineering" (1992)), etc.

When bacteria, particularly E. coli are used as host cells, an expression vector generally comprises, at least, a promoter/operator region, an initiation codon, the DNA encoding the protein termination codon, terminator region, and replicon.

When yeast, animal cells, or insect cells are used as hosts, an expression vector is preferably comprises, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used.

A promoter/operator region to express the protein in bacteria comprises a promoter, an operator, and a Shine-Dalgarno (SD) sequence (for example, AAGG). For example, when the host is Escherichia, it preferably comprises Trp promoter, lac promoter, recA promoter, lambda.PL promoter, b 1 pp promoter, tac promoter, or the like. Examples of a promoter to express the protein in yeast are PH05 promoter, PGK promoter, GAP promoter, ADH promoter, and so on. When the host is Bacillus, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon. Usually, used natural or synthetic terminators are used as a terminator region.

A "replicon" means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for E. coli, yeast 2.mu. plasmid or yeast chromosomal DNA for yeast, and pRSVneo ATCC 37198, pSV2dhfr ATCC 37145, pdBPV-MMTneo ATCC 37224, pSV2neo ATCC 37149, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phophotransferase gene, aspartate transcarbamylase gene, etc. It should also be noted that these are also selection genes, except for use in mammalian cells instead of the genes described in the paragraph above, which are used in bacteria. Usually the genes described in the paragraph above are used for plasmid amplification in bacterial cells and the ones in this paragraph are used for selection of mammalian cells.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

As used herein, "transformants" can be prepared by introducing the expression vector mentioned above into host cells.

As used herein, "host" cells are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces, Pichia*, and such), animal cells, or insect cells).

Specific examples are *E. coli* (DH5alpha, TB1, HB101, and such), mouse-derived cells (COP, L, C127, Sp2/0, NS-1, NIH 3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed/transfected/transduced/electroporated) into host cells by known methods.

Transformation can be performed, for example, according to the method of Cohen et al. (Proc. Natl. Acad. Sci. USA, 69:2110 (1972)), protoplast method (Mol, Gen. Genet., 168: 111 (1979)), or competent method (J. Mol. Biol., 56:209 (1971)) when the hosts are bacteria (*E. coli, Bacillus subtilis*, and such), the method of Hinnen et al. (Proc. Natl. Acad. Sci. USA, 75:1927 (1978)), or lithium method (J. Bacteriol., 153: 163 (1983)) when the host is *Saccharomyces cerevisiae*, the method of Graham (Virology, 52:456 (1973)) when the hosts are animal cells, and the method of Summers et al. (Mol. Cell. Biol., 3:2156-2165 (1983)) when the hosts are insect cells.

The protein disclosed herein, can be produced by cultivating transformants (in the following, this term includes transfectants) comprising an expression vector prepared as mentioned in nutrient media.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation of cell lines is performed by a method known in the art. Cultivation conditions such as temperature, pH of the media, and cultivation time are selected appropriately so that the protein is produced in large quantities.

Examples of the isolation and purification method are a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charges, such as ion exchange chromatography and hydroxylapatite chromatography; a method utilizing specific affinity, such as affinity column chromatography; a method utilizing the difference in hydrophobicity, such as reverse phase high performance liquid chromatography; and a method utilizing the difference in isoelectric point, such as isoelectric focusing.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal virus genome, or viral DNA, or may contain elements of both.

"Operably linked" refers to an arrangement of elements wherein the components so described are configured so as to perform their usual function. For example, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. The promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The terms "chimeric", "fusion" and "composite" are used to denote a protein, peptide domain or nucleotide sequence or molecule containing at least two component portions that are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences that encode them, are recombinant in the sense that they contain at least two constituent portions that are not otherwise found directly linked (covalently) together in nature.

The term "domain" in this context is not intended to be limited to a single discrete folding domain.

A "reporter polynucleotide" includes any gene that expresses a detectable gene product, which may be RNA or a reporter polypeptide. Reporter genes include coding sequences for which the transcriptional and/or translational products are readily detectable or selectable.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

A "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is a heritable change in a DNA sequence relative to a reference "wild-type" DNA sequence. Mutations can occur as a result of a single base change, multiple base changes, or the addition or deletion of more than one nucleotide to a DNA sequence.

The term "genotoxicity" is used to broadly refer to any deleterious change in the genetic material of a cell, regardless of the mechanism by which the change is induced.

As used herein the term mutagenicity and genotoxic activity are used to refer to the ability of an agent (e.g., a chemical compound or a drug candidate) to cause a permanent change in the structure of the genetic material of a cell, which causes a heritable change in the effected cell. Contemplated changes include alterations in the sequences of the bases in the nucleic acid (gene mutation), structural changes to chromosomes (clastogenicity) and/or changes to the number of chromosomes present.

A "mutagen" or a "genotoxic agent" is an agent that creates or causes mutations. It is well-established that chemical mutagens vary in their modes of action. However, in general terms, a chemical mutagen changes a nucleic acid or nucleoside relative to the nucleotide sequence of a reference or "wild-type" genome. Generally speaking a mutagen or genotoxic agent increases the frequency of reversion or forward mutation.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

A "gene mutation" refers to a mutation that occurs entirely within one gene, or its upstream regulatory sequences and can comprise either a point mutation or other disruption of normal chromosomal structure that occurs entirely within one gene.

A "reversion assay" is an assay of genotoxic activity that detects a reverse mutation that confers normal function to a mutant gene thereby causing a gain of function. Typically, the genotoxic activity of compounds are evaluated using a bacterial reverse mutation assay that utilizes an amino acid-requiring (i.e., auxotrophic) tester strains of *Salmonella typhimurium* (*S. typhimurium*) or *Escherichia coli* (*E. coli*) to evaluate the genotoxic activity of a compound. Generally speaking, reversion assays are capable of detecting point mutations, such as a substitution, an addition or a deletion of one or more DNA bases, which are introduced into the genome of an affected tester strain.

A "forward mutation assay" is an assay of genotoxic activity, which detects "forward" mutations that alter a functional gene in a way that causes a loss, rather than a gain, of function.

A "wild-type" strain is capable of a full range of metabolic activities. For example, wild-type strains of *Salmonella* can synthesize all 20 amino acids from a single carbon source.

A "mutant" strain is not capable of all of the activities of the wild-type strain from which it is derived. For example, a mutant bacterial strain that is defective in its ability to synthesize the amino acid histidine (his strain) requires the presence of exogenous histidine in order to grow.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than tranversions because the former are not detected by the proof-reading enzymes.

Alternatively, point mutation can also cause a nonsense mutation resulting from the insertion of a stop codon (amber, ochre, opal). Base pair mutations that generate a translation stop codon causes premature termination of translation of the coded protein.

A "frameshift mutation" results from the insertion or deletion of one or more nucleotides within a gene. The "reading frame" of a gene refers to the order of the bases with respect to the starting point for translation of the mRNA. Deletion of a single base pair results in moving ahead one base in all of the codons, and is often referred to as a positive frameshift. Addition of one base pair (or loss of two base pairs) shifts the reading frame behind by one base, and is often referred to as a negative frameshift.

As used herein the term "DNA Repair Mechanism" refers to any one of the potential repair mechanisms that exist in both prokaryotes and eukaryotes. For example: postreplication; mismatch repair; nucleotide excision-repair and photoreactivation or light-dependent repair (not found in mammals).

A "base pair substitution mutagen" is an agent that causes a base (i.e., nucleotide) change in DNA. In the context of a reversion test this change may occur at the site of the original mutation, or at a second site in the bacterial genome.

A "frameshift mutagen" is an agent that causes the addition or deletion of one or more base pairs in the DNA, thus changing the reading frame in the RNA.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used.

In accordance with the present disclosure, "a detectably effective amount" of embodiments of the present disclosure is defined as an amount sufficient to yield an acceptable image using equipment that is available for clinical use. A detectably effective amount of the embodiments of the present disclosure may be administered in more than one injection. The detectably effective amount of embodiments of the present disclosure can vary according to factors such as the degree of susceptibility of the individual, the age, sex, and weight of the individual, idiosyncratic responses of the individual, the dosimetry, and the like. Detectably effective amounts of embodiments of the present disclosure can also vary according to instrument and film-related factors. Optimization of such factors is well within the level of skill in the art.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. In particular, the host is a human subject. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

The term "link" as used herein refers to a physical linkage as well as linkage that occurs by virtue of co-existence within a biological particle, e.g., phage, bacteria, yeast or other eukaryotic cell.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the CaCl method by procedures well known in the art. Alternatively, MgCl or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the calcium sensing system of the present disclosure, and a second foreign DNA molecule encoding a selectable phenotype, such as the herpes simplex virus thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the embodiments of the present disclosure may be by any conventional means such as, for example, preparative chromatographic separations and immunological separations such as those involving the use of monoclonal or polyclonal antibodies or antigen.

A variety of host-expression vector systems may be utilized to express the bioluminescent indicator coding sequence. These include, but are not limited to, microorganisms such as bacteria transformed with recombinant bacteriophage DNA, plasmid DNA or cosmid DNA expression vectors containing the calcium sensing system sequences; yeast transformed with recombinant yeast expression vectors containing the calcium sensing system sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid vectors containing the calcium sensing system sequences); insect cell systems infected with recombinant virus expression vectors (e.g., baculovirus vectors) containing the calcium sensing system sequences; or animal cell systems infected with recombinant virus expression vectors (e.g., retroviruses, adenovirus, vaccinia virus vectors containing the calcium sensing system sequences) or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (See, e.g., Bitter, et al., Methods in Enzymology 153:516-544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for calcium sensing system.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the mutation assay system may be driven by any of a number of promoters. For example, viral promoters such as the 35S RNA and 19S RNA promoters of CaMV (Brisson, et al., Nature 310:511-514, 1984), or the coat protein promoter to TMV (Takamatsu, et al., EMBO J. 6:307-311, 1987) may be used; alternatively, plant promoters such as the small subunit of RUBISCO (Coruzzi, et al., 1984, EMBO J. 3:1671-1680; Broglie, et al., Science 224:838-843, 1984); or heat shock promoters, e.g., soybean hsp17.5-E or hsp17.3-B (Gurley, et al., Mol. Cell. Biol. 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, N.Y., Section VIII, pp. 421-463, 1988; and Grierson & Corey, Plant Molecular Biology, 2d Ed., Blackie, London, Ch. 7-9, 1988.

An alternative expression system, which could be used to express mutation assay system, is an insect system. In one such system, *Autographa californica* nuclear polyhedrosis virus (AcNPV) is used as a vector to express foreign genes. The virus grows in *Spodoptera frugiperda* cells. The calcium sensing system sequences may be cloned into non-essential regions (for example, the polyhedrin gene) of the virus and placed under control of an AcNPV promoter (for example the polyhedrin promoter). Successful insertion of the calcium sensing system sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

DNA sequences encoding the mutation assay system of the present disclosure can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

As used herein, "linker" or "spacer" refers to a molecule or group of molecules that connects two molecules, such as, for example, a fluorescent binding ligand and a display protein or nucleic acid, and serves to place the two molecules in a preferred configuration.

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA, which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes used herein include DNA sequences that encode the fluorescent indicator that may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. As used herein, the term "transgenic" includes any transgenic technology familiar to those in the art which can produce an organism carrying an introduced transgene or one in which an endogenous gene has been rendered non-functional or "knocked out."

An "imaging reporter gene" is here defined as any gene that can encode a protein that can be detected in a living subject using an imaging modality. The protein product of an imaging reporter gene may itself emit a signal that is detectable by an imaging system; otherwise it can be detected using a signal emitting probe (imaging reporter probe). The protein product of the imaging reporter gene may emit fluorescence upon excitation by a specific range of wavelengths. The protein may be able to phosphorylate some nucleotide analogs that can be detected by a nuclear imaging system (e.g., PET, SPECT, and the like).

"Bioluminescent initiator molecule" is a molecule that can react with a bioluminescent protein to generate bioluminescence.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, etc.).

As used herein, the terms "prophylactically treat" or "prophylactically treating" refers completely or partially preventing a disease or symptom thereof and/or may be therapeutic in terms of a partial or complete cure for a disease and/or adverse effect attributable to the disease.

General Discussion

Embodiments of the present disclosure include double-fusion human embryonic stem cells, methods of imaging double-fusion human embryonic stem cells, double-fusion polynucleotides, double-fusion proteins, triple-fusion human embryonic stem cells, methods of imaging triple-fusion human embryonic stem cells, triple-fusion polynucleotides, triple-fusion proteins, methods of monitoring the progression of human embryonic stem cells, methods of making isolated double-fusion human embryonic stem cells, methods of making isolated triple-fusion human embryonic stem cells, and the like. Embodiments of the present disclosure can be used to image, detect (and visualize), quantitate, study, monitor, evaluate, and/or screen, biological events (e.g., progression of the stem cells and progeny thereof) in vivo or in vitro. Additional details are also provided in Examples 1, 2, 3, and 4.

In particular, embodiments of the present disclosure provide for: isolated double-fusion human embryonic stem cell (hESC), methods of preparing isolated double-fusion hESC, methods of monitoring double-fusion human embryonic stem cell, isolated double-fusion hESC, isolated triple-fusion hESC, methods of preparing isolated double-fusion hESC, methods of preparing isolated triple-fusion hESC, and the like.

Embryonic Stem Cells

It should be noted that embryonic stem cells (ESCs) are pluripotent cells derived from the inner cell mass of blastocyst-stage embryos. Their importance to modern biology and regenerative medicine derives from two unique characteristics that distinguish them from all other organ-specific stem cells identified so far. First, ESCs can be maintained and expanded as pure populations of undifferentiated cells for extended periods of time in culture. Second, ESCs possess the capacity to differentiate into every cell type in the body, including neuronal, cardiac, hepatic, and endothelial cells. Thus, the self renewal and pluripotency characteristics distinguish ESCs from adult stem cells. The discovery of mouse embryonic stem cells (mESCs) in 1981 represented a major advance in cell biology as it enabled the routine manipulation of the mouse genome for studying mammalian development (*Nature* 1981; 292:154-6; *Proc Natl Sci USA* 1981; 78:7634-8). Almost two decades later, the first successful cultivation of human embryonic stem cells (hESCs) was reported in 1998 by Thomson et al. who isolated cells from the inner cell mass and grew them onto mitotically inactivated mouse embryonic fibroblast (MEF) feeder layers (*Science* 1998; 282:1145-7). Two years later, Rubinoff et al. demonstrated the differentiation potential of hESCs under in vitro conditions (*Nat Biotechnol* 2000; 18:399-404).

Over the following years, scientists have learned that mESCs and hESCs indeed have quite different biological properties (see Table 1) (*Physiol Rev* 2005; 85:635-78). For example, whereas leukemia inhibitory factor (LIF) signaling plays a key role in maintaining the self-renewal of mESCs, the same factor fails to maintain hESCs in an undifferentiated state. Unlike mESCs, hESCs are able to differentiate into trophoblast-like cells (*Stem Cells* 2001; 19:193-204). Telomerase biology and regulation are also different between mESCs and hESCs (*Differentiation* 2002; 69:188-97). Ginis et al. have reported significant differences in gene expression profiles among mESCs versus hESCs (*Dev Biol* 2004; 269:360-80). These differences suggest that caution must be exercised in extrapolation of data directly from mESCs to hESCs and that additional studies will be required. In addition, the growth conditions, propagation time, and differentiation procedure for mESCs and hESCs are quite different. For these reasons, the creation of a genetically modified hESC line expressing either the double fusion (DF) or a triple fusion (TF) will be difficult to achieve and irrespective of any previous success with mESC lines. One skilled in the art can not predict with any confidence how changing one or more variables will impact the outcome and would not have an expectation of success based on mESC lines. As discussed above in the noted references the mere substitution would not yield predictable results and experiments conducted with mESC lines would not provide motivation to conduct similar experiments in hESC lines since mESC and hESC are significantly different. It should be noted that each of the references in the two paragraphs above are incorporated herein by reference.

TABLE 1

Comparison of some properties of mouse and human embryonic stem cells

| Marker | Mouse ES Cells | Human ES Cells |
|---|---|---|
| SSEA-1 | + | − |
| SSEA-3/-4 | − | + |
| TRA-1-60/81 | − | + |
| TRA-2-54 | − | + |
| GCTM-2 | − | + |
| TG 343 | ? | + |
| TG 30 | ? | + |
| CD 9 | + | + |
| CD 133/prominin | + | + |
| Alkaline phosphatase | + | + |
| Oct-4 | + | + |
| Nanog | + | + |
| Sox-2 | + | + |
| FGF4 | + | − |
| LIF receptor | + | +/− |
| Telomerase activity | + | + |
| Regulation of self-renewal | Via gp 130 receptors, MEF feeder layer, Nanog, BMP-4 | Feeder cells (MEF or human cells), serum, bFGF, Matrigel |
| Growth characteristics in vitro | Tight, rounded, multilayer clusters | Flat, loose aggregates |
| EB formation | Simple and cystic EBs | Cystic EBs |
| Teratoma formation in vivo | + | + |

Double-Fusion Human Embryonic Stem Cells

In general, embodiments of the present disclosure include isolated double-fusion human embryonic stem cells (hESC) or populations thereof. In an embodiment, the double-fusion hESC expresses a firefly luciferase reporter gene encoding a firefly luciferase protein and express an enhanced green fluorescent reporter gene encoding an enhanced green fluorescent protein. The progeny of the double-fusion hESC also express the firefly luciferase reporter gene and the enhanced green fluorescent reporter gene. The double-fusion hESC can be disposed (e.g., engraphed) into a host (e.g., a tissue or organ of the human subject) and can be monitored (e.g., detected, imaged, and the like) as the double-fusion hESC proliferates and/or differentiates. In particular, embodiments of the present disclosure provide the ability to monitor the proliferation rate, the localization, and lifetime, of the double-fusion hESC and the progeny thereof. The double-fusion hESC and the progeny thereof can be monitored without sacrificing the host. In this regard, the in vivo monitoring can be conducted non-invasively for extended periods of time, maybe for an indefinite period of time, using a fluorescence and/or bioluminescence imaging system. In addition, the ability to non-invasively monitor the double-fusion hESC and the progeny thereof in vivo allows for experiments to evaluate growth factors to enhance the survival rate of the double-fusion hESC, assess immunosuppressive regimen that can prevent immune rejection of the double-fusion hESC, screen specific protocols aimed at deriving purely differentiated cells that are incapable of forming teratomas, correlate the survival of transplanted cells in relation to functional improvement of recipient hosts, and the like.

In an embodiment, the firefly luciferase reporter gene and the enhanced green fluorescent reporter gene are not silenced after 44 passages. In addition, embodiments of the present disclosure also express SSEA 4 and Oct-4 (stem cell markers) and are alkaline phosphatase positive, which illustrates that the transduction of the firefly luciferase reporter gene and the enhanced green fluorescent reporter gene did not alter the stem cell relative to stem cells that were not transduced with these genes.

Furthermore, embodiments of the present disclosure examine the use of reporter gene-induced perturbations at the genetic level by expression profiling of Fluc+/eGFP+hES cell-derived EBs as they differentiated into mature lineages over the course of 42 days. Specifically, expression of stem cell markers (Oct-4, Nanog, Rex-1) was unchanged following transduction, as was the expression time course of early stage cardiac transcriptional factors (Nkx2.5, MEF-2c). Cardiac specific markers (a-MHC, ANF) appeared by day 14 and persisted through terminal differentiation into cardiomyocytes. Overall, the data is consistent with prior studies using lentiviral vectors to stably express transgenes in hES cells.

The fluorescence imaging system can include, but is not limited to, FACS, Maestro spectral fluorescent imager, Cellvizio fiber-based fluorescent confocal microscope, Olympus intravital microscopy, and the like. The bioluminescence imaging system can include, but is not limited to, Xenogen IVIS system.

As mentioned above, the double-fusion hESC express a firefly luciferase reporter gene encoding a firefly luciferase protein and express an enhanced green fluorescent reporter gene encoding an enhanced green fluorescent protein. The hESC is from the H9 human embryonic stem cell line.

The firefly luciferase reporter gene and the enhanced green fluorescent reporter gene are transduced into the human embryonic stem cells using a LV-pUP-Fluc-eGFP, where LV is lentivirus (SEQ ID NO: 16), pUP is constitutive human ubiquitin promoter, Fluc is a firefly luciferase reporter gene, and eGFP is enhanced green fluorescent reporter gene. The two genes are linked together by a 14 amino acid linker (SEQ ID NO: 21, LENSHASAGYQAST). The Fluc ID# in genebank is M15077 (SEQ ID NO: 1). The GFP ID# in genebank is U55763 (SEQ ID NO: 2). Additional details regarding transduction and the like are described in Examples 1, 2, 3, and 4.

Embodiments of the present disclosure include double fusion polynucleotides that include the firefly luciferase reporter gene and the enhanced green fluorescent reporter gene. In particular, the double fusion polynucleotide includes LV-pUP-Fluc-eGFP (SEQ ID NO: 11). In an embodiment the firefly luciferase reporter gene and the enhanced green fluorescent reporter gene are linked with a linker such as (SEQ ID NO: 21, LENSHASAGYQAST). In an embodiment, the double fusion polynucleotide LV-pUP-Fluc-eGFP has a nucleotide sequence listing corresponding to SEQ ID NO: 10

Embodiments of the present disclosure include double fusion polypeptide that includes the firefly luciferase reporter protein and the enhanced green fluorescent reporter protein.

In an embodiment, the double fusion polypeptide has a polypeptide sequence corresponding to SEQ ID NO: 11.

The firefly luciferase reporter gene can include a nucleotide sequence described in SEQ ID NO: 1, portions thereof, mutants thereof, or variants thereof, as well as the corresponding proteins.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, brightness, and the like and in vivo and/or in vitro stability (e.g., half-life), and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the Luciferase mutants retain Luciferase activity (e.g., catalyze the conversion of a coelenterazine substrate into a luminescent product in the presence of molecular oxygen). In an embodiment, the Luciferase mutants have at least one of the following properties relative to their corresponding reference wild-type protein: modulated stability, enhanced light output, and/or modulated emission wavelength maximum and modulated substrate utilization.

The firefly luciferase reporter protein produced the firefly luciferase reporter gene can react with a bioluminescence initiating compound to produce a radiation emission. The bioluminescence initiating compound can include, but is not limited to, D-luciferin analogs, and functional derivatives thereof.

The enhanced green fluorescent reporter gene can include a nucleotide sequence described in SEQ ID NO: 2, portions thereof, mutants thereof, or variants thereof, and the corresponding proteins.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, brightness, and the like and in vivo and/or in vitro stability (e.g., half-life), and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the enhanced green fluorescent reporter gene mutants retain enhanced green fluorescent reporter gene activity. In an embodiment, the enhanced green fluorescent reporter gene mutants have at least one of the following properties relative to their corresponding reference wild-type protein: modulated stability, enhanced light output, and/or modulated emission wavelength maximum and modulated substrate utilization.

In another embodiment, the double-fusion hESC express a humanized firefly luciferase reporter gene encoding a humanized firefly luciferase protein and express a humanized enhanced green fluorescent reporter gene encoding a humanized enhanced green fluorescent protein. The humanized form of these genes and proteins are less immunogenic than their non-humanized counterparts. The two genes are linked together by a 5 amino acid linker (GSHGD, amino acids 589-593 of SEQ ID NO: 20) (SEQ ID NO: 19 represents the nucleotide sequence for the double-fusion hESC, and SEQ ID NO: 20 is the corresponding protein sequence, with the linker (GSHGD) at amino acids 589-593 of SEQ ID NO: 20). The humanized Fluc ID# in genebank is AY73822 (SEQ ID NO: 3). The humanized GFP ID# in genebank is XXU50963 (SEQ ID NO: 4).

In another embodiment, the double-fusion hESC express a red fluorescent reporter gene encoding a red fluorescent protein and express a renilla luciferase reporter gene encoding a renilla luciferase protein. The two genes are linked together by a 5 amino acid linker (GSHGD). The mRFP ID# in genebank is AF506027 (SEQ ID NO: 6). The GFP ID# in genebank is XXU50963 (SEQ ID NO: 2). The renilla luciferase ID# in genebank is M63501 (SEQ ID NO: 5).

In another embodiment, the double-fusion hESC express a Herpes Simplex Virus 1 thymidine kinase (HSV1-tk) (SEQ ID NO: 12) positron emission tomography (PET) reporter gene encoding an enzyme protein (HSV1-TK) (SEQ ID NO: 13) and express an enhanced green fluorescent reporter gene encoding an enhanced green fluorescent protein. The enzyme protein (HSV1-TK) can phosphorylate some nucleotide analogs that can be detected by a nuclear imaging system (e.g., PET).

In embodiments including renilla luciferase, portions thereof, mutants thereof, variants thereof, the bioluminescence initiating compound can include, but is not limited to, coelenterazine, analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp, coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750; and 5,874,304).

In general, coelenterazines are known to luminesce when acted upon by a wide variety of bioluminescent proteins, specifically luciferases. Useful, but non-limiting, coelenterazines are disclosed in U.S. patent application Ser. No. 10/053, 482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

Triple-Fusion Human Embryonic Stem Cells

In general, embodiments of the present disclosure include isolated triple-fusion human embryonic stem cells (hESC) or populations thereof. In an embodiment, the triple-fusion hESC expresses a firefly luciferase reporter gene encoding a firefly luciferase protein, expresses a red fluorescent reporter gene encoding a red fluorescent protein, and expresses a Herpes Simplex Virus 1 thymidine kinase (HSV1-tk) positron emission tomography (PET) reporter gene (or a truncated HSV1-tk (HSV1-ttk) SEQ ID NO: 14) encoding an enzyme protein (HSV1-TK) (or a truncated HSV1-TK (HSV1-tTK, (SEQ ID NO: 15)). The progeny of the triple-fusion hESC also express the firefly luciferase reporter gene, the red fluorescent reporter gene, and the HSV1-tk PET reporter gene. The triple-fusion hESC can be disposed (e.g., engraphed) into a host (e.g., a tissue or organ of the human subject) and can be monitored (e.g., detected, imaged, and the like) as the triple-fusion hESC proliferates and/or differentiates. In particular, embodiments of the present disclosure provide the ability to monitor the proliferation rate, the localization, and lifetime, of the triple-fusion hESC and the progeny thereof. The triple-fusion hESC and the progeny thereof can be monitored without sacrificing the host. In this regard, the in vivo monitoring can be conducted non-invasively for extended periods of time, maybe for an indefinite period of time, using a fluorescence and/or bioluminescence imaging system and/or nuclear imaging system. In addition, the ability to non-invasively monitor the triple-fusion hESC and the progeny thereof in vivo allows for experiments to evaluate growth factors to enhance the survival rate of the triple-fusion hESC, assess immunosuppressive regimen that can prevent immune rejection of the triple-fusion hESC, screen specific protocols aimed at deriving purely differentiated cells that are incapable of forming teratomas, correlate the survival of transplanted cells in relation to functional improvement of recipient hosts, and the like.

In an embodiment, the firefly luciferase reporter gene, the red fluorescent reporter gene, and the HSV1-tk PET reporter gene are not significantly silenced after 30 passages. In addition, embodiments of the present disclosure also express SSEA 4 and Oct-4 (stem cell markers) and are alkaline phosphatase positive, which illustrates that the transduction of the firefly luciferase reporter gene, the red fluorescent reporter gene, and the HSV1-tk PET reporter gene did not alter the stem cell relative to stem cells that were not transduced with these genes.

Furthermore, embodiments of the present disclosure examine the use of reporter gene-induced perturbations at the genetic level by expression profiling of hESC cell-derived EBs as they differentiated into mature lineages over the course of 42 days. Specifically, expression of stem cell markers (Oct-4, Nanog, Rex-1) was unchanged following transduction, as was the expression time course of early stage cardiac transcriptional factors (Nkx2.5, MEF-2c). Cardiac specific markers (a-MHC, ANF) appeared by day 14 and persisted through terminal differentiation into cardiomyocytes. Overall, the data is consistent with prior studies using lentiviral vectors to stably express transgenes in hES cells.

The fluorescence imaging system can include, but is not limited to, FACS, Maestro spectral fluorescent imager, Cellvizio fiber-based fluorescent confocal microscope, Olympus intravital microscopy, and the like. The bioluminescence imaging system can include, but is not limited to, Xenogen IVIS system. The enzyme protein (HSV1-TK or HSV1-tTK) can phosphorylate some nucleotide analogs that can be detected by a nuclear imaging system (e.g., PET and SPECT).

In an embodiment, the triple-fusion hESC expresses a firefly luciferase reporter gene encoding a firefly luciferase protein, expresses a red fluorescent reporter gene encoding a red fluorescent protein, and expresses a Herpes Simplex Virus 1 thymidine kinase (HSV1-tk) positron emission tomography (PET) reporter gene (or a truncated HSV1-tk (HSV1-ttk)) encoding a enzyme protein (HSV1-TK) (or a truncated HSV1-TK (HSV1-tTK)). The enzyme protein (HSV1-TK or HSV1-tTK) can phosphorylate some nucleotide analogs that can be detected by a nuclear imaging system (e.g., PET). The hESC is from the H9 human embryonic stem cell line.

In an embodiment, the firefly luciferase reporter gene, the mutated red fluorescent reporter gene, and the truncated HSV1-tk PET reporter gene are transduced into the human embryonic stem cells using a LV-pUB-Fluc-RFP-tTK (the nucleotide sequence associated with the amino acid sequence SEQ ID NO: 18 or the nucleotide sequence SEQ ID NO: 8 without the LV portion, where the LV is SEQ ID NO: 16), where LV is lentivirus (SEQ ID NO: 16), pUB (part of SEQ ID NO: 18) is constituitve human ubiquitin promoter, Fluc is a firefly luciferase reporter gene, mRFP is the red fluorescent reporter gene, and tTK is the truncated HSV1-tk PET reporter gene. The firefly luciferase reporter gene and the red fluorescent reporter gene are linked together by a 5 amino acid linker (EAAAR). The red fluorescent reporter gene and the truncated HSV1-tk PET reporter gene are linked together by a 8 amino acid linker (TAGPGSAT). The Fluc ID# in genebank is M15077 (SEQ ID NO: 1). The mRFP ID# in genebank is AF506027 (SEQ ID NO: 6). The tTK ID# in genebank is AF057310 (SEQ ID NO: 7). Additional details regarding transduction and the like are described in Examples 1, 2, 3, and 4.

Embodiments of the present disclosure include triple fusion polynucleotides that include the firefly luciferase reporter gene, the red fluorescent reporter gene, and the HSV1-tk PET reporter gene. In particular, the triple fusion polynucleotide includes LV-pUB-Fluc-RFP-tTK. The firefly luciferase reporter gene and the red fluorescent reporter gene are linked together by a 5 amino acid linker (EAAAR) (amino acids 551-555 of SEQ ID No: 9). The red fluorescent reporter gene and the truncated HSV1-tk PET reporter gene are linked together by a 8 amino acid linker (TAGPGSAT ((SEQ ID NO: 22)). In an embodiment, the triple fusion polynucleotide LV-pUB-Fluc-RFP-tTK has a nucleotide sequence as defined as the following: (the nucleotide sequence associated with the amino acid sequence SEQ ID NO: 18 or the nucleotide sequence SEQ ID NO: 8 without the LV portion, where the LV is SEQ ID NO: 16). The protein sequence of Ub-Fluc-rfp-TtK is shown in SEQ ID NO: 9.

Embodiments of the present disclosure include triple fusion polypeptide that includes the firefly luciferase reporter protein, the red fluorescent reporter protein, and the HSV1-tk PET reporter protein. In an embodiment, the triple fusion polypeptide has a polypeptide sequence corresponding to SEQ ID NO: 18.

The firefly luciferase reporter gene can include a nucleotide sequence described in SEQ ID NO: 1, portions thereof, mutants thereof, or variants thereof, as well as the corresponding proteins.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, brightness, and the like and in vivo and/or in vitro stability (e.g., half-life), and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the Luciferase mutants retain Luciferase activity (e.g., catalyze the conversion of a coelenterazine substrate into a luminescent product in the presence of molecular oxygen). In an embodiment, the Luciferase mutants have at least one of the following properties relative to their corresponding reference wild-type protein: modulated stability, enhanced light output, and/or modulated emission wavelength maximum and modulated substrate utilization.

The firefly luciferase reporter protein produced the firefly luciferase reporter gene can react with a bioluminescence initiating compound to produce a radiation emission. The bioluminescence initiating compound can include, but is not limited to, D-luciferin analogs, and functional derivatives thereof.

The mutated red fluorescent reporter gene can include a nucleotide sequence described in SEQ ID NO: 6, portions thereof, mutants thereof, or variants thereof, as well as the corresponding proteins.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, brightness, and the like and in vivo and/or in vitro stability (e.g., half-life), and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In another embodiment, the humanized firefly luciferase reporter gene and the humanized red fluorescent reporter gene are linked together by a 5 amino acid linker (GSHGD) (the nucleotide sequence and the polypeptide sequence for the fusion of the humanized firefly luciferase reporter gene and the humanized red fluorescent reporter are SEQ ID NO: 19 and 20, respectively, with the linker at amino acids 589-593 of SEQ ID NO: 20). The humanized Fluc ID# in genebank is AY73822 (SEQ ID NO: 3). The humanized form of these genes and proteins are less immunogenic than their non-humanized counterparts.

Methods of Use

Embodiments of the present disclosure can be used to image, detect (and visualize), quantitate, study, monitor, evaluate, and/or screen, biological events (e.g., progression of the stem cells and progeny thereof) in vivo or in vitro.

In particular, embodiments of the present disclosure can be used to monitor double-fusion human embryonic stem cells or monitor the progression of the double-fusion human embryonic stem cells. In this regard, the method includes providing an isolated double-fusion human embryonic stem cells (hESC) as described herein and detecting fluorescence, bioluminescence, or both fluorescence and bioluminescence emitted from the double-fusion hESC and progeny thereof. Thus, embodiments of the present disclosure provide the ability to monitor the proliferation rate, the localization, and lifetime, of the double-fusion hESC and the progeny thereof. Additional details are provided in Examples 1, 2, 3, and 4.

In particular, embodiments of the present disclosure can be used to monitor triple-fusion human embryonic stem cells or monitor the progression of the triple-fusion human embryonic stem cells. In this regard, the method includes providing an isolated triple-fusion human embryonic stem cells (hESC) as described herein and detecting fluorescence, bioluminescence, radiation (e.g., gamma radiation) or combinations (any combination of 2 or all 3) of these emitted from the triple-fusion hESC and progeny thereof. Thus, embodiments of the present disclosure provide the ability to monitor the proliferation rate, the localization, and lifetime, of the triple-fusion hESC and the progeny thereof. Additional details are provided in Examples 1, 2, 3, and 4.

The term "monitor" or "monitoring" includes detecting, identifying, imaging, or otherwise establishing the presence or absence of double-fusion human embryonic stem cells or the triple-fusion human embryonic stem cells using the fluorescence, and/or bioluminescence and/or radiation, or imaging, ascertaining, establishing, or otherwise determining one or more characteristics of the double-fusion human embryonic stem cells or the triple-fusion human embryonic stem cells using the fluorescence and/or bioluminescence and/or radiation.

Kits

This disclosure encompasses kits that include, but are not limited to, double-fusion human embryonic stem cells and directions (written instructions for their use). In addition, the kit may include other reagents that can be used with the double-fusion human embryonic stem cells.

In addition, this disclosure encompasses kits that include, but are not limited to, triple-fusion human embryonic stem cells and directions (written instructions for their use). The kit may include other reagents that can be used with the triple-fusion human embryonic stem cells.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

EXAMPLES

Now having described the embodiments of the disclosure, in general, the examples describe some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction

Human embryonic stem (hES) cells are derived from the inner cell mass of pre-implanted blastocysts. They have been shown to differentiate into a variety of cell types that represent endoderm, ectoderm, and mesoderm origins via three-dimensional structures called embryoid bodies (EBs), which at least partially mimic the spatial organization of the embryo. Various lineages have been derived from hES cells, including neurons, cardiomyocytes, hematopoietic cells, osteogenic cells, hepatocytes, insulin-producing cells, keratinocytes and endothelial cells. Furthermore, these cells appear to be weakly immunogenic, with absent MHC-II and only low levels of MHC-I molecules. Given their unlimited self-renewal and pluripotency capacity, hES cells represent a new and exciting avenue for stem cell therapy. In cell culture, hES cells can differentiate into endothelial cells through successive maturation steps. Therefore, the isolation and use of hES-derived endothelial cells (hESC-ECs) have potential therapeutic applications, including cell transplantation for repair of ischemic tissues and tissue-engineered vascular grafts.

Stem cell therapy is an exciting area of research that promises future treatment of many diseases. However, to fully understand the beneficial effects of stem cell therapy, investigators must be able to track the biology and physiology of transplanted cells in living subjects over time. At present, most cell therapy protocols require histological analysis to determine viable engraftment of the transplanted cells. The development of sensitive, noninvasive technologies to monitor this fundamental engraftment parameter will greatly aid clinical implementation of cell therapy. In reporter gene imaging, stem cells can be genetically engineered to express various reporter genes before transplantation. The reporter genes can be detected by sensitive imaging devices such as the optical coupled device (CCD), single photon emission computed tomography (SPECT), or positron emission tomography (PET). Magnetic resonance (MR) imaging of stem cells is also an emerging application for monitoring cell engraftment. In particular, stem cells labeled with superparamagnetic iron oxide (SPIO) particles can be identified in vivo as hypointensities in MR images, as the iron shortens transverse proton relaxation times. The spatial and temporal resolution of MR imaging allow the location of iron-labeled donor cells to be monitored noninvasively over several weeks in vivo. A fundamental drawback of hypointense signal is the difficulty in distinguishing iron-labeled cells from the surrounding air, hemorrhage, necrosis, and macrophages. To address these problems, techniques to generate positive contrast to enhance signal- and contrast-to-noise ratios of the iron-labeled stem cells have been developed. Cunningham et al. have reported off-resonance (OR) MR imaging of iron-labeled mouse ES cells to generate positive contrasts through suppression of background tissue. However, whether these different methodologies can be applied for studying the engraftment of hES cells and their derivatives in vivo has yet to be examined. To help answer these important questions, we performed a head-to-head comparison of tracking undifferentiated hES cells and differentiated hESC-ECs using reporter gene and iron particle imaging.

As mentioned above, human embryonic stem (hES) cells are pluripotent stem cells capable of self-renewal and differentiation into virtually all cell types. Thus, they hold tremendous potential as cell sources for regenerative therapies. The concurrent development of accurate, sensitive, and noninvasive technologies capable of monitoring hES cells engraftment in vivo can greatly expedite basic research prior to future clinical translation.

In this example, hES cells were stably transduced with a lentiviral vector carrying a novel double-fusion reporter gene that consists of firefly luciferase and enhanced green fluorescence protein (Fluc-eGFP). Reporter gene expression had no adverse effects on cell viability, proliferation, or differentiation to endothelial cells (hESC-ECs). To compare the two popular imaging modalities, hES cells and hESC-ECs were then co-labeled with superparamagnetic iron oxide (SPIO) particles before transplantation into murine hindlimbs. Longitudinal magnetic resonance (MR) imaging showed persistent MR signals in both cell populations that lasted up to 4 weeks. By contrast, bioluminescence imaging indicated divergent signal patterns for hES cells and hESC-ECs. In particular, hESC-ECs showed significant bioluminescence signals at day 2, which decreased progressively over the following 4 weeks, whereas bioluminescence signals from undifferentiated hES cells increased dramatically during the same period. Postmortem histology and immunohistochemistry confirmed teratoma formation after injection of undifferentiated hES cells, but not hESC-ECs. Taken together, we conclude that reporter gene is a better marker for monitoring cell viability, whereas iron particle labeling is a better marker for high-resolution detection of cell location by MR. Furthermore, transplantation of pre-differentiated rather than undifferentiated hES cells would be more suited for avoiding teratoma formation.

Materials and Methods

Maintenance and Differentiation of Human Embryonic Stem Cells.

Undifferentiated hES cells (H9 line from Wicell, passages 35 to 45) were grown on an inactivated mouse embryonic fibroblast (MEF) feeder layer as previously described (Stem Cells, 2007. 25(2): p. 392-401). Briefly, the cell was maintained at an undifferentiated stage on irradiated low-passage MEF feeder layers on 0.1% gelatin-coated plates. The medium was changed daily. The medium consisted of Dulbecco's modified Eagle's medium (DMEM)/F-12, 20% knockout serum replacement, 0.1 mM nonessential amino acids, 2 mM L-glutamine, 0.1 mM β-mercaptoethanol, and 4 ng/ml rhFGF-2 (R&D Systems Inc., Minneapolis). The undifferentiated hES cells were treated by 1 mg/ml collagenase type IV in DMEM/F12 and scraped mechanically on the day of passage. Prior to iron labeling and endothelial differentiation, hES cell were seeded onto Matrigel-coated plates in conditioned medium (CM) prepared from MEF as follows (Nat Biotechnol, 2001. 19(10): p. 971-4). MEF cells were harvested and irradiated with 50 Gy, and cultured with hES medium without bFGF. CM was collected daily and supplemented with an additional 4 ng/ml of bFGF before feeding hES cells.

In Vitro Differentiation of hESC-ECs.

To induce hES cell differentiation, undifferentiated hES cells were cultured in differentiation medium containing Iscove's modified Dulbecco's medium (IMDM) and 15% defined fetal bovine serum (FBS) (Hyclone, Logan, Utah), 0.1 mM nonessential amino acids, 2 mM L-glutamine, 450 µM monothioglycerol (Sigma, St. Louis, Mo.), 50 U/ml penicillin, and 50 µg/ml streptomycin, either in ultra-low attachment plates for the formation of suspended embryoid bodies (EBs) as previously described (Proc Natl Acad Sci USA, 2002. 99(7): p. 4391-6 and Stem Cells, 2007. 25(2): p. 392-401). Briefly, hES cells cultured on Matrigel coated plate with CM were treated by 2 mg/ml dispase (Invitrogen, Carlsbad, Calif.) for 15 minutes at 37° C. to loosen the colonies. The colonies were then scraped off, and transferred into ultra low-attachment plates (Corning Incorporated, Corning, N.Y.) for EB formation.

Whole-Mount Immunostaining of Human Embryoid Bodies (hEBs).

Whole-mount immunohistostaining of hEBs was performed as previously described with minor modifications. The hEBs were fixed in methanol and DMSO (4:1) at 4° C. overnight. For staining, the rehydrated hEBs were first blocked by two incubations in PBSBT (2% BSA and 0.2% TWEEN-20™ (Polysorbate 20) in PBS), then with PBSBT containing mouse anti-human MoAb CD31 (Becton Dickinson) overnight at 4° C. The hEBs were washed five times in PBSBT each for 1 h at 4° C. for the initial three washes and at room temperature for the final two. The primary antibody was labeled by incubating the hEBs with Alex 594-conjugated goat anti-mouse IgG (Invitrogen) in PBSBT overnight at 4° C. and nuclear counterstained with DAPI.

Flow Cytometry Sorting (FCS) of hESC-ECs.

Single cell suspensions from day 12 of differentiated hEBs were obtained by treatment with 0.56 units/ml of Liberase Blendzyme IV (Roche, Indianapolis) at 37° C. for 20-30 min. Cells were passed through a 40-μm cell strainer [7]. Cells were incubated for 30 min at 4° C. with mouse phycoerythrin (PE) conjugated anti-human CD31 (BD). The CD31+ cells were isolated using FACScan™ (Becton Dickinson). To generate hESC-ECs, the isolated CD31+ cells were grown on 0.1% gelatin or 4 μg/cm² human fibronectin (Calbiochem, San Diego, Calif.) coated plates in EGM-2 with 5% FBS. The medium was changed every 2-3 days.

Biological Characteristics of hESC-ECs.

Flow cytometry analysis, DiI-ac-LDL uptake assay, and Matrigel assay were used to confirm endothelial cell phenotype within these CD31+ purified hES cells. Antibodies used in this study were phycoerythrin (PE) conjugated anti-CD31 (BD Pharmingen) and Allophycocyanin (APC) conjugated anti-KDR(R&D Systems), APC conjugated anti-mouse IgG2a, and mouse anti-human VE-cadherin (BD Pharmingen). The stained cells were analyzed using BD FACSVANTAGE™ (Becton-Dickinson, MA). Dead cells stained by propidium-iodide (P1) were excluded from the analysis. Isotype-identical antibodies served as controls (BD Pharmingen). Approximately $5 \times 10^5$ undifferentiated hES cells and $2 \times 10^5$ differentiated hESC-ECs were used to run the FACS. For DiI-ac-LDL uptake assay, hESC-ECs were incubated with 10 μg/ml of DiI-Ac-LDL (Molecular Probes, Eugene, Oreg.) at 37° C. for 6 hours. After washing with PBS twice, the slides were fixed and counterstained with DAPI (4, 6-diamidino-2-phenylindole), mounted with mounting medium (Vector Laboratories, Burlingame, Calif.), and covered with coverslips prior to detection with fluorescence microscopy as described (Stem Cells, 2007. 25(2): p. 392-401). The formation of endothelial tubes was assessed by seeding cells in 24-well plates coated with Matrigel™ (BD Pharmingen) and incubating them at 37° for 12 hours as described (Circulation, 2007. 116(11): p. I46-54 and Nature, 2000. 408(6808): p. 92-6).

Real Time RT-PCR (qRT-PCR).

qRT-PCR assays were performed using the human endothelial cell biology $RT^2$ Profiler™ PCR Array (SuperArray Bioscience, Frederick, Md.) on an ABI PRISM 7900 HT (Applied Biosystems, Foster City, Calif.). Data analysis are available at the company website (www.superarray.com/per/arrayanalysis.php). Briefly, total RNAs were isolated using RNeasy® (Qiagen, Waltham, Mass.) from undifferentiated hES cells at day 0, differentiated hEBs at day 12, hESC-derived endothelial cells (after CD31 sort), and human umbilical endothelial cells (HUVEC) as positive control. First-strand cDNAs were generated using iScript Select cDNA Synthesis Kit (BioRad, Hercules, Calif.). For real-time PCR reaction, first-strand cDNAs were added to RT qPCR Master Mix (SuperArray Bioscience). Samples were heated for 10 min at 95° C. and then subjected to 40 cycles of denaturation at 95° C. for 15 sec and annealing and elongation at 60° C. for 1 min. Methods for conventional RT-PCR analysis and primer sequences for endothelial specific genes (CD31, VE-cadherin, KDR, Oct-4, GAPDH) are described in Supplemental Methods (See below), respectively.

Lentiviral Transduction of hES Cells with Double Fusion (DF) Reporter Gene.

In order to track transplanted cells in vivo, hES cells were transduced at multiplicity of infection (MOI) of 10 with self-inactivating (SIN) lentiviral vector carrying a human ubiquitin promoter driving firefly luciferase and enhanced green fluorescence protein (Fluc-eGFP). Stable clones were isolated using FACS for eGFP expression. Afterwards, Fluc activity within different cell numbers was confirmed ex vivo using Xenogen IVIS® 200 system (Xenogen, Alameda, Calif.) as described (Circulation, 2006. 113(7): p. 1005-14). Non-transduced hES cells (control) and hES cells with DF reporter gene (hESC-DF) were stained for Oct-4 (Chemicon, Temecula, Calif.). The undifferentiated hES cell colonies were fixed in 4% paraformaldehyde in PBS for 15 minutes. Nonspecific binding was blocked with 4% normal goat serum for 30 minutes, following which the colonies were stained with antibodies to Oct-4 and incubated with Alexa 594-conjugated rabbit anti-goat secondary antibodies (Invitrogen) for 30 minutes and nuclear counterstained with DAPI. Images were obtained with a Zeiss Axiovert microscopy (Sutter Instrument Co., USA). Subsequently, the processes for in vitro endothelial cell differentiation and characterization were the same as control non-transduced hES cells described earlier.

Labeling of hES Cells and hESC-ECs with Iron Particles.

Transduced hES cells and derived hESC-ECs were labeled with Feridex IV-protamine sulfate (FE-Pro) as described [25] with minor modifications. The commercially available superparamagnetic iron oxide (SPIO) suspension, (Feridex IV®, Berlex Laboratories, Inc, Wayne, N.J.) contains particles approximately 80-150 nm in size and has a total iron content of 11.2 mg/ml. Preservative-free protamine sulfate (American Pharmaceuticals Partner Inc., Schaumburg, Ill.), 10 mg/ml, was prepared as a fresh stock solution of 1 mg/ml in distilled water at the time of use. SPIO at a concentration of 100 μg/ml was put into a mixing tube containing serum-free culture medium. Protamine sulfate (12 μg/ml) was added and the entire suspension was mixed for 5-10 minutes. The final FE-Pro suspension was added directly to the existing medium, incubated overnight. The final concentration of Feridex IV and protamine sulfate was 50 μg/ml and 6 μg/ml of medium, respectively. After overnight incubation, the hES cells and hESC-ECs were washed twice with phosphate-buffered saline (PBS), and harvested by treating with collagenase IV and trypsin, respectively. Next, the trypan blue exclusion assay was used to assess viability and cytotoxicity of iron labeling on hES cells and hESC-ECs. Six samples were performed and averaged for these assays.

Transplantation of hES Cells and hESC-ECs Into Murine Hindlimbs.

All procedures were performed on 8-10 week old female SCID beige mice (Charles River Laboratories, Inc.) (n=15) according to the Stanford University Animal Care and Use Committee guidelines. Mice were anesthetized with inhaled isoflurane (2% to 3%). Approximately $1 \times 10^6$ undifferentiated hES cells and $1 \times 10^6$ hESC-ECs (both stably transduced with DF reporter gene and co-labeled with SPIO particles) were injected into right and left hind limbs of the same mouse, respectively, in 100 μl PBS.

Optical Bioluminescence Imaging of Transplanted Cell Fate in Living Mice.

Bioluminescence imaging was performed using the Xenogen IVIS® 200 system. After intraperitoneal injections of reporter probe D-Luciferin (150 mg luciferin/kg), animals were imaged for 2 seconds to 2 minutes. The same mice were scanned for 4 weeks. Imaging signals were quantified in units of maximum photons per second per centimeter square per steridian (photons/sec/cm$^2$/sr). Bioluminescence imaging was performed by an investigator blinded to the study conditions.

MR Imaging of Transplanted Cell Fate in Living Mice.

Afterwards, in vivo MR imaging was performed on the 1.5 T-MR scanner (Signa, GE Medical Systems, Milwaukee, Wis.) using a 3-inch surface coil. The mice were anesthetized with intraperitoneal injection of ketamine (100 mg/kg) and xylazine (20 mg/kg) and imaged in a prone position. After 3D-plane localization, images were acquired in a coronal plane using gradient-recalled echo (GRE) sequence (TR=100 msec, TE=10 msec, Flip angle=30°, FOV=8×8 cm, slice thickness=1 mm, slice gap=0 mm, matrix=256×256, NEX=4). Multiple contiguous coronal slices consisting of 9-10 slices were acquired for complete coverage of the mice hind limb. Following GRE, Off-Resonance (OR) sequence was applied to the transplanted labeled cells. Briefly, OR utilizes spectrally selective radiofrequency (RF) pulses to excite and refocus the off-resonance water surrounding the labeled cells while suppressing on-resonance signal. This generates positive contrast from the hydrogen protons adjacent to the labeled cells and helps identify and estimate the volume of the labeled cells (Magn Reson Med, 2005. 53(5): p. 999-1005). Projectional OR imaging was performed with TR=800 msec, TE=14 msec, FOV=20 cm, and matrix=256× 128 with 2 discrete Fourier transformation (DFT) encoding and an 8-ms readout. Measurement of signals in the region of interest (ROI) was performed with the Image J software. The signal volume of GRE images was measured by summation of hypointense area of each slice. The OR signal enhancement area was obtained by measuring the area of projectional OR image. MR imaging was performed by an investigator blinded to the study condition (YS). Protocol for ex vivo MR imaging of cell suspension is included in the Supplementary Methods.

Immunohistochemical Staining for Macrophages, Iron Particles, and Various Cell Types.

Mice were euthanized at four weeks after cell transplantation. Both hind limbs were embedded in paraffin and cut into 5 μm sections. H&E and Prussian staining were carried out to identify the fate of transplanted hES cells and hESC-ECs doubly labeled with iron particles and reporter genes. To examine whether the iron particles are localized in the macrophages, staining of macrophages (Mac-3) and iron particles were performed. Sections were first incubated with the monoclonal rat anti-mouse macrophage Mac-3 antibody (BD Parmingen) for one hour and then with a second antibody, biotinylated goat anti-rat secondary antibody (Invitrogen), for another hour. Streptavidin-horseradish peroxidase (HRP) was then applied for 30 minutes and HRP activity was detected by with 3,3'-Diaminobenzidine (DAB). For iron particle staining, sections were incubated with Perls reagent in the dark for 30 minutes and counterstained with fast red. For immunofluorescence histology, both hind limbs were embedded into OCT compound (Miles Scientific, Elkhart, Ind.) and 5 μm frozen sections were cut. For immunostaining, sections were incubated with primary antibodies, rat anti-mouse macrophage Mac-3 antibody (BD Pharmingen), rabbit anti-GFP (Invitrogen), and goat anti-mouse CD31 (Santa Cruz Biotechnology), followed by incubation with secondary antibody, APC-conjugated mouse anti-rat IgG (BD Pharmingen), Alex 488 conjugated donkey anti-rabbit IgG (Invitrogen), Alex 594 conjugated donkey anti-goat IgG (Invitrogen), then counter stained with DAPI. Histologic interpretation was performed by a pathologist blinded to the study conditions (AJC).

Statistical Analysis.

ANOVA and repeated measures ANOVA with post-hoc testing as well as the two-tailed Student's t-test were used. Differences were considered significant at P-values of <0.05. Unless otherwise specified, data are expressed as mean±standard deviation.

Results

Characterization and Differentiation of hES Cells.

Figure 1:
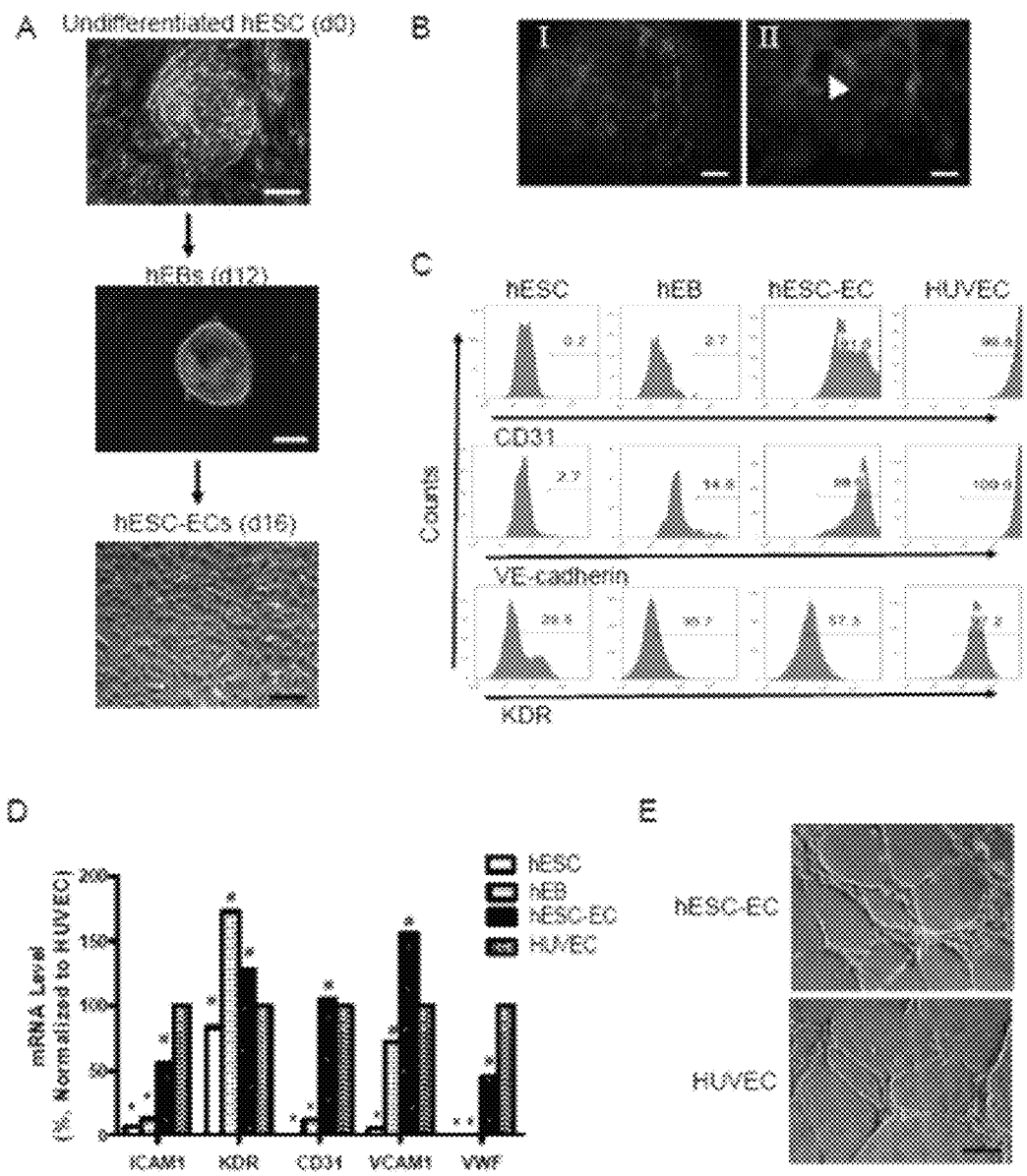
FIGS. 1(A)-1(E) illustrate in vitro endothelial differentiation of hES cells.

In order to compare the fate of undifferentiated versus differentiated hES cells in vivo, we first established a differentiation protocol to induce hESC-ECs (FIG. 1A). Undifferentiated hES cell (H9 line) were maintained either on irradiated MEF feeder cells or on Matrigel coated plates in the presence of MEF condition medium (Stem Cells, 2007. 25(2): p. 392-401). To isolate endothelial cells from hES cells, undifferentiated hES cells cultured on Matrigel coated plated were placed into Petri dishes with differentiation medium for induction of EB formation. Previous studies have shown that differentiated hEBs from hES cells contain endothelial cells which can be isolated by CD31 (Proc Natl Acad Sci USA, 2002. 99(7): p. 4391-6) or CD34 markers (Stem Cells, 2007. 25(2): p. 392-401). In this study, whole-mount immunostaining confirmed that within day-12 hEBs, the CD31$^+$ endothelial cells were organized in specific channel-like structures (FIG. 1B). These data confirm that hES cells cultivated as hEBs spontaneously differentiated to endothelial cells and formed blood vessel-like structures. Initial FACS analysis showed that ~3% cells expressed CD31 marker. This population of CD31$^+$ was sorted, cultured, and propagated for further analysis to confirm endothelial cell traits. In particular, we examined CD31, VE-cadherin, and KDR, which are known to be markers for endothelial differentiation of ES cells (J Cell Biochem, 2005. 95(3): p. 559-70, Proc Natl Acad Sci USA, 2002. 99(7): p. 4391-6, Stem Cells, 2007. 25(2): p. 392-401, Endothelium, 2003. 10(6): p. 329-36, and N Engl J Med, 2003. 348(7): p. 581-2). As expected, both FACS and quantitative RT-PCR analysis indicated undifferentiated hES cells expressed endothelial markers at low level. After endothelial induction, ICAM1, CD31, VCAM1, vWF, and VE-cadherin were upregulated while Oct-4 expression (marker for undifferentiated state) was downregulated (FIGS. 1C, 1D, and 7A). Quantitative RT-PCR analysis showed similar endothelial gene expression pattern of hES-ECs compared to HUVECs but great disparity between hESC-ECs and hES cells (FIGS. 1D, 7B, and 7C). Interestingly, KDR was continuously expressed in both undifferentiated and differentiated hES cells as shown by RT-PCR and FACS (FIGS. 1C, 1D, and 7A). This pattern of expression is unlike mouse ES cells whereby KDR is specifically expressed on hemagioblasts but not on undifferentiated ES cells (J Cell Biochem, 2005. 95(3): p. 559-70). After 1 week of culturing, flow cytometry was again performed using antibodies directed against endothelial markers such as VE-cadherin and CD31. Isolated cells continued to express robust levels of both VE-cadherin and CD31 (>80%). These CD31 cells morphologically resembled HUVECs and can form tube-like structure on Matrigel (FIG. 1E).

Genetic Labeling of hES Cells with Double Fusion (DF) Reporter Gene.

Figure 2:
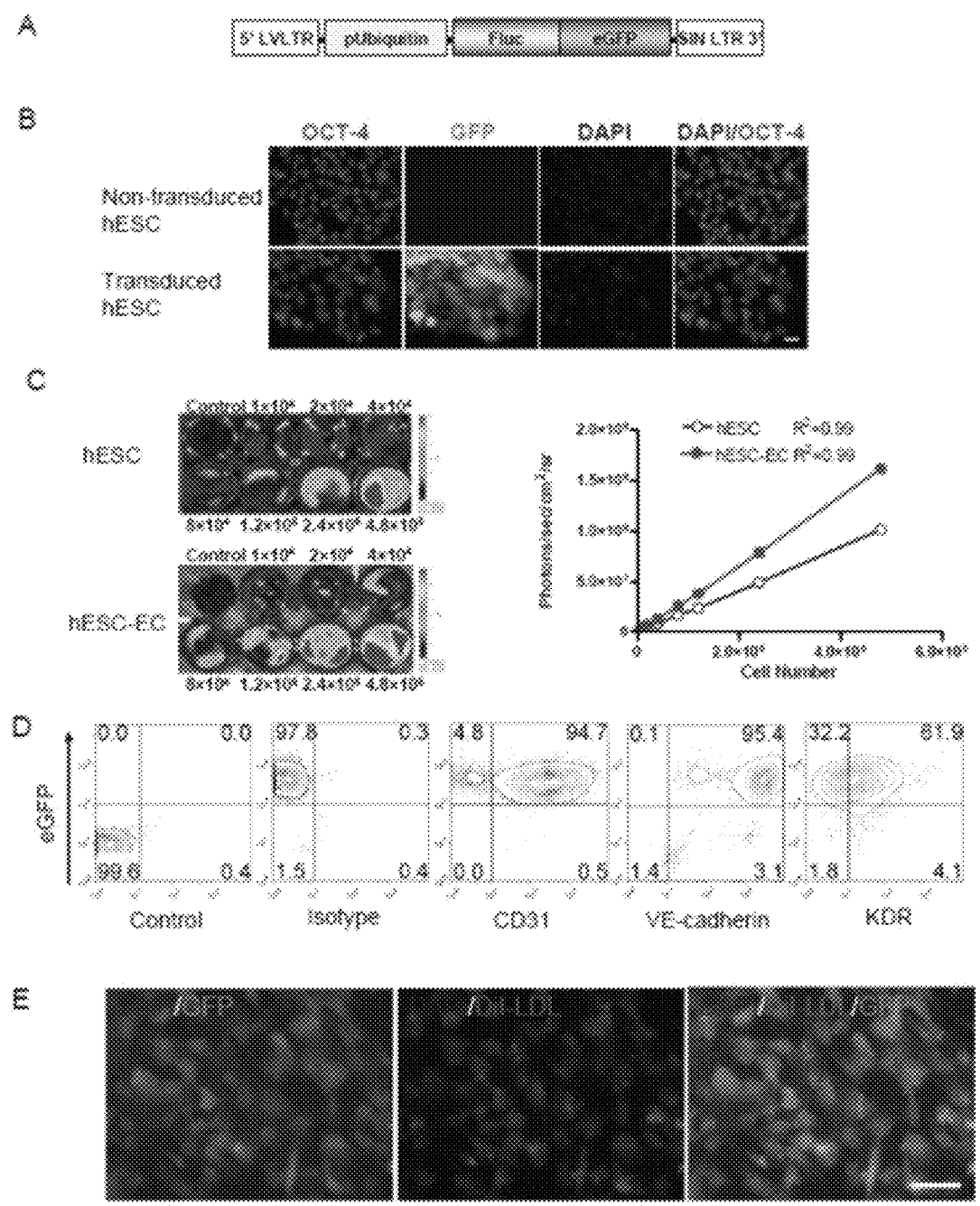
FIGS. 2(A)-2(E) illustrate stable lentiviral transduction of hES cells with the double fusion reporter genes.

In order to develop an imaging platform for tracking transplanted hES cells and hESC-ECs in living animals, we used a DF reporter gene consisting of Fluc-eGFP (FIG. 2A). The efficiency of self-inactivating lentiviral vector for transducing hES cells was ~20% (data not show). Both control non-transduced hES cells and stably transduced hES cells showed similar expression patterns of stem cell markers Oct-4 on immunostaining, suggesting minimal side effects by reporter gene on maintaining stem cell state (FIG. 2B). Upon culturing onto 24-well plates, we also observed a strong correlation ($r^2=0.99$) between Fluc activity and cell numbers ex vivo using the Xenogen IVIS system (FIG. 2C). The cell proliferation and cell viability data are also similar between control hES cells and transduced hES cells (data not shown). Overall, these data are consistent with our previous studies showing minimal effects of reporter genes on mouse ES cell survival, proliferation, and differentiation (Circulation, 2006. 113(7): p. 1005-14, Proteomics, 2006. 6(23): p. 6234-49, and Physiol Genomics, 2006. 25(1): p. 29-38). In addition, the differentiation procedure and differentiation efficiency of stably transduced hES cells were similar to control non-transduced hES cells. Isolated cells express robust levels of both VE-cadherin and CD31, and avidly incorporate Dil-ac-LDL (FIGS. 2D & 2E). Uptake of Dil-ac-LDL has been used to characterize mature endothelial cells (J Cell Biol, 1984. 99(6): p. 2034-40). The isolated cells similarly can form tube-like structure on Matrigel (data not shown). Overall, reporter gene expression did not seem to significantly affect the typical characteristics of endothelial cells as measured by immunostainings, Dil-ac-LDL uptake, and Matrigel angiogenesis assay.

Physical Labeling of hES Cells with Iron Particle.

In order to track transplanted cells using MR imaging in vivo, hES cells and hESC-ECs (both stably expressing the DF reporter gene) were co-labeled with iron particles. After staining with Prussian Blue, iron labeled cells were found to have cytosolic accumulation of iron. Interestingly, the iron uptake of hES cells was less than hESC-ECs, which is likely due to difference in their physical size (FIG. 3A). Similarly, in vitro cellular MR imaging demonstrated that dephasing signals in hES cells were weaker than those in hESC-ECs. Representative in vitro cellular MRI of labeled cells is shown in FIG. 3B. Finally, the cell viability assay showed no significant difference between control unlabeled hES cells versus iron particle labeled hES cells (FIG. 3C).

Longitudinal MR Imaging of hES Cell Survival in Living Animals.

In order to evaluate whether MR imaging can be used to serially monitor cell survival following transplantation, we injected $1 \times 10^6$ iron-labeled hES cells into left hind limbs and $1 \times 10^6$ iron-labeled hESC-ECs into right hind limbs of SCID beige mice. We then imaged these iron-labeled cells repetitively for up to 4 weeks. Representative serial MR images of iron-labeled cells by GRE and OR (Magn Reson Med, 2005. 53(5): p. 999-1005) sequences during the 4-week period are shown in FIGS. 4A and 4C, respectively. Control animals injected with unlabeled cells showed no MR signals as expected. Similar to the in vitro data showing more cytosolic accumulation of iron particles within the larger size hESC-ECs (FIG. 3A), we noted the GRE and OR signals were also stronger in the right (hESC-ECs) compared to left (hESC) hind limbs. Four weeks after cell transplantation, MR imaging with GRE sequence showed a significant increase in the physical size of the left hind limb injected with iron-labeled hES cells, which is due to teratoma formation (FIG. 4A). However, when normalized to day 2, analysis of both MR imaging signals (GRE and OR) produced no difference at 4 weeks as shown in FIGS. 4B and 4D ($P=0.001$).

Longitudinal Reporter Gene Imaging of hES Cell Survival in Living Animals.

Since the same animals described above were injected with hES cells and hESC-ECs double labeled with iron particles and Fluc-eGFP, we decided to analyze the ability of reporter gene imaging for assessing stem cell fate (e.g., engraftment, proliferation, and death). Longitudinal bioluminescence imaging was also performed in the same animals for 4 weeks (FIG. 5A). In both hind limbs, bioluminescence signals were most robust immediately after transplantation (day 2). In the hESC-EC group, bioluminescence signals progressively decreased from day 2 to day 28 ($P=0.001$ vs. control for all time points), indicating acute donor cell loss. Control animals injected with PBS showed no imaging signals as expected. Quantitative analysis shows that the hESC-ECs survival activity at day 21 was less than 1.5% compared to day 2. This survival pattern of differentiated hESC-ECs is markedly different when compared to undifferentiated hES cells, which was >40-fold higher compared to day 2 (FIG. 5B). Interestingly, the undifferentiated hES cell survival activity decreased to about 25% baseline from day 2 to day 7, followed by a robust rebound of cell survival activity from day 14 to day 28. This dichotomous pattern of hES cell death followed by hES cell proliferation was seen in most animals analyzed.

Postmortem Histology and Immunohistochemistry.

In order to confirm our in vivo imaging data (both MR and bioluminescence), all animals were sacrificed 4 weeks after cell transplantation. Teratoma formation was observed uniformly within the left hind limbs injected with undifferentiated hES cells (FIG. 8A), but not in the right hind limbs injected with differentiated hESC-ECs. Immunostaining for macrophages (Mac-3) reveals that in the right hind limbs injected with hESC-ECs, most of the iron particles were deposited between muscle bundles and taken up by macrophages, thus accounting for the persistent MR signals seen at 4 weeks (FIG. 6A). Immunofluorescence staining showed similar macrophage deposition pattern and GFP$^+$hESC-ECs were seldom found but few integrated into host microvasculatures (FIGS. 6B and 8B). In the left hind limbs injected with undifferentiated hES cells, macrophage infiltration was distributed between muscle fibers. As expected, the teratoma formation stained GFP$^+$uniformly throughout (FIGS. 6C & 6D). The unique morphology of hES cells, which are round and small with relatively large nuclei, make them easily identifiable from the surrounding muscle.

Discussion

This example identified suitable molecular markers for serial monitoring of hES cell survival following transplantation and compared to the in vivo behavior of differentiated versus undifferentiated hES cells. Here for the first time we have compared the use of two popular cell markers, Fluc reporter gene and SPIO MR contrast agent, for labeling hES cells and their derived endothelial cells ex vivo. Under proper differentiation conditions, hES cells can be differentiated into functional endothelial cells, which express high levels of CD31 and VE-cadherin and can form tube-like structures on Matrigel assay and uptake Dil-ac-LDL. After double labeling, the fate of transplanted hES cells and hESC-ECs can be monitored by both imaging techniques. For bioluminescence imaging, a time-dependent decrease of cell signal activity was observed in the hESC-EC group, indicating significant acute donor cell loss. By contrast, engraftment of undifferentiated hES cells was followed by dramatic increases in bioluminescence signals from week 2 to week 4, which were confirmed as teratoma formation by postmortem analysis. For MR imaging, persistent and stable signals (both GRE and OR) were seen within both hind limbs injected with undifferentiated hES cells and differentiated hESC-ECs. The negative contrast GRE sequence of MR revealed higher anatomic resolution of the teratoma formation, and the positive contrast OR sequence readily showed the cell location after injection. However, overall MR imaging was unable to distinguish cell viability from cell proliferation as its signals remained relatively constant over the 4 week time span.

MRI has been used for tracking mouse ES cells (Magn Reson Med, 2004. 52(5): p. 1214-9) and mesenchymal stem cells (Stem Cells, 2006. 24(8): p. 1968-75, Circulation, 2003. 107(18): p. 2290-3, and Proc Natl Acad Sci USA, 2007. 104(24): p. 10211-6) in the heart and brain. However, in this study, MR imaging demonstrated stable signals in both hind limbs implanted with undifferentiated hES cells and undifferentiated hESC-ECs over 4 weeks. Thus, MR imaging was unable to specifically distinguish viable from non-viable cells or proliferating from non-proliferating cell populations. This is not surprising because, as the cells proliferate, the constant number of SPIO nanoparticles is merely divided among the daughter cells (Magn Reson Med, 2007. 57(6): p. 1173-9 and Curr Cardiol Rep, 2007. 9(1): p. 45-50). Moreover, the iron from cells undergoing apoptosis or cell lyses can be internalized by resident macrophages or remain in the local tissue. Altogether, these findings suggest that MR imaging, at least in the way utilized in this study, cannot distinguish iron-labeled cells from free iron released upon cell death, making iron labeling a less suitable marker for tracking long-term cell survival. Finally, the divergent pattern of survival (hESC-ECs vs. hES cells) seen in our reporter gene data are also consistent with previous studies showing poor donor cell survival after adult stem cell transplantation and uncontrolled teratoma formation after introduction of undifferentiated ES cells (Circulation, 2007. 116(11): p. I46-54, Circulation, 2006. 113(7): p. 1005-14, Cloning Stem Cells, 2007. 9(1): p. 107-17, and J Mol Cell Cardiol, 2002. 34(3): p. 251-3).

For bioluminescence imaging, several studies have found a close relationship between cell numbers and imaging signals (Circulation, 2007. 116(11): p. I46-54, Circulation, 2006. 113(7): p. 1005-14, Cloning Stem Cells, 2007. 9(1): p. 107-17, and J Nucl Cardiol, 2006. 13(4): p. 554-69). In this study, we were able to determine the kinetics of hES cell and hESC-EC survival over time. By imaging the same individual animal, we avoided the sampling biases and errors that bedevil conventional studies in which groups of animals have to be sacrificed at different time points for histology purpose (J Nucl Cardiol, 2006. 13(4): p. 554-69). Nevertheless, at present bioluminescence imaging still lacks adequate tomographic resolution (FIG. 5) due to attenuation of photons within tissues. To solve this problem, a combined multimodality approach (e.g., bioluminescence imaging with MR or PET) may be designed in the future as a more suitable approach to monitor the spatial and temporal kinetics of transplanted hES donor cells in animal models in vivo.

Human ES cells are remarkable for their unlimited self-renewal and pluripotency capacity, making them highly desirable candidates for cell replacement therapy (Science, 1998. 282(5391): p. 1145-7). One major risk involving the use of hES cells, however, is the possibility of cell misbehavior following transplantation. This potentially serious complication may occur if any of the transplanted undifferentiated ES cells take on teratoma formation (Circulation, 2007. 116(11): p. I46-54 and Circulation, 2006. 113(7): p. 1005-14). In our study, the survival kinetics of undifferentiated hES cells was different compared to pre-differentiated hESC-ECs, with acute donor cell loss from day 2 to day 14 followed by a strong rebound of cell survival and proliferation from week 2 to week 4 due to subsequent teratoma formation. Thus, the ability to visualize cellular proliferation and differentiation in vivo in both pre-differentiated and undifferentiated populations would be of great benefit in monitoring cellular behavior. On the other hand, endothelial cells are promising key factors for the repair of ischemic tissues and formation of new blood vessels (Blood, 2007. 110(3): p. 806-14, J Mol Cell Cardiol, 2006. 40(1): p. 1-8, and Nat Biotechnol, 2005. 23(7): p. 879-84). Several studies have explored the endothelial potential of hES cells, mainly by demonstrating the spontaneous differentiation of EBs to vascular-like structures and isolating hESC-ECs (Proc Natl Acad Sci USA, 2002. 99(7): p. 4391-6, Stem Cells, 2007. 25(2): p. 392-401, and Nat Biotechnol, 2007. 25(3): p. 317-8). In this study, hESC-ECs isolated from hEBs after 12 days of differentiation displayed characteristics similar to vascular endothelium and expressed typical EC markers similar to those expressed in HUVECs such as VE-cadherin, CD31 and Dil-ac-LDL uptake. However, bioluminescence imaging data suggest that by week 4, <1.5% of the transplanted hESC-ECs are still alive. This observation conforms with other studies showing poor donor cell survival using serial histology, TUNEL apoptosis assay, or Taqman Sty PCR techniques (J Mol Cell Cardiol, 2002. 34(3): p. 251-3). Thus, the application of bioengineering methods or pro-survival cocktails (Nat Biotechnol, 2007. 25(9): p. 1015-1024), rather than direct stem cell injection, may prove to be a more viable approach for achieving long-term engraftment in the future (Nat Biotechnol, 2005. 23(7): p. 879-84).

In conclusion, though pluripotent hES cells represent a potentially unlimited source of cells for regeneration medicine, teratoma formation observed in this study and other reports (Circulation, 2007. 116(11): p. I46-54 and Circulation, 2006. 113(7): p. 1005-14) recommends that extreme caution be exercised. Careful and precise protocols for acquiring differentiated cells are needed. To confirm the fate of hES cells in vivo, it is crucial to continue the development and further refinement of noninvasive imaging techniques. To that end, we compared the effects of labeling hES cells with reporter gene and iron particles. We showed that MR signals were persistent over a span of 4 weeks regardless of imaging undifferentiated hES cells (leads to teratoma formation) or differentiated hESC-ECs (leads to acute donor cell death). These data lead us to believe that reporter gene imaging is a better technique for monitoring long-term cell viability, death, and proliferation, while MR imaging is a better technique for high-resolution detection of cell location post transplantation.

RT-PCR Analysis.

For RT-PCR analysis, total RNA was isolated using RNeasy (Qiagen, Waltham, Mass.) from undifferentiated hES cells at day 0, differentiated hEBs at day 12, hESC-derived endothelial cells (after CD31 sorting), and human umbilical endothelial cells (HUVEC) as positive control. First-strand cDNAs were generated using M-MLV Reverse Transcriptase (Invitrogen, Carlsbad, Calif.). For the PCR reaction, first-strand cDNAs were amplified at a final volume of 50 μL with 1U Taq DNA polymerase (Invitrogen). In addition, all cDNA samples were adjusted to yield equal amplification of glyceraldehyde-3-phosphate dehydrogenase (GAPDH) as an internal standard. Primer sequences for these endothelial specific genes (CD31, VE-cadherin, KDR, Oct-4, GAPDH) are listed in Table 1, Example 1. Unless stated otherwise, all experiments were performed in triplicates.

TABLE 1

| Example 1 | | |
|---|---|---|
| Name | Sequences, SEQ ID NOs: 23-32 | |
| CD31 F | 5'-GAAGTTGGCTGGAGGTGCTC-3' | (23) |
| CD31 R | 5'-GCTGTTGGTGGAAGGAGTGC-3' | (24) |
| VE-cadherin F | 5'-ATCCCATTGTCTGAGATGACC-3' | (25) |

TABLE 1-continued

Example 1

| Name | Sequences, SEQ ID NOs: 23-32 |
|---|---|
| VE-cadherin R | 5'-GAATCCATTGTGCAAGTCCAC-3' (26) |
| KDR F | 5'-ACAAAGTCGGGAGAGGAG-3' (27) |
| KDR R | 5'-ATGACGATGGACAAGTAGCC-3' (28) |
| Oct-4 F | 5'-CTCACTCGGTTCTCGATACTGGTT-3' (29) |
| Oct-4 R | 5'-GGAAGGTATTCAGCCAAACGACCA-3' (30) |
| GAPDH F | 5'-ACCCCTTCATTGACCTCAA-3' (31) |
| GAPDH R | 5'-GCATGGACTGTGGTCATGAGT-3' (32) |

Example 2

Introduction

Myocardial infarction is a major cause of morbidity and mortality worldwide. The limited ability of the surviving cardiac cells to proliferate following an ischemic attack renders the damaged heart susceptible to unfavorable remodeling processes and heart failure. Currently, pharmaceutical and implantable device management of heart failure seek only to preserve existing viable myocardium after an ischemic attack, and thus merely slows the progression of cardiac dysfunction. Ultimately, heart transplantation is the only viable treatment option for end-stage heart failure patients. To "regenerate" the heart and not only preserve cardiac function but also recover lost or diseased muscle, stem cell therapy has emerged as a promising therapy for heart disease because it can provide a virtually unlimited source of cardiomyocytes, endothelial cells, and other differentiated cell types. The hope is to use these cells to replace diseased myocardium that would otherwise progress to outright failure and regenerate the heart to its former, healthy self.

Recently, human embryonic stem cells (hESCs) have generated much interest because of their capacity for self-renewal and pluripotency. In practical terms, hESCs can be cultured indefinitely ex vivo, and can differentiate into virtually any cell type in the adult body. hESCs are thus an attractive source for the derivation of large numbers of cells to be used in various tissue repair and cell replacement therapies. However, upon transplantation into living organisms, undifferentiated hESCs can spontaneously differentiate into rapidly proliferating teratomas, which are disordered amalgams of all three germs layers. Nevertheless, under the appropriate conditions, ex vivo hESCs can be directed to differentiate into beating cardiomyocytes via an embryoid body (EB) intermediate. Subsequently, the cardiomyocyte sub-population is enriched several-fold using discontinuous density gradient separation. Therefore, coaxing hESCs into cardiomyocytes for therapeutic applications is an innovative and feasible strategy that can minimize the risk of cellular misbehavior and teratoma formation.

In order to define at a molecular level the changes occurring at each stage of hESC differentiation into cardiomyocytes, we performed transcriptional profiling of the cells using whole human genome microarrays. This allowed us to examine the activation of specific genes as well as broader developmental processes during the progression from hESC to fetal cardiomyocyte, and to identify novel genes that are potentially important in mediating differentiation and development as well as potential novel markers of each stage. In the future, such genes may prove vital in efforts to more closely direct and assess differentiation of potential therapeutic pre-cardiomyocytes or cardiomyocytes in the repair of injured cardiac tissues. To monitor cell survival after transplantation, we then employ molecular imaging techniques that allow repetitive, noninvasive assessment of transplanted ES cell engraftment, viability, and proliferation in small animal models. Using these genomic and imaging tools, we investigate the molecular networks governing our differentiating cardiomyocytes, with an eye toward transplantation and assessment of cell survival and proliferation in vivo in a myocardial ischemia reperfusion model.

As mentioned above, human embryonic stem cells (hESCs) can serve as a potentially limitless source of cells that may enable regeneration of diseased tissue and organs. In this example we investigate the use of human embryonic stem cell-derived cardiomyocytes (hESC-CMs) in promoting recovery from cardiac ischemia reperfusion injury in a mouse model. Using microarrays, we have described the hESC-CM transcriptome within the spectrum of changes that occur between undifferentiated hESCs and fetal heart cells. The hESC-CMs expressed cardiomyocyte genes at levels similar to those found in 20-week fetal heart cells, making this population a good source of potential replacement cells in vivo. Echocardiographic studies showed significant improvement in heart function by 8 weeks after transplantation. Finally, we demonstrate long-term engraftment of hESC-CMs by using molecular imaging to track cellular localization, survival, and proliferation in vivo. Taken together, global gene expression profiling of hESC differentiation enables a systems-based analysis of the biological processes, networks, and genes that drive hESC fate decisions, and studies such as this will serve as the foundation for future clinical applications of stem cell therapies.

Results

Differentiation of hESCs to Cardiomyocytes.

We differentiated hESCs into cardiomyocytes as shown in FIG. 9a. To understand the time course of transcriptional changes occurring in these cells, we performed RT-PCR analysis of hESC-derived EBs as they differentiated over the course of 42 days into beating clusters (FIG. 9b). Expression of stem cell markers (Oct4, NANOG, Rex1) decreased substantially by day 28, while early stage cardiac transcriptional factors (Nkx2.5, MEF2c) appeared between days 14-28. As expected, cardiac specific markers (aMHC, ANF) appeared by day 14 and persisted through terminal differentiation into beating EBs. Before enrichment, only 2-5% of the cells within beating EBs expressed cardiac marker troponin-T as determined by FACS analysis. However, by utilizing Percoll density gradient separation, we were able to achieve cardiomyocyte-enriched populations ranging from 40-45%, a tenfold increase (FIG. 9c).

Major Changes in Gene Expression Between Stages Highlight Developmental Progression.

cRNA derived from four independent biological replicates at the three stages of differentiation, and from cells isolated from four individual human fetal hearts (19, 19, 20, and 21 weeks), was hybridized into individual whole human genome microarrays. Because fetal and adult hearts are composed of numerous cell types, including cardiomyocytes, endothelial cells, smooth muscle, fibroblasts, and many others, we isolated only primary cardiomyocytes for microarray analysis (see below). Doing so prevented non-cardiac cell types from contaminating our gene expression data. The resulting data were analyzed using the SAM algorithm (Proc Natl Acad Sci USA 98: 5116-5121) to identify genes which had changed expression significantly between stages. A summary of our major findings is shown in FIG. 10a. To obtain an overview of the transcriptional landscape, we looked at the data using principal components analysis (PCA), a dimensional reduction technique which identifies "principal components" or major trends in gene expression in the overall data (FIG. 10b). PCA demonstrates that each of the four replicates from each stage has very similar transcriptional profiles to one another, but distinctly different between stages, as expected. "Adjacent" stages show a progression of gene expression changes primarily along component one, a pattern of continuously decreasing gene expression across time, a pattern that we also identified as prominent in clustering analyses. A hierarchical clustering overview of the microarray experiments as a whole (FIG. 10c) likewise shows that the overall gene expressions among replicates of each stage are very similar, with progressive differences between more distantly separated stages.

hESCs Exhibit Unique Biologic Processes and Molecular Signature.

To better understand which cellular processes are important in the undifferentiated hESC stage, we performed statistical Gene Ontology (GO) biological process overrepresentation analysis and found that the most highly upregulated processes involved almost exclusively cell cycling and mitosis, as well as nucleic acid synthesis and metabolism.

This was not surprising given that hESCs' primary mission is to self renew. hESCs are also characterized by a network of genes important for pluripotency, including the unique homeobox transcription factor NANOG, which is the main downstream effector of this network. When we compared expression patterns in hESCs to EB cells, we found that there were 2,219 genes expressed much more highly in hESCs. The most dramatically elevated transcript in hESCs was NANOG, which is expressed at a level 250 times higher in hESCs than in EB (Cell 113: 643-655 and Cell Res 17: 42-49). POU5F1 (also known as Oct4), upstream of NANOG, is one of the critical regulators of pluripotency in the mammalian embryo, and our results show that it is expressed 106-160 fold more highly in the undifferentiated hESCs when compared to EB. SOX2, another key pluripotency gene, is expressed at 7.4 times the level in hESCs as in EB (Epigenetics 2: 37-42). Other known markers of ES cell status are also clearly present at high levels: TDGF1 and 3 (Cryptol and 3) (J Biol Chem 281: 33497-33504), expressed at ~100 fold higher levels in hESCs; the SRC family kinase LCK (40 fold higher), whose repression is associated with ES differentiation (Mol Pharmacol 68: 1320-1330); the ES cell markers such as developmental pluripotency-associated 4 (Dppa4) (15.7 fold) (J Biol Chem 282: 33034-33042) and homeobox expressed in ES cells 1 (Hesx1, 10 fold) (Genomics 18: 464-466). Further discussion can be found below.

Beating EB Cells Express Many Mesodermal and Cardiac Specific Gene Programs.

Differentiation to the beating EB stage is a very exciting and complex time in the life of the cell population. Our microarray results showed significant upregulation of master cardiac transcriptional regulators, as well as cardiac-specific structural and functional genes (FIG. 10a). Although this population of cells had clearly differentiated with a significant bias toward mesodermal and cardiac lineages, we could still see expression of genes characteristic of all three cell layers. Analysis of the biological processes in the beating EBs confirms these observations, with overexpression of embryonic and organ system developmental categories including nervous system development, kidney development, skeletal muscle development, and heart development.

hESC-CMs Downregulate Early Mesodermal Genes and Upregulate Cardiovascular and Structural Genes.

Differentiation of beating EBs to cardiomyocytes is marked by a transcriptional downregulation of 2,389 genes, including early mesodermal genes such as TWIST1, whose expression goes down substantially by 5 fold between the EB and CM stages, and MEOX2, with a 15 fold reduction. There are also considerable reductions in the expression of a number of homeobox genes (HOXB3, 4, IRX, HHEX, HESX1). At the same time, we observe substantial increases in expression of 1,012 genes, including cardiac structural genes such as tropomyosin 1 and 2 (TPM1, 2, ~3 fold upregulated) (Circ Res 91: 255-262), the heart and muscle gene LMO7 (3.5 fold) (Hum Mol Genet. 15: 3459-3472), and a number of actins and actin-regulatory genes such as beta actin (ACTNB, 3.4 fold), alpha actinin (5 fold), coronin (2.5 fold), transgelin (4.6 fold) (Dev Biol 187: 311-321), and caldesmon 1 (5 fold) (J Anat 203: 369-377). Cells in this population also exhibit evidence of maturation with the increased expression of extracellular structural components such as vascular collagens COL8A1 (18 fold) (Eur J Biochem 197: 615-622), COL4A3 and 4 (11 fold and 16 fold) (N Engl J Med 357: 2687-2695), COL6A3 (4 fold) (Ann Neurol 62: 390-405), and COL2A1 (2.4 fold) (Dev Biol 305: 120-132). Nevertheless, there is still transcriptional evidence for the presence of other mesodermal derivatives such as hematopoietic derivatives with the increased expression of IL1A (10-20 fold), toll like receptor 3 (TLR 3, 3 fold), skeletogenic genes such as RUNX1 (4 fold), sclerostosis (SOST, 8.7 fold), osteoprotogerin (TNFSFR11, 7 fold). Some neuroectodermal genes are also upregulated, including neuralized (NEURL, 2.7 fold) and neurofilament light peptide (NEFL, 2.3 fold).

Significant Changes in Energy Metabolism Between CM and Fetal Heart Cardiomyocytes.

One of our goals in this study is to compare our CM population to a cell population that would likely be optimal for cell transplantation into the damaged heart. An optimal cell type would be committed to the cardiomyocyte lineage but would still retain the capacity to undergo mitosis and thereby regenerate damaged heart muscle. We therefore chose primary fetal heart (FH) cardiomyocytes as the gold standard for comparison since they retain some proliferative capacity while also maintaining a cardiac phenotype. In general, we found that expression of cardiac structural and force generating protein genes in the FH cells was not significantly higher than in the CM populations. This suggests that the CM population, while still somewhat heterogeneous, is composed of differentiated cardiomyocytes that are capable of contraction but have not yet faced the biomechanical stresses in vivo required for cardiac development. This is further corroborated when we looked at the GO processes that are more active in the FH cells and found a pattern suggesting increased metabolic activity but not structural protein biogenesis. Specifically, many of the increased processes in FH cells include the TCA cycle, cellular respiration, mitochondrial biogenesis, and lipid metabolism. These energy-related pathways are necessary for the mature cardiomyocyte to contract forcefully, and their expression timing may correlate with the necessity for active cardiac contraction in the fetus that continues up to and beyond birth, with an interesting shift to a lipid-based metabolism in the postnatal heart.

Electrophysiological Recordings of hESC-CMs.

Figure 11:
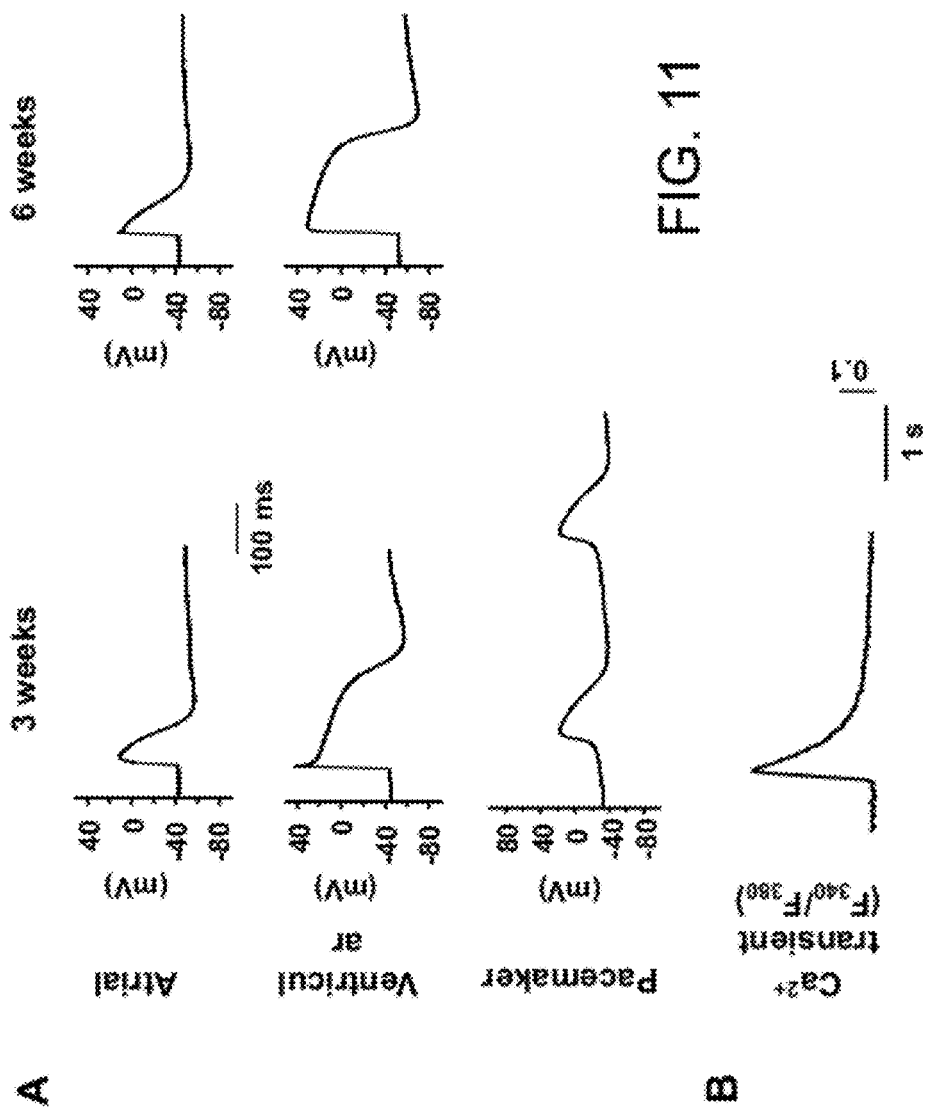

Previous groups have studied the electrophysiology of hESC-CMs and have reported significant heterogeneity within the population (Circulation 107: 2733-2740, Circulation research 93: 32-39, and Circulation research 91: 659-661). To understand the electrophysiological properties of our hESC-CMs, we took action potential (AP) recordings from single cells using whole-cell patch-clamps. hESC-CMs were categorized into pacemaker-, atrial-, or ventricular-like phenotypes, based on such common electrophysiological characteristics as the AP amplitude, upstroke velocity, as well as the resting membrane potential. $Ca^{2+}$ transients that are crucial for excitation-contraction coupling were also recorded. At 3 and 6 weeks post-differentiation, ventricular-, atrial-, and pacemaker-like derivatives were readily observed (FIG. 11). Noticeably, ventricular-like hESC-CMs were most similar to fetal rather than adult ventricular cells as indicated by their depolarized resting membrane potential. Nonetheless, the AP profiles did not appear to change significantly over the time course of our experiments. Ideally, we would like to isolate only the ventricular-like hESC-CMs and use those cells for transplantation studies in ischemic left ventricles. Given the lack of specific cellular markers for identifying ventricular/atrial/pacemaker CM types, we were limited to using the whole population for transplantation studies.

hESC-CM Transplantation Improves Left Ventricular Function in a Mouse Myocardial Infarction Model.

After analyzing the molecular changes underlying hESC differentiation as well as their electrophysiological phenotypes, we then assessed the effect of hESC-CM transplantation on myocardial function. Using SCID-Beige mice, one million hESC-CMs were transplanted by direct injection into ischemic regions of the left ventricle after 30 minutes of temporary left anterior descending (LAD) coronary artery occlusion. To characterize potential functional improvements, we performed echocardiography on post-transplant animals that received either hESC-CMs (n=21) or PBS (n=12) as a control. Left ventricular fractional shortening (LVFS), which is a common method for quantifying cardiac contractility or ability of the ventricle to eject blood, was used as the metric for comparison of the two groups' outcomes. Expressed as a percentage of the ventricle's volume, diminished LVFS is associated with a failing heart. Animals receiving hESC-CMs showed a 12.5±4.2% improvement over controls at 8 weeks as measured by LVFS (P=0.03, FIG. 12). This was primarily due to improvements in the left ventricular end systolic dimension (LVESD), as the left ventricular end diastolic dimension (LVEDD) remained constant between the two groups.

We also noted evidence of increased angiogenesis in the ischemic regions of explanted mouse hearts (FIG. 14), and histology confirmed that the fibrotic scar was attenuated at 8 weeks post-transplantation in animals that underwent hESC-CM transplantation (FIGS. 12c and 15). Using NIH Image J software, the quantified infarct sizes (percent of LV) in hESC-CM-treated mice and PBS controls were 21%±3% (n=6) and 25%±2% (n=6) (P=0.041), respectively. However, improved LVFS was not sustained at later time point (16 weeks) (data not shown). Although the reasons for this are unclear, we suspect that acute donor cell death within the first month is responsible for attenuation of the positive remodeling processes initiated by hESC-CM paracrine effectors. To confirm this hypothesis, we decided to use molecular imaging to track hESC-CM fate noninvasively in living mice.

Lentiviral Transduction with Reporter Genes does not Alter hESC Characteristics.

Figure 16:
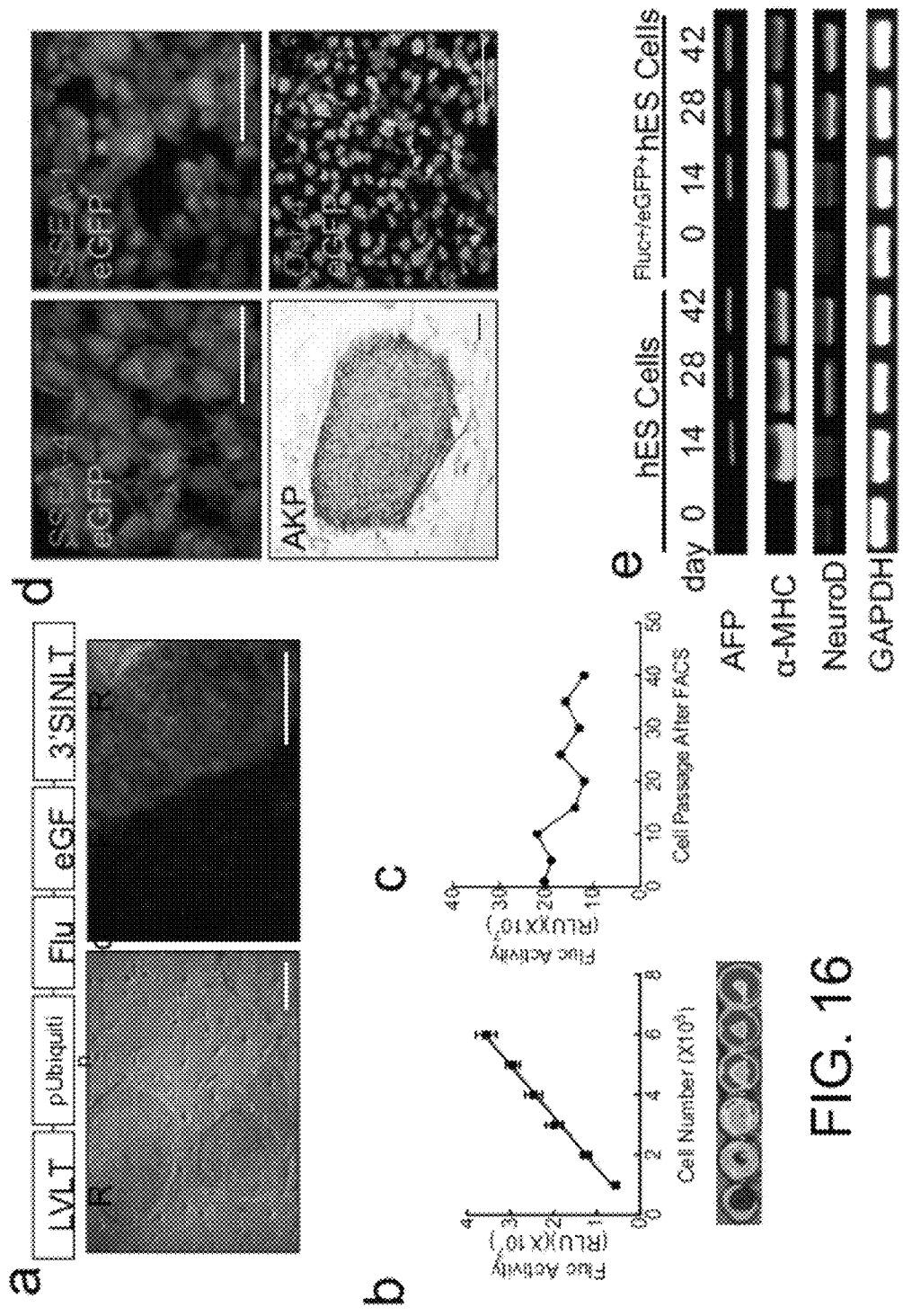

In order to follow the fate of transplanted hESC-CMs noninvasively and longitudinally, we next employed reporter gene imaging. Undifferentiated hESCs were stably transduced with a firefly luciferase (Fluc) and enhanced green fluorescent protein (eGFP) double fusion reporter gene driven by a constitutive human ubiquitin promoter (pUB) using a lentiviral vector. The double fusion reporter gene can be stably expressed and does not alter hESC and hESC-CM characteristics (FIGS. 13a, 13b, and 16).

Reporter Gene Imaging for Tracking Transplanted hESC-CM Fate In Vivo.

Figure 18:
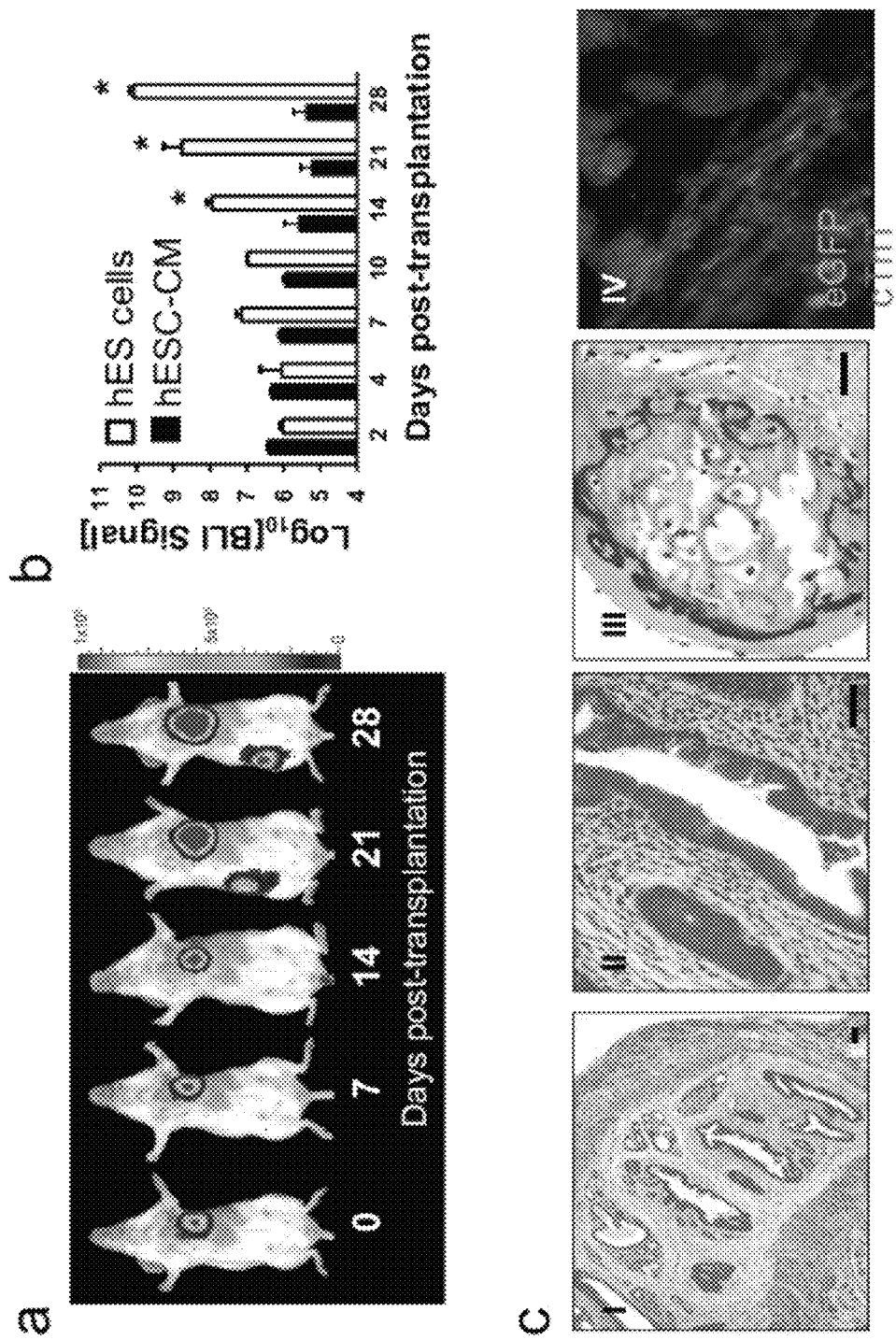

To understand the fate of transplanted cells in vivo, one million $^{Fluc+/eGFP+}$hESC-CMs were injected into peri-infarct regions of the myocardium. $^{Fluc+/eGFP+}$hESC-CMs engrafted successfully, emitting a robust and stable bioluminescent signal for 8 weeks following transplantation (FIG. 13c). Quantitative imaging analysis revealed that signal intensity declined logarithmically during the first 3 weeks post-injection and remained constant thereafter (FIG. 13d). This initial drop in bioluminescence correlates with the death of roughly 90% of the administered cell population. Importantly, $^{Fluc+/eGFP+}$hESC-CMs remained localized to the heart throughout our studies. Imaging did not reveal any cellular misbehavior, and no histological evidence of teratoma formation was observed in any animal within this group (n=15) (FIGS. 13d, 13e and 17). In contrast, injection of one million undifferentiated $^{Fluc+/eGFP+}$hESCs into the heart led to both intra-cardiac and extra-cardiac teratoma formation in 7 out of 7 mice (FIG. 18). We also performed spike-in studies to mimic clinically relevant scenarios in which contaminating undifferentiated hESCs are injected along with hESC-CMs. Our results show teratoma formation with 100 k hESCs (+400 k hESC-CMs), but not with 1 k hESCs (+499k hESC-CMs) or 10 k hESCs (+490k hESC-CMs) (FIG. 19). Thus, these data suggest there is likely a threshold for the number of contaminating hESCs within an injected hESC-CM population that can lead to teratoma formation in the heart.

Histologic Evaluation of Transplanted hESC-CMs.

Importantly, our histologic studies revealed minimal integration of the $^{Fluc+/eGFP+}$hESC-CMs into infarcted areas of the left ventricle. Though small clusters of injected cells appeared to engraft and then persist for many weeks after transplantation (emitting measurable bioluminescent signal), they did not exhibit functional organization with the surrounding host myocardium. These findings confirm previous reports which have also found minimal organized integration of hESC-CMs with host myocardium (Nature 435: 944-947, Circulation research 102: 1008-1010, and Nature 453: 524-528). It is therefore difficult to explain the transient improvement in cardiac contractility at 8 weeks given the underwhelming evidence for robust integration of transplanted cells (FIGS. 13e and 17). Such findings have led us and others to hypothesize that paracrine factors may be involved by helping to increase angiogenesis or preventing apoptosis of ischemic host myocardial tissues (See, Gnecchi M et al, Nature Medicine 2005; 11:367-368, which is incorporated herein by reference).

Discussion

In this Example, we have described the hESC-CM transcriptome within the spectrum of changes that occur between undifferentiated hESCs and fetal heart cells, and used molecular imaging to follow their survival and engraftment in the heart. Global gene expression profiling of hESC differentiation thus enables a systems-based analysis of the biological processes, networks, and genes that drive hESC fate decisions. This systems biology approach has obvious benefits over traditional PCR-based methods, which measure only a limited number of transcripts and so cannot define the complex regulatory networks of genes and pathways important for hESC differentiation.

Previous studies have also analyzed the transcriptional profiles of hESC-CMs (Stem cells 26: 1831-1840). However, these studies focused on un-purified beating clusters of cells with significant non-cardiac and non-mesodermal cell contamination. Using purified hESC-CMs, our comprehensive, systems-based approach to transcriptional analyses supports the case that each of the stages of differentiation and selection results in a significant enrichment in cells of the cardiomyocyte lineage, expresses appropriate stage specific genes, and turns on appropriate biological processes corresponding to these stages. Given the robustness of our differentiation method, we believe the hESC-CM population would be an ideal source of replacement cells in the in vivo setting. We also demonstrate that hESC-CMs can successfully engraft in the ischemic heart for an extended duration that result in improved cardiac function, though only transiently. This latter finding may be partly attributed to the activation of paracrine signaling mechanisms by transplanted cells on host cells and themselves, which then attenuates after acute donor cell death. Lastly, we show that cardiac differentiation prior to transplantation can prevent teratoma formation, which remains a major safety concern for investigators exploring the therapeutic uses of hESCs.

In our microarray analysis, we observed high expression of pluripotency-related genes involved in the core hESC regulatory circuitry, including OCT4, SOX2, and NANOG, as well as CRYPTO 1 and 3, LCK, and HESX1. Differentiation into beating EBs was accompanied by mesodermal differentiation and dramatic activation of TWIST1, TBX5, and MEOX transcription, as well as the very clear induction of nearly all of the early cardiogenic genes, including FOXC1, ISL2, HAND1, GATA4, 5, and 6, FOXH1, and MEF2C. While it is clear that other developmental lineages are still present in the EB population, it is also clear from the high levels of cardiac gene expression that this population is significantly enriched for the cardiac lineage even at an early stage. The transcriptional analysis of the final differentiation and selection of the hESC-derived CMs indicates that this enrichment continues, with the CM population expressing differentiated cardiomyocyte genes at levels similar to our more advanced FH cells. Importantly, because of the cell type heterogeneity in the fetal heart, we specifically isolated cardiomyocytes from the fetal left ventricles for microarray analysis.

We now briefly discuss the four major trends in the microarray data seen in the K-means clustering analysis (FIG. 10d), which will allow us to explore the major themes within an enormous amount of expression data. Cluster 1 is composed of 1775 genes whose expression increases at each stage from hESC to EB to hESC-CM to FH (FIG. 10d). Overrepresentation analysis of this cluster of genes shows that the GO processes to which these genes contribute include many basic differentiated cell functions such as the establishment of cellular transport and secretory processes, regulation of cell localization, response to cellular stresses and hypoxia, cytoskeletal biogenesis, control of apoptosis, and interestingly, cardioblast cell fate commitment. This cluster of genes has a substantial overlap with the component genes of principal component 1 from the PCA analysis (FIG. 10b), demonstrating how two analytic approaches can result in similar significant findings.

The converse expression pattern is seen in the 2,453 genes composing cluster 2, which are sequentially downregulated across the groups from hESC to EB to hESC-CM to FH. The processes overrepresented in this cluster primarily involve nucleic acid synthesis, DNA replication and chromatin maintenance, cell cycle, and transcription in general. This theme is consistent with patterns seen in normal embryonic development in both *drosophila* and mouse (Dev Biol 288: 595-611), and reflects the fact that earlier undifferentiated cells are undergoing rapid replication and production of broad ranges of transcripts, while cell cycling slows dramatically later in development as cells begin to express a more limited number of genes that are appropriate for the differentiated state.

Cluster 3 is comprised of 1,009 genes whose expression increases at each stage from hESC to EB to hESC-CM, but which are expressed significantly less in the FH cells. The overrepresented processes in this cluster correspond to non-cardiac cell differentiation pathways, particularly neuroectodermal differentiation, that compose a portion of the hESC-CM population which we have differentiated and purified it from hESC precursors, but are not present in the harvested fetal heart cells. The final interesting cluster of genes is cluster 4, representing genes which generally increase in expression across all stages from hESC to EB to hESC-CM to FH, but which are expressed at considerably higher levels in the two older FH samples, 3 and 4 (at 20 and 21 weeks, respectively), than in FH1 and 2 (19 weeks each). The processes overrepresented in this gene group are heavily weighted toward cardiac muscle contraction, muscle development, heart development and other cardiac specific processes, and the genes contributing to these processes include dozens of cardiac structural proteins such as cardiac myosin heavy and light chains, cardiomyocyte potassium channels such as KCNE1 (J Cell Physiol 212: 358-367), KCNQ1 (Hum Genet. 120: 912) and KCNH2 (Circulation 116: 1128-1136), cardiomyocyte troponins including T2 and C1, as well as cardiac phospholamban and cardiac actin 1. Thus, the hESC-CM population's expression of terminal cardiac differentiation markers at a level intermediate between younger and older FH cardiomyocytes suggests that this population is sufficiently advanced developmentally to serve as a potential replacement population for cells lost to ischemia.

With these very interesting and detailed gene expression studies, we began focusing on cellular transplantation to the ischemic heart. We observed significant improvements in echocardiographic metrics when comparing treated and control animals. Histologic analysis revealed reduced scar formation, but there was underwhelming evidence of functional myocardium regeneration, confirming previous reports (Circulation research 102: 1008-1010, Nature 453: 524-528, and Heart 93: 1278-1284). To explain this disparity, the improvement in cardiac function may be due to paracrine factors, as suggested by Dzau and colleagues (Nature medicine 11: 367-368, The FASEB journal 20: 661-669, and Proceedings of the National Academy of Sciences of the United States of America 104: 1643-1648). Our own studies indicate some increased cytokine signaling in hypoxic hESC-CMs (FIG. 20). However, if paracrine signaling is the primary mechanism of improvement, then long-term generation of these factors from sufficient numbers of transplanted hESC-CMs may be required for a sustained improvement in cardiac function. Until now no studies have analyzed the overall survival and growth kinetics of transplanted hESC-CMs in ischemic myocardium.

To address this lack of understanding, we employed molecular imaging technology for understanding the fate of cells following transplantation (Nuclear medicine and biology 26: 481-490). Longitudinal imaging of transplanted hESC-CMs exposes the limitations of cardiac stem cell therapy, as ~90% of cells die within the first three weeks of delivery. Though we did not address the specific mechanism of death in this study, poor cell survival is likely due to widespread apoptosis and anoikis of cells injected into an inhospitable environment. Improving cell survival by subjecting hESC-CMs to the appropriate anti-apoptotic and pro-survival cues may alleviate some of the survival issues, and efforts to this end have been reported since completion of this work (Nat Biotech 25: 1015-1024). Other methods that take advantage of tissue engineering technologies in which biopolymers and synthetic tissue constructs are used to organize and support transplanted cells may offer another means for increasing cell survival (Circulation research 97: 1220-1231). Delivery techniques other than intra-myocardial injection, such as intracoronary or retrograde coronary venous, may also improve cell survival (Circulation 112: 1150-156). Another confounding factor is the host immune response, which we did not address in this study (as SCID mice were used). With a functioning host immune system, we would expect to see a further reduction in cell survival. Nevertheless, it is important to note that even in our SCID mice, transplantation of $^{Fluc/+eGFP+}$hESC-CMs did not form teratomas in the post-transplantation period. The lack of teratoma formation emphasizes the robustness of our hESC-CM purification protocol in removing undifferentiated cell contaminants.

In summary, hESC-CMs hold potential promise for treatment of cardiovascular disease. The molecular processes that control stem cell pluripotency, differentiation, and proliferation are complex, justifying the need for a broad investigation that integrates systems biological tools for transcriptome analysis with molecular imaging tools for confirmation of survival, engraftment and functional benefit in the in vivo setting. We found that the enriched hESC-CMs expresses cardiomyocyte genes at levels similar to 20-week fetal heart cells, making this population a good source of potential replacement cells in the in vivo setting. Beyond a characterization of the overall transcriptional characteristics of our differentiated cells, we have also identified a large number of potentially important new genes that are expressed at high levels at distinct stages and that may play roles in the cardiogenic developmental program. These genes may also act as specific markers of cell differentiation in addition to being inducers of cardiogenic differentiation, thus opening new avenues of investigation into the basic biology of cardiovascular development. However, understanding the molecular networks of differentiation is not enough to predict the fate of differentiated cells once transplanted in a living host. To address this lack of knowledge, we have shown molecular imaging to be a powerful method for assessing cellular localization, engraftment, survival, and proliferation in vivo. Taken together, gene expression and molecular imaging studies such as this will serve as a crucial foundation for future clinical applications of stem cell therapies.

Methods and Materials

Culture of undifferentiated hESCs. hESCs (H9 line) from passage 35-40 were initially maintained on top of murine embryonic fibroblasts (MEF) feeder layers, seeded onto 0.1% gelatin coated plastic dishes, and inactivated by 10 μg/ml of mitomycin C. hESCs were maintained in ES medium containing 80% Dulbecco's modified Eagle's medium/F12, 1 mM L-glutamine, 0.1 mM β-mercaptoethanol, 0.1 mN non-essential amino acids, 20% Knockout Serum Replacement, and 8 ng/ml hbFGF. The ES cell culture medium was changed daily and hESCs were passaged every 4-5 days.

Lentiviral Production and Generation of Stable hESC Lines.

SIN lentivirus was prepared by transient transfection of 293T cells. hESCs were stably transduced with LV-pUB-Fluc-eGFP at a multiplicity of infection (MOI) of 10. The infectivity was determined by eGFP expression as analyzed on FACScan (BD Bioscience). The eGFP positive cell populations were isolated by fluorescence activated cell sorting (FACS) Vantage SE cell sorter (Becton Dickinson) followed by plating on the feeder layer cells for long-term culturing. Flow cytometry data were analyzed with FlowJo (Treestar, San Carlos, Calif.) analysis software.

Embryoid Body Formation and Cardiac Specific Differentiation.

hESC colonies were dispersed into cell aggregates containing approximately 500 to 1,000 cells using 1 mg/mL collagenase IV. The cell aggregates were then suspension-cultured in ultra-low attachment cell culture dishes with hESC differentiated medium (without basic fibroblast growth factor) for 9 days with the media changed every two days. To promote cardiac differentiation, 9-day old EBs were transferred to 10 cm dishes coated with 0.1% gelatin and grown in media consisting of DMEM supplemented with 20% FBS and 2 mmol/L L-glutamine. During differentiation, the media was changed every two days. Spontaneously contracting cells appeared as clusters in outgrowths from the EBs at day 10 after differentiation. These beating EBs were maintained in long-term cultures for up to 103 days.

Isolation of hESC-CMs.

Differentiated cultures containing beating cardiomyocytes were washed with phosphate buffered saline (PBS) and incubated with 0.56 units/ml Liberase Blendzyme IV (Roche, Indianapolis, Ind.) at 37° C. for 25 min. After dissociation, the cell suspension was separated by Percoll density (58.5% and 40.5%) centrifugation at 1500 g for 30 minutes at room temperature.

Cell Samples Collection and RNA Preparation.

The undifferentiated hESC, day 10 beating whole embryoid bodies (Beating EBs), day 14 Percoll-enriched cardiomyocytes derived from human hESCs (hESC-CM) and human fetus heart-derived left ventricular cardiomyocytes (FH-CM) at 19, 19, 20, and 21 weeks were collected at chosen time points. Four samples from each group (for a total of 16 unique samples) were harvested for RNA isolation. Total RNA was isolated as described previously in Trizol (Invitrogen) followed by purification over a Qiagen RNeasy column (Qiagen).

Microarray Hybridization and Data Acquisition.

A full description of RNA quality control, and labeling reaction and hybridization is included in Supplemental Information. Using Agilent Low RNA Input Fluorescent Linear Amplification Kits, cDNA was reverse transcribed from each of 16 RNA samples representing four biological quadruplicates, as well as the pooled reference control, and cRNA was then transcribed and fluorescently labeled with Cy5/Cy3. cRNA was purified using an RNeasy kit (Qiagen, Valencia, Calif., USA). 825 ng of Cy3- and Cy5-labeled and amplified cRNA was hybridized to Agilent 4×44K whole human genome microarrays (G4112F) and processed according to the manufacturer's instructions. The array was scanned using Agilent G2505B DNA microarray scanner. The image files were extracted using Agilent Feature Extraction software version 9.5.1 applying LOWESS background subtraction and dye-normalization.

Microarray Data Analysis.

The data were analyzed using the SAM algorithm [7] with multiple testing correction to identify genes which had statistically significantly changed expression between each stage, and K-means clustering to identify clusters of genes having unique temporal expression profiles. For hierarchical clustering, we used positive correlation for distance determination and required complete linkage. Gene Ontology over-representation analysis was performed using Fisher's Exact test and High Throughput GOMiner software.

Electrophysiology Analysis.

Action potential (AP) recordings from single cells were done using the whole-cell patch-clamp technique. Patch pipettes were prepared from 1.5 mm thin-walled borosilicate glass tubes using a Sutter Micropipette Puller (P-97) and typically had resistances of 4-6 MO when filled with an internal solution containing (mM): 110 $K^+$ aspartate, 20 KCl, 1 $MgCl_2$, 0.1 Na-GTP, 5 Mg-ATP, 5 $Na_2$-phosphocreatine, 1 EGTA, 10 HEPES, pH adjusted to 7.3 with KOH. The external Tyrode's bath solution consisted of (mM): 140 NaCl, 5 KCl, 1 $CaCl_2$, 1 $MgCl_2$, 10 glucose, 10 HEPES, pH adjusted to 7.4 with NaOH. Upon seal formation and following patch break, APs were recorded using the current-clamp mode. Voltage recordings were filtered at 10 KHz. Axopatch 200B, Digitize 1322 and pClamp8 (Axon Burlingame, Calif., USA) were used for data amplification and acquisition. hESC-CMs were categorized into pacemaker-, atrial- or ventricular-like phenotypes, based on such common electrophysiological characteristics as the AP amplitude (mV), upstroke velocity (mV/ms), APD50 and APD90 (ms), as well as the resting membrane potential (RMP, mV). We primarily used the AP profiles as signatures of different CM types. Nodal-like AP phenotype was defined as those that exhibited: a) prominent phase-4 depolarization, b) slow upstroke (dV/dt), c) small action potential amplitude (APA), d) relatively depolarized MDP, and e) spontaneous firing. By contrast, like others, we defined the ventricular-like phenotype as those that displayed: i) a significant plateau phase, ii) longer APD (vs. those of atrial and nodal), iii) rapid upstroke, and iv) a flat phase 4. Atrial APs were those that displayed a triangular shape. Of note, in comparison to neonatal and adult human ventricular and atrial CMs, the AP parameters of hESC-CMs exhibit MDP and upstroke velocities that are positive (~−40 vs. ~−80 mV) and slow (~10V/s vs. 100-300V/s), respectively. (See Supplemental Information for further Electrophysiology Methods).

Measurements of Cytosolic $Ca^{2+}$.

A spectrofluorometric method with Fura-2/AM as the $Ca^{2+}$ indicator was used for measuring $[Ca^{2+}]_i$. FLV- or hESC-CMs were incubated with 5 μM Fura-2/AM and 0.2% pluronic F-127 for 30 min at 37° C. Fluorescent signals obtained upon excitation at 340 nm (F340) and 380 nm (F380) were recorded from cells perfused with Tyrode solution containing (mM): 140 NaCl, 5.0 KCl, 1.0 $CaCl_2$, 1.0 $MaCl_2$, 10.0 glucose and 10 HEPES (pH 7.4) unless otherwise indicated. Data were analyzed using the Ionwizard software (Version 5, Ion-Optix) to generate the Ca transient parameters reported in this study. The F340/F380 ratio was used to represent cytosolic $[Ca^{2+}]$. To induce cytoplasmic $Ca^{2+}$ transients, hESC-CMs were electrically stimulated. $Ca^{2+}$ transients were recorded and analyzed after a series of depolarizations that enabled each transient to fully decay so as to establish a steady-state SR content.

Effect of Reporter Genes on hESC Proliferation and Differentiation.

Reverse transcription polymerase chain reaction (RT-PCR) was used to compare the expression of embryonic markers (Oct4, NANOG, Rex1), cardiac transcription factors (Nkx2.5, MEF2C), ventricular specific proteins (αMHC, ANF), and Fluc reporter gene between control non-transduced hES and $^{Fluc+/eGFP+}$hESCs. RNA was isolated from hES and $^{Fluc+/eGFP+}$hESCs using Trizol reagent. Two pg of total RNA extracted from EBs was reverse-transcribed using ThermoScript RT-PCR system (Invitrogen, Carlsbad, Calif.). One μl of cDNA sample was PCR amplified with gene-specific primers (see Supplemental Information) using optimized PCR cycles to obtain amplified reactions in a linear range. PCR products were separated on 1% agarose gel by electrophoresis and quantified by using Labworks 4.6 Image Acquisition and analysis software (UVP Bio-imaging systems, Upland, Calif.).

Transplantation of hESC-CMs into Ischemic Myocardium.

A total of 50 adult female SCID Beige mice (Charles River Laboratories) weighing 18-20 gm were used. All procedures were performed in accordance with protocols approved by the Stanford Animal Research Committee guidelines. Following induction of anesthesia with isoflurane (3-4%), animals were orotracheally intubated and ventilated with a mixture of oxygen and 2-3% isoflurane with a volume-cycled rodent ventilator as described (Nature 428: 668-673). A lateral thoracotomy was performed followed by ligation of the mid left anterior descending (LAD) artery for 30 minutes. Myocardial infarction was confirmed by blanching and EKG changes. Subsequently, 3 groups received direct myocardial injection of: (1) $1\times10^{6}$ $^{Fluc+/eGFP+}$hESC-derived cardiomyocytes in 40 μl of PBS (n=16), (2) $1\times10^6$ non-transduced hESC-derived cardiomyocytes (n=6), and (3) 40 μl of PBS as control (n=12). Another set of 16 animals were used to evaluate the potential for teratoma formation following intramyocardial injection of undifferentiated $^{Fluc+/eGFP+}$hESCs. Animals were injected with $1\times10^6$ undifferentiated $^{Fluc+/eGFP+}$hESCs (n=7), $1\times10^5$ undifferentiated $^{Fluc+/eGFP+}$hESCs spiked with $4\times10^6$ non-transduced hESC-CMs (n=3), $1\times10^4$ undifferentiated $^{Fluc+/eGFP+}$hESCs spiked with $4.9\times10^5$ non-transduced hESC-CMs (n=3), and $1\times10^3$ undifferentiated $^{Fluc+/eGFP+}$hESCs spiked with $4.99\times10^5$ non-transduced hESC-CMs (n=3). Post-operative analgesia was provided by a one-time, subcutaneous injection of buprenorphine (0.1 mg/kg body weight). Animals were recovered in a warmed, humidified chamber.

Bioluminescence Imaging (BLI) of hESC and hESC-CM Transplantation.

Cardiac BLI was performed by an independent, blinded operator using the Xenogen In Vivo Imaging System. Mice were anesthetized with 2% isoflurane and D-Luciferin was administered intraperitoneally at a dose of 375 mg/kg body weight. At the time of imaging, animals were placed in a light-tight chamber, and photons emitted from luciferase expressing hESCs transplanted into the animals were collected with integration times of 1-10 min, depending on the intensity of the bioluminescence emission. Ventral images were obtained to better determine the origin of photon emission. The same mice were scanned repetitively over 12 months as per the study design. Bioluminescence was quantified in units of maximum photons per second per centimeter square per steridian (p/s/$cm^2$/sr).

Assessment of Left Ventricular Contractility.

Echocardiography was performed by an independent, blinded operator using the Siemens-Acuson Sequioa C512 system equipped with a multi-frequency (8-14 MHz) 15L8 transducer. Mice were assessed pre-operatively, and 2, 4, 8, and 16 weeks post-transplant. Animals received continuous inhaled isoflurane (1.5-2%) for the duration of the imaging session (10-15 minutes). Animals were imaged in the supine position resting on a specialized platform allowing for continual inhaled anesthesia while maintaining optimal exposure of the left chest. M-mode short axis views of the LV were obtained and archived. Analysis of the M-Mode images was performed using the Siemens built-in analysis software. Left ventricular end diastolic diameter (LVEDD) and end-systolic diameter (LVESD) were measured and used to calculate fractional shortening (FS) by the following formula: FS=[LVEDD-LVESD]/LVEDD.

Immunohistochemical Analysis.

To confirm their undifferentiated state, cultured hESCs were plated onto 8 chamber slides and fixed with acetone on ice for 20 minutes, then stained for immunofluorescence with the appropriate antibodies. Microscopy was performed using a ZEISS Axiovert microscropy (Sutter Instrument).

Tissue Fixation.

Hearts were excised two months after transplantation and prepared into 10-micron thick frozen sections. Immunofluorescent labeling was analyzed using a Zeiss LSM 510 Confocal Laser Scanning Microscope equipped with a Coherent Mira 900 tunable Ti:Sapphire laser for two-photon excitation (Zeiss, Minneapolis, Minn.).

Statistical Analysis.

Unless otherwise noted, non-microarray data are presented as mean±S.D. Data were compared using standard or repeated measures, using ANOVA where appropriate. Pairwise comparisons were performed using a two-tailed Student's t-test. For electrophysiology data, data are expressed as mean±SEM. One-way ANOVA followed by Newman-Keuls multiple comparison tests or paired t test was carried out to test for differences between the mean values within the same study. For all data, differences were considered significant for P-values<0.05.

Supplemental Information for Example 2

Microarray Analysis of Novel hESC Markers.

In addition to these known ES markers, however, we have also identified a significant number of novel genes with elevated expression in hESCs that may play important roles in the developmental or pluripotentiality. Of particular interest is FzdS, the receptor for Wnt5a, which is 15-19 fold more highly expressed in hESCs, suggesting some canonical Wnt signaling occurring in this population, although there also appears to be a significant upregulation of a number of Wnt ligands at the EB stage. PIM2, an anti-apoptotic kinase whose relatives PIM1 and PIM3 are involved in ESC self-renewal, is also expressed 20 fold higher in hESCs than in EB, suggesting that it too plays a role in self-renewal, a role it may reprise in several hematopoietic malignancies. Another gene that appears prominently in our experiments is phorbol-12-myristate-13-acetate-induced protein 1 (PMAIP1), whose RNA is 10 fold more highly expressed in hESCs. PMAIP1, a BH3-only member of the Bcl2 family, appears to be a mediator of p53 dependent apoptosis, and is highly expressed in adult T-cell leukemia cell lines.

Microarray Analysis of Embryoid Bodies.

Between the hESC and EB stages, we identified 4,407 genes that are significantly upregulated. Importantly, the most significantly upregulated gene is TWIST1, a bHLH family member which is one of the master regulators of mesodermal differentiation, and which is upregulated by 22 fold in the EB cells while MEOX1, a gene necessary for somitogenesis, is 4 fold upregulated. Almost as statistically significant, and much more highly upregulated at 46 fold, is Tbx2, a gene involved in regulating mesodermal genes and which is important later in regulating angiogenesis and cardiac development. Others include the closely related Tbx5 gene, which at 222 fold is one of the most highly upregulated genes in EB, and the cardiac regulator Tbx1 (22 fold). Other early regulators of cardiac and vascular differentiation are also highly upregulated, including the forkhead box gene Foxc1 (50 fold induction), the second heart field regulator Isl1 (35 fold induction), the master muscle regulator Mef2C (28 fold induction), and the cardiac morphogenetic gene Hand2 (6.4 fold induction) and FoxH1 (5.2 fold induction). GATA4, a highly dosage sensitive regulator of cardiac development, is upregulated at a comparatively modest but still substantial level (6.7 fold induction), and so are its relatives GATA5 (16 fold induction) and GATA6 (12 fold induction), as well as Irx5 (8 fold induction).

The elevated expression levels of these cardiac master transcriptional regulators are reflected in very significantly upregulated cardiac specific structural and functional genes, including the following: Myoz2 (Calsarcin1), a calcineurin binding Z-disc protein implicated in cardiomyopathy, which is the most highly upregulated gene at 250 fold; phospholamban (PLN), a major mediator of cardiomyocyte SERCA pump activity (upregulated 218 fold); cardiac muscle myosin alpha heavy chain 6 (MYH6, 100 fold); ventricular myosin light chain 3 (MYL3, 30 fold); cardiac troponin T 2 (TNNT2, 27 fold), atrial myosin light chain 4 (MYL4, 19 fold); cardiac myosin binding protein C (MYBPC3, 13 fold); cardiac myosin heavy chain (MYH7, 8.4 fold); cardiac myosin heavy chain 7B (MYH7B, 6.4 fold); myosin light chain 3 (MYL3, 6 fold); cardiac alpha actin 1 (ACTC1, 4.7 fold); and ATPA2 (SERCA2, 2.6 fold).

Clearly, this population of cells has differentiated with a significant bias toward mesodermal and cardiac lineages, but we do still see at this stage expression of genes characteristic of all three cell layers, endoderm, mesoderm and ectoderm. These include endodermal genes such as Foxa1 (HNF3A, 20 fold), liver genes such as complement factor I (CFI, 120-170 fold) and liver arginase (ARG1, 89 fold), skeletal muscle genes such as fast skeletal myosin light chain 2 (MYLPF, 25 fold) and skeletal myosin light chain 1 (MYL1, 7 fold), and neuroectodermal genes such as ectodermal-neural cortex (ENC1, 6 fold) and neural cell adhesion molecule (NCAM, 3 fold), demonstrating that beating EBs still contain cells from each lineage. Many developmental regulatory genes are also very much active in the beating EBs population, including Wnts (Wnt1, 2, 2b, 3a, 5a, 10b, and 11, and FZD1, 3, 4, and 10, all significantly upregulated), and homeobox genes (HOXA2, A3, A4, B2, B3, B4, B5, C5, D1, D2, D3, MSX1, 2, MEOX1, and a number of others), demonstrating the multiplicity of developmental lineages represented.

Microarray Analysis of hESC-CM Biological Processes.

Biological process analysis of the hESC-CMs shows that cellular maturation processes such as cytoskeletal organization and biogenesis, cell localization, and developmental processes such as muscle development and angiogenesis predominate in the CMs when compared to the beating EB populations. This maturation of the CMs, which are still somewhat heterogeneous, is a necessary intermediate step between undifferentiated, rapidly cycling cells and the stable cells possessing a solid cytoskeleton that are beginning to become firmly anchored into place with ECM and ready to contract with significant force. We can also see that the cells in this population are continuing to slow the rampant cell cycling, nucleotide synthesis, transcription, and mRNA processing seen in the hESC populations, as well as to down-regulate non-cardiac developmental programs such as mesenchymal cell differentiation, kidney development, and neural development, among others.

Microarray Analysis of Fetal Heart Cells.

Comparing the transcriptional profile of the CM cells to cultured primary fetal cardiomyocytes (FH), we find that 1,451 genes are expressed at lower levels in the FH population, and that many of these genes are associated with differentiation programs other than the cardiomyocyte program, highlighting the fact that the FH cells are less heterogeneous than our differentiated CM cell populations. For example, the early pan-mesodermal gene Dkk2 is expressed 92 fold less in FH, the skeletogenic gene sclerostosis (SOST) is expressed 406 fold less, and a significant number of neurogenic genes including synaptotagmins-4 (141 fold) and -13 (88 fold), neurofilament light (23 fold), medium (86 fold), and heavy chains (4.8 fold), as well as regulatory genes such as EPHB1 (5 fold) and DCX (72 fold) are also expressed at much lower levels in FH than CM.

Compared to the CM cell population, we find that a total of 684 genes are expressed more highly in the transcriptional program of the FH cells. Among the most differentially elevated transcripts are several encoding tumor suppressor genes, including tumor suppressor candidate 1 (TUSC1, 42 fold more highly expressed), cervical cancer suppressor gene 5 (ZNF434, 33 fold), TSPYL5 (56 fold), XAF1 (BIRC4BP, 20 fold), and OSGIN1 (4.6 fold), as well as the serum deprivation response gene (SDPR, 42 fold), consistent with a terminally differentiated cell population. We also see much higher expression of the later cardiac developmental genes CSRP1 (Heart L1m Protein, 26 fold), FHL2 (5 fold), and natriuretic peptide receptor 1 (NPR1, 5.2 fold) in the FH population, consistent with their known developmental expression patterns. Other very interesting differences between our CM population and the primary FH cardiomyocytes are revealed when we perform GO process analysis. As might be expected, we see that processes that are less active in the FH cells include many having to do with developmental processes of other tissues, particularly neural developmental processes, body plan regulatory processes, and diverse signaling families such as Wnt pathways. This suggests, as would be expected, that the FH cells are a somewhat more pure cardiomyocyte population than our differentiated CMs.

Isolation of Human Fetal Cardiomyocytes from 20-Week Hearts.

Hearts were placed in 10 cm dishes and great vessels, atria, and right ventricle removed. The left ventricle was then submersed in buffer (116 mM NaCl, 20 mM Hepes, 0.8 mM $Na_2HPO4$, 5.6 mM glucose, 5.4 mM KCl, 0.8 mM $MgSO_4$) and minced with forceps and micro-scissors. The resulting cell/tissue suspension was transferred to sterilized 15 ml centrifuge tube containing 10 ml of 0.4 mg/ml Collagenase Type II and agitated at approximately 80 rpms in a 37° C. incubator. After 10 minutes, the suspension is discarded since most cells at this point are erythrocytes. The minced tissue is resuspended in Collagenase Type II followed by collection of the suspension after another 10 mins (repeat this step twice). After each digestion repeat, the cell suspension is placed immediately in 2 ml of neonatal calf serum and centrifuged at 660 rpm for 5 minutes. The resulting pellet is then resuspended in 4 ml of cell medium and kept at 37° C. The collected cell-suspensions can be pooled and centrifuged again for 5 minutes at 660 rpm. The pellet is then resuspended in plating media and pre-plated for 60 minutes. After pre-plating, fibroblasts will adhere to the plate while cardiomyocytes remain in suspension. The cardiomyocyte-enriched fraction is removed and plated onto 10 $cm^2$ gelatin-coated plates (4-8 million cells per plate). Cytosine arabinoside.HCl (Sigma Chemical Co., St Louis, Mo., U.S.A.) at a final concentration of 10 M in the serum-free medium was added to prevent the growth of any residual fibroblasts as described (American journal of physiology 255: C19-27, which is incorporated herein by reference).

RNA Quality Control.

RNA concentration was measured by spectrophotometry, and RNA integrity assessed with an Agilent 2100 bioanalyzer with 6000 Nano Chips. RNA was judged as suitable for array hybridization only if samples exhibited intact bands corresponding to 18S and 28S ribosomal RNA subunits and had an RNA Integrity Number (RIN) greater than six. A pool of all samples was used as microarray reference controls.

Labeling Reaction and Hybridization.

All sample processing was performed at the same time to negate any potential technical variability. Using Low RNA Input Fluorescent Linear Amplification Kits (Agilent Technologies, Santa Clara, Calif., USA), cDNA was reverse transcribed from each RNA sample, and cRNA was then transcribed and fluorescently labeled from each cDNA sample. The 16 cRNA samples representing four biological quadruplicates, as well as the pooled reference control, were labeled with Cy5/Cy3. The resulting cRNA was purified using an RNeasy kit (Qiagen, Valencia, Calif., USA) followed by quantification of the cRNA by spectroscopy using an ND-1000 spectrophotometer (NanoDrop Technologies, Wilmington, Del., USA). 825 ng of Cy3- and Cy5-labeled and amplified cRNA was mixed and fragmented according to the Agilent technology protocol. cRNA was hybridized to 4×44K whole human genome microarray slides from Agilent (Part G4112F) according to the manufacturer's instructions. The hybridization was carried in a rotating hybridization chamber in the dark at 65° C. for 17 h.

RT-PCR Primer Sets Used for Transcriptional Analysis.

The primer sets used in the amplification reaction are as follows: (SEQ ID NOs: 33-52)

```
Human Oct-4 forward primer:
5'-GGCGTTCTCTTTGCAAAGGTGTTC-3'  (33)

Human Oct-4 reverse primer:
5'-CTCGAACCACATCCTTCTCT-3'  (34)

Human Nanog forward primer:
5'-GGCGTTCTCTTTGCAAAGGTGTTC-3'  (35)

Human Nanog reverse primer:
5'-CTCGAACCACATCCTTCTCT-3'  (36)

Human Rex-1 forward primer:
5'-CGTACGCAAATTAAAGTCCAGA-3'  (37)

Human Rex-1 reverse primer:
5'-CAGCATCCTAAACAGCTCGCAGAAT-3'  (38)

Human NeuroD forward primer:
5'-AAGCCATGAACGCAGAGGAGGACT-3'  (39)

Human NeuroD reverse primer:
5'-AGCTGTCCATGGTACCGTAA-3'  (40)

Human AFP forward primer:
5'-AGAACCTGTCACAAGCTGTG-3'  (41)

Human AFP reverse primer:
5'-GACAGCAAGCTGAGGATGTC-3'  (42)

Human Nkx2.5 forward primer:
5'-CTTCAAGCCAGAGGCCTACG-3'  (43)

Human Nkx2.5 reverse primer:
5'-CCGCCTCTGTCTTCTTCAGC-3'  (44)

Human α-MHC forward primer:
5'-GTCATTGCTGAAACCGAGAATG-3'  (45)

Human α-MHC reverse primer:
5'-GCAAAGTACTGGATGACACGCT-3'  (46)

Human ANP forward primer:
5'-GAACCAGAGGGGAGAGACAGAG-3'  (47)

Human ANP reverse primer:
5'-CCCTCAGCTTGCTTTTTAGGAG-3'  (48)

Fluc forward primer:
5'-ATCTACTGGTCTGCCTAAAG-3'  (49)
```

```
Fluc reverse primer:
5'-CAGCTCTTCTTCAAATCTATAC-3'  (50)

Human GAPDH forward primer:
5'-TGAAGGTCGGAGTCAACGGATTTGGT-3'  (51)

Human GAPDH reverse primer:
5'-CATGTGGGCCATGAGGTCCACCAC-3'  (52)
```

Quantitation of Scar Formation.

Hearts subjected to I/R injury were perfusion fixed in 10% neutral buffered formalin at 2, 4, 6, 8 weeks after I/R injury. Two 5-μm sections from each paraffin-embedded slice (i.e., basal and apical) were obtained (one just below the ligature and the other from the basal side of the apical part of LV) and were stained with hematoxylin/eosin. Scar and spared myocardium area were assessed and calculated using NIH Image J software. Infarct area was calculated as the ratio between scar area and the area of the whole-LV section and expressed in percentages. Measurements obtained in the two representative sections of each heart were averaged.

Quantitative Analysis of the Endothelial Cell Marker (Mouse CD31) Positive Capillary Density in Ischemic Hearts at Week 8.

Capillary densities were examined by counting the number of capillaries stained with anti-CD31 in five random fields on two different sections (approximately 3 mm apart) from each mouse. Images were analyzed using Image J software as described (PloS one 3: e1666, 20008).

Induction of Hypoxia and Angiogenesis Antibody Array.

The effect of angiogenesis induction was analyzed by comparing the expression of angiogenesis inhibitors and activators in media from cultured hESC-CMs exposed to hypoxia versus normoxia. Plates with hESC-CMs were placed in a humidified Billups-Rothenberg modular incubation chamber (model MIC-101, Billups-Rothenberg, Del Mar, Calif.), charged with a gas mixture of 1% $O_2$/5% $CO_2$/94% $N_2$ and sealed prior to placement into a tissue culture incubator set at 37° C. Hypoxic exposure was carried out for 12 hours and control hESCs were kept alongside at ambient oxygen concentrations. Culture medium was harvested following hypoxic exposure, and total cell protein was analyzed with the Bio-Rad protein assay. Cytokines were measured by the TranSignal™ Human Angiogenesis Antibody Array (Panomics, Fremont, Calif.). The following angiogenic growth factors were evaluated: angiogenin (ang), basic fibroblast growth factor (bFGF), FGF-α, interleukin 6 (IL-6), IL-8, hepatocyte growth factor (HGF), tumor necrosis factor alpha (TNF-α), and vascular endothelial growth factor (VEGF).

Electrophysiology Methods.

Cells were grown on mouse embryonic fibroblasts (MEFs) pre-treated with 10 μg/ml mitomycin C (Sigma; St Louis, Mo., USA) for 3 hr, as previously described [39,40]. Culture medium consisted of DMEM (Invitrogen, Carlsbad, Calif., USA) containing 2 mM I-glutamine (Invitrogen, Carlsbad, Calif., USA), insulin-transferrin-selenium (Invitrogen, Carlsbad, Calif., USA), non-essential amino acids (Invitrogen, Carlsbad, Calif., USA), β-mercaptoethanol (Gibco, Carlsbad, Calif., USA), 20 U/ml penicillin (Invitrogen, Carlsbad, Calif., USA), 20 μg/mL streptomycin (Invitrogen, Carlsbad, Calif., USA), and 20% fetal calf serum (FCS) (Hyclone, Logan, Utah). The HES2 line was passaged manually ("cut-and-paste"), by cutting colony pieces and removing them from the MEFs using dispase (10 mg/mL) for 2 min. The resulting HES2 colony pieces were washed twice in PBS then placed on fresh MEFs. For differentiation to cardiomyocytes, co-culture of the HES2 and END2 cells was carried out as described previously [39,40]. In brief, END2 cells were grown to 100% confluence and treated with 10 pg/mL mitomycin C (Sigma; St Louis, Mo.) for 3 hr. Undifferentiated HES2 cells were removed from the MEFs using 10 mg/mL dispase (Invitrogen, Carlsbad, Calif.). Colonies were then washed twice with PBS, resuspended in hESC media and broken into pieces by repeated pipeting. These pieces were then transferred to the END2 cell layer and incubated at 37° C. for 2-3 weeks in hESC medium lacking serum. The co-cultures were refreshed with medium lacking serum every 4-5 days. Areas of beating cardiomyocytes were scored by visual examination from day 7 onwards.

Example 3

Introduction

Human embryonic stem cells (hESCs) have generated great interest given their pluripotency and capacity to self-renew. Specifically, hESCs can be cultured indefinitely in vitro, and can differentiate into virtually any cell type in the adult body. Given the limited potential for regeneration of most adult tissues following injury and the prevalence of numerous chronic diseases involving cell death and dysfunction, hESCs are an attractive source for tissue regeneration and repair therapies. Successful in vitro differentiation of hESCs into multiple somatic cell types has been reported, including cardiomyocytes, hematopoietic cells, neurons, pancreatic islet cells and hepatocytes. Furthermore, there is a growing number of reports showing the therapeutic benefit of hESC derivatives following transplantation into animal models of disease. Although such data are encouraging, significant hurdles remain before hESC-based treatments can be safely and successfully translated into clinical therapy.

An important obstacle facing in vivo engraftment and function of hESCs is the potential immunologic barrier. hESCs express low levels of Class I Human Leukocyte Antigen (HLA), which moderately increases as these cells differentiate. The presence of distinct major histocompatibility complex (MHC) antigens suggests that hESCs may elicit an immune response and be at risk for immune rejection when introduced in vivo across histocompatibility barriers. At the same time, hESCs theoretically represent an immune-privileged cell population, as embryos consisting of 50% foreign paternal material are usually not rejected by the maternal host. Recent reports have indeed shown that both mouse embryonic stem cells (mESCs) and hESCs seem to have the capability to evade immune recognition in allogeneic as well as in xenogeneic hosts. mESCs have been shown to survive in immunocompetent mice, as well as in rats and sheep for many weeks after transplantation. Similarly, rat ESC-like cells were demonstrated to permanently engraft in allogeneic recipients leading to allospecific down-regulation of the host immune response. In addition, not only have hESCs been reported to inhibit allogeneic T-cell proliferation in vitro, but also to evade immune recognition in xenogeneic immunocompetent mice.

Nevertheless, our group and others have found that following transplantation into allogeneic murine hearts, mESCs triggered progressive immune cell infiltration and were subsequently rejected. Others have concluded that hESC grafts are infiltrated by inflammatory cells and do not form teratomas in immunocompetent mice, suggesting rejection. Clearly, questions of whether hESCs have immune-privileged properties and whether immunological rejection of transplanted hESCs and hESC derivatives is something that must be addressed remains to be clarified.

In this Example, we used novel, non-invasive molecular imaging techniques to longitudinally track hESC fate following transplantation. We present evidence of an adaptive donor-specific xenogeneic immune response that is launched against hESCs shortly after transplantation into immunocompetent mice, resulting in rejection. We further delineate the role of T-lymphocyte subsets in mediation of the murine anti-hESC immune response. Finally, we compared the efficacy of various combinations of clinically available immunosuppressive regimens for enhancing survival of transplanted hESCs in vivo.

Given their self-renewing and pluripotent capabilities, human embryonic stem cells (hESCs) are well-poised as a cellular source for tissue regeneration therapy. However, the host immune response against transplanted hESCs is not well characterized. In fact, controversy remains as to whether hESCs have immune-privileged properties.

To address this issue, we used in vivo bioluminescent imaging to track the fate of transplanted hESCs stably transduced with a double fusion reporter gene consisting of firefly luciferase (fLuc) and enhanced green fluorescent protein (eGFP). We show that post-transplant survival is significantly limited in immunocompetent as opposed to immunodeficient mice. Repeated transplantation of hESCs into immunocompetent hosts results in accelerated hESC death, suggesting an adaptive donor-specific immune response. Our data demonstrate that transplanted hESCs trigger robust cellular and humoral immune responses, resulting in intra-graft infiltration of inflammatory cells and subsequent hESC rejection. Moreover, we have found $CD4^+$T-cells to be an important modulator of hESC immune-mediated rejection. Finally, we show that immunosuppressive drug regimens can mitigate the anti-hESC immune response and that a regimen of combined tacrolimus (TAC) and sirolimus (SIR) therapy significantly prolongs survival of hESCs for up to 28 days. Taken together, these data suggest that hESCs are immunogenic, trigger both cellular and humoral-mediated pathways and, as a result, are rapidly rejected in xenogeneic hosts. This process can be mitigated by a combined immunosuppressive regimen as assessed by novel molecular imaging approaches.

Results

Characterization of hESCs Expressing a Double Fusion (DF) Reporter Gene.

To date, most studies on hESC therapy have relied on conventional reporter gene technology such as green fluorescent protein (GFP) and β-galactosidase (LacZ) to monitor cell survival and behavior following transplantation. These reporter genes are typically identified by immunohistochemical staining techniques, which provide only a "snapshot" representation rather than a comprehensive picture of cell survival over time. Such limited techniques may, in part, contribute to the conflicting observations of hESC survival in xenogeneic hosts. Results from previous studies range from no signs of rejection to complete rejection of hESCs following transplantation into mice. To circumvent these issues, a double fusion (DF) reporter gene construct carrying firefly luciferase (fLuc) and enhanced green fluorescent protein (eGFP) driven by a constitutive human ubiquitin promoter (pUB) was successfully transduced into undifferentiated hESCs (H9 line), using a self-inactivating (SIN) lentiviral vector (FIG. 21A). This enabled us to track the hESCs in vivo by bioluminescent imaging (fLuc) as well as ex vivo by immunohistochemistry (eGFP). After 2 to 3 passages of feeder-free culture in mTersh culture medium, FACS analysis of $H9^{DF}$ hESCs revealed robust expression of eGFP concomitant with expression of pluripotent hESC markers ($SSEA-4^+$ and $SSEA-1^-$) (FIG. 21B). The cells exhibited a robust correlation between fLuc expression and hESC number ($r^2$=0.99, FIG. 21C). In vitro analysis showed that $H9^{DF}$ hESCs were able to proliferate and differentiate into cells of all three germ layers at a frequency similar to control H9 hESCs (data not shown).

The major system of alloantigens responsible for cell incompatibility is the major histocompatibility complex (MHC) (Transpl Immunol 10:101-108). In agreement with previous reports (Proc Natl Acad Sci USA 99:9864-9869 and J Anat 200:249-258), we found low expression levels of both MHC-I and $β_2$-microglobulin proteins and no expression of MHC-II on both H1 and H9 hESCs, as compared to a positive control (human lymphocytes). Importantly, these profiles were not altered by the introduction of our reporter genes (FIG. 26A). Also, lentiviral transduction did not result increased autocrine secretion of interferon (IFN)-γ, a cytokine known to induce MHC expression (Proc Natl Acad Sci USA 99:9864-9869) (FIGS. 26B and 26C).

Monitoring of Transplanted hESCs in Immunocompetent and Immunodeficient Mice.

We investigated longitudinal hESC survival following intramuscular (gastrocnemius muscle) transplantation of $1\times10^6$ $H9^{DF}$ hESCs into immunodeficient (NOD/SCID, n=5) versus two strains of immunocompetent mice (BALB/c and C57BI/6a, n=5 per group) by in vivo bioluminescent imaging (BLI). hESC survival was significantly limited in immunocompetent animals as compared to NOD/SCID mice. (Day 5 BLI signal: NOD/SCID 7.37±0.3; BALB/c 5.91±0.47; C57BL/6a 6.1±0.19 $Log^{[photons/sec]}$; P<0.05 immunodeficient vs. immunocompetent). BLI signal completely disappeared in immunocompetent animals between 7 and 10 days post-transplant (FIGS. 22A and 22B). Repeated transplantation of $H9^{DF}$ hESCs in the contralateral gastocnemius muscle at two weeks following primary injection resulted in accelerated hESC death in immunocompetent animals, with BLI signal reaching background levels by post-transplant day 3 (NOD/SCID 7.95±0.29; BALB/c 4.97±0.10; C57BI/6a 4.97±0.19 $Log^{[photons/sec]}$; P<0.001 immunodeficient vs. immunocompetent), suggesting an adaptive, donor-specific immune response (FIGS. 22A and 22C). Post-transplant hESC death in immunocompetent mice was confirmed in a control experiment, in which $1\times10^6$ H1 hESC were transplanted into an additional group of BALB/c animals (n=5). Detailed histological evaluation of the graft site at 10 days following hESC injection revealed no signs of hESC survival (FIGS. 27A and 27B). By contrast, $H9^{DF}$ hESC survived well in NOD/SCID animals with progressively increasing BLI signal intensity starting at post-transplant day 10, suggesting hESC proliferation (FIG. 2B). At 42 days following primary transplantation, intramuscular teratomas were found in transplanted NOD/SCID animals (FIGS. 27C and 27D), whereas neither teratomas nor persistent hESCs were seen in immunocompetent animals (data not shown).

To exclude the possibility that the adaptive immune reaction was launched against xenoantigens produced by the reporter genes introduced into the cells, rather than against hESC xenoantigens, we next transplanted $1\times10^6$ non-transduced H9 hESCs into a second group of BALB/c mice (n=3), followed by re-transplantation of $1\times10^6$ $H9^{DF}$ hESCs into the contralateral leg at two weeks following primary injection. BLI following re-transplantation showed a similar loss of signal as compared to animals that were primarily stimulated with $H9^{DF}$ hESCs (FIGS. 28A and 28B), indicating that the adaptive immune response was in fact directed towards the hESCs.

To determine whether hESC differentiation would influence their capacity to escape immunological rejection, we next injected 1×10⁶ hESC-derivatives after spontaneous in vitro differentiation during 14 days before transplantation into BALB/c mice (n=5). Overall, our results did not show a significant difference in their survival compared with undifferentiated hESCs (FIG. 28C).

Transplantation of hESCs Triggers Severe Graft Infiltration by a Variety of Immune Cells.

Five days following transplantation of either 1×10⁶ H9$^{DF}$ or H1 hESCs (n=6) or PBS (n=3) as a control, gastrocnemius muscles of BALB/c animals were analyzed for graft infiltrating cells. Histological analysis demonstrated severe intramuscular infiltration of inflammatory cells (FIGS. 23A and 23B). Immunofluorescent staining showed that a large percentage of infiltrating cells stained positive for the T-lymphocyte surface marker CD3 (FIGS. 23C and 23D). Quantification and further characterization of graft infiltrating cells was carried out by enzymatic digestion of the explanted muscles followed by FACS analysis. Comparison of the control PBS to the hESC injected muscles confirmed that both H9$^{DF}$ and H1 hESC transplantation elicited severe infiltration of various types of immune cells involved in both adaptive and innate types of immunity (FIG. 23E). Interestingly, both CD3⁺T-cells (H9$^{DF}$: 4.5±0.3%; H1: 4.3±0.5% vs. PBS control: 0.5±0.1%, P<0.01) and B220⁺B-cells (H9$^{DF}$: 3.4±0.5%; H1: 4.9±0.7% vs. PBS control: 1.0±0.1%, P<0.01) were present at a high frequency, suggesting a prominent role for adaptive immunity in hESC rejection. Furthermore, CD4⁺T-cells, CD8⁺T-cells and Mac-1⁺Gr-1⁺neutrophils, and Mac-1⁺Gr-1⁻ macrophages (the latter only in the H1 group) infiltrated into the hESC graft at a significantly higher frequency as compared to PBS controls (FIG. 23E).

hESC Transplantation Triggers Systemic Cellular and Humoral Murine Immune Responses.

To investigate the cellular immune response, we next performed ELISPOT assays using splenocytes of both H9$^{DF}$ and H1 hESC recipient animals. Cytokine release was abundant in these animals. At 5 days following transplantation, splenocytes from hESC recipients secreted significant amounts of both IFN-γ and Interleukin-4 (IL-4), compared to wild type animals (H9$^{DF}$: IFN-γ: 488±91, IL-4:529±57; H1: IFN-γ: 495±106, IL-4: 563±87 vs. WT group: IFN-γ: 0.5±0.3, IL-4: 8.5±2, P<0.001) (FIG. 24A). IFN-γ is produced by T-helper (Th)-1 cells and induces cellular immune activity, whereas IL-4 produced by Th-2 cells activates humoral immune pathways. Thus, our data suggests the involvement of an antibody-mediated B-cell response. Indeed, FACS analysis showed a significantly higher presence of circulating xeno-reactive antibodies in hESC recipient sera, as compared to wild type animals (mean fluorescent intensity (MFI): H9$^{DF}$: 7.0±1.2; H1: 6.8±1.5 vs. WT group: 3.8±0.6, P<0.05) (FIG. 24B).

Prominent Role for CD4⁺T-Cells in Mouse Anti-hESC Rejection.

The phylogenetic disparity between mice and humans may lead to a lower affinity of mouse T-cell receptors (TCR) for human MHC molecules (*Annu Rev Immunol* 16:433-470). Therefore, the indirect pathway of immune recognition, whereby the recipient's antigen presenting cells (APC) process and present xenoantigens to recipient CD4⁺T cells, plays a major role in discordant cellular xenorejection (*Annu Rev Immunol* 16:433-470). For these reasons, combined with the fact that hESCs lack expression of MHC-II antigens (FIG. 21D) necessary for direct xenograft recognition by recipient CD4⁺T cells, we hypothesized that indirect immune recognition by CD4⁺T cells could play an important role in mouse anti-h ESC rejection. To further delineate the role of T-cell subsets in hESC rejection, we transplanted 1×10⁶ H9$^{DF}$ hESCs into T-cell deficient BALB/c Nude, CD4⁺T-cell knockout (CD4-KO), and CD8⁺T-cell knockout (CD8-KO) animals (n=4 or 5 per group) and followed cell survival by BLI. In agreement with prior data (20), hESCs survived in Nude mice over the 42 day study course (FIGS. 25A and 25B), and were able to form teratomas. Interestingly, hESCs survived significantly longer in CD4-KO compared to CD8-KO animals (BLI signal at post-transplant day 5: CD4-KO: 6.5±0.6 vs. CD8-KO: 5.0±0.3 Log$^{[photons/sec]}$; P<0.05). However in both groups, hESC xenografts were eventually rejected (FIGS. 29A and 29B).

Immunosuppressive Therapy Prolongs Survival of hESCs Following Transplantation.

Since post-transplant hESC death appears largely due to T-cell mediated donor-specific immune response, we next investigated the efficacy of single and combined immunosuppressive drug regimens for preventing post-transplant hESC rejection. Clinically available immunosuppressants were chosen based on different mechanism of action: (1) calcineurin inhibitors (tacrolimus=TAC), (2) target of rapamycin (TOR) inhibitors (sirolimus=SIR), and (3) anti-proliferatives (mycophenolate mofetil=MMF). A group of BALB/c mice (n=30) were randomized to receive daily TAC, SIR, MMF, TAC+MMF, SIR+MMF or TAC+SIR (n=5 per group) treatment following transplantation of 1×10⁶ H9$^{DF}$ hESCs into the gastrocnemius muscle. The therapeutic dose range was confirmed by serum drug trough level measurements (SI Table 1).

Figure 25:
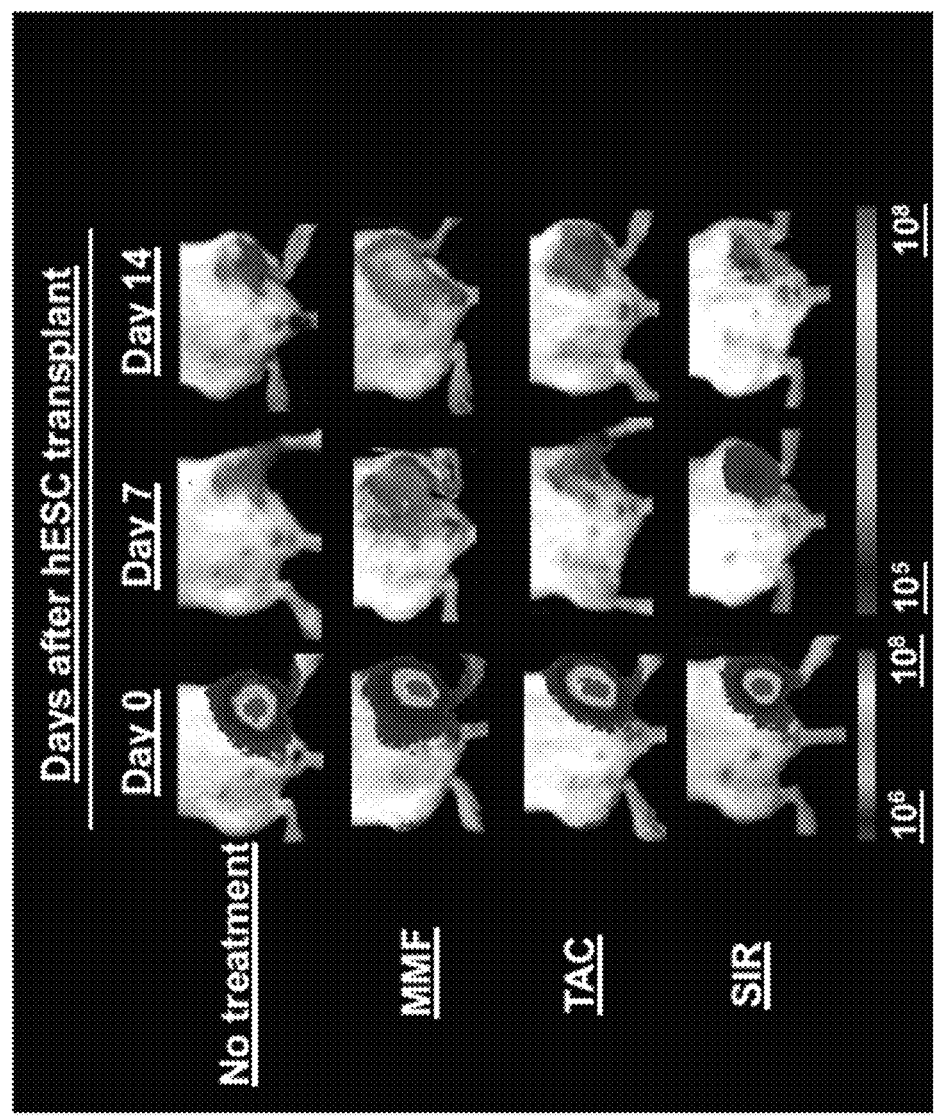
Figure 25B:
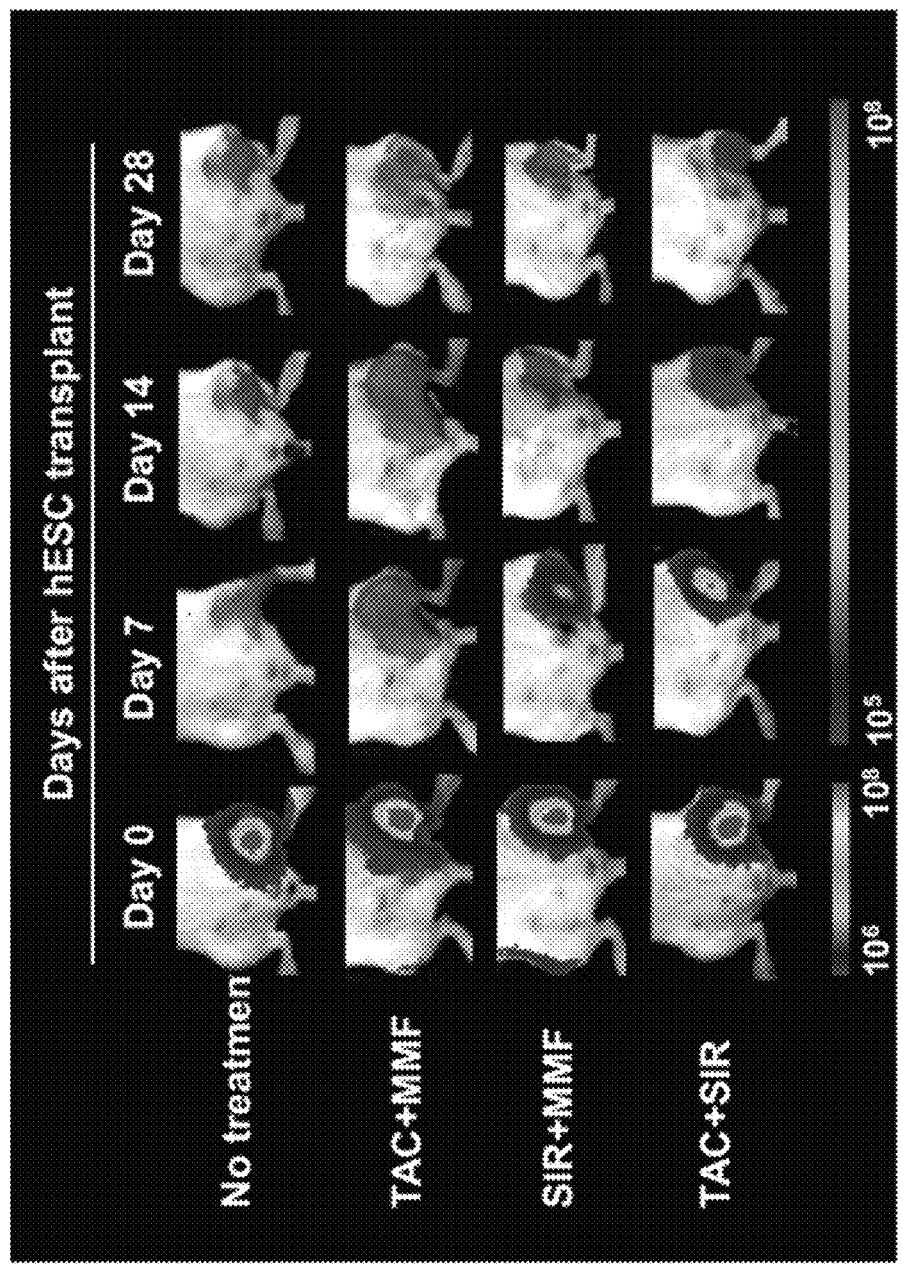
Figure 25:
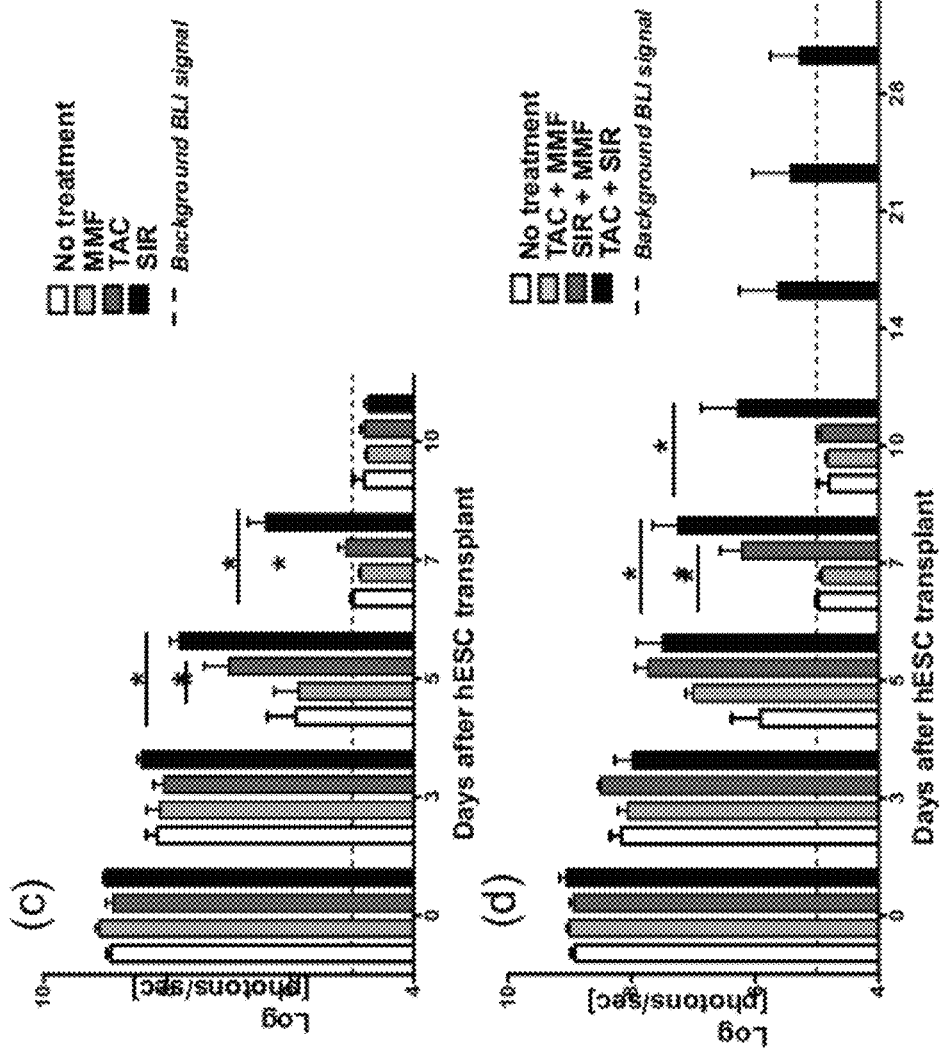
Figure 25:
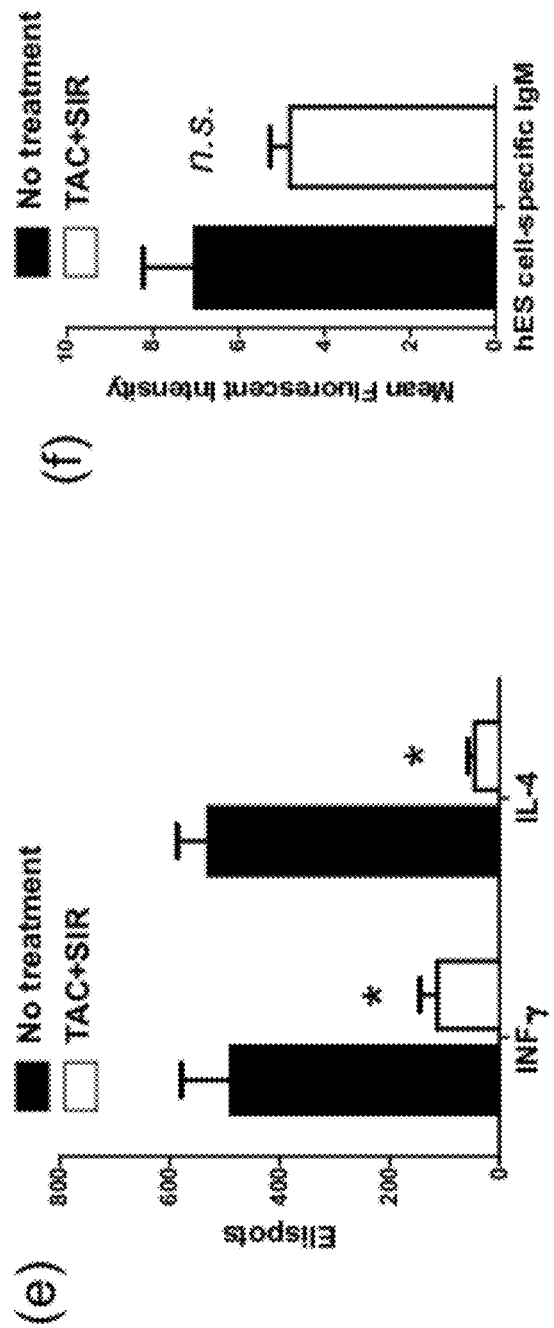

As monotherapy, SIR extended hESC survival to the greatest degree. Significantly higher BLI signals from the SIR treated animals were seen up to 7 days after transplantation, as compared to the no treatment (NT) group (BLI signal at day 7: SIR: 6.4±0.29 vs. NT: 4.98±0.04 Log$^{[photons/sec]}$; P<0.05). However, the signal in all single drug treatment groups (TAC, SIR, MMF) had decreased to background levels by post-transplant day 10 (FIGS. 25A and 25C), emphasizing the strong anti-hESC immune response despite high dose immunosuppressive treatment. In our model, addition of MMF did not result in significant improvement of hESC survival over single TAC and/or SIR treatment (FIGS. 25B and 25D). Combined TAC+SIR treatment, however, markedly improved survival of hESCs. BLI signals from the TAC+SIR treated animals were significantly higher starting at 7 days following transplantation and could be followed out to post-transplant day 28 (FIGS. 26B and 26D). Finally, the efficacy of combined TAC+SIR treatment for effective suppression of the recipient anti-h ESC immune response was confirmed by in vitro analysis. ELISPOT assay showed a significant inhibition of effector cytokine production (TAC+SIR: INF-γ: 113±32; IL-4: 45±12 vs. NT: INF-γ: 488±91, IL-4: 529±57, P<0.01) (FIG. 25E) and FACS analysis revealed a strong trend in reduction of circulating xeno-reactive antibodies (TAC+SIR: 4.8±0.5 vs. NT: 7.0±1.2, P=0.14) (FIG. 25F).

Discussion

The field of hESC-based therapy is advancing rapidly. Although federal regulations still restrict the generation of new hESC lines in the United States, regional funding institutions such as the California Institute of Regenerative Medicine foresee hESC-based therapies to go into phase I clinical trails within the next 10 years. To accomplish such goals, several significant hurdles that preclude clinical translation of such therapy need to be overcome, of which hESC immunogenicity is a major concern.

This study was designed to characterize hESC immunogenicity in a human-to-mouse transplantation model, and to evaluate the efficacy of different immunosuppressive drug regimens to improve transplanted hESC survival. Specifically, we have demonstrated that: (1) molecular imaging can be used to quantify hESC survival and non-invasively follow donor cell fate; (2) hESCs can trigger potent cellular and humoral immune responses following transplantation into immunocompetent mice, resulting in intra-graft infiltration of a variety of inflammatory cells, leading to rejection; (3) CD4$^+$ T-lymphocytes play an important role in mouse anti-hESC rejection; and (4) an immunosuppressive drug regimen consisting of tacrolimus (TAC) and sirolimus (SIR) significantly mitigates the host immune response to prolong hESC survival.

Specific studies evaluating immunogenicity of hESCs in vivo are few and have yielded mixed conclusions regarding hESC's potential to induce immune response and/or survive in xenogeneic hosts. In these studies, results were based on histological techniques to evaluate hESC survival and potential immunological rejection. Histological analysis is susceptible to sampling error, as each tissue section represents only one layer of the hESC graft and surrounding tissue at one time-point. To address these shortcomings, our group has been developing and validating reporter gene-based molecular imaging techniques. In particular, fLuc-based optical bioluminescent imaging has proven to be a reliable technique for assessing engraftment and survival of stem cells following transplantation in vivo (30). An important advantage in using bioluminescent imaging to track cell transplantation is that the expression of the fLuc reporter gene, which is integrated into the DNA of the transplanted cells, is expressed only by living cells, making it a highly accurate tool for following cell graft rejection in the living subject (*Transplantation* 80:134-139). Using this approach in this report, we have clearly showed impaired survival of hESCs in immunocompetent versus immunodeficient mice, a phenomenon which was even more pronounced after repeated transplantation of the hESCs.

Xenotransplantation of cells or organs is usually complicated by severe immunological responses (*Annu Rev Immunol* 16:433-470). Previous studies have addressed murine xenogeneic immune responses to adult human cells or tissues following transplantation. For example, human-to-mouse pancreatic islet transplants trigger progressive infiltration of lymphocytes leading to rejection within 5-6 days (*Science* 257:789-792). Human skin transplants are rejected by immunocompetent mice within 10 days, and a delay of rejection is seen when skin is transplanted onto mice lacking CD4$^+$T-cells, but not on those lacking CD8$^+$T cells (*Transplantation* 68:1721-1727). A comparison of these data to the results of our study, in which we show a similar time course of rejection of hESCs (7-10 days) that seems largely mediated by CD4$^+$T cells, suggests that hESCs are recognized by the murine immune system in a comparable way as adult human cells. This leads us to conclude that, in a discordant xenotransplant model, hESCs do not retain immune-privileged and/or immunosuppressive properties. During the first 10 days after transplantation, spontaneous non-immune related hESC death also occurred in immunodeficient mice (FIG. 22). In immunocompetent mice, spontaneous hESC death could have lead to activation of the adaptive immune system through the indirect pathway, in which intracellular antigens shed by hESC debris are phagocytosed by host APCs and presented to CD4$^+$T lymphocytes. This would explain the major role of CD4$^+$cells that we found in our study.

Studies addressing the character and intensity of immune responses towards hESCs in a human allogeneic setting in vivo raises ethical considerations and thus are currently not feasible. However, the results of this study emphasize that solutions which can reduce or eliminate potential immune responses need to be evaluated. Strategies that could prevent hESC immune recognition include: (1) forming MHC isotyped hES cell-line banks; (2) creating a universal donor cell by genetic modification; (3) inducing tolerance by hematopoietic chimerism; (4) generating isogeneic hESC lines by somatic nuclear transfer; (5) and/or using immunosuppressive medication (*Springer Semin Immunopathol* 26:201-213 and *Adv Drug Deliv Rev* 57:1944-1969). In the near future, successful clinical application of hESC-based transplantation will most likely rely on immunosuppressive therapy based in part on the experience learned from organ transplantation. Thus, the significance of evaluating the effects of immunosuppressive drugs upon hESC survival in our animal model is two-fold: (1) to investigate the efficacy of various compounds that may be used in conjunction with clinical hESC-based therapies in the future, and (2) to develop an immunosuppressive drug regimen that optimizes transplanted hESC survival in animal models. Our results show that, in a xenogeneic murine setting, a combined immunosuppressive drug regimen consisting of TAC and SIR optimally suppressed anti-hESC immune response and prolonged their survival to 28 days following transplantation. TAC and SIR are a potential combination for an immunosuppressive strategy because of their different side mechanisms of action, side-effect profiles, and apparent synergism when used together (*N Engl J Med* 343:230-238). TAC and SIR are structurally similar macrolide immunosuppressants. Both drugs bind to a common family of immunophilins called FK506 binding proteins (FKBPs). SIR binds to FKBP, thereby blocking signal transduction by inhibiting two kinases late in the $G_1$ cell cycle progression. These kinases have been designated TOR-1 and -2, targets of Rapamycin. TAC exerts its effect through the inhibition of calcineurin, by the FK506/FKBP complex. Calcineurin plays a critical role in interleukin-2 promoter induction after T-cell activation (*Crit Rev Oncol Hematol* 56:23-46). Although this combination is used with caution in clinical transplantation because of potential adverse drug effects, we recommend applying this treatment protocol to studies in pre-clinical animal models that address the biology and therapeutic efficacy of hESC-derivatives.

In summary, our data show that hESC xenografts are effectively recognized and rejected by the adaptive murine immune system following transplantation. We also show that standard immunosuppressive drugs have the potency to prolong survival of the transplanted cells but cannot completely prevent rejection. Finally, the integration of molecular imaging techniques for development and validation of different strategies to improve post-transplant survival of hESC-derivatives should accelerate progress in this field.

Methods and Materials

Lentiviral Production and Generation of Stable hESC Line.

SIN lentivirus (LV) was prepared by transient transfection of 293T cells. H9 hESCs (Wicell) were transduced with LV-pUB-fLuc-eGFP double fusion (DF) reporter gene at a multiplicity of infection (MOI) of 10. The infectivity was determined by eGFP expression as analyzed on FACScan (BD Bioscience, San Jose, Calif.). The eGFP positive cell populations (~20%) were isolated by fluorescence activated cell sorting (FACS) Vantage SE cell sorter (Becton Dickinson Immunocytometry Systems) followed by plating on the feeder layer cells for culturing.

Culture and Transplantation of hESCs.

H1, H9 and H9DF hESCs were initially maintained on top of murine embryonic fibroblasts feeder (MEF) layers as detailed in SI Methods. To prevent contamination of the transplanted hESC population with MEF, hESC colonies were separated from MEF by incubation with dispase (Invitrogen) and subcultured on feeder-free matrigel (hESC qualified, BD Biosciences) coated 6-well plates in mTeSR™ 1 maintenance medium (Stem Cell Technologies) for 2 to 5 passages. MHC expression on hESCs was evaluated by flow cytometry as detailed in SI Methods. Shortly prior to transplantation, hESCs were trypsinated, and resuspended in sterile PBS at $1 \times 10^6$ cells per 20 µl. hESC transplantation was performed by direct injection into gastrocnemius muscles of recipient mice (using a 29.5 gauge insulin syringe.

Animal Experiments.

All animal procedures were approved by the Animal Care and Use Committee of Stanford University. Mouse stains are detailed in SI Methods.

Optical Bioluminescent Imaging of hESC Transplanted Animals.

BLI was performed using the Xenogen In Vivo Imaging System as previously described (38). Briefly, mice were anesthetized with isoflurane and D-luciferin was administered intraperitoneally at a dose of 375 mg/kg body weight. At the time of imaging, animals were placed in a light-tight chamber, and photons emitted from luciferase expressing hESCs transplanted into the animals were collected with integration times of 5 sec-5 min, depending on the intensity of the bioluminescence emission. The same mice were scanned repetitively as per the study design. BLI signal was quantified in units of photons per second (Total flux) and presented as Log[photons/sec].

Quantification of Graft Infiltrating Cells.

Intra-hESC graft infiltrating cells were measured by FACS analysis of enzymatically digested gastrocnemius muscles as detailed in SI Methods.

Quantification of Cellular Immune Response.

During animal sacrifice on day 5, the spleens were harvested and splenocytes were isolated. Enzyme-linked immunosorbent spot (ELISPOT) assays using $1 \times 10^5$ γ-irradiated hESCs (1500 RAD) as stimulator cells and $1 \times 10^6$ recipient splenocytes as responder cells were performed according to the manufacturer's protocol (BD Bioscience) using IFN-γ and IL-4-coated plates. Spots were automatically enumerated using an ELISPOT plate reader (CTL) for scanning and analyzing.

Quantification of Humoral Immune Response.

Donor-specific xenoreactive antibodies were detected by FACS analysis of target hESCs following incubation with recipient mouse serum as detailed in SI Methods.

Immunosuppressive Therapy.

Tacrolimus (TAC, 4 mg/kg/d; Sigma-Aldrich), sirolimus (SIR, 3 mg/kg/d; Rapamune oral solution; Sigma-Aldrich) and mycophenolat mofetil (MMF, 30 mg/kg/d; Roche) were administered once daily as detailed in SI Methods.

Statistical Analysis.

Data are presented as mean±SEM. Comparisons between groups were done by independent sample t-tests or analysis of variance (ANOVA) with LSD post hoc tests, where appropriate. Differences were considered significant for P-values<0.05. Statistical analysis was performed using SPSS statistical software for Windows (SPSS).

Supplemental Information for Example 2

Culture and Transplantation of hESCs.

H1, H9, and, H9DF hESCs were initially maintained on top of murine embryonic fibroblasts feeder (MEF) layers seeded onto 0.1% gelatin-coated plastic dishes and inactivated by γ-irradiation (6,000 RAD). hESCs were maintained in hESC medium containing 80% Dulbecco's modified Eagle's medium/F12 (DMEM/F12, Invitrogen), 1 mM L-glutamine, 0.1 mM 13-mercaptoethanol, 0.1 mM non-essential amino acids (Invitrogen), 20% Knockout Serum Replacement (Invitrogen), and 8 ng/ml human basic fibroblast growth factor (bFGF; Invitrogen) (*Dev Biol* 227:271-278, which is incorporated herein by reference). MEF were derived from CF-1 E12.5 embryos as previously described (*Science* 282:1145-1147, which is incorporated herein by reference). The hESC culture medium was changed daily and hESCs were passaged every 4-5 days. hESC differentiation was induced by embryoid body (EB) formation. hESC colonies were dispersed into cell aggregates using 1 mg/ml collagenase IV. These aggregates were then cultured in suspension in ultra-low attachment plates (Corning) in hESC differentiation medium, consisting of DMEM high glucose supplemented with 20% FBS (HyClone), 1 mM Lglutamine, 0.1 mM 2-mercaptoethanol, and 0.1 mM nonessential amino acids for 7 days. Then, EBs were transferred to 10-cm culture dishes coated with 0.1% gelatin and cultured for an additional 7 days. hESC differentiation medium was changed every two days.

FACS Analysis of hESC Surface Marker Expression.

H1, H9, and, H9DF hESCs were trypsinated, washed, and incubated with PEconjugated mouse anti-human HLA-ABC (G46-2.6), β2-microglobulin (Tu99), HLA-DR, DP, DQ (Tu39), or their respective isotype control antibodies (all BD Biosciences) in FACS buffer (PBS 2% FCS) for 45 min at 4° C. Cells were washed, incubated with 7-amino-actinomycin D (7-AAD) cell viability solution (eBiosciences), and analyzed on a FACSCalibur system (BD Biosciences). For analysis of pluripotency markers, a similar protocol was followed, using PE-conjugated anti-human SSEA-1 (MC-480) and purified anti-human SSEA-4 (MC-813-70) antibodies (R&D Systems). The latter followed by incubation with PE-conjugated anti-IgG secondary antibody (eBioscience) for 30 min at 4° C.

Quantification of IFN-α Secretion by hESC.

CytokineAntibody Array (Raybiotech) were used to identify the H9 and H9DF hESC secretion profiles of IFN-α. Membranes were covered with 24-hour supernatant of H9 hESC, H9DF hESC, medium alone as well as medium containing 25 ng/ml recombinant IFN-α (Peprotech) as a positive control. Membranes were developed according to the manufacturer's protocol. Integrated densities were calculated using National Institutes of Health imageJ 1.38. Values were normalized to the integrated positive control on each membrane.

Animal Experiments.

Six- to 10-week-old female BALB/c (wildtype), C57BL/6J-Tyrc-2J/J (C57BL/6 albino or C67BI/6a), NOD.CB17-Prkdcscid/J (NOD/SCID), B6.12952-Cd4tm1Mak/J (CD4 knockout), B6.12952-Cd8 atml Mak/J (CD8 knockout) mice (The Jackson Laboratory), and BALB/c Nude (T cell deficient, Charles River laboratories) mice were housed at no more than five per cage in our American Association for Accreditation of Laboratory Animal Care-approved facility with 12:12-h lightdark cycles and free access to standard rodent chow and water. All animal procedures were approved by the Animal Care and Use Committee of Stanford University.

Tissue Collection, Immunofluorescent and Histological Analysis.

Explanted muscles were fixed in 2% paraformaldehyde for 2 h at room temperature and cryoprotected in 30% sucrose overnight at 4° C. Tissue was frozen in optimum cutting temperature compound (OCT compound, Sakura Finetek) and sectioned at 5 µm on a cryostat. Serial sections were blocked and incubated with hamster anti-CD3 (clone G4.18) (BD Biosciences) for 1 h at room temperature, followed by goat anti-hamster Texas Red (Santa Cruz Biotechnology) Sections were counterstained with 4,6-diamidino-2-phenylindole (DAPI, Molecular Probes) and analyzed with a Leica DMRB fluorescent microscope (Leica Microsystems, Frankfurt, Germany). Hematoxylin and Eosin staining (Sigma) was performed according to established protocols. For histopathogical evaluation of hESC survival 6 sections of each explanted muscle were stained with H&E and carefully analyzed by a blinded pathologist (H.V.).

Quantification of Graft Infiltrating Cells.

Gastrocnemius muscles were surgically explanted, minced, and digested for 2 h in Collagenase D (2 mg/ml; Worthington Biochemical) at room temperature in RPMI 1640 media (Sigma Chemical Co.) with 10% FCS (FCS; Life Technologies). Muscle cell suspensions were ran through a 70-pm cell strainer, washed in FACS buffer (PBS 2% FCS), and incubated with PE-conjugated CD3e (145-2C11), CD8a (53-6.7), Mac-1/CD11b (M1/70), and allophycocyanin (APC)-conjugated CD4 (GK1.5), B220 (RA3-6B2), and Gr-1 (RB6-8C5) antibodies (CD4 and CD8: eBiosciences, all others: BD Bioscience) for 45 min at 4° C. Cells were washed, incubated with 7-AAD cell viability solution (eBiosciences), and analyzed on a FACSCalibur system (BD Biosciences).

Quantification of Humoral Immune Response.

Sera from recipient mice were decomplemented by heating to 56° C. for 30 min and subsequently diluted by 33% in PBS containing 3% FCS and 0.1% NaN3. Equal amounts of sera and hESC (1 106 cells per milliliter) suspensions were incubated for 30 min at 4° C. and washed with PBS through a calf-serum cushion. IgM xenoreactive antibodies were stained by incubation of the cells with PE-conjugated goat antibodies specific for the Fc portion of mouse IgM (BD Bioscience) at 4° C. for 45 min. Cells from all groups were washed twice with PBS containing 2% FCS and then analyzed on a FACSCalibur system (BD Biosciences). Fluorescence data were collected by use of logarithmic amplification and expressed as mean fluorescent intensity.

Immunosuppressive Therapy Protocol.

Adult female BALB/c mice (n=30) were randomized to receive Tacrolimus (TAC; Sigma-Aldrich), sirolimus (SIR; Rapamune oral solution; Sigma-Aldrich), and mycophenolat mofetil (MMF; Roche). All drugs were administered once daily by oral gavage, using the following doses for TAC, SIR, and MMF: 4, 3, and 30 mg kg 1d 1, respectively, to achieve drug serum levels comparable to clinical trough levels of 10-15 ng/ml for TAC and SIR and 3.5-5.5 ng/ml for MMF. Blood was drawn during animal sacrifice and 12- or 24-hour drug trough levels were quantified by high-performance liquid chromatography (HPLC) as described earlier (*Ther Drug Monit* 22:608-612, which is incorporated herein by reference).

SUPPLEMENTAL TABLE 1

Example 3. Immunosuppressive treatment dosages and serum drug through levels.

|     | Dosage (mg/kg/d) | Trough levels ± SEM (ng/ml) | Target values (ng/ml) |
| --- | --- | --- | --- |
| TAC | 4 | 11.4 ± 3.6 | 10-15 |
| SIR | 3 | 11.6 ± 3.8 | 10-15 |
| MMF | 30 | 3.8 ± 1.2 | 3.5-5.5 |

TAC = Tacrolimus, SIR = Sirolimus, MMF = mycophenolate mofetil (n = 5 per group).

Example 4

Figure 30:
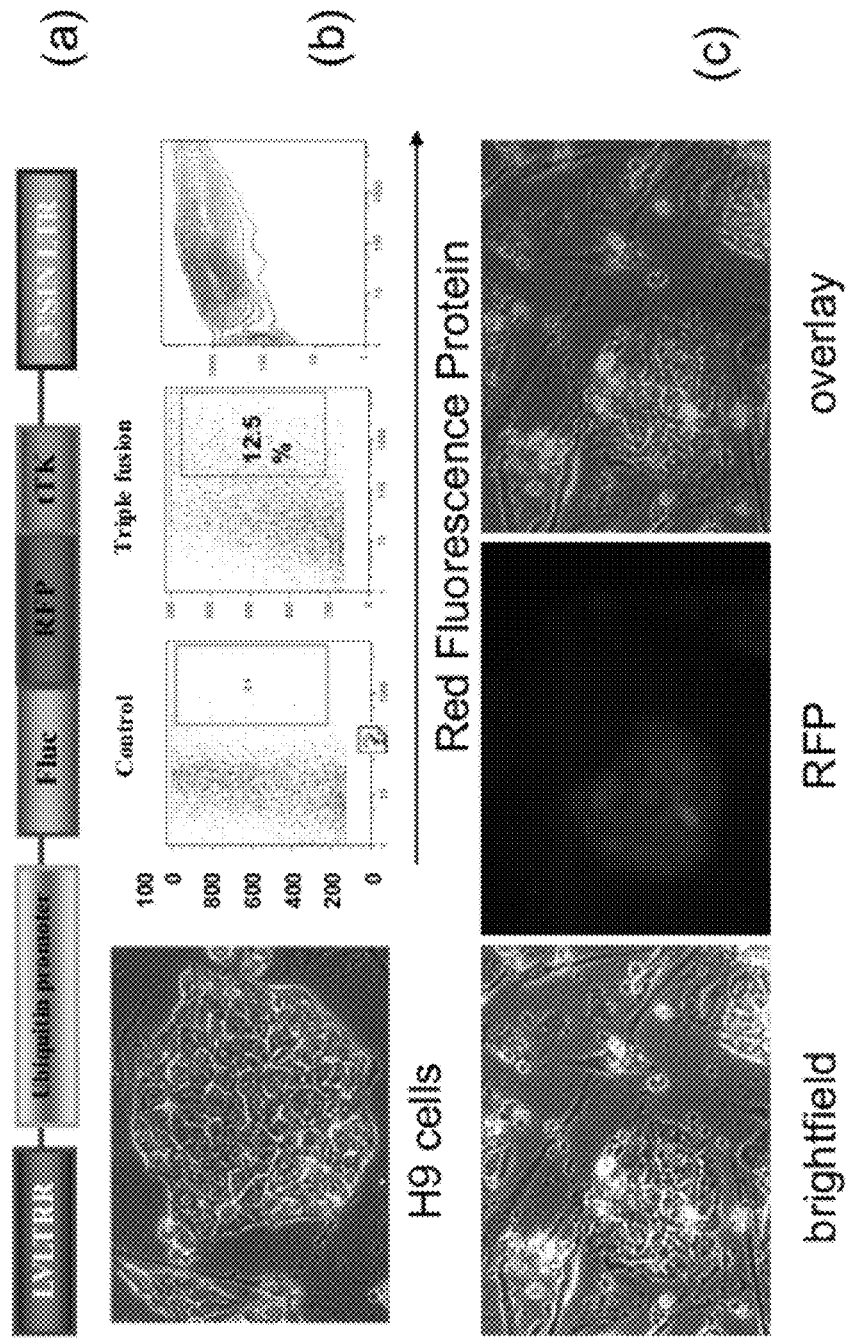

Stable lentiviral transduction of hESCs with the triple fusion (TF) reporter gene can be done. FIG. 30(*a*) is a achema of the TF reporter gene containing fusion of Fluc-RFP-HS-Vttk. The TF reporter gene was cloned into a SIN lentiviral vector downstream from the ubiquitin promoter. The three fusion proteins are joined by a 14-(LENSHASAGYQAST) (SEQ ID NO: 21) and 8-amino acid (TAGPGSAT) (SEQ ID NO: 22) linker, respectively. The Fluc is a bioluminescence reporter gene that allows imaging of cells in small animals. The RFP is a fluorescence reporter gene that allows FACS and single cell microscopy imaging. The HSVttk is a PET reporter gene that allows imaging of cells in small animal, large animal, and humans. FIG. 30(*b*) illustrates FACS histograms of hESCss 48 hours after transduction with lentivirus carrying the TF reporter gene shows ~12.5% RFP+ cells. FIG. 30(*c*) illustrates brightfiled and fluorescence images of stably transduced cells.

Figure 31:
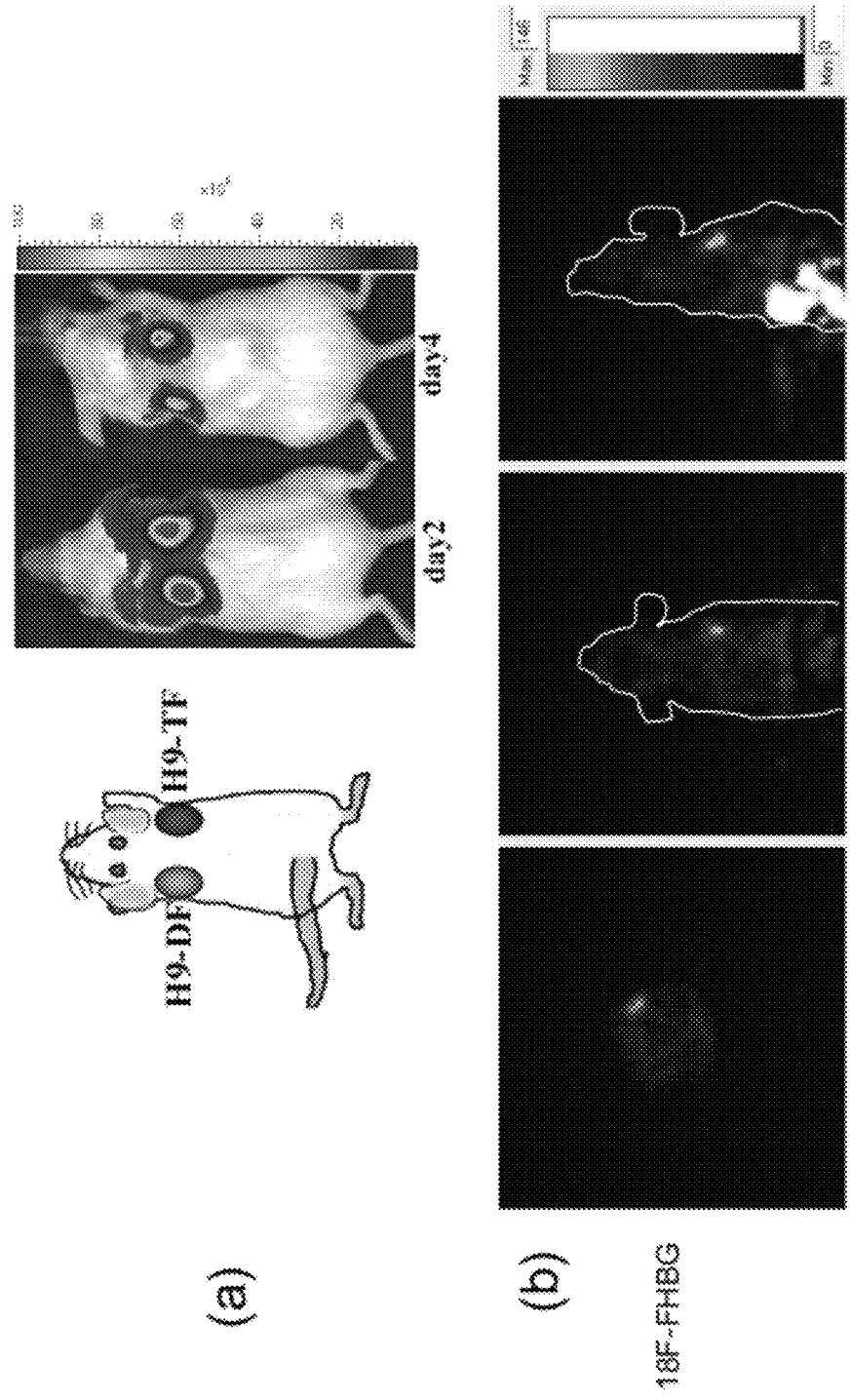

FIG. 31 shows imaging of hESCs stably transduced with double or triple fusion reporter gene. FIG. 31(*a*) illustrates that 1×10⁶ hESCs were transplanted into the shoulders of animals. Bioluminescence imaging at day 2 and 4 show robust signals in both shoulders. FIG. 31(*b*) illustrates a PET image at day 14 in coronal, horizontal, and sagittal views show signals in the right shoulder (triple fusion cells) but not left shoulder (double fusion cells lacking HSVttk).

FIG. 32 illustrates immunostaining of triple (Fluc-RFP—HSVttk) and double (Fluc-GFP) fusion hESCs confirms red fluorescence (left) and green fluorescence (right).

FIG. 33 illustrates the histology of explanted teratomas at 8 weeks show (I):squamous cell differentiation with keratin pearl; (II) respiratory epithelium with ciliated columnar and mucin producing goblet cells; (III):osteoid (non-mineralized bonn formation; (IV) cartilage formation; V:osteoid formation; and (VI): rosette consistent with neuroectodermal (400×).

SEQUENCES

```
SEQ ID NO: 1, Firefly luciferase nucleotide sequence
ATGGAAGACGCCAAAAACATAAAGAAAGGCCCGGCGCCATTCTATCCGCTGGAAGATGGA

ACCGCTGGAGAGCAACTGCATAAGGCTATGAAGAGATACGCCCTGGTTCCTGGAACAATT

GCTTTTACAGATGCACATATCGAGGTGGACATCACTTACGCTGAGTACTTCGAAATGTCCG

TTCGGTTGGCAGAAGCTATGAAACGATATGGGCTGAATACAAATCACAGAATCGTCGTATG

CAGTGAAAACTCTCTTCAATTCTTTATGCCGGTGTTGGGCGCGTTATTTATCGGAGTTGCA

GTTGCGCCCGCGAACGACATTTATAATGAACGTGAATTGCTCAACAGTATGGGCATTTCGC

AGCCTACCGTGGTGTTCGTTTCCAAAAAGGGGTTGCAAAAAATTTTGAACGTGCAAAAAAA

GCTCCCAATCATCCAAAAAATTATTATCATGGATTCTAAAACGGATTACCAGGGATTTCAGT
```

-continued

CGATGTACACGTTCGTCACATCTCATCTACCTCCCGGTTTTAATGAATACGATTTTGTGCCA

GAGTCCTTCGATAGGGACAAGACAATTGCACTGATCATGAACTCCTCTGGATCTACTGGTC

TGCCTAAAGGTGTCGCTCTGCCTCATAGAACTGCCTGCGTGAGATTCTCGCATGCCAGAG

ATCCTATTTTTGGCAATCAAATCATTCCGGATACTGCGATTTTAAGTGTTGTTCCATTCCATC

ACGGTTTTGGAATGTTTACTACACTCGGATATTTGATATGTGGATTTCGAGTCGTCTTAATG

TATAGATTTGAAGAAGAGCTGTTTCTGAGGAGCCTTCAGGATTACAAGATTCAAAGTGCGC

TGCTGGTGCCAACCCTATTCTCCTTCTTCGCCAAAAGCACTCTGATTGACAAATACGATTTA

TCTAATTTACACGAAATTGCTTCTGGTGGCGCTCCCCTCTCTAAGGAAGTCGGGGAAGCGG

TTGCCAAGAGGTTCCATCTGCCAGGTATCAGGCAAGGATATGGGCTCACTGAGACTACATC

AGCTATTCTGATTACACCCGAGGGGGATGATAAACCGGGCGCGGTCGGTAAAGTTGTTCC

ATTTTTTGAAGCGAAGGTTGTGGATCTGGATACCGGGAAAACGCTGGGCGTTAATCAAAGA

GGCGAACTGTGTGTGAGAGGTCCTATGATTATGTCCGGTTATGTAAACAATCCGGAAGCGA

CCAACGCCTTGATTGACAAGGATGGATGGCTACATTCTGGAGACATAGCTTACTGGGACGA

AGACGAACACTTCTTCATCGTTGACCGCCTGAAGTCTCTGATTAAGTACAAAGGCTATCAG

GTGGCTCCCGCTGAATTGGAATCCATCTTGCTCCAACACCCCAACATCTTCGACGCAGGTG

TCGCAGGTCTTCCCGACGATGACGCCGGTGAACTTCCCGCCGCCGTTGTTGTTTTGGAGC

ACGGAAAGACGATGACGGAAAAAGAGATCGTGGATTACGTCGCCAGTCAAGTAACAACCG

CGAAAAAGTTGCGCGGAGGAGTTGTGTTTGTGGACGAAGTACCGAAAGGTCTTACCGGAA

AACTCGACGCAAGAAAAATCAGAGAGATCCTCATAAAGGCCAAGAAGGGCGGAAAGATCG

CCGTGTAA

SEQ ID NO: 2, GFP nucleotide sequence
ATGGTGAGCAAGGGCGAGGAGCTGTTCACCGGGGTGGTGCCCATCCTGGTCGAGCT

GGACGGCGACGTAAACGGCCACAAGTTCAGCGTGTCCGGCGAGGGCGAGGGCGATG

CCACCTACGGCAAGCTGACCCTGAAGTTCATCTGCACCACCGGCAAGCTGCCCGTGC

CCTGGCCCACCCTCGTGACCACCCTGACCTACGGCGTGCAGTGCTTCAGCCGCTACC

CCGACCACATGAAGCAGCACGACTTCTTCAAGTCCGCCATGCCCGAAGGCTACGTCC

AGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAA

GGAGGACGGCAACATCCTGGGGCACAAGCTGGAGTACAACTACAACAGCCACAACG

TCTATATCATGGCCGACAAGCAGAAGAACGGCATCAAGGTGAACTTCAAGATCCGC

CACAACATCGAGGACGGCAGCGTGCAGCTCGCCGACCACTACCAGCAGAACACCCC

CATCGGCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTCGTGA

CCGCCGCCGGGATCACTCTCGGCATGGACGAGCTGTACAAGTAA

SEQ ID NO: 3, hFluc nucleotide sequence
ATGGAAGATGCCAAAAACATTAAGAAGGGCCCAGCGCCATTCTACCCACTC

GAAGACGGGACCGCCGGCGAGCAGCTGCACAAAGCCATGAAGCGCTACGC

CCTGGTGCCCGGCACCATCGCCTTTACCGACGCACATATCGAGGTGGACA

TTACCTACGCCGAGTACTTCGAGATGAGCGTTCGGCTGGCAGAAGCTATG

AAGCGCTATGGGCTGAATACAAACCATCGGATCGTGGTGTGCAGCGAGAA

TAGCTTGCAGTTCTTCATGCCCGTGTTGGGTGCCCTGTTCATCGGTGTGG

-continued

```
CTGTGGCCCCAGCTAACGACATCTACAACGAGCGCGAGCTGCTGAACAGC
ATGGGCATCAGCCAGCCCACCGTCGTATTCGTGAGCAAGAAAGGGCTGCA
AAAGATCCTCAACGTGCAAAAGAAGCTACCGATCATACAAAAGATCATCA
TCATGGATAGCAAGACCGACTACCAGGGCTTCCAAAGCATGTACACCTTC
GTGACTTCCCATTTGCCACCCGGCTTCAACGAGTACGACTTCGTGCCCGA
GAGCTTCGACCGGGACAAAACCATCGCCCTGATCATGAACAGTAGTGGCA
GTACCGGATTGCCCAAGGGCGTAGCCCTACCGCACCGCACCGCTTGTGTC
CGATTCAGTCATGCCCGCGACCCCATCTTCGGCAACCAGATCATCCCCGA
CACCGCTATCCTCAGCGTGGTGCCATTTCACCACGGCTTCGGCATGTTCA
CCACGCTGGGCTACTTGATCTGCGGCTTTCGGGTCGTGCTCATGTACCGC
TTCGAGGAGGAGCTATTCTTGCGCAGCTTGCAAGACTATAAGATTCAATC
TGCCCTGCTGGTGCCCACACTATTTAGCTTCTTCGCTAAGAGCACTCTCA
TCGACAAGTACGACCTAAGCAACTTGCACGAGATCGCCAGCGGCGGGGCG
CCGCTCAGCAAGGAGGTAGGTGAGGCCGTGGCCAAACGCTTCCACCTACC
AGGCATCCGCCAGGGCTACGGCCTGACAGAAACAACCAGCGCCATTCTGA
TCACCCCCGAAGGGGACGACAAGCCTGGCGCAGTAGGCAAGGTGGTGCCC
TTCTTCGAGGCTAAGGTGGTGGACTTGGACACCGGTAAGACACTGGGTGT
GAACCAGCGCGGCGAGCTGTGCGTCCGTGGCCCCATGATCATGAGCGGCT
ACGTTAACAACCCCGAGGCTACAAACGCTCTCATCGACAAGGACGGCTGG
CTGCACAGCGGCGACATCGCCTACTGGGACGAGGACGAGCACTTCTTCAT
CGTGGACCGGCTGAAGAGCCTGATCAAATACAAGGGCTACCAGGTAGCCC
CAGCCGAACTGGAGAGCATCCTGCTGCAACACCCCAACATCTTCGACGCC
GGGGTCGCCGGCCTGCCCGACGACGATGCCGGCGAGCTGCCCGCCGCAGT
CGTCGTGCTGGAACACGGTAAAACCATGACCGAGAAGGAGATCGTGGACT
ATGTGGCCAGCCAGGTTACAACCGCCAAGAAGCTGCGCGGTGGTGTTGTG
TTCGTGGACGAGGTGCCTAAAGGACTGACCGGCAAGTTGGACGCCCGCAA
GATCCGCGAGATTCTCATTAAGGCCAAGAAGGGCGGCAAGATCGCCGTGT
AA
```

SEQ ID NO: 4, hGFP nucleotide sequence

```
ATGGTGAGCAAGCAGATCCTGAAGAACACCGGCCTGCAGGAGATCATGAGCTTCAA
GGTGAACCTGGAGGGCGTGGTGAACAACCACGTGTTCACCATGGAGGGCTGCGGCA
AGGGCAACATCCTGTTCGGCAACCAGCTGGTGCAGATCCGCGTGACCAAGGGCGCC
CCCCTGCCCTTCGCCTTCGACATCCTGAGCCCCGCCTTCCAGTACGGCAACCGCACC
TTCACCAAGTACCCCGAGGACATCAGCGACTTCTTCATCCAGAGCTTCCCCGCCGGC
TTCGTGTACGAGCGCACCCTGCGCTACGAGGACGGCGGCCTGGTGGAGATCCGCAG
GACATCAACCTGATCGAGGAGATGTTCGTGTACCGCGTGGAGTACAAGGGCCGCAA
CTTCCCCAACGACGGCCCCGTGATGAAGAAGACCATCACCGGCCTGCAGCCCAGCT
TCGAGGTGGTGTACATGAACGACGGCGTGCTGGTGGGCCAGGTGATCCTGGTGTAC
CGCCTGAACAGCGGCAAGTTCTACAGCTGCCACATGCGCACCCTGATGAAGAGCAA
GGGCGTGGTGAAGGACTTCCCCGAGTACCACTTCATCCAGCACCGCCTGGAGAAGA
```

CCTACGTGGAGGACGGCGGCTTCGTGGAGCAGCACGAGACCGCCATCGCCCAGCTG

ACCAGCCTGGGCAAGCCCCTGGGCAGCCTGCACGAGTGGGTGTAA

SEQ ID NO: 5, Renilla Luciferse nucleotide sequence
ATGGCTTCGAAAGTTTATGATCCAGAACAAAGGAAACGGATGATAACTGGTCCGCA

GTGGTGGGCCAGATGTAAACAAATGAATGTTCTTGATTCATTTATTAATTATTATGA

TTCAGAAAAACATGCAGAAAATGCTGTTATTTTTTTACATGGTAACGCGGCCTCTTC

TTATTTATGGCGACATGTTGTGCCACATATTGAGCCAGTAGCGCGGTGTATTATACC

AGACCTTATTGGTATGGGCAAATCAGGCAAATCTGGTAATGGTTCTTATAGGTTACT

TGATCATTACAAATATCTTACTGCATGGTTTGAACTTCTTAATTTACCAAAGAAGATC

ATTTTTGTCGGCCATGATTGGGGTGCTTGTTTGGCATTTCA'TTATAGCTATGAGCATC

AAGATAAGATCAAAGCAATAGTTCACGCTGAAAGTGTAGTAGATGTGATTGAATCA

TGGGATGAATGGCCTGATATTGAAGAAGATATTGCGTTGATCAAATCTGAAGAAGG

AGAAAAAATGGTTTTGGAGAATAACTTCTTCGTGGAAACCATGTTGCCATCAAAAAT

CATGAGAAAGTTAGAACCAGAAGAATTTGCAGCATATCTTGAACCATTCAAAGAGA

AAGGTGAAGTTCGTCGTCCAACATTATCATGGCCTCGTGAAATCCCGTTAGTAAAAG

GTGGTAAACCTGACGTTGTACAAATTGTTAGGAATTATAATGCTTATCTACGTGCAA

GTGATGATTTACCAAAAATGTTTATTGAATCGGACCCAGGATTCTTTTCCAATGCTAT

TGTTGAAGGTGCCAAGAAGTTTCCTAATACTGAATTTGTCAAAGTAAAAGGTCTTCA

TTTTTCGCAAGAAGATGCACCTGATGAAATGGGAAAATATATCAAATCGTTCGTTGA

GCGAGTTCTCAAAAATGAACAAAGATCTACAAGTTTGTACAAAAAAGCTGAACGAG

AAACGTAA

SEQ ID NO: 6, mRFP nucleotide sequence
ATGGCCTCCTCCGAGGACGTCATCAAGTTCATGCGCTTCAAGGTGCGCATGGAGGGC

TCCGTGAACGGCCACGAGTTCGAGATCGAGGGCGAGGGCGAGGGCCGCCCCTACGA

GGGCACCCAGACCGCCAAGCTGAAGGTGACCAAGGGCGGCCCCCTGCCCTTCGCCT

GGGACATCCTGTCCCCTCAGTTCCAGTACGGCTCCAAGGCCTACGTGAAGCACCCCG

CCGACATCCCCGACTACTTGAAGCTGTCCTTCCCCGAGGGCTTCAAGTGGGAGCGCG

TGATGAACTTCGAGGACGGCGGCGTGGTGACCGTGACCCAGGACTCCTCCCTGCAG

GACGGCGAGTTCATCTACAAGGTGAAGCTGCGCGGCACCAACTTCCCCTCCGACGG

CCCCGTAATGCAGAAGAAGACCATGGGCTGGGAGGCCTCCACCGAGAGGATGTACC

CCGAGGACGGCGCCCTGAAGGGCGAGATCAAGATGAGGCTGAAGCTGAAGGACGG

CGGCCACTACGACGCCGAGGTCAAGACCACCTACATGGCCAAGAAGCCCGTGCAGC

TGCCCGGCGCCTACAAGACCGACATCAAGCTGGACATCACCTCCCACAACGAGGAC

TACACCATCGTGGAACAGTACGAGCGCGCCGAGGGCCGCCACTCCACCGGCGCCTA

A

SEQ ID NO: 7 TTK nucleotide sequence
ATG CCC ACG CTA CTG CGG GTT TAT ATA GAC GGT CCC CAC GGG ATG GGG AAA
ACC ACC ACC ACC ACG CAA CTG CTG GTG GCC CTG GGT TCG CGC GAC GAT ATC
GTC TAC GTA CCC GAG CCG ATG ACT TAC TGG CGG GTG CTG GGG GCT TCC GAG
ACA ATC GCG AAC ATC TAC ACC ACA CAA CAC CGC CTC GAC CAG GGT GAG ATA TCG
GCC GGG GAC GCG GCG GTG GTA ATG ACA AGC GCC CAG ATA ACA ATG CCT TAT
GCC GTG ACC GAC GCC GTT CTG GCT CCT CAT ATC GGG GGG GAG GCT GGG AGC -continued

```
TCA CAT GCC CCG CCC CCG GCC CTC ACC ATC TTC CTC GAC CGC CAT CCC ATC
GCC TTC ATG CTG TGC TAC CCG GCC GCG CGG TAC CTT ATG GGC AGC ATG ACC
CCC CAG GCC GTG CTG GCG TTC GTG GCC CTC ATC CCG CCG ACC TTG CCC GGC
ACC AAC ATC GTG CTT GGG GCC CTT CCG GAG GAC AGA CAC ATC GAC CGC CTG
GCC AAA CGC CAG CGC CCC GGC GAG CGG CTG GAC CTG GCT ATG CTG GCT GCG
ATT CGC CGC GTT TAC GGG CTA CTT GCC AAT ACG GTG CGG TAT CTG CAG TGC
GGC GGG TCG TGG CGG GAG GAC TGG GGA CAG CTT TCG GGG ACG GCC GTG CCG
CCC CAG GGT GCC GAG CCC CAG AGC AAC GCG GGC CCA CGA CCC CAT ATC GGG
GAC ACG TTA TTT ACC CTG TTT CGG GCC CCC GAG TTC ATG GCC CCC AAC GGC
GAC CTG TAT AAC GTG TTT GCC TGG GCC TTG GAC GTC TTG GCC AAA CGC CTC CGT
TCC ATG CAC GTC TTT ATC CTG GAT TAC GAC CAA TCG CCC GCC GGC TGC CGG
GAC GCC CTG CTG CAA CTT ACC TCC GGG ATG GTC CAG ACC CAC GTC ACC ACC
CCC GGC TCC ATA CCG ACG ATA TGC GAC CTG GCG CGC ACG TTT GCC CGG GAG
ATG GGG GAG GCT AAC TGA
```

SEQ ID NO: 8, Ub-Fluc-rfp-Ttk nucleic acid sequence
```
ATGGAAGACGCCAAAAACATAAAGAAAGGCCCGGCGCCATTCTATCCTCTAGAGGATGGAACCGCT
GGAGAGCAACTGCATAAGGCTATGAAGAGATACGCCCTGGTTCCTGGAACAATTGCTTTTACAGATG
CACATATCGAGGTGAACATCACGTACGCGGAATACTTCGAAATGTCCGTTCGGTTGGCAGAAGCTAT
GAAACGATATGGGCTGAATACAAATCACAGAATCGTCGTATGCAGTGAAAACTCTCTTCAATTCTTTA
TGCCGGTGTTGGGCGCGTTATTTATCGGAGTTGCAGTTGCGCCCGCGAACGACATTTATAATGAACG
TGAATTGCTCAACAGTATGAACATTTCGCAGCCTACCGTAGTGTTTGTTTCCAAAAAGGGGTTGCAAA
AAATTTTGAACGTGCAAAAAAAATTACCAATAATCCAGAAAATTATTATCATGGATTCTAAAACGGATT
ACCAGGGATTTCAGTCGATGTACACGTTCGTCACATCTCATCTACCTCCCGGTTTTAATGAATACGAT
TTTGTACCAGAGTCCTTTGATCGTGACAAAACAATTGCACTGATAATGAATTCCTCTGGATCTACTGG
GTTACCTAAGGGTGTGGCCCTTCCGCATAGAGCTGCCTGCGTCAGATTCTCGCATGCCAGAGATCC
TATTTTTGGCAATCAAATCGCTCCGGATACTGCGATTTTAAGTGTTGTTCCATTCCATCACGGTTTTG
GAATGTTTACTACACTCGGATATTTGATATGTGGATTTCGAGTCGTCTTAATGTATAGATTTGAAGAAG
AGCTGTTTTTACGATCCCTTCAGGATTACAAAATTCAAAGTGCGTTGCTAGTACCAACCCTATTTTCAT
TCCTGGCCAAAAGCACTCTGATTGACAAATACGATTTATCTAATTTACACGAAATTGCTTCTGGGGGC
GCACCTCTTTCGAAAGAAGTCGGGGAAGCGGTTGCAAAACGCTTCCATCTTCCAGGGATACGACAA
GGATATGGGCTCACTGAGACTACATCAGCTATTCTGATTACACCCAAGGGGGATGATAAACCGGGC
GCGGTCGGTAAAGTTGTTCCATTTTTTGAAGCGAAGGTTGTGGATCTGGATACCGGGAAAACGCTGG
GCGTTAATCAGAGAGGCGAATTATGTGTCAGAGGACCTATGATTATGTCCGGTTATGTAAACAATCC
GGAAGCGACCAACGCCTTGATTGACAAGGATGGATGGCTACATTCTGGAGACATAGCTTACTGGGA
CGAAGACGAACACTTCTTCATAGTTGACCGCTTGAAGTCTTTAATTAAATACAAAGGATATCAGGTGG
CCCCCGCTGAATTGGAATCGATATTGTTACAACACCCCAACATCTTCGACGCGGGCGTGGCAGGTCT
TCCCGACGATGACGCCGGTGAACTTCCCGCCGCCGTTGTTGTTTTGGAGCACGGAAAGACGATGAC
GGAAAAAGAGATCGTGGATTACGTCGCCAGTCAAGTAACAACCGCGAAAAAGTTGCGCGGAGGAGT
TGTGTTTGTGGACGAAGTACCGAAAGGTCTTACCGGAAAACTCGACGCAAGAAAAATCAGAGAGATC
CTCATAAAGGCCAAGAAGGGCGGAAAGTCCAAATTG GAAATCATAATGAGA ATG GCC TCC TCC
GAG GAC GTC ATC AAG GAG TTC ATG CGC TTC AAG GTG CGC ATG GAG GGC TCC
```

-continued

<u>GTG AAC GGC CAC GAG</u> TTC GAG ATC GAG GGC GAG GGC GAG GGC CGC CCC TAC
GAG GGC ACC CAG ACC GCC AAG CTG AAG GTG ACC AAG GGC GGC CCC CTG CCC
TTC GCC TGG GAC ATC CTG TCC CCT CAG TTC CAG TAC GGC TCC AAG GCC TAC
GTG AAG CAC CCC GCC GAC ATC CCC GAC TAC TTG AAG CTG TCC TTC CCC GAG
GGC TTC AAG TGG GAG CGC GTG ATG AAC TTC GAG GAC GGC GGC GTG GTG ACC
GTG ACC CAG GAC TCC TCC CTG CAG GAC GGC GAG TTC ATC TAC AAG GTG AAG
CTG CGC GGC ACC AAC TTC CCC TCC GAC GGC CCC GTA ATG CAG AAG AAG ACC
ATG GGC TGG GAG GCC TCC ACC GAG CGG ATG TAC CCC GAG GAC GGC GCC CTG
AAG GGC GAG ATC AAG ATG AGG CTG AAG CTG AAG GAC GGC GGC CAC TAC GAC
GCC GAG GTC AAG ACC ACC TAC ATG GCC AAG AAG CCC GTG CAG CTG CCC GGC
GCC TAC AAG ACC GAC ATC AAG CTG GAC ATC ACC TCC CAC AAC GAG GAC TAC
ACC ATC GTG GAA CAG TAC GAG CGC GCC <u>GAG GGC CGC CAC TCC</u> ACC GGC GCC
<u>ACC GCG GGC CCG GGA TCC GCC ACC</u> ATG CCC ACG CTA CTG CGG GTT TAT ATA
GAC GGT CCC CAC GGG ATG <u>GGG AAA ACC ACC ACC ACC</u> ACG CAA CTG CTG GTG
GCC CTG GGT TCG CGC GAC GAT ATC GTC TAC GTA CCC GAG CCG ATG ACT TAC
TGG CGG GTG CTG GGG GCT TCC GAG ACA ATC GCG AAC ATC TAC ACC ACA CAA
CAC CGC CTC GAC CAG GGT GAG ATA TCG GCC GGG GAC GCG GCG GTG GTA ATG
ACA AGC GCC CAG ATA ACA ATG CCT TAT GCC GTG ACC GAC GCC GTT CTG GCT CCT
CAT ATC GGG GGG GAG GCT GGG AGC TCA CAT GCC CCG CCC CCG GCC CTC ACC
<u>A</u>TC <u>T</u>TC <u>C</u>TC GAC CGC CAT CCC ATC GCC <u>T</u>TC <u>A</u>TG CTG TGC TAC CCG GCC GCG
CGG TAC CTT ATG GGC AGC ATG ACC CCC CAG GCC GTG CTG GCG TTC GTG GCC
CTC ATC CCG CCG ACC TTG CCC GGC ACC AAC ATC GTG CTT GGG GCC CTT CCG
GAG GAC AGA CAC ATC GAC CGC CTG GCC AAA CGC CAG CGC CCC GGC GAG CGG
CTG GAC CTG GCT ATG CTG GCT GCG ATT CGC CGC GTT TAC GGG CTA CTT GCC
AAT ACG GTG CGG TAT CTG CAG TGC GGC GGG TCG TGG CGG GAG GAC TGG GGA
CAG CTT TCG GGG ACG GCC GTG CCG CCC CAG GGT GCC GAG CCC CAG AGC AAC
GCG GGC CCA CGA CCC CAT ATC GGG GAC ACG TTA TTT ACC CTG TTT CGG GCC
CCC GAG TTG ATG GCC CCC AAC GGC GAC CTG TAT AAC GTG TTT GCC TGG GCC
TTG GAC GTC TTG GCC AAA CGC CTC CGT TCC ATG CAC GTC TTT ATC CTG GAT TAC
GAC CAA TCG CCC GCC GGC TGC CGG GAC GCC CTG CTG CAA CTT ACC TCC GGG
ATG GTC CAG ACC CAC GTC ACC ACC CCC GGC TCC ATA CCG ACG ATA TGC GAC
CTG GCG CGC ACG TTT GCC CGG GAG ATG GGG GAG GCT AAC TGA

SEQ ID NO: 9, Ub-Fluc-rfp-Ttk protein sequence
MEDAKNIKKGPAPFYPLEDGTAGEQLHKAMKRYALVPGTIAFTDAHIEVNITYAEYFEMSVRLAE

AMKRYGLNINHRIVVCSENSLQFFMPVLGALFIGVAVAPANDIYNERELLNSMNISQPTVVFVS

KKGLQKILNVQKKLPIIQKIIIMDSKTDYQGFQSMYTFVTSHLPPGFNEYDFVPESFDRDKTIALIM

NSSGSTGLPKGVALPHRAACVRFSHARDPIFGNQIAPDTAILSVVPFHHGFGMFTTLGYLICGF

RVVLMYRFEEELFLRSLQDYKIQSALLVPTLFSFLAKSTLIDKYDLSNLHEIASGGAPLSKEVGEA

VAKRFHLPGIRQGYGLTETTSAILITPKGDDKPGAVGKVVPFFEAKVVDLDTGKTLGVNQRGEL

CVRGPMIMSGYVNNPEATNALIDKDGWLHSGDIAYWDEDEHFFIVDRLKSLIKYKGYQVAPAEL

ESILLQHPNIFDAGVAGLPDDDAGELPAAVVVLEHGKTMTEKEIVDYVASQVTTAKKLRGGVVF

VDEVPKGLTGKLDARKIREILIKAKKGGKSKLEAAARMASSEDVIKEFMRFKVRMEGSVNGHEF

EIEGEGEGRPYEGTQTAKLKVTKGGPLPFAWDILSPQFQYGSKAYVKHPADIPDYLKLSFPEGF

KWERVMNFEDGGVVTVTQDSSLQDGEFIYKVKLRGTNFPSDGPVMQKKTMGWEASTERMYP

EDGALKGEIKMRLKLKDGGHYDAEVKTTYMAKKPVQLPGAYKTDIKLDITSHNEDYTIVEQYER

AEGRHSTGATAGPGSATMPTLLRVYIDGPHGMGKTTTTTQLLVALGSRDDIVYVPEPMTYWRV

LGASETIANIYTTQHRLDQGEISAGDAAVVMTSAQITMPYAVTDAVLAPHIGGEAGSSHAPPPAL

TIFLDRHPIAFMLCYPAARYLMGSMTPQAVLAFVALIPPTLPGTNIVLGALPEDRHIDRLAKRQRP

GERLDLAMLAAIRRVYGLLANTVRYLQCGGSWREDWGQLSGTAVPPQGAEPQSNAGPRPHIG

DTLFTLFRAPELMAPNGDLYNVFAWALDVLAKRLRSMHVFILDYDQSPAGCRDALLQLTSGMV

QTHVTTPGSIPTICDLARTFAREMGEAN

SEQ ID NO: 10, LV-pUP-Fluc-eGFP polynucleotide sequence
AACCCGTGTCGGCTCCAGATCTGGCCTCCGCGCCGGGTTTTGGCGCCTCCCGCGGGCGC

CCCCCTCCTCACGGCGAGCGCTGCCACGTCAGACGAAGGGCGCAGCGAGCGTCCTGATC

CTTCCGCCCGGACGCTCAGGACAGCGGCCCGCTGCTCATAAGACTCGGCCTTAGAACCC

CAGTATCAGCAGAAGGACATTTTAGGACGGGACTTGGGTGACTCTAGGGCACTGGTTTTCT

TTCCAGAGAGCGGAACAGGCGAGGAAAAGTAGTCCCTTCTCGGCGATTCTGCGGAGGGAT

CTCCGTGGGCGGTGAACGCCGATGATTATATAAGGACGCGCCGGGTGTGGCACAGCTA

GTTCCGTCGCAGCCGGGATTTGGGTCGCGGTTCTTGTTTGTGGATCGCTGTGATCGTCAC

TTGGTGAGTAGCGGGCTGCTGGGCTGGCCGGGGCTTTCGTGGCCGCCGGGCCGCTCGG

TGGGACGGAAGCGTGTGGAGAGACCGCCAAGGGCTGTAGTCTGGGTCCGCGAGCAAGGT

TGCCCTGAACTGGGGGTTGGGGGGAGCGCACAAAATGGCGGCTGTTCCCGAGTCTTGAA

TGGAAGACGCTTGTGAGGCGGGCTGTGAGGTCGTTGAAACAAGGTGGGGGGCATGGTGG

GCGGCAAGAACCCAAGGTCTTGAGGCCTTCGCTAATGCGGGAAAGCTCTTATTCGGGTGA

GATGGGCTGGGGCACCATCTGGGGACCCCTGACGTGAAGTTTGTCACTGACTGGAGAAAC

TCGGGTTTGTCGTCTGTTGCGGGGCGGCAGTTATGGCGGTGCCGTTGGGCAGTGCACC

CGTACCTTTGGGAGCGCGCGCCCTCGTCGTGTCGTGACGTCACCCGTTCTGTTGGCTTAT

AATGCAGGGTGGGGCCACCTGCCGGTAGGTGTGCGGTAGGCTTTTCTCCGTCGCAGGAC

GCAGGGTTCGGGCCTAGGGTAGGCTCTCCTGAATCGACAGGCGCCGGACCTCTGGTGAG

GGGAGGGATAAGTGAGGCGTCAGTTTCTTTGGTCGGTTTTATGTACCTATCTTCTTAAGTA

GCTGAAGCTCCGGTTTTGAACTATGCGCTCGGGGTTGGCGAGTGTGTTTTGTGAAGTTTTT

TAGGCACCTTTTGAAATGTAATCATTTGGGTCAATATGTAATTTTCAGTGTTAGACTAGTAAA

TTGTCCGCTAAATTCTGGCCGTTTTTGGCTTTTTTGTTAGACATGGAAGACGCCAAAAACAT

AAAGAAAGGCCCGGCGCCATTCTATCCGCTGGAAGATGGAACCGCTGGAGAGCAACTGCA

TAAGGCTATGAAGAGATACGCCCTGGTTCCTGGAACAATTGCTTTTACAGATGCACATATC

GAGGTGGACATCACTTACGCTGAGTACTTCGAAATGTCCGTTCGGTTGGCAGAAGCTATGA

AACGATATGGGCTGAATACAAATCACAGAATCGTCGTATGCAGTGAAAACTCTCTTCAATTC

TTTATGCCGGTGTTGGGCGCGTTATTTATCGGAGTTGCAGTTGCGCCCGCGAACGACATTT

ATAATGAACGTGAATTGCTCAACAGTATGGGCATTTCGCAGCCTACCGTGGTGTTCGTTTC

CAAAAAGGGGTTGCAAAAAATTTTGAACGTGCAAAAAAAGCTCCCAATCATCCAAAAAATTA

TTATCATGGATTCTAAAACGGATTACCAGGGATTTCAGTCGATGTACACGTTCGTCACATCT

CATCTACCTCCCGGTTTTAATGAATACGATTTTGTGCCAGAGTCCTTCGATAGGGACAAGA

```
CAATTGCACTGATCATGAACTCCTCTGGATCTACTGGTCTGCCTAAAGGTGTCGCTCTGCC

TCATAGAACTGCCTGCGTGAGATTCTCGCATGCCAGAGATCCTATTTTTGGCAATCAAATCA

TTCCGGATACTGCGATTTTAAGTGTTGTTCCATTCCATCACGGTTTTGGAATGTTTACTACA

CTCGGATATTTGATATGTGGATTTCGAGTCGTCTTAATGTATAGATTTGAAGAAGAGCTGTT

TCTGAGGAGCCTTCAGGATTACAAGATTCAAAGTGCGCTGCTGGTGCCAACCCTATTCTCC

TTCTTCGCCAAAAGCACTCTGATTGACAAATACGATTTATCTAATTTACACGAAATTGCTTCT

GGTGGCGCTCCCCTCTCTAAGGAAGTCGGGGAAGCGGTTGCCAAGAGGTTCCATCTGCCA

GGTATCAGGCAAGGATATGGGCTCACTGAGACTACATCAGCTATTCTGATTACACCCGAGG

GGGATGATAAACCGGGCGCGGTCGGTAAAGTTGTTCCATTTTTTGAAGCGAAGGTTGTGG

ATCTGGATACCGGGAAAACGCTGGGCGTTAATCAAAGAGGCGAACTGTGTGTGAGAGGTC

CTATGATTATGTCCGGTTATGTAAACAATCCGGAAGCGACCAACGCCTTGATTGACAAGGA

TGGATGGCTACATTCTGGAGACATAGCTTACTGGGACAAGACGAACACTTCTTCATCGTT

GACCGCCTGAAGTCTCTGATTAAGTACAAAGGCTATCAGGTGGCTCCCGCTGAATTGGAAT

CCATCTTGCTCCAACACCCCAACATCTTCGACGCAGGTGTCGCAGGTCTTCCCGACGATG

ACGCCGGTGAACTTCCCGCCGCCGTTGTTGTTTTGGAGCACGGAAAGACGATGACGGAAA

AAGAGATCGTGGATTACGTCGCCAGTCAAGTAACAACCGCGAAAAAGTTGCGCGGAGGAG

TTGTGTTTGTGGACGAAGTACCGAAAGGTCTTACCGGAAAACTCGACGCAAGAAAAATCAG

AGAGATCCTCATAAAGGCCAAGAAGGGCGGAAAGATCGCCGTGTAATTCGGATCCCACGG

CGATATGAGCGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTGCCC

TGGCCCACCCTCGTGACCACCCTGACCTACGGCGTGCAGTGCTTCAGCCGCTACCCCGAC

CACATGAAGCAGCACGACTTCTTCAAGTCCGCCATGCCCGAAGGCTACGTCCAGGAGCGC

ACCATCTTCTTCAAGGACGACGGCAACTACAAGACCCGCGCCGAGGTGAAGTTCGAGGGC

GACACCCTGGTGAACCGCATCGAGCTGAAGGGCATCGACTTCAAGGAGGACGGCAACATC

CTGGGGCACAAGCTGGAGTACAACTACAACAGCCACAACGTCTATATCATGGCCGACAAG

CAGAAGAACGGCATCAAGGTGAACTTCAAGATCCGCCACAACATCGAGGACGGCAGCGTG

CAGCTCGCCGACCACTACCAGCAGAACACCCCCATCGGCGACGGCCCCGTGCTGCTGCC

CGACAACCACTACCTGAGCACCCAGTCCGCCCTGAGCAAAGACCCCAACGAGAAGCGCG

ATCACATGGTCCTGCTGGAGTTCGTGACCGCCGCCGGGATCACTCTCGGCATGGACGAGC

TGTACAAAAT

SEQ ID NO: 11, LV-pUP-Fluc-eGFP protein sequence
GRRQKHKERPGAILSAGRWNRWRATAGYEEIRPGSWNNCFYRCTYRGGHHLRVLRNIVRSVG

RSYETIWAEYKSQNRRMQKLSSILYAGVGRVIYRSCSCARERHLTIAQQYGHFAAYRGVRFQK

GVAKNFERAKKAPNHPKNYYHGFNGLPGISVDVHVRHISSTSRFIRFCARVLRGQDNCTDHEL

LWIYWSARCRSASNCLREILACQRSYFWQSNHSGYCDFKCCSIPSRFWNVYYTRIFDMWISSR

LNVIRRAVSEEPSGLQDSKCAAGANPILLLRQKHSDQIRFIFTRNCFVVWRSPLGSRGSGCQEV

PSARYQARIWAHDYISYSDYTRGGTGRGRSCSIFSEGCGSGYRENAGRSKRRTVCERSYDYV

RLCKQSGSDQRLDQGWMATFWRHSLLGRRRTLLHRPPEVSDVQRLSGGSRIGIHLAPTPQHL

RRRCRRSSRRRRTSRRRCCFGARKDDDGKRDRGLRRQSSNNREKVARRSCVCGRSTERSY

RKTRRKKNQRDPHKGQEGRKDRRVIRIPRRYEREQGRGAVHRGGAHPGRAGRRRKRPQVQ
```

RVRRGRGRCHLRQADPEVHLHHRQAARALAHPRDHPDLRRAVLQPLPRPHEAARLLQVRHA

RRLRPGAHHLLQGRRQLQDPRRGEVRGRHPGEPHRAEGHRLQGGRQHPGAQAGVQLQQP

QRLYHGRQAEERHQGELQDPPQHRGRQRAARRPLPAEHPHRRRPRAAARQPLPEHPVRPE

QRPQREARSHGPAGVRDRRRDHSRHGRAVQN

SEQ ID NO: 12, HSV1-TK nuclei acid sequence (accession No. ACC91769.1)
ATGGCTTCGTACCCCGGCCATCAACACGCGTCTGCGTTCGACCAGGCTGCGCGTTCT

CGCGGCCATAGCAACCGACGTACGGCGTTGCGCCCTCGCCGGCAGCAAGAAGCCAC

GGAAGTCCGCCCGGAGCAGAAAATGCCCACGCTACTGCGGGTTTATATAGACGGTC

CCCACGGGATGGGGAAAACCACCACCACGCAACTGCTGGTGGCCCTGGGTTCGCGC

GACGATATCGTCTACGTACCCGAGCCGATGACTTACTGGCGGGTGCTGGGGGCTTCC

GTGCTACCCGGCCGCGCGGTACCTTATGGGCAGCATGACCCCCCAGGCCGTGCTGGC

GTTCGTGGCCCTCATCCCGCCGACCTTGCCCGGCACCAACATCGTGCTTGGGGCCCT

TCCGGAGGACAGACACATCGACCGCCTGGCCAAACGCCAGCGCCCCGGCGAGCGGC

TGGACCTGGCTATGCTGGCTGCGATTCGCCGCGTTTACGGGCTACTTGCCAATACGG

TGCGGTATCTGCAGTGCGGCGGGTCGTGGCGGGAGGACTGGGGACAGCTTTCGGGG

ACGGCCGTGCCGCCCCAGGGTGCCGAGCCCCAGAGCAACGCGGGCCCACGACCCCA

TATCGGGACACGTTATTTACCCTTTCGGGCCCCGAGTTGCTGGCCCCAACGG

CGACCTGTATAACGTGTTTGCCTGGGCCTTGGACGTCTTGGCCAAACGCCTCCGTTC

CATGCACGTCTTTATCCTGGATTTACGACCAATCGCCCGCCGGCTGCCGGGACGCCCT

GCTGCAACTTACCTCCGGGATGGTCCAGACCCACGTCACCACCCCCGGCTCCATACC

GACGATATGCGACCTGGCGCGCACGTTTGCCCGGGAGATGGGGGAGGCTAACTGA

SEQ ID NO: 13, HSV-1TK protein sequence
GFVPRPSTRVCVRPGCAFSRPQPTYGVAPSPAARSHGSPPGAENAHATAGLYRRSPRDGEN

HHHATAGGPGFARRYRLRTRADDLLAGAGGFRATRPRGTLWAAPPRPCWRSWPSSRRPCP

APTSCLGPFRRIDTSTAWPNASAPASGVVTWLCWLRFAAFTGYLPIRCGICSAAGRGGRTGDS

FRGRPCRPRVPSPRATRAHDPISGTRYLPCFGPPSCWPPTATCITCLPGPVVTSWPNASVPCT

SLSWITTNRPPAAGTPCCNLPPGWSRPTSPPPAPYRRYATWRARLPGRWGRLTE

SEQ ID NO: 14, tTK nuclei acid sequence (accession No. BAD20746.1)
ATGGCTTCTCACGCCGGCCAACAGCACGCGCCTGCGTTCGGTCAGGCTGCTCGTGCG

AGCGGGCCTACCGACGGCCGCGCGGCGTCCCGTCCTAGCCATCGCCAGGGGCCTC

CGGAGCCCGCGGGGATCCGGAGCTGCCCACGCTGCTGCGGGTTTATATAGACGGAC

CCCACGGGGTGGGGAAGACCACCACCTCCGCGCAGCTGATGGAGGCCCTGGGGCCG

CGCGACAATATCGTCTACGTCCCCGAGCCGATGACTTACTGGCAGGTGCTGGGGGCC

TCCGAGACCCTGACGAACATCTACAACACGCAGCACCGTCTGGACCGCGGCGAGAT

ATCGGCCGGGGAGGCGGCGGTGGTAATGACCAGCGCCCAGATAACAATGAGCACGC

CTTATGCGGCGACGGACGCCGTTTTGGCTCCTCATATCGGGGGGGAGGCTGTGGGCC

CGCAAGCCCCGCCCCGGCCCTCACCCTTGTTTTCGACCGGCACCCTATCGCCTCCCT

GCTGTGCTACCGGCCGCGCGGTACCTCATGGGAAGCATGACCCCCCAGGCCGTGTT

GGCGTTCGTGGCCCTCATGCCCCCGACCGCGCCCGGCACGAACCTGGTCCTGGGTGT

CCTTCCGGAGGCCGAACACGCCGACCGCCTGGCCAGACGCCAACGCCCGGGCGAGC

GGCTTGACCTGGCCATGCTGTCCGCCATTCGCCGTGTCTACGATCTACTCGCCAACA

CGGTGCGGTACCTGCAGCGCGGCGGGAGGTGGCGGGAGGACTGG

SEQ ID NO: 15, tTK protein sequence
GFSRRPTARACVRSGCSCERAYRRPRGVPSPSPGGLRSPRGSGAAHAAAGLYRRTPRGG

EDHHLRAADGGPGAARQYRLRPRADDLLAGAGGLRDPDEHLQHAAPSGPRRDIGRGG

GGGNDQRPDNNEHALCGDGRRFGSSYRGGGCGPASPAPGPHPCFRPAPYRLPAVLPGR

AVPHGKHDPPGRVGVRGPHAPDRAREEPGPGCPSGGRTRRPPGQTPTPGRAAPGHAVR

HSPCLRSTRQHGAVPAARREVAGGLGPADGGRRGDPAPDPEDGAGSLPRIEDTLFALFR

VPELLAPNGDLYHIFAWVLDVLADRLLPMHLFVLDYDQSPVGCRDALLRLTAGMIPTR

VTTAGSIAEIRDLARTFAREVGGV

SEQ ID NO: 16, LV nucleotide sequence
TAATCAACCTCTGGATTACAAAATTTGTGAAAGATTGACTGGTATTCTTAACTATGTT

GCTCCTTTTACGCTATGTGGATACGCTGCTTTAATGCCTTTGTATCATGCTATTGCTT

CCCGTATGGCTTTCATTTTCTCCTCCTTGTATAAATCCTGGTTGCTGTCTCTTTATGAG

GAGTTGTGGCCCGTTGTCAGGCAACGTGGCGTGGTGTGCACTGTGTTTGCTGACGCA

ACCCCCACTGGTTGGGGCATTGCCACCACCTGTCAGCTCCTTTCCGGGACTTTCGCTT

TCCCCCTCCCTATTGCCACGGCGGAACTCATCGCCCGCCTGCCTTGCCCGCTGCTGG

ACAGGGGCTCGGCTGTTGGGCACTGACAATTCCGTGGTGTTGTCGGGGAAATCATCG

TCCTTTCTTGGCTGCTCGCCTGTGTTGCCACCTGGATTCTGCGCGGGACGTCCTTCT

GCTACGTCCTTCGGCCCTCAATCCAAGCGGACCTTCCTTCCCGCGGCCTGCTGCCGG

CTCTGCGGGCCTCTTCCGCGTCTTTCGCCTTCGCCCTCAGACGAGTCGGATCTCCCTT

TGGGCGCTCCCCGCATCGATGTCGACCTCGAGACCGGCCGAACTCGAAGACCTAGA

AAAAACATTGGAGCAATCACAAGTAGCAATACAGCAGCTACCAATGCTGATTGTGC

CTGGCTAGAAGCACAAGAGGAGGAGGAGGTGGGTTTTCCAGTCACACCTCAGGTAC

CTTTAAGACCAATGACTTACAAGGCAGCTGTAGATCTTAGCCACTTTTTAAAAGAAA

AGGGGGGACTGGAAGGGCTAATTCACTCCCAACGAAGACAAGATATCCTTGATCTG

TGGATCTACCACACACAAGGCTACTTCCCTGATTGGCAGAACTACACACCAGGGCC

AGGGATCAGATATCCACTGACCTTTGGATGGTGCTACAAGCTAGTACCAGTTGAGCA

AGAGAAGGTAGAAGAAGCCAATGAAGGAGAGAACACCCGCTTGTTACACCCTGTGA

GCCTGCATGGGATGGATGACCCGGAGAGAGAAGTATTAGAGTGGAGGTTTGACAGC

CGCCTAGCATTTCATCACATGGCCCGAGAGCTGCATCCGGACTGTACTGGGTCTCTC

TGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGT

GACTCTGGTAACTAGAGATCCCTCAGACCCTTTTAGTCAGTGTGGAAAATCTCTAGC

AGGGCCCGTTTAAACCCGCTGATCAGCCTCGACTGTGCCTTCTAGTTGCCAGCCATC

TGTTGTTTGCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCATTCTATTC

TGGGGGGTGGGGTGGGGCAGGACAGCAAGGGGGAGGATTGGGAAGACAATAGCAG

GCATGCTGGGGATGCGGTGGGCTCTATGGCTTCTGAGGCGGAAAGAACCAGCTGGG

GCTCTAGGGGGTATCCCCACGCGCCCTGTAGCGGCGCATTAAGCGCGGCGGGTGTG

GTGGTTACGCGCAGCGTGACCGCTACACTTGCCAGCGCCCTAGCGCCCGCTCCTTTC

GCTTTCTTCCCTTCCTTTCTCGCCACGTTCGCCGGCTTTCCCCGTCAAGCTCTAAATC

GGGGCATCCCTTTAGGGTTCCGATTTAGTGCTTTACGGCACCTCGACCCCAAAAAAC

-continued
TTGATTAGGGTGATGGTTCACGTAGTGGGCCATCGCCCTGATAGACGGTTTTTCGCC
CTTTGACGTTGGAGTCCACGTTCTTTAATAGTGGACTCTTGTTCCAAACTGGAACAA
CACTCAACCCTATCTCGGTCTATTCTTTTGATTTATAAGGGATTTTGGGGATTTCGGC
CTATTGGTTAAAAAATGAGCTGATTTAACAAAAATTTAACGCGAATTAATTCTGTGG
AATGTGTGTCAGTTAGGGTGTGGAAAGTCCCCAGGCTCCCCAGCAGGCAGAAGTAT
GCAAAGCATGCATCTCAATTAGTCAGCAACCAGGTGTGGAAAGTCCCCAGGCTCCC
CAGCAGGCAGAAGTATGCAAAGCATGCATCTCAATTAGTCAGCAACCATAGTCCCG
CCCCTAACTCCGCCCATCCCGCCCCTAACTCCGCCCAGTTCCGCCCATTCTCCGCCCC
ATGGCTGACTAATTTTTTTATTTATGCAGAGGCCGAGGCCGCCTCGGCCTCTGAGCT
ATTCCAGAAGTAGTGAGGAGGCTTTTTTGGAGGCCTAGGCTTTTGCAAAAAGCTCCC
GGGAGCTTGTATATCCATTTTCGGATCTGATCAGCACGTGTTGACAATTAATCATCG
GCATAGTATATCGGCATAGTATAATACGACAAGGTGAGGAACTAAACCATGGCCAA
GTTGACCAGTGCCGTTCCGGTGCTCACCGCGCGCGACGTCGCCGGAGCGGTCGAGTT
CTGGACCGACCGGCTCGGGTTCTCCCGGGACTTCGTGGAGGACGACTTCGCCGGTGT
GGTCCGGGACGACGTGACCCTGTTCATCAGCGCGGTCCAGGACCAGGTGGTGCCGG
ACAACACCCTGGCCTGGGTGTGGGTGCGCGGCCTGGACGAGCTGTACGCCGAGTGG
TCGGAGGTCGTGTCCACGAACTTCCGGGACGCCTCCGGGCCGGCCATGACCGAGAT
CGGCGAGCAGCCGTGGGGCGGGAGTTCGCCCTGCGCGACCCGGCCGGCAACTGCG
TGCACTTCGTGGCCGAGGAGCAGGACTGACACGTGCTACGAGATTTCGATTCCACCG
CCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGC
AGCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATGTCT
GTATACCGTCGACCTCTAGCTAGAGCTTGGCGTAATCATGGTCATAGCTGTTTCCTGT
GTGAAATTGTTATCCGCTCACAATTCCACACAACATACGAGCCGGAAGCATAAAGT
GTAAAGCCTGGGGTGCCTAATGAGTGAGCTAACTCACATTAATTGCGTTGCGCTCAC
TGCCCGCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTC
TCCTGTTCCGACCCTGCCGCTTACCGGATACCTGTCCGCCTTTCTCCCTTCGGGAAGC
GTGGCGCTTTCTCAATGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTG
AAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAA

```
AGGATCTCAAGAAGATCCTTTGATCTTTTCTACGGGGTCTGACGCTCAGTGGAACGA

AAACTCACGTTAAGGGATTTTGGTCATGAGATTATCAAAAAGGATCTTCACCTAGAT

CCTTTTAAATTAAAAATGAAGTTTTAAATCAATCTAAAGTATATATGAGTAAACTTG

GTCTGACAGTTACCAATGCTTAATCAGTGAGGCACCTATCTCAGCGATCTGTCTATTT

CGTTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTCCA

GATTTATCAGCAATAAACCAGCCAGCCGGAAGGGCCGAGCGCAGAAGTGGTCCTGC

AACTTTATCCGCCTCCATCCAGTCTATTAATTGTTGCCGGGAAGCTAGAGTAAGTAG

TTCGCCAGTTAATAGTTTGCGCAACGTTGTTGCCATTGCTACAGGCATCGTGGTGTC

ACGCTCGTCGTTTGGTATGGCTTCATTCAGCTCCGGTYCCCAACGATCAAGGCGAGT

TACATGATCCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCACTGCATAA

TTCTCTTACTGTCATGCCATCCGTAAGATGCTTYTCTGTGACTGGTGAGTACTCAACC

AAGTCATTCTGAGAATAGTGTATGCGGCGACCGAGTTGCTCTTGCCCGGCGTCAATA

CGGGATAATACCGCGCCACATAGCAGAACTTTAAAAGTGCTCATCATTGGAAAACG

TTCTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTGGG

TGAGCAAAAACAGGAAGGCAAAATGCCGCAAAAAAGGGAATAAGGGCGACACGGA

AATGTTGAATACTCATACTCTTCCTTTTTCAATATTATTGAAGCATTTATCAGGGTTA

TTGTCTCATGAGCGGATACATATTTGAATGTATTTAGAAAAATAAACAAATAGGGGT

TCCGCGCACATTTCCCCGAAAAGTGCCACCTGACGTCGACGGATCGGGAGATCTCCC

GATCCCCTATGGTGCACTCTCAGTACAATCTGCTCTGATGCCGCATAGTTAAGCCAG

TATCTGCTCCCTGCTTGTGTGTTGGAGGTCGCTGAGTAGTGCGCGAGCAAAATTTAA

GCTACAACAAGGCAAGGCTTGACCGACAATTGCATGAAGAATCTGCTTAGGGTTAG

GCGTTTTGCGCTGCTTCGCGATGTACGGGCCAGATATACGCGTTGACATTGATTATT

GACTAGTTATTAATAGTAATCAATTACGGGGTCATTAGTTCATAGCCCATATATGGA

GTTCCGCGTTACATAACTTACGGTAAATGGCCCGCCTGGCTGACCGCCCAACGACCC

CCGCCCATTGACGTCAATAATGACGTATGTTCCCATAGTAACGCCAATAGGGACTTT

CCATTGACGTCAATGGGTGGACTATTTACGGTAAACTGCCCACTTGGCAGTACATCA

AGTGTATCATATGCCAAGTACGCCCCCTATTGACGTCAATGACGGTAAATGGCCCGC

CTGGCATTATGCCCAGTACATGACCTTACGGGACTTTCCTACTTGGCAGTACATCTA

CGTATTAGTCATCGCTATTACCATGGTGATGCGGTTTTGGCAGTACACCAATGGGCG

TGGATAGCGGTTTGACTCACGGGGATTTCCAAGTCTCCACCCCATTGACGTCAATGG

GAGTTTGTTTTGGCACCAAAATCAACGGGACTTTCCAAAATGTCGTAACAACTCCGC

CCCATTGACGCAAATGGGCGGTAGGCGTGTACGGTGGGAGGTCTCTGTACTGGGTCT

CTCTGGTTAGACCAGATCTGAGCCTGGGAGCTCTCTGGCTAACTAGGGAACCCACTG

CTTAAGCCTCAATAAAGCTTGCCTTGAGTGCTTCAAGTAGTGTGTGCCCGTCTGTTGT

GTGACTCTGGTAACTAGAGATCCCTCAGACCCTTTTAGTCAGTGTGGAAAATCTCTA

GCAGTGGCGCCCGAACAGGGACTTGAAAGCGAAAGGGAAACCAGAGGAGCTCTCT

CGACGCAGGACTCGGCTTGCTGAAGCGCGCACGGCAAGAGGCGAGGGGCGGCGAC
```

```
                            -continued
TGGTGAGTACGCCAAAAATTTTGACTAGCGGAGGCTAGAAGGAGAGATGGGTGC

GAGAGCGTCAGTATTAAGCGGGGGAGAATTAGATCGCGATGGGAAAAAATTCGGTT

AAGGCCAGGGGGAAAGAAAAAATATAAATTAAAACATATAGTATGGGCAAGCAGG

GAGCTAGAACGATTCGCAGTTAATCCTGGCCTGTTAGAAACATCAGAAGGCTGTAG

ACAAATACTGGGACAGCTACAACCATCCCTTCAGACAGGATCAGAAGAACTTAGAT

CATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCAC

CGCACAGCAAGCGGCCGCTGATCTTCAGACCTGGAGGAGGAGATATGAGGGACAAT

TGGAGAAGTGAATTATATAAATATAAAGTAGTAAAAATTGAACCATTAGGAGTAGC

ACCCACCAAGGCAAAGAGAAGAGTGGTGCAGAGAGAAAAAAGAGCAGTGGGAATA

GGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAA

CAATTTGCTGAGGGCTATTGAGGCGCAACAGCATCTGTTGCAACTCACAGTCTGGGG

CATCAAGCAGCTCCAGGCAAGAATCCTGGCTGTGGAAAGATACCTAAAGGATCAAC

AGCTCCTGGGGATTTGGGGTTGCTCTGGAAAACTCATTTGCACCACTGCTGTGCCTT

GGAATGCTAGTTGGAGTAATAAATCTCTGGAACAGATTTGGAATCACACGACCTGG

ATGGAGTGGGACAGAGAAATTAACAATTACACAAGCTTAATACACTCCTTAATTGA

AGAATCGCAAAACCAGCAAGAAAAGAATGAACAAGAATTATTGGAATTAGATAAAT

GGGCAAGTTTGTGGAATTGGTTTAACATAACAAATTGGCTGTGGTATATAAAATTAT

TCATAATGATAGTAGGAGGCTTGGTAGGTTTAAGAATAGTTTTTGCTGTACTTTCTAT

AGTGAATAGAGTTAGGCAGGGATATTCACCATTATCGTTTCAGACCCACCTCCCAAC

CCCGAGGGGACCCGACAGGCCCGAAGGAATAGAAGAAGAAGGTGGAGAGAGAGAC

AGAGACAGATCCATTCGATTAGTGAACGGATCGGCACTGCGTGCGCCAATTCTGCA

GACAAATGGCAGTATTCATCCACAATTTTAAAAGAAAAGGGGGGATTGGGGGGTAC

AGTGCAGGGGAAAGAATAGTAGAAATAATAGCAACAGACATACAAACTAAAGAAT

TACAAAAACAAATTACAAAAATTCAAAATTTTCGGGTTTATTACAGGGA

SEQ ID NO: 17, UP sequence
GTGTCGGCTCCAGATCTGGCCTCCGCGCCGGGTTTTGGCGCCTCCCGCGGGCGCCCC

CCTCCTCACGGCGAGCGCTGCCACGTCAGACGAAGGGCGCAGCGAGCGTCCTGATC

CTTCCGCCCGGACGCTCAGGACAGCGGCCCGCTGCTCATAAGACTCGGCCTTAGAAC

CCCAGTATCAGCAGAAGGACATTTTAGGACGGGACTTGGGTGACTCTAGGGCACTG

GTTTTCTTTCCAGAGAGCGGAACAGGCGAGGAAAAGTAGTCCCTTCTCGGCGATTCT

GCGGAGGGATCTCCGTGGGGCGGTGAACGCCGATGATTATATAAGGACGCGCCGGG

TGTGGCACAGCTAGTTCCGTCGCAGCCGGGATTTGGGTCGCGGTTCTTGTTTGTGGA

TCGCTGTGATCGTCACTTGGTGAGTAGCGGGCTGCTGGGCTGGCCGGGGCTTTCGTG

GCCGCCGGGCCGCTCGGTGGGACGGAAGCGTGTGGAGAGACCGCCAAGGGCTGTAG

TCTGGGTCCGCGAGCAAGGTTGCCCTGAACTGGGGGTTGGGGGGAGCGCACAAAAT

GGCGGCTGTTCCCGAGTCTTGAATGGAAGACGCTTGTGAGGCGGGCTGTGAGGTCGT

TGAAACAAGGTGGGGGGCATGGTGGGCGGCAAGAACCCAAGGTCTTGAGGCCTTCG

CTAATGCGGGAAAGCTCTTATTCGGGTGAGATGGGCTGGGGCACCATCTGGGGACC

CCTGACGTGAAGTTTGTCACTGACTGGAGAAACTCGGGTTTGTCGTCTGTTGCGGGG
```

```
GCGGCAGTTATGGCGGTGCCGTTGGGCAGTGCACCCGTACCTTTGGGAGCGCGCGC

CCTCGTCGTGTCGTGACGTCACCCGTTCTGTTGGCTTATAATGCAGGGTGGGGCCAC

CTGCCGGTAGGTGTGCGGTAGGCTTTTCTCCGTCGCAGGACGCAGGGTTCGGGCCTA

GGGTAGGCTCTCCTGAATCGACAGGCGCCGGACCTCTGGTGAGGGGAGGGATAAGT

GAGGCGTCAGTTTCTTTGGTCGGTTTTATGTACCTATCTTCTTAAGTAGCTGAAGCTC

CGGTTTTGAACTATGCGCTCGGGGTTGGCGAGTGTGTTTTGTGAAGTTTTTTAGGCAC

CTTTTGAAATGTAATCATTTGGGTCAATATGTAATTTTCAGTGTTAGACTAGTAAATT

GTCCGCTAAATTCTGGCCGTTTTTGGCTTTTT
```

SEQ ID NO: 18, LV-UB-FIREFLY-RFP-Ttk protein sequence
```
GRRQKHKERPGAILSAGRWNRWRATAGYEEIRPGSWNNCFYRCTYRGGHHLRVLRNV

RSVGRSYETIWAEYKSQNRRMQKLSSILYAGVGRVIYRSCSCARERHLTIAQQYGHFAA

YRGVRFQKGVAKNFERAKKAPNHPKNYYHGFNGLPGISVDVHVRHISSTSRFIRFCARV

LRGQDNCTDHELLWIYWSARCRSASNCLREILACQRSYFWQSNHSGYCDFKCCSIPSRF

WNVYYTRIFDMWISSRLNVIRRAVSEEPSGLQDSKCAAGANPILLLRQKHSDQIRFIFTR

NCFWWRSPLGSRGSGCQEVPSARYQARIWAHDYISYSDYTRGGTGRGRSCSIFSEGCGS

GYRENAGRSKRRTVCERSYDYVRLCKQSGSDQRLDQGWMATFWRHSLLGRRRTLLHR

PPEVSDVQRLSGGSRIGIHLAPTPQHLRRRCRRSSRRRRTSRRRCCFGARKDDDGKRDRG

LRRQSSNNREKVARRSCVCGRSTERSYRKTRRKKNQRDPHKGQEGRKDRRVIPREFSRV

CRISSFHHGLLRGRHQVHALQGAHGGLRERPRVRDRGRGRGPPLRGHPDRQAEGDQGR

PPALRLGHPVPSVPVRLQGLREAPRRHPRLLEAVLPRGLQVGARDELRGRRRGDRDPGL

LPAGRRVHLQGEAARHQLPLRRPRNAEEDHGLGGLHREDVPRGRRPEGRDQDEAEAEG

RRPLRRRGQDHLHGQEARAAARRLQDRHQAGHHLPQRGLHHRGTVRARRGPPLHRRH

RGPGIRHHAHATAGLYRRSPRDGENHHHHATAGGPGFARRYRLRTRADDLLAGAGGF

RDNREHLHHTTPPRPGDIGRGRGGGNDKRPDNNALCRDRRRSGSSYRGGGWELTCPAP

GPHELPRPPSHRLHAVLPGRAVPYGQHDPPGRAGVRGPHPADLARHQHRA WGPSGGQ

THRPPGQTPAPRRAAGPGYAGCDSPRLRATCQYGAVSAVRRVVAGGLGTAFGDGRAA

PGCRAPEQRGPTTPYRGHVIYPVSGPRVDGPQRRPVRVCLGLRLGQTPPFHARLYPGL

RPIARRLPGRPAATYLRDGPDPRHHPRLHTDDMRPGAHVCPGDGGGLI
```

SEQ ID NO: 19, Humanized Fluc & humanized GFP (nucleotide sequence)
```
ATGCCAAAAACATTAAGAAGGGCCCAGCGCCATTCTACCCACTCGAAGACGGGACC

GCCGGCGAGCAGCTGCACAAAGCCATGAAGCGCTACGCCCTGGTGCCCGGCACCAT

CGCCTTTACCGACGCACATATCGAGGTGGACATTACCTACGCCGAGTACTTCGAGAT

GAGCGTTCGGCTGGCAGAAGCTATGAAGCGCTATGGGCTGAATACAAACCATCGGA

TCGTGGTGTGCAGCGAGAATAGCTTGCAGTTCTTCATGCCCGTGTTGGGTGCCCTGT

TCATCGGTGTGGCTGTGGCCCCAGCTAACGACATCTACAACGAGCGCGAGCTGCTGA

ACAGCATGGGCATCAGCCAGCCCACCGTCGTATTCGTGAGCAAGAAAGGGCTGCAA

AAGATCCTCAACGTGCAAAAGAAGCTACCGATCATACAAAGATCATCATCATGGA

TAGCAAGACCGACTACCAGGGCTTCCAAAGCATGTACACCTTCGTGACTTCCCATTT

GCCACCCGGCTTCAACGAGTACGACTTCGTGCCCGAGAGCTTCGACCGGGACAAA

CCATCGCCCTGATCATGAACAGTAGTGGCAGTACCGGATTGCCCAAGGGCGTAGCC

CTACCGCACCGCACCGCTTGTGTCCGATTCAGTCATGCCCGCGACCCCATCTTCGGC

AACCAGATCATCCCCGACACCGCTATCCTCAGCGTGGTGCCATTTCACCACGGCTTC
```

```
GGCATGTTCACCACGCTGGGCTACTTGATCTGCGGCTTTCGGGTCGTGCTCATGTAC

CGCTTCGAGGAGGAGCTATTCTTGCGCAGCTTGCAAGACTATAAGATTCAATCTGCC

CTGCTGGTGCCCACACTATTTAGCTTCTTCGCTAAGAGCACTCTCATCGACAAGTAC

GACCTAAGCAACTTGCACGAGATCGCCAGCGGCGGGGCGCCGCTCAGCAAGGAGGT

AGGTGAGGCCGTGGCCAAACGCTTCCACCTACCAGGCATCCGCCAGGGCTACGGCC

TGACAGAAACAACCAGCGCCATTCTGATCACCCCCGAAGGGGACGACAAGCCTGGC

GCAGTAGGCAAGGTGGTGCCCTTCTTCGAGGCTAAGGTGGTGGACTTGGACACCGG

TAAGACACTGGGTGTGAACCAGCGCGGCGAGCTGTGCGTCCGTGGCCCCATGATCA

TGAGCGGCTACGTTAACAACCCCGAGGCTACAAACGCTCTCATCGACAAGGACGGC

TGGCTGCACAGCGGCGACATCGCCTACTGGGACGAGGACGAGCACTTCTTCATCGTG

GACCGGCTGAAGAGCCTGATCAAATACAAGGGCTACCAGGTAGCCCCAGCCGAACT

GGAGAGCATCCTGCTGCAACACCCCAACATCTTCGACGCCGGGGTCGCCGGCCTGC

CCGACGACGATGCCGGCGAGCTGCCCGCCGCAGTCGTCGTGCTGGAACACGGTAAA

ACCATGACCGAGAAGGAGATCGTGGACTATGTGGCCAGCCAGGTTACAACCGCCAA

GAAGCTGCGCGGTGGTGTTGTTCGTGGACGAGGTGCCTAAAGGACTGACCGGCA

AGTTGGACGCCCGCAAGATCCGCGAGATTCTCATTAAGGCCAAGAAGGGCGGCAAG

ATCGCCGTGAATTCTCACGGCTTCCCTCCCGAGGTGGAGGAGCAGGCCGCCGGCACC

CTGCCCATGAGCTGCGCCCAGGAGAGCGGCATGGATAGACACCCTGCTGCTTGCGC

CAGCGCCAGGATCAACGTCGGATCCCACGGCGATATGACACCCACTCGTGCAGGCT

GCCCAGGGGCTTGCCCAGGCTGGTCAGCTGGGCGATGGCGGTCTCGTGCTGCTCCAC

GAAGCCGCCGTCCTCCACGTAGGTCTTCTCCAGGCGGTGCTGGATGAAGTGGTACTC

GGGGAAGTCCTTCACCACGCCCTTGCTCTTCATCAGGGTGCGCATGTGGCAGCTGTA

GAACTTGCCGCTGTTCAGGCGGTACACCAGGATCACCTGGCCCACCAGCACGCCGTC

GTTCATGTACACCACCTCGAAGCTGGGCTGCAGGCCGGTGATGGTCTTCTTCATCAC

GGGGCCGTCGTTGGGGAAGTTGCGGCCCTTGTACTCCACGCGGTACACGAACATCTC

CTCGATCAGGTTGATGTCGCTGCGGATCTCCACCAGGCCGCCGTCCTCGTAGCGCAG

GGTGCGCTCGTACACGAAGCCGGCGGGGAAGCTCTGGATGAAGAAGTCGCTGATGT

CCTCGGGGTACTTGGTGAAGGTGCGGTTGCCGTACTGGAAGGCGGGGCTCAGGATG

TCGAAGGCGAAGGGCAGGGGGGCGCCCTTGGTCACGCGGATCTGCACCAGCTGGTT

GCCGAACAGGATGTTGCCCTTGCCGCAGCCCTCCATGGTGAACACGTGGTTGTTCAC

CACGCCCTCCAGGTTCACCTTGAAGCTCATGATCTCCTGCAGGCCGGTGTTCTTCAG

GATCTGCTTGCTCACCATGGTGA
```

SEQ ID NO: 20, Humanized Fluc & humanized GFP PROTEIN SEQUNCE
AKNIKKGPAPFYPLEDGTAGEQLHKAMKRYALVPGTIAFTDAHIEVDITYAEYFEMSVRLAEAMK

RYGLNTNHRIVVCSENSLQFFMPVLGALFIGVAVAPANDIYNERELLNSMGISQPTVVFVSKKGL

QKILNVQKKLPIIQKIIIMDSKTDYQGFQSMYTFVTSHLPPGFNEYDFVPESFDRDKTIALIMNSS

GSTGLPKGVALPHRTACVRFSHARDPIFGNQIIPDTAILSVVPFHHGFGMFTTLGYLICGFRVVL

MYRFEEELFLRSLQDYKIQSALLVPTLFSFFAKSTLIDKYDLSNLHEIASGGAPLSKEVGEAVAKR

FHLPGIRQGYGLTETTSAILITPEGDDKPGAVGKVVPFFEAKVVDLDTGKTLGVNQRGELCVRG

PMIMSGYVNNPEATNALIDKDGWLHSGDIAYWDEDEHFFIVDRLKSLIKYKGYQVAPAELESILL

QHPNIFDAGVAGLPDDDAGELPAAVVVLEHGKTMTEKEIVDYVASQVTTAKKLRGGVVFVDEV

```
PKGLTGKLDARKIREILIKAKKGGKIAVNSHGFPPEVEEQAAGTLPMSCAQESGMDRHPAACAS

ARINVGSHGDMTPTRAGCPGACPGWSAGRWRSRAAPRSRRPPRRSSPGGAGSGTRGSPSP

RPCSSSGCACGSCRTCRCSGGTPGSPGPPARRRSCTPPRSWAAGRWSSSSRGRRWGSCG

PCTPRGTRTSPRSGCRCGSPPGRRPRSAGCARTRSRRGSSGRSRCPRGTWRCGCRTGRR

GSGCRRRRAGGRPWSRGSAPAGCRTGCCPCRSPPWTRGCSPRPPGSPSSSPAGRCSSGS

ACSPW (The linker (GSHGD), indicated by underlining, appears at amino acids
589-593 of SEQ ID NO: 20, above)
SEQ ID NO: 21, linker: LENSHASAGYQAST SEQ ID NO: 22, linker: TAGPGSAT
```

The invention claimed is:

1. A method of monitoring human embryonic stem cells (hESCs) comprising:
providing human embryonic stem cells;
transducing the hESCs with a triple-fusion expression vector to produce triple-fusion hESCs, wherein the triple-fusion expression vector comprises a firefly luciferase reporter gene (Fluc) having a nucleotide sequence selected from the group consisting of: SEQ ID NO: 1 and SEQ ID NO: 3, a red fluorescent reporter gene (RFP) having a nucleotide sequence of SEQ ID NO: 6, and a truncated HSV1-tK positron emission tomography (PET) reporter gene (HSV1-tTK) having a nucleotide sequence selected from the group consisting of: SEQ ID NO: 7 and SEQ ID NO: 14; and
detecting fluorescence, bioluminescence, a nuclear signal from a PET reporter, or a combination thereof, emitted from the triple-fusion hESCs and any progeny of the triple-fusion hESCs.

2. The method of claim 1, wherein the expression vector is LV-pUP-Fluc-RFP-tTK, where LV is lentivirus, pUP is constitutive human ubiquitin promoter, Fluc is firefly luciferase reporter gene, RFP is the red fluorescent reporter gene, and tTK is the truncated HSV1-tk PET reporter gene.

3. The method of claim 1, wherein the triple-fusion expression vector comprises a gene having SEQ ID NO: 8.

4. The method of claim 1, wherein the triple-fusion expression vector comprises a gene encoding a triple-fusion protein having SEQ ID NO: 9.

5. The method of claim 1, wherein the triple-fusion expression vector comprises a gene encoding a triple-fusion protein having SEQ ID NO: 18.

6. A method of monitoring human embryonic stem cells (hESCs) in a subject comprising:
providing triple-fusion hESCs having a triple-fusion expression vector comprising a firefly luciferase reporter gene (Fluc) having a nucleotide sequence selected from the group consisting of: SEQ ID NO: 1 and SEQ ID NO: 3, a red fluorescent reporter gene (RFP) having a nucleotide sequence of SEQ ID NO: 6, and a truncated HSV1-tK positron emission tomography (PET) reporter gene (HSV1-tTK) having a nucleotide sequence selected from the group consisting of: SEQ ID NO: 7 and SEQ ID NO: 14;
administering the triple-fusion hESCs to the subject; and
detecting fluorescence, bioluminescence, a nuclear signal from a PET reporter, or a combination thereof, emitted from the triple-fusion hESCs and any progeny of the triple-fusion hESCs.

7. The method of claim 6, wherein the expression vector is LV-pUP-Fluc-RFP-tTK, where LV is lentivirus, pUP is constitutive human ubiquitin promoter, Fluc is firefly luciferase reporter gene, RFP is the red fluorescent reporter gene, and tTK is the truncated HSV1-tk PET reporter gene.

8. The method of claim 6, wherein the triple-fusion expression vector comprises a gene having SEQ ID NO: 8.

9. The method of claim 6, wherein the triple-fusion expression vector comprises a gene encoding a triple-fusion protein having SEQ ID NO: 9.

10. The method of claim 6, wherein the triple-fusion expression vector comprises a gene encoding a triple-fusion protein having SEQ ID NO: 18.

11. A triple-fusion construct comprising:
a firefly luciferase reporter gene (Fluc) having a nucleotide sequence selected from the group consisting of: SEQ ID NO: 1 and SEQ ID NO:3;
a red fluorescent reporter gene (RFP) having a nucleotide sequence SEQ ID NO: 6; and a truncated Herpes Simplex Virus 1 thymidine kinase positron emission tomography (PET) reporter gene (HSV1-tTK) having a nucleotide sequence selected from the group consisting of: SEQ ID NO: 7 and SEQ ID NO: 14.

12. A method of monitoring stem cells comprising:
providing stem cells;
transducing the stem cells with a triple-fusion expression vector to produce triple-fusion stem cells, wherein the triple-fusion expression vector comprises a firefly luciferase reporter gene (Fluc) having a nucleotide sequence selected from the group consisting of: SEQ ID NO: 1 and SEQ ID NO: 3, a red fluorescent reporter gene (RFP) having a nucleotide sequence of SEQ ID NO: 6, and a truncated HSV1-tK positron emission tomography (PET) reporter gene (HSV1-tTK) having a nucleotide sequence selected from the group consisting of: SEQ ID NO: 7 and SEQ ID NO: 14; and
detecting fluorescence, bioluminescence, a nuclear signal from a PET reporter, or a combination thereof, emitted from the triple-fusion stem cells and any progeny of the triple-fusion stem cells.

13. The method of claim 12, wherein the stem cells are human stem cells.

14. A method of monitoring human stem cells in a subject comprising:
providing triple fusion human stem cells having a triple-fusion expression vector comprising a firefly luciferase reporter gene (Fluc) having a nucleotide sequence selected from the group consisting of: SEQ ID NO: 1 and SEQ ID NO: 3, a red fluorescent reporter gene (RFP) having a nucleotide sequence of SEQ ID NO: 6, and a truncated HSV1-tK positron emission tomography (PET) reporter gene (HSV1-tTK) having a nucleotide sequence selected from the group consisting of: SEQ ID NO: 7 and SEQ ID NO: 14;
administering the triple-fusion human stem cells to the subject; and
detecting fluorescence, bioluminescence, a nuclear signal from a PET reporter, or a combination thereof, emitted from the triple-fusion human stem cells and any progeny of the triple-fusion human stem cells.

* * * * *

UNITED STATES PATENT AND TRADEMARK OFFICE
CERTIFICATE OF CORRECTION

| | |
|---|---|
| PATENT NO. | : 8,945,862 B2 |
| APPLICATION NO. | : 13/358838 |
| DATED | : February 3, 2015 |
| INVENTOR(S) | : Wu et al. |

It is certified that error appears in the above-identified patent and that said Letters Patent is hereby corrected as shown below:

In the Specification

At column 1, lines 31-36, in the paragraph entitled "Statement Regarding Federally Sponsored Research or Development", delete:

"This invention was made with Government support under contract HL089027 awarded by the National Institutes of Health. The Government has certain rights in this invention. This invention also had support under grant #RS1-00322 from the California Institute of Regenerative Medicine."

and replace with:

"This invention was made with Government support under contract HL089027 awarded by the National Institutes of Health. The Government has certain rights in the invention."

Signed and Sealed this
Twenty-ninth Day of March, 2016

Michelle K. Lee
*Director of the United States Patent and Trademark Office*

SEQUENCE LISTING

```
<160> NUMBER OF SEQ ID NOS: 52

<210> SEQ ID NO 1
<211> LENGTH: 1653
<212> TYPE: DNA
<213> ORGANISM: Photinus pyralis

<400> SEQUENCE: 1
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caatcacag aatcgtcgta     240 tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aaggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttc tgaggagcct tcaggattac     840
aagattcaaa gtgcgctgct ggtgccaacc ctattctcct tcttcgccaa agcactctg      900 attgacaaat acgatttatc taatttacac gaaattgctt ctggtggcgc tcccctctct    960
aaggaagtcg ggaagcggt tgccaagagg ttccatctgc caggtatcag gcaaggatat   1020
gggctcactg agactacatc agctattctg attacacccg aggggatga taaaccgggc   1080 gcggtcggta agttgttcc attttttgaa gcgaaggttg tggatctgga taccgggaaa   1140
acgctgggcg ttaatcaaag aggcgaactg tgtgtgagag gtcctatgat tatgtccggt   1200
tatgtaaaca tccggaagc gaccaacgcc ttgattgaca aggatggatg ctacattct    1260 ggagacatag cttactggga cgaagacgaa cacttcttca tcgttgaccg cctgaagtct   1320
ctgattaagt acaaaggcta tcaggtggct cccgctgaat tggaatccat cttgctccaa   1380 cacccccaaca tcttcgacgc aggtgtcgca ggtcttcccg acgatgacgc cggtgaactt   1440
```

```
cccgccgccg ttgttgtttt ggagcacgga aagacgatga cggaaaaaga gatcgtggat    1500
tacgtcgcca gtcaagtaac aaccgcgaaa agttgcgcg gaggagttgt gtttgtggac    1560
gaagtaccga aaggtcttac cggaaaactc gacgcaagaa aaatcagaga gatcctcata   1620
aaggccaaga agggcggaaa gatcgccgtg taa                                1653
```

```
<210> SEQ ID NO 2
<211> LENGTH: 720
<212> TYPE: DNA
<213> ORGANISM: Artificial Sequence
<220> FEATURE:
<223> OTHER INFORMATION: Chemically synthesized enhanced green
      fluorescent protein nucleotide sequence

<400> SEQUENCE: 2
```

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

```
<210> SEQ ID NO 3
<211> LENGTH: 1653
<212> TYPE: DNA
<213> ORGANISM: Artificial Sequence
<220> FEATURE:
<223> OTHER INFORMATION: Synthesized Humanized firefly luciferase
      sequence

<400> SEQUENCE: 3
```

```
atggaagatg ccaaaaacat taagaagggc ccagcgccat tctacccact cgaagacggg     60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg atcgtggtg    240 tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatccccg acaccgctat cctcagcgtg    720
```

```
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgcccaca ctatttagct tcttcgctaa gagcactctc      900
atcgacaagt acgacctaag caacttgcac gagatcgcca cgggcggggc gccgctcagc      960
aaggaggtag gtgaggccgt ggccaaacgc ttccacctac caggcatccg ccagggctac     1020
ggcctgacag aaacaaccag cgccattctg atcacccccg aaggggacga caagcctggc     1080
gcagtaggca aggtggtgcc cttcttcgag gctaaggtgg tggacttgga caccggtaag     1140
acactgggtg tgaaccagcg cggcgagctg tgcgtccgtg gccccatgat catgagcggc     1200
tacgttaaca accccgaggc tacaaacgct ctcatcgaca aggacggctg gctgcacagc     1260
ggcgacatcg cctactggga cgaggacgag cacttcttca tcgtggaccg gctgaagagc     1320
ctgatcaaat acaagggcta ccaggtagcc ccagccgaac tggagagcat cctgctgcaa     1380
caccccaaca tcttcgacgc cggggtcgcc ggcctgcccg acgacgatgc cggcgagctg     1440
cccgccgcag tcgtcgtgct ggaacacggt aaaaccatga ccgagaagga gatcgtggac     1500
tatgtggcca gccaggttac aaccgccaag aagctgcgcg tggtgttgt gttcgtggac     1560 gaggtgccta aaggactgac cggcaagttg acgcccgca gatccgcga gattctcatt     1620 aaggccaaga agggcggcaa gatcgccgtg taa                                 1653
```

<210> SEQ ID NO 4
<211> LENGTH: 719
<212> TYPE: DNA
<213> ORGANISM: Artificial Sequence
<220> FEATURE:
<223> OTHER INFORMATION: Synthesized Humanized green fluorescent protein
      sequence

<400> SEQUENCE: 4

```
atggtgagca agcagatcct gaagaacacc ggcctgcagg agatcatgag cttcaaggtg       60
aacctggagg gcgtggtgaa caaccacgtg ttcaccatgg agggctgcgg caagggcaac      120
atcctgttcg gcaaccagct ggtgcagatc cgcgtgacca agggcgcccc cctgcccttc      180
gccttcgaca tcctgagccc cgccttccag tacggcaacc gcaccttcac caagtacccc      240
gaggacatca gcgacttctt catccagagc ttccccgccg gcttcgtgta cgagcgcacc      300
ctgcgctacg aggacggcgg cctggtggag atccgcagga catcaacctg atcgaggaga      360
tgttcgtgta ccgcgtggag tacaagggcc gcaacttccc caacgacggc cccgtgatga      420
agaagaccat caccggcctg cagcccagct tcgaggtggt gtacatgaac gacggcgtgc      480
tggtgggcca ggtgatcctg gtgtaccgcc tgaacagcgg caagttctac agctgccaca      540
tgcgcacccc tgatgaagag caagggcgtg tgaaggactt ccccgagtac cacttcatcc      600
agcaccgcct ggagaagacc tacgtggagg acggcggctt cgtggagcag cacgagaccg      660
ccatcgccca gctgaccagc ctgggcaagc ccctgggcag cctgcacgag tgggtgtaa      719
```

<210> SEQ ID NO 5
<211> LENGTH: 975
<212> TYPE: DNA
<213> ORGANISM: Renilla reniformis

<400> SEQUENCE: 5

```
atggcttcga aagtttatga tccagaacaa aggaaacgga tgataactgg tccgcagtgg       60
tgggccagat gtaaacaaat gaatgttctt gattcattta ttaattatta tgattcagaa      120
```

| | |
|---|---:|
| aaacatgcag aaaatgctgt tattttttta catggtaacg cggcctcttc ttatttatgg | 180 |
| cgacatgttg tgccacatat tgagccagta gcgcggtgta ttataccaga ccttattggt | 240 |
| atgggcaaat caggcaaatc tggtaatggt tcttataggt tacttgatca ttacaaatat | 300 |
| cttactgcat ggtttgaact tcttaattta ccaagaaga tcattttgt cggccatgat | 360 |
| tggggtgctt gtttggcatt tcattatagc tatgagcatc aagataagat caaagcaata | 420 |
| gttcacgctg aaagtgtagt agatgtgatt gaatcatggg atgaatggcc tgatattgaa | 480 |
| gaagatattg cgttgatcaa atctgaagaa ggagaaaaaa tggttttgga gataacttc | 540 |
| ttcgtggaaa ccatgttgcc atcaaaaatc atgagaaagt tagaaccaga gaatttgca | 600 |
| gcatatcttg aaccattcaa agagaaaggt gaagttcgtc gtccaacatt atcatggcct | 660 |
| cgtgaaatcc cgttagtaaa aagtggtaaa cctgacgttg tacaaattgt taggaattat | 720 |
| aatgcttatc tacgtgcaag tgatgattta ccaaaaatgt ttattgaatc ggacccagga | 780 |
| ttctttttcca atgctattgt tgaaggtgcc aagaagtttc ctaatactga atttgtcaaa | 840 |
| gtaaaaggtc ttcattttc gcaagaagat gcacctgatg aaatgggaaa atatatcaaa | 900 |
| tcgttcgttg agcgagttct caaaaatgaa caaagatcta caagtttgta caaaaaagct | 960 |
| gaacgagaaa cgtaa | 975 |

<210> SEQ ID NO 6
<211> LENGTH: 675
<212> TYPE: DNA
<213> ORGANISM: Artificial Sequence
<220> FEATURE:
<223> OTHER INFORMATION: Chemically synthesized monomeric red
      fluorescent protein gene

<400> SEQUENCE: 6

| | |
|---|---:|
| atggcctcct ccgaggacgt catcaagttc atgcgcttca aggtgcgcat ggagggctcc | 60 |
| gtgaacggcc acgagttcga gatcgagggc gagggcgagg ccgcccccta cgagggcacc | 120 |
| cagaccgcca agctgaaggt gaccaagggc ggccccctgc ccttcgcctg ggacatcctg | 180 |
| tcccctcagt tccagtacgg ctccaaggcc tacgtgaagc accccgccga catccccgac | 240 |
| tacttgaagc tgtccttccc cgagggcttc aagtgggagc gcgtgatgaa cttcgaggac | 300 |
| ggcggcgtgg tgaccgtgac ccaggactcc tccctgcagg acggcgagtt catctacaag | 360 |
| gtgaagctgc gcggcaccaa cttccccctcc gacggccccg taatgcagaa gaagaccatg | 420 |
| ggctgggagg cctccaccga ggatgtatac cccgaggacg cgccctgaa gggcgagatc | 480 |
| aagatgaggc tgaagctgaa ggacggcggc cactacgacg ccgaggtcaa gaccacctac | 540 |
| atggccaaga gcccgtgca gctgcccggc cctacaaga ccgacatcaa gctggacatc | 600 |
| acctcccaca cgaggacta caccatcgtg aacagtacg agcgcgccga gggccgccac | 660 |
| tccaccggcg cctaa | 675 |

<210> SEQ ID NO 7
<211> LENGTH: 993
<212> TYPE: DNA
<213> ORGANISM: herpes simplex virus 1

<400> SEQUENCE: 7

| | |
|---|---:|
| atgcccacgc tactgcgggt ttatatagac ggtccccacg ggatggggaa aaccaccacc | 60 |
| accacgcaac tgctggtggc cctgggttcg cgcgacgata tcgtctacgt acccgagccg | 120 |
| atgacttact ggcgggtgct gggggcttcc gagacaatcg cgaacatcta caccacacaa | 180 |

```
caccgcctcg accagggtga gatatcggcc ggggacgcgg cggtggtaat gacaagcgcc      240
cagataacaa tgccttatgc cgtgaccgac gccgttctgg ctcctcatat cgggggggag      300
gctgggagct cacatgcccc gccccggcc ctcaccatct tcctcgaccg ccatcccatc       360
gccttcatgc tgtgctaccc ggccgcgcgg taccttatgg gcagcatgac cccccaggcc     420
gtgctggcgt tcgtggccct catcccgccg accttgcccg gcaccaacat cgtgcttggg     480
gcccttccgg aggacagaca catcgaccgc ctggccaaac gccagcgccc cggcgagcgg     540
ctggacctgg ctatgctggc tgcgattcgc cgcgtttacg ggctacttgc caatacggtg     600
cggtatctgc agtgcggcgg tcgtggcgg gaggactggg gacagctttc ggggacggcc      660
gtgccgcccc agggtgccga gccccagagc aacgcgggcc cacgaccca tatcggggac      720 acgttattta ccctgtttcg ggccccgag ttgatggccc caacggcga cctgtataac      780 gtgtttgcct gggccttgga cgtcttggcc aaacgcctcc gttccatgca cgtctttatc     840
ctggattacg accaatcgcc cgccggctgc cgggacgccc tgctgcaact tacctccggg    900
atggtccaga cccacgtcac cacccccggc tccataccga cgatatgcga cctggcgcgc    960
acgtttgccc gggagatggg ggaggctaac tga                                    993
```

<210> SEQ ID NO 8
<211> LENGTH: 3357
<212> TYPE: DNA
<213> ORGANISM: Artificial Sequence
<220> FEATURE:
<223> OTHER INFORMATION: Synthesizzed nucleotide encoding fusion protein with sequences from homo sapiens, synthetic red fluorescent protein, photinus pyralis, and herpes simplex virus

<400> SEQUENCE: 8

```
atggaagacg ccaaaaacat aaagaaaggc ccggcgccat tctatcctct agaggatgga      60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt   300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggcccttt ccgcatagag ctgcctgcgt cagattctcg   660
catgccagag atcctatttt tggcaatcaa atcgctccgg atactgcgat tttaagtgtt   720
gttccattcc atcacggttt tggaatgttt actacactcg atatttgat atgtggattt   780 cgagtcgtct taatgtatag atttgaagaa gagctgtttt tacgatccct tcaggattac    840
aaaattcaaa gtgcgttgct agtaccaacc ctatttttcat tcctggccaa agcactctg   900 attgacaaat acgatttatc taatttacac gaaattgctt ctggggcgc acctcttcg     960 aaagaagtcg ggaagcggt tgcaaaacgc ttccatcttc cagggatacg acaaggatat    1020 ggctcactg agactacatc agctattctg attacaccca agggggatga taaaccgggc   1080
gcggtcggta aagttgttcc atttttttgaa gcgaaggttg tggatctgga taccgggaaa   1140
acgctgggcg ttaatcagag aggcgaatta tgtgtcagag gacctatgat tatgtccggt   1200
```

```
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
cacccccaaca tcttcgacgc gggcgtggca ggtcttcccg acgatgacgc cggtgaactt    1440
cccgccgccg ttgttgtttt ggagcacgga agacgatga cggaaaaaga gatcgtggat    1500
tacgtcgcca gtcaagtaac aaccgcgaaa agttgcgcg gaggagttgt gtttgtggac    1560
gaagtaccga aggtcttac cggaaaactc gacgcaagaa aaatcagaga gatcctcata    1620
aaggccaaga agggcggaaa gtccaaattg gaaatcataa tgagaatggc ctcctccgag    1680
gacgtcatca aggagttcat gcgcttcaag gtgcgcatgg agggctccgt gaacggccac    1740
gagttcgaga tcgagggcga gggcgagggc cgccctacg agggcacccca gaccgccaag    1800
ctgaaggtga ccaagggcgg ccccctgccc ttcgcctggg acatcctgtc ccctcagttc    1860
cagtacggct ccaaggccta cgtgaagcac cccgccgaca tccccgacta cttgaagctg    1920
tccttccccg agggcttcaa gtgggagcgc gtgatgaact tcgaggacgg cggcgtggtg    1980
accgtgaccc aggactcctc cctgcaggac ggcgagttca tctacaaggt gaagctgcgc    2040
ggcaccaact tcccctccga cggccccgta atgcagaaga gaccatggg ctgggaggcc    2100
tccaccgagc ggatgtaccc cgaggacggc gccctgaagg gcgagatcaa gatgaggctg    2160
aagctgaagg acggcggcca ctacgacgcc gaggtcaaga ccacctacat ggccaagaag    2220
cccgtgcagc tgcccggcgc ctacaagacc gacatcaagc tggacatcac ctcccacaac    2280
gaggactaca ccatcgtgga acagtacgag cgcgccgagg ccgccactc caccggcgcc    2340
accgcgggcc cggatccgc caccatgccc acgctactgc gggtttatat agacggtccc    2400
cacgggatgg ggaaaaccac caccaccacg caactgctgg tggccctggg ttcgcgcgac    2460
gatatcgtct acgtacccga gccgatgact tactggcggg tgctgggggc ttccgagaca    2520
atcgcgaaca tctacaccac acaacaccgc ctcgaccagg gtgagatatc ggccggggac    2580
gcggcggtgg taatgacaag cgcccagata acaatgcctt atgccgtgac cgacgccgtt    2640
ctggctcctc atatcggggg ggaggctggg agctcacatg ccccgccccc ggccctcacc    2700
atcttcctcg accgccatcc catcgccttc atgctgtgct acccggccgc gcggtacctt    2760
atgggcagca tgaccccccca ggccgtgctg gcgttcgtgg ccctcatccc gccgaccttg    2820
cccggcacca acatcgtgct tggggcccctt ccggaggaca gacacatcga ccgcctggcc    2880
aaacgccagc gccccggcga gcggctggac ctggctatgc tggctgcgat cgccgcgtt    2940
tacgggctac ttgccaatac ggtgcggtat ctgcagtgcg gcgggtcgtg gcgggaggac    3000
tggggacagc tttcggggac ggccgtgccg ccccagggtg ccgagcccca gagcaacgcg    3060
ggcccacgac cccatatcgg ggacacgtta tttaccctgt ttcgggcccc cgagttgatg    3120
gcccccaacg cgacctgta taacgtgttt gcctgggcct tggacgtctt ggccaaacgc    3180
ctccgttcca tgcacgtctt tatcctggat tacgaccaat cgcccgccgg ctgccgggac    3240
gccctgctgc aacttacctc cgggatggtc cagacccacg tcaccacccc cggctccata    3300
ccgacgatat gcgacctggc gcgcacgttt gcccgggaga tggggaggc taactga       3357
```

<210> SEQ ID NO 9
<211> LENGTH: 1118
<212> TYPE: PRT
<213> ORGANISM: Artificial Sequence
<220> FEATURE:

<223> OTHER INFORMATION: Synthesized fusion protein with sequences from
      homo sapiens, synthetic red fluorescent protein, photinus pyralis,
      and herpes simplex virus

<400> SEQUENCE: 9

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Ala Ala Cys Val Arg Phe Ser His Ala Arg Asp
210                 215                 220
Pro Ile Phe Gly Asn Gln Ile Ala Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Leu Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Lys Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
```

```
                385                 390                 395                 400

Tyr Val Asn Asn Pro Glu Ala Thr Asn Ala Leu Ile Asp Lys Asp Gly
                            405                 410                 415

Trp Leu His Ser Gly Asp Ile Ala Tyr Trp Asp Glu Asp His Phe
                        420                 425                 430

Phe Ile Val Asp Arg Leu Lys Ser Leu Ile Lys Tyr Lys Gly Tyr Gln
                        435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Ala Gly Glu Leu
        465                 470                 475                 480

Pro Ala Ala Val Val Val Leu Glu His Gly Lys Thr Met Thr Glu Lys
                            485                 490                 495

Glu Ile Val Asp Tyr Val Ala Ser Gln Val Thr Thr Ala Lys Lys Leu
                        500                 505                 510

Arg Gly Gly Val Val Phe Val Asp Glu Val Pro Lys Gly Leu Thr Gly
                        515                 520                 525

Lys Leu Asp Ala Arg Lys Ile Arg Glu Ile Leu Ile Lys Ala Lys Lys
        530                 535                 540

Gly Gly Lys Ser Lys Leu Glu Ala Ala Ala Arg Met Ala Ser Ser Glu
        545                 550                 555                 560

Asp Val Ile Lys Glu Phe Met Arg Phe Lys Val Arg Met Glu Gly Ser
                            565                 570                 575

Val Asn Gly His Glu Phe Glu Ile Glu Gly Glu Gly Glu Gly Arg Pro
                        580                 585                 590

Tyr Glu Gly Thr Gln Thr Ala Lys Leu Lys Val Thr Lys Gly Gly Pro
                    595                 600                 605

Leu Pro Phe Ala Trp Asp Ile Leu Ser Pro Gln Phe Gln Tyr Gly Ser
                    610                 615                 620

Lys Ala Tyr Val Lys His Pro Ala Asp Ile Pro Asp Tyr Leu Lys Leu
        625                 630                 635                 640

Ser Phe Pro Glu Gly Phe Lys Trp Glu Arg Val Met Asn Phe Glu Asp
                            645                 650                 655

Gly Gly Val Val Thr Val Thr Gln Asp Ser Ser Leu Gln Asp Gly Glu
                        660                 665                 670

Phe Ile Tyr Lys Val Lys Leu Arg Gly Thr Asn Phe Pro Ser Asp Gly
                        675                 680                 685

Pro Val Met Gln Lys Lys Thr Met Gly Trp Glu Ala Ser Thr Glu Arg
        690                 695                 700

Met Tyr Pro Glu Asp Gly Ala Leu Lys Gly Glu Ile Lys Met Arg Leu
        705                 710                 715                 720

Lys Leu Lys Asp Gly Gly His Tyr Asp Ala Glu Val Lys Thr Thr Tyr
                            725                 730                 735

Met Ala Lys Lys Pro Val Gln Leu Pro Gly Ala Tyr Lys Thr Asp Ile
                        740                 745                 750

Lys Leu Asp Ile Thr Ser His Asn Glu Asp Tyr Thr Ile Val Glu Gln
                        755                 760                 765

Tyr Glu Arg Ala Glu Gly Arg His Ser Thr Gly Ala Thr Ala Gly Pro
        770                 775                 780

Gly Ser Ala Thr Met Pro Thr Leu Leu Arg Val Tyr Ile Asp Gly Pro
        785                 790                 795                 800

His Gly Met Gly Lys Thr Thr Thr Thr Gln Leu Leu Val Ala Leu
                            805                 810                 815
```

Gly Ser Arg Asp Asp Ile Val Tyr Val Pro Glu Pro Met Thr Tyr Trp
            820                 825                 830

Arg Val Leu Gly Ala Ser Glu Thr Ile Ala Asn Ile Tyr Thr Thr Gln
            835                 840                 845

His Arg Leu Asp Gln Gly Glu Ile Ser Ala Gly Asp Ala Ala Val Val
            850                 855                 860

Met Thr Ser Ala Gln Ile Thr Met Pro Tyr Ala Val Thr Asp Ala Val
865                 870                 875                 880

Leu Ala Pro His Ile Gly Gly Glu Ala Gly Ser Ser His Ala Pro Pro
                885                 890                 895

Pro Ala Leu Thr Ile Phe Leu Asp Arg His Pro Ile Ala Phe Met Leu
            900                 905                 910

Cys Tyr Pro Ala Ala Arg Tyr Leu Met Gly Ser Met Thr Pro Gln Ala
            915                 920                 925

Val Leu Ala Phe Val Ala Leu Ile Pro Pro Thr Leu Pro Gly Thr Asn
930                 935                 940

Ile Val Leu Gly Ala Leu Pro Glu Asp Arg His Ile Asp Arg Leu Ala
945                 950                 955                 960

Lys Arg Gln Arg Pro Gly Glu Arg Leu Asp Leu Ala Met Leu Ala Ala
            965                 970                 975

Ile Arg Arg Val Tyr Gly Leu Leu Ala Asn Thr Val Arg Tyr Leu Gln
            980                 985                 990

Cys Gly Gly Ser Trp Arg Glu Asp Trp Gly Gln Leu Ser Gly Thr Ala
            995                 1000                1005

Val Pro Pro Gln Gly Ala Glu Pro Gln Ser Asn Ala Gly Pro Arg
            1010                1015                1020

Pro His Ile Gly Asp Thr Leu Phe Thr Leu Phe Arg Ala Pro Glu
            1025                1030                1035

Leu Met Ala Pro Asn Gly Asp Leu Tyr Asn Val Phe Ala Trp Ala
            1040                1045                1050

Leu Asp Val Leu Ala Lys Arg Leu Arg Ser Met His Val Phe Ile
            1055                1060                1065

Leu Asp Tyr Asp Gln Ser Pro Ala Gly Cys Arg Asp Ala Leu Leu
            1070                1075                1080

Gln Leu Thr Ser Gly Met Val Gln Thr His Val Thr Thr Pro Gly
            1085                1090                1095

Ser Ile Pro Thr Ile Cys Asp Leu Ala Arg Thr Phe Ala Arg Glu
            1100                1105                1110

Met Gly Glu Ala Asn
            1115

<210> SEQ ID NO 10
<211> LENGTH: 3629
<212> TYPE: DNA
<213> ORGANISM: Artificial Sequence
<220> FEATURE:
<223> OTHER INFORMATION: Synthesized Humanized nucleotide encoding
      fusion protein with sequences from homo sapiens, synthetic green
      fluorescent protein, photinus pyralis, and lentvirus

<400> SEQUENCE: 10
aacccgtgtc ggctccagat ctggcctccg cgccgggttt tggcgcctcc cgcgggcgcc     60
cccctcctca cggcgagcgc tgccacgtca gacgaagggc gcagcgagcg tcctgatcct    120
tccgcccgga cgctcaggac agcggcccgc tgctcataag actcggcctt agaacccag    180

```
tatcagcaga aggacatttt aggacgggac ttgggtgact ctagggcact ggttttcttt    240
ccagagagcg gaacaggcga ggaaaagtag tcccttctcg gcgattctgc ggagggatct    300
ccgtggggcg gtgaacgccg atgattatat aaggacgcgc cgggtgtggc acagctagtt    360
ccgtcgcagc cgggatttgg gtcgcggttc ttgtttgtgg atcgctgtga tcgtcacttg    420
gtgagtagcg ggctgctggg ctggccgggg ctttcgtggc cgccgggccg ctcggtggga    480
cggaagcgtg tggagagacc gccaagggct gtagtctggg tccgcgagca aggttgccct    540
gaactggggg ttggggggag cgcacaaaat ggcggctgtt cccgagtctt gaatggaaga    600
cgcttgtgag gcgggctgtg aggtcgttga acaaggtgg ggggcatggt gggcggcaag    660
aacccaaggt cttgaggcct tcgctaatgc gggaaagctc ttattcgggt gagatgggct    720
ggggcaccat ctgggaccc ctgacgtgaa gtttgtcact gactggagaa actcgggttt    780
gtcgtctgtt gcggggcgg cagttatggc ggtgccgttg ggcagtgcac ccgtaccttt    840
gggagcgcgc gccctcgtcg tgtcgtgacg tcacccgttc tgttggctta taatgcaggg    900
tggggccacc tgccggtagg tgtgcggtag gcttttctcc gtcgcaggac gcaggggttcg    960 ggcctagggt aggctctcct gaatcgacag gcgccggacc tctggtgagg ggagggataa   1020
gtgaggcgtc agtttctttg gtcggttta tgtacctatc ttcttaagta gctgaagctc   1080
cggttttgaa ctatgcgctc ggggttggcg agtgtgtttt gtgaagtttt ttaggcacct   1140
tttgaaatgt aatcatttgg gtcaatatgt aattttcagt gttagactag taaattgtcc   1200
gctaaattct ggccgttttt ggcttttttg ttagacatgg aagacgccaa aaacataaag   1260
aaaggcccgg cgccattcta tccgctggaa gatggaaccg ctggagagca actgcataag   1320
gctatgaaga gatacgccct ggttcctgga acaattgctt ttacagatgc acatatcgag   1380
gtggacatca cttacgctga gtacttcgaa atgtccgttc ggttggcaga agctatgaaa   1440
cgatatgggc tgaatacaaa tcacagaatc gtcgtatgca gtgaaaactc tcttcaattc   1500
tttatgccgg tgttgggcgc gttatttatc ggagttgcag ttgcgcccgc gaacgacatt   1560
tataatgaac gtgaattgct caacagtatg ggcatttcgc agcctaccgt ggtgttcgtt   1620
tccaaaaagg ggttgcaaaa aattttgaac gtgcaaaaaa agctcccaat catccaaaaa   1680
attattatca tggattctaa aacggattac cagggatttc agtcgatgta cacgttcgtc   1740
acatctcatc tacctcccgg ttttaatgaa tacgattttg tgccagagtc cttcgatagg   1800
gacaagacaa ttgcactgat catgaactcc tctggatcta ctggtctgcc taaaggtgtc   1860
gctctgcctc atagaactgc ctgcgtgaga ttctcgcatg ccagagatcc tatttttggc   1920
aatcaaatca ttccggatac tgcgatttta agtgttgttc cattccatca cggttttgga   1980
atgtttacta cactcggata tttgatatgt ggatttcgag tcgtcttaat gtatagattt   2040
gaagaagagc tgtttctgag gagccttcag gattacaaga ttcaaagtgc gctgctggtg   2100
ccaaccctat tctccttctt cgccaaaagc actctgattg acaaatacga tttatctaat   2160
ttacacgaaa ttgcttctgg tggcgctccc ctctctaagg aagtcgggga gcggttgcc    2220 aagaggttcc atctgccagg tatcaggcaa ggatatgggc tcactgagac tacatcagct   2280
attctgatta cacccgaggg ggatgataaa ccgggcgcgg tcgtaaagt tgttccattt   2340 tttgaagcga aggttgtgga tctggatacc gggaaaacgc tgggcgttaa tcaaagaggc   2400
gaactgtgtg tgagaggtcc tatgattatg tccggttatg taaacaatcc ggaagcgacc   2460
aacgccttga ttgacaagga tggatggcta cattctggag acatagctta ctgggacgaa   2520
gacgaacact tcttcatcgt tgaccgcctg aagtctctga ttaagtacaa aggctatcag   2580
```

```
gtggctcccg ctgaattgga atccatcttg ctccaacacc ccaacatctt cgacgcaggt    2640
gtcgcaggtc ttcccgacga tgacgccggt gaacttcccg ccgccgttgt tgttttggag    2700
cacggaaaga cgatgacgga aaaagagatc gtggattacg tcgccagtca agtaacaacc    2760
gcgaaaaagt tgcgcggagg agttgtgttt gtggacgaag taccgaaagg tcttaccgga    2820
aaactcgacg caagaaaaat cagagagatc ctcataaagg ccaagaaggg cggaaagatc    2880
gccgtgtaat tcggatccca cggcgatatg agcgtgagca agggcgagga gctgttcacc    2940
ggggtggtgc ccatcctggt cgagctggac ggcgacgtaa acggccacaa gttcagcgtg    3000
tccggcgagg gcgagggcga tgccacctac ggcaagctga ccctgaagtt catctgcacc    3060
accggcaagc tgcccgtgcc ctggcccacc ctcgtgacca ccctgaccta cggcgtgcag    3120
tgcttcagcc gctaccccga ccacatgaag cagcacgact tcttcaagtc cgccatgccc    3180
gaaggctacg tccaggagcg caccatcttc ttcaaggacg acggcaacta caagacccgc    3240
gccgaggtga agttcgaggg cgacaccctg gtgaaccgca tcgagctgaa gggcatcgac    3300
ttcaaggagg acggcaacat cctggggcac aagctggagt acaactacaa cagccacaac    3360
gtctatatca tggccgacaa gcagaagaac ggcatcaagg tgaacttcaa gatccgccac    3420
aacatcgagg acggcagcgt gcagctcgcc gaccactacc agcagaacac ccccatcggc    3480
gacggccccg tgctgctgcc cgacaaccac tacctgagca cccagtccgc cctgagcaaa    3540
gaccccaacg agaagcgcga tcacatggtc ctgctggagt tcgtgaccgc cgccgggatc    3600
actctcggca tggacgagct gtacaaaat                                      3629
```

<210> SEQ ID NO 11
<211> LENGTH: 768
<212> TYPE: PRT
<213> ORGANISM: Artificial Sequence
<220> FEATURE:
<223> OTHER INFORMATION: Synthesized Humanizezd fusion protein with
      sequences from homo sapiens, synthetic green fluorescent protein,
      photinus pyralis, and lentvirus

<400> SEQUENCE: 11

```
Gly Arg Arg Gln Lys His Lys Glu Arg Pro Gly Ala Ile Leu Ser Ala
1               5                   10                  15

Gly Arg Trp Asn Arg Trp Arg Ala Thr Ala Gly Tyr Glu Glu Ile Arg
            20                  25                  30

Pro Gly Ser Trp Asn Asn Cys Phe Tyr Arg Cys Thr Tyr Arg Gly Gly
        35                  40                  45

His His Leu Arg Val Leu Arg Asn Val Arg Ser Val Gly Arg Ser Tyr
    50                  55                  60

Glu Thr Ile Trp Ala Glu Tyr Lys Ser Gln Asn Arg Arg Met Gln Lys
65                  70                  75                  80

Leu Ser Ser Ile Leu Tyr Ala Gly Val Gly Arg Val Ile Tyr Arg Ser
                85                  90                  95

Cys Ser Cys Ala Arg Glu Arg His Leu Thr Ile Ala Gln Gln Tyr Gly
            100                 105                 110

His Phe Ala Ala Tyr Arg Gly Val Arg Phe Gln Lys Gly Val Ala Lys
        115                 120                 125

Asn Phe Glu Arg Ala Lys Lys Ala Pro Asn His Pro Lys Asn Tyr Tyr
    130                 135                 140

His Gly Phe Asn Gly Leu Pro Gly Ile Ser Val Asp Val His Val Arg
145                 150                 155                 160
```

-continued

```
His Ile Ser Ser Thr Ser Arg Phe Ile Arg Phe Cys Ala Arg Val Leu
                165                 170                 175
Arg Gly Gln Asp Asn Cys Thr Asp His Glu Leu Leu Trp Ile Tyr Trp
            180                 185                 190
Ser Ala Arg Cys Arg Ser Ala Ser Asn Cys Leu Arg Glu Ile Leu Ala
        195                 200                 205
Cys Gln Arg Ser Tyr Phe Trp Gln Ser Asn His Ser Gly Tyr Cys Asp
    210                 215                 220
Phe Lys Cys Cys Ser Ile Pro Ser Arg Phe Trp Asn Val Tyr Tyr Thr
225                 230                 235                 240
Arg Ile Phe Asp Met Trp Ile Ser Ser Arg Leu Asn Val Ile Arg Arg
                245                 250                 255
Ala Val Ser Glu Glu Pro Ser Gly Leu Gln Asp Ser Lys Cys Ala Ala
            260                 265                 270
Gly Ala Asn Pro Ile Leu Leu Leu Arg Gln Lys His Ser Asp Gln Ile
        275                 280                 285
Arg Phe Ile Phe Thr Arg Asn Cys Phe Trp Trp Arg Ser Pro Leu Gly
    290                 295                 300
Ser Arg Gly Ser Gly Cys Gln Glu Val Pro Ser Ala Arg Tyr Gln Ala
305                 310                 315                 320
Arg Ile Trp Ala His Asp Tyr Ile Ser Tyr Ser Asp Tyr Thr Arg Gly
                325                 330                 335
Gly Thr Gly Arg Gly Arg Ser Cys Ser Ile Phe Ser Glu Gly Cys Gly
            340                 345                 350
Ser Gly Tyr Arg Glu Asn Ala Gly Arg Ser Lys Arg Thr Val Cys
        355                 360                 365
Glu Arg Ser Tyr Asp Tyr Val Arg Leu Cys Lys Gln Ser Gly Ser Asp
    370                 375                 380
Gln Arg Leu Asp Gln Gly Trp Met Ala Thr Phe Trp Arg His Ser Leu
385                 390                 395                 400
Leu Gly Arg Arg Arg Thr Leu Leu His Arg Pro Pro Glu Val Ser Asp
                405                 410                 415
Val Gln Arg Leu Ser Gly Gly Ser Arg Ile Gly Ile His Leu Ala Pro
            420                 425                 430
Thr Pro Gln His Leu Arg Arg Arg Cys Arg Arg Ser Arg Arg Arg
        435                 440                 445
Arg Thr Ser Arg Arg Arg Cys Cys Phe Gly Ala Arg Lys Asp Asp Asp
    450                 455                 460
Gly Lys Arg Asp Arg Gly Leu Arg Arg Gln Ser Ser Asn Asn Arg Glu
465                 470                 475                 480
Lys Val Ala Arg Ser Cys Val Cys Gly Arg Ser Thr Glu Arg Ser
                485                 490                 495
Tyr Arg Lys Thr Arg Arg Lys Lys Asn Gln Arg Asp Pro His Lys Gly
            500                 505                 510
Gln Glu Gly Arg Lys Asp Arg Arg Val Ile Arg Ile Pro Arg Arg Tyr
        515                 520                 525
Glu Arg Glu Gln Gly Arg Gly Ala Val His Arg Gly Ala His Pro
    530                 535                 540
Gly Arg Ala Gly Arg Arg Lys Arg Pro Gln Val Gln Arg Val Arg
545                 550                 555                 560
Arg Gly Arg Gly Arg Cys His Leu Arg Gln Ala Asp Pro Glu Val His
                565                 570                 575
Leu His His Arg Gln Ala Ala Arg Ala Leu Ala His Pro Arg Asp His
```

```
                580               585                590
Pro Asp Leu Arg Arg Ala Val Leu Gln Pro Leu Pro Arg Pro His Glu
            595                 600                605
Ala Ala Arg Leu Leu Gln Val Arg His Ala Arg Arg Leu Arg Pro Gly
    610                 615                 620
Ala His His Leu Leu Gln Gly Arg Arg Gln Leu Gln Asp Pro Arg Arg
625                 630                 635                 640
Gly Glu Val Arg Gly Arg His Pro Gly Glu Pro His Arg Ala Glu Gly
                645                 650                 655
His Arg Leu Gln Gly Gly Arg Gln His Pro Gly Ala Gln Ala Gly Val
            660                 665                 670
Gln Leu Gln Gln Pro Gln Arg Leu Tyr His Gly Arg Gln Ala Glu Glu
        675                 680                 685
Arg His Gln Gly Glu Leu Gln Asp Pro Pro Gln His Arg Gly Arg Gln
    690                 695                 700
Arg Ala Ala Arg Arg Pro Leu Pro Ala Glu His Pro His Arg Arg
705                 710                 715                 720
Pro Arg Ala Ala Ala Arg Gln Pro Leu Pro Glu His Pro Val Arg Pro
                725                 730                 735
Glu Gln Arg Pro Gln Arg Glu Ala Arg Ser His Gly Pro Ala Gly Val
            740                 745                 750
Arg Asp Arg Arg Arg Asp His Ser Arg His Gly Arg Ala Val Gln Asn
        755                 760                 765

<210> SEQ ID NO 12
<211> LENGTH: 904
<212> TYPE: DNA
<213> ORGANISM: Herpes simplex virus 1

<400> SEQUENCE: 12
atggcttcgt accccggcca tcaacacgcg tctgcgttcg accaggctgc gcgttctcgc      60
ggccatagca accgacgtac ggcgttgcgc cctcgccggc agcaagaagc cacggaagtc     120
cgcccggagc agaaaatgcc cacgctactg cgggtttata tagacggtcc ccacggggatg    180
ggaaaaacca ccaccacgca actgctggtg gccctgggtt cgcgcgacga tatcgtctac     240
gtacccgagc cgatgactta ctggcgggtg ctgggggctt ccgtgctacc cggccgcgcg     300
gtaccttatg ggcagcatga cccccaggc cgtgctggcc ttcgtggccc tcatcccgcc     360
gaccttgccc ggcaccaaca tcgtgcttgg ggccccttccg gaggacagac acatcgaccg    420
cctggccaaa cgccagcgcc ccggcgagcg gctggacctg ctatgctggc tgcgattcg     480
ccgcgtttac gggctacttg ccaatacggt gcggtatctg cagtgcggcg gtcgtggcg     540
ggaggactgg ggacagcttt cggggacggc cgtgccgccc cagggtgccg agccccagag    600
caacgcgggc ccacgacccc atatcgggga cacgttattt accctgtttc gggccccga    660
gttgctggcc cccaacggcg acctgtataa cgtgtttgcc tgggccttgg acgtcttggc    720
caaacgcctc cgttccatgc acgtctttat cctggattac gaccaatcgc ccgccggctg    780
ccgggacgcc ctgctgcaac ttaccctccgg gatggtccag acccacgtca ccaccccgg    840
ctccataccg acgatatgcg acctggcgcg cacgtttgcc cgggagatgg gggaggctaa    900
ctga                                                                  904

<210> SEQ ID NO 13
<211> LENGTH: 299
<212> TYPE: PRT
```

<213> ORGANISM: Herpes simplex virus 1

<400> SEQUENCE: 13

```
Gly Phe Val Pro Arg Pro Ser Thr Arg Val Cys Val Arg Pro Gly Cys
1               5                   10                  15
Ala Phe Ser Arg Pro Gln Pro Thr Tyr Gly Val Ala Pro Ser Pro Ala
            20                  25                  30
Ala Arg Ser His Gly Ser Pro Pro Gly Ala Glu Asn Ala His Ala Thr
        35                  40                  45
Ala Gly Leu Tyr Arg Arg Ser Pro Arg Asp Gly Glu Asn His His His
    50                  55                  60
Ala Thr Ala Gly Gly Pro Gly Phe Ala Arg Arg Tyr Arg Leu Arg Thr
65                  70                  75                  80
Arg Ala Asp Asp Leu Leu Ala Gly Ala Gly Gly Phe Arg Ala Thr Arg
                85                  90                  95
Pro Arg Gly Thr Leu Trp Ala Ala Pro Pro Arg Pro Cys Trp Arg Ser
            100                 105                 110
Trp Pro Ser Ser Arg Arg Pro Cys Pro Ala Pro Thr Ser Cys Leu Gly
        115                 120                 125
Pro Phe Arg Arg Thr Asp Thr Ser Thr Ala Trp Pro Asn Ala Ser Ala
    130                 135                 140
Pro Ala Ser Gly Trp Thr Trp Leu Cys Trp Leu Arg Phe Ala Ala Phe
145                 150                 155                 160
Thr Gly Tyr Leu Pro Ile Arg Cys Gly Ile Cys Ser Ala Ala Gly Arg
                165                 170                 175
Gly Gly Arg Thr Gly Asp Ser Phe Arg Gly Arg Pro Cys Arg Pro Arg
            180                 185                 190
Val Pro Ser Pro Arg Ala Thr Arg Ala His Asp Pro Ile Ser Gly Thr
        195                 200                 205
Arg Tyr Leu Pro Cys Phe Gly Pro Pro Ser Cys Trp Pro Pro Thr Ala
    210                 215                 220
Thr Cys Ile Thr Cys Leu Pro Gly Pro Trp Thr Ser Trp Pro Asn Ala
225                 230                 235                 240
Ser Val Pro Cys Thr Ser Leu Ser Trp Ile Thr Thr Asn Arg Pro Pro
                245                 250                 255
Ala Ala Gly Thr Pro Cys Cys Asn Leu Pro Pro Gly Trp Ser Arg Pro
            260                 265                 270
Thr Ser Pro Pro Pro Ala Pro Tyr Arg Arg Tyr Ala Thr Trp Arg Ala
        275                 280                 285
Arg Leu Pro Gly Arg Trp Gly Arg Leu Thr Glu
    290                 295
```

<210> SEQ ID NO 14
<211> LENGTH: 780
<212> TYPE: DNA
<213> ORGANISM: Herpes simplex virus 2

<400> SEQUENCE: 14

```
atggcttctc acgccggcca acagcacgcg cctgcgttcg gtcaggctgc tcgtgcgagc      60
gggcctaccg acggccgcgc ggcgtcccgt cctagccatc gccaggggc ctccggagcc     120
cgcggggatc cggagctgcc cacgctgctg cgggtttata tagacggacc ccacggggtg     180
gggaagacca ccacctccgc gcagctgatg gaggccctgg ggccgcgcga caatatcgtc     240
tacgtccccg agccgatgac ttactggcag gtgctggggg cctccgagac cctgacgaac     300
```

```
atctacaaca cgcagcaccg tctggaccgc ggcgagatat cggccgggga ggcggcggtg    360
gtaatgacca cgcgcccagat aacaatgagc acgccttatg cggcgacgga cgccgttttg    420
gctcctcata tcgggggga ggctgtgggc ccgcaagccc cgccccggc cctcacccctt      480 gttttcgacc ggcaccctat cgcctccctg ctgtgctacc cggccgcgcg gtacctcatg    540
ggaagcatga ccccccaggc cgtgttggcg ttcgtggccc tcatgccccc gaccgcgccc    600
ggcacgaacc tggtcctggg tgtccttccg gaggccgaac acgccgaccg cctggccaga    660
cgccaacgcc cgggcgagcg gcttgacctg gccatgctgt ccgccattcg ccgtgtctac    720
gatctactcg ccaacacggt gcggtacctg cagcgcggcg ggaggtggcg ggaggactgg    780
```

<210> SEQ ID NO 15
<211> LENGTH: 373
<212> TYPE: PRT
<213> ORGANISM: Herpes simplex virus 2

<400> SEQUENCE: 15

```
Gly Phe Ser Arg Arg Pro Thr Ala Arg Ala Cys Val Arg Ser Gly Cys
1               5                   10                  15

Ser Cys Glu Arg Ala Tyr Arg Arg Pro Arg Gly Val Pro Ser Pro Ser
            20                  25                  30

Pro Gly Gly Leu Arg Ser Pro Arg Gly Ser Gly Ala Ala His Ala Ala
        35                  40                  45

Ala Gly Leu Tyr Arg Arg Thr Pro Arg Gly Gly Glu Asp His His Leu
    50                  55                  60

Arg Ala Ala Asp Gly Gly Pro Gly Ala Ala Arg Gln Tyr Arg Leu Arg
65                  70                  75                  80

Pro Arg Ala Asp Asp Leu Leu Ala Gly Ala Gly Gly Leu Arg Asp Pro
                85                  90                  95

Asp Glu His Leu Gln His Ala Ala Pro Ser Gly Pro Arg Arg Asp Ile
            100                 105                 110

Gly Arg Gly Gly Gly Gly Asn Asp Gln Arg Pro Asn Asn Glu
        115                 120                 125

His Ala Leu Cys Gly Asp Gly Arg Arg Phe Gly Ser Ser Tyr Arg Gly
    130                 135                 140

Gly Gly Cys Gly Pro Ala Ser Pro Ala Pro Gly Pro His Pro Cys Phe
145                 150                 155                 160

Arg Pro Ala Pro Tyr Arg Leu Pro Ala Val Leu Pro Gly Arg Ala Val
                165                 170                 175

Pro His Gly Lys His Asp Pro Pro Gly Arg Val Gly Val Arg Gly Pro
            180                 185                 190

His Ala Pro Asp Arg Ala Arg His Glu Pro Gly Pro Gly Cys Pro Ser
        195                 200                 205

Gly Gly Arg Thr Arg Arg Pro Pro Gly Gln Thr Pro Thr Pro Gly Arg
    210                 215                 220

Ala Ala Pro Gly His Ala Val Arg His Ser Pro Cys Leu Arg Ser Thr
225                 230                 235                 240

Arg Gln His Gly Ala Val Pro Ala Ala Arg Arg Glu Val Ala Gly Gly
                245                 250                 255

Leu Gly Pro Ala Asp Gly Gly Arg Arg Gly Asp Pro Ala Pro Asp Pro
            260                 265                 270

Glu Asp Gly Ala Gly Ser Leu Pro Arg Ile Glu Asp Thr Leu Phe Ala
        275                 280                 285

Leu Phe Arg Val Pro Glu Leu Leu Ala Pro Asn Gly Asp Leu Tyr His
```

```
                290                 295                 300
Ile Phe Ala Trp Val Leu Asp Val Leu Ala Asp Arg Leu Leu Pro Met
305                 310                 315                 320

His Leu Phe Val Leu Asp Tyr Asp Gln Ser Pro Val Gly Cys Arg Asp
            325                 330                 335

Ala Leu Leu Arg Leu Thr Ala Gly Met Ile Pro Thr Arg Val Thr Thr
                340                 345                 350

Ala Gly Ser Ile Ala Glu Ile Arg Asp Leu Ala Arg Thr Phe Ala Arg
            355                 360                 365

Glu Val Gly Gly Val
        370

<210> SEQ ID NO 16
<211> LENGTH: 7881
<212> TYPE: DNA
<213> ORGANISM: Lentvirus

<400> SEQUENCE: 16
taatcaacct ctggattaca aaatttgtga agattgact ggtattctta actatgttgc      60
tccttttacg ctatgtggat acgctgcttt aatgcctttg tatcatgcta ttgcttcccg    120
tatggctttc attttctcct ccttgtataa atcctggttg ctgtctcttt atgaggagtt    180
gtggcccgtt gtcaggcaac gtggcgtggt gtgcactgtg tttgctgacg caaccccac     240 tggttggggc attgccacca cctgtcagct cctttccggg actttcgctt tccccctccc    300
tattgccacg gcggaactca tcgcccgcct gccttgcccg ctgctggaca ggggctcggc    360
tgttgggcac tgacaattcc gtggtgttgt cggggaaatc atcgtccttt ccttggctgc    420
tcgcctgtgt tgccacctgg attctgcgcg gacgtccttc tgctacgtc cttcggccct     480 caatccaagc ggaccttcct tcccgcggcc tgctgccggc tctgcgggcc tcttccgcgt    540 cttcgcctt cgcctcaga cgagtcgat ctccctttgg gcgctcccg catcgatgtc        600 gacctcgaga ccggccgaac tcgaagacct agaaaaaaca ttggagcaat acaagtagc     660 aatacagcag ctaccaatgc tgattgtgcc tggctagaag cacaagagga ggaggaggtg    720
ggttttccag tcacacctca ggtacctta agaccaatga cttacaaggc agctgtagat     780
cttagccact ttttaaaaga aaggggggga ctggaagggc taattcactc ccaacgaaga    840
caagatatcc ttgatctgtg gatctaccac acacaaggc acttccctga ttggcagaac    900
tacacaccag ggccagggat cagatatcca ctgacctttg gatggtgcta caagctagta    960
ccagttgagc aagagaaggt agaagaagcc aatgaaggag agaacacccg cttgttacac   1020
cctgtgagcc tgcatgggat ggatgacccg gagagagaag tattagagtg gaggtttgac   1080
agccgcctag catttcatca catggcccga gagctgcatc cggactgtac tgggtctctc   1140
tggttagacc agatctgagc ctgggagctc tctggctaac tagggaaccc actgcttaag   1200
cctcaataaa gcttgccttg agtgcttcaa gtagtgtgtg cccgtctgtt gtgtgactct   1260
ggtaactaga gatccctcag acccttttag tcagtgtgga aaatctctag cagggcccgt   1320
ttaaacccgc tgatcagcct cgactgtgcc ttctagttgc cagccatctg ttgtttgccc   1380
ctcccccgtg ccttccttga ccctggaagg tgccactccc actgtccttt cctaataaaa   1440
tgaggaaatt gcatcgcatt gtctgagtag gtgtcattct attctggggg gtggggtggg   1500
gcaggacagc aagggggagg attgggaaga caatagcagg catgctgggg atgcggtggg   1560
ctctatggct tctgaggcgg aaagaaccag ctggggctct aggggg tatc cccacgcgcc   1620
```

| | |
|---|---|
| ctgtagcggc gcattaagcg cggcgggtgt ggtggttacg cgcagcgtga ccgctacact | 1680 |
| tgccagcgcc ctagcgcccg ctcctttcgc tttcttccct tcctttctcg ccacgttcgc | 1740 |
| cggctttccc cgtcaagctc taaatcgggg catcccttta gggttccgat ttagtgcttt | 1800 |
| acggcacctc gaccccaaaa aacttgatta gggtgatggt tcacgtagtg gccatcgcc | 1860 |
| ctgatagacg gttttccgcc cttttgacgtt ggagtccacg ttctttaata gtggactctt | 1920 |
| gttccaaact ggaacaacac tcaaccctat ctcggtctat tcttttgatt tataagggat | 1980 |
| tttggggatt tcggcctatt ggttaaaaaa tgagctgatt taacaaaaat ttaacgcgaa | 2040 |
| ttaattctgt ggaatgtgtg tcagttaggg tgtggaaagt ccccaggctc ccagcaggc | 2100 |
| agaagtatgc aaagcatgca tctcaattag tcagcaacca ggtgtggaaa gtccccaggc | 2160 |
| tccccagcag gcagaagtat gcaaagcatg catctcaatt agtcagcaac catagtcccg | 2220 |
| cccctaactc cgcccatccc gcccctaact ccgcccagtt ccgcccattc tccgcccat | 2280 |
| ggctgactaa ttttttttat ttatgcagag gccgaggccg cctcggcctc tgagctattc | 2340 |
| cagaagtagt gaggaggctt ttttggaggc ctaggctttt gcaaaaagct cccgggagct | 2400 |
| tgtatatcca ttttcggatc tgatcagcac gtgttgacaa ttaatcatcg gcatagtata | 2460 |
| tcggcatagt ataatacgac aaggtgagga actaaaccat ggccaagttg accagtgccg | 2520 |
| ttccggtgct caccgcgcgc gacgtcgccg gagcggtcga ttctggacc gaccggctcg | 2580 |
| ggttctcccg ggacttcgtg gaggacgact tcgccggtgt ggtccgggac gacgtgaccc | 2640 |
| tgttcatcag cgcggtccag gaccaggtgg tgccggacaa caccctggcc tgggtgtggg | 2700 |
| tgcgcggcct ggacgagctg tacgccgagt ggtcggaggt cgtgtccacg aacttccggg | 2760 |
| acgcctccgg gccggccatg accgagatcg gcgagcagcc gtggggcgg gagttcgccc | 2820 |
| tgcgcgaccc ggccggcaac tgcgtgcact tcgtggccga ggagcaggac tgacacgtgc | 2880 |
| tacgagattt cgattccacc gccgccttct atgaaaggtt gggcttcgga atcgttttcc | 2940 |
| gggacgccgg ctggatgatc ctccagcgcg ggatctcat gctggagttc ttcgcccacc | 3000 |
| ccaacttgtt tattgcagct tataatggtt acaaataaag caatagcatc acaaatttca | 3060 |
| caaataaagc atttttttca ctgcattcta gttgtggttt gtccaaactc atcaatgtat | 3120 |
| cttatcatgt ctgtataccg tcgacctcta gctagagctt ggcgtaatca tggtcatagc | 3180 |
| tgtttcctgt gtgaaattgt tatccgctca caattccaca caacatacga gccgaagca | 3240 |
| taaagtgtaa agcctggggt gcctaatgag tgagctaact cacattaatt gcgttgcgct | 3300 |
| cactgcccgc tttccagtcg ggaaacctgt cgtgccagct gcattaatga atcggccaac | 3360 |
| gcgcggggag aggcggtttg cgtattgggc gctcttccgc ttcctcgctc actgactcgc | 3420 |
| tgcgctcggt cgttcggctg cggcgagcgg tatcagctca ctcaaaggcg gtaatacggt | 3480 |
| tatccacaga atcaggggat aacgcaggaa agaacatgtg agcaaaaggc cagcaaaagg | 3540 |
| ccaggaaccg taaaaaggcc gcgttgctgg cgtttttcca taggctccgc cccctgacg | 3600 |
| agcatcacaa aaatcgacgc tcaagtcaga ggtggcgaaa cccgacagga ctataaagat | 3660 |
| accaggcgtt tcccctgga agctccctcg tgcgctctcc tgttccgacc ctgccgctta | 3720 |
| ccggatacct gtccgccttt ctcccttcgg aagcgtggc gctttctcaa tgctcacgct | 3780 |
| gtaggtatct cagttcggtg taggtcgttc gctccaagct gggctgtgtg cacgaaccc | 3840 |
| ccgttcagcc cgaccgctgc gccttatccg gtaactatcg tcttgagtcc aacccggtaa | 3900 |
| gacacgactt atcgccactg gcagcagcca ctggtaacag gattagcaga gcgaggtatg | 3960 |
| taggcggtgc tacagagttc ttgaagtggt ggcctaacta cggctacact agaaggacag | 4020 |

```
tatttggtat ctgcgctctg ctgaagccag ttaccttcgg aaaaagagtt ggtagctctt    4080
gatccggcaa acaaaccacc gctggtagcg gtggttttt tgtttgcaag cagcagatta     4140
cgcgcagaaa aaaggatct caagaagatc ctttgatctt ttctacgggg tctgacgctc     4200
agtggaacga aaactcacgt taagggattt tggtcatgag attatcaaaa aggatcttca    4260
cctagatcct tttaaattaa aaatgaagtt ttaaatcaat ctaaagtata tatgagtaaa    4320
cttggtctga cagttaccaa tgcttaatca gtgaggcacc tatctcagcg atctgtctat    4380
ttcgttcatc catagttgcc tgactccccg tcgtgtagat aactacgata cgggagggct    4440
taccatctgg ccccagtgct gcaatgatac cgcgagaccc acgctcaccg gctccagatt    4500
tatcagcaat aaaccagcca gccggaaggg ccgagcgcag aagtggtcct gcaactttat    4560
ccgcctccat ccagtctatt aattgttgcc gggaagctag agtaagtagt tcgccagtta    4620
atagtttgcg caacgttgtt gccattgcta caggcatcgt ggtgtcacgc tcgtcgtttg    4680
gtatggcttc attcagctcc ggttcccaac gatcaaggcg agttacatga tcccccatgt    4740
tgtgcaaaaa agcggttagc tccttcggtc ctccgatcgt tgtcagaagt aagttggccg    4800
cagtgttatc actcatggtt atggcagcac tgcataattc tcttactgtc atgccatccg    4860
taagatgctt ttctgtgact ggtgagtact caaccaagtc attctgagaa tagtgtatgc    4920
ggcgaccgag ttgctcttgc ccggcgtcaa tacgggataa taccgcgcca catagcagaa    4980
ctttaaaagt gctcatcatt ggaaaacgtt cttcggggcg aaaactctca aggatcttac    5040
cgctgttgag atccagttcg atgtaaccca ctcgtgcacc caactgatct tcagcatctt    5100
ttactttcac cagcgtttct gggtgagcaa aaacaggaag gcaaaatgcc gcaaaaaagg    5160
gaataagggc gacacggaaa tgttgaatac tcatactctt cctttttcaa tattattgaa    5220
gcatttatca gggttattgt ctcatgagcg gatacatatt tgaatgtatt tagaaaaata    5280
aacaaatagg ggttccgcgc acatttcccc gaaaagtgcc acctgacgtc gacggatcgg    5340
gagatctccc gatcccctat ggtgcactct cagtacaatc tgctctgatg ccgcatagtt    5400
aagccagtat ctgctccctg cttgtgtgtt ggaggtcgct gagtagtgcg cgagcaaaat    5460
ttaagctaca acaaggcaag gcttaccgga caattgcatg aagaatctgc ttagggttag    5520
gcgttttgcg ctgcttcgcg atgtacgggc cagatatacg cgttgacatt gattattgac    5580
tagttattaa tagtaatcaa ttacggggtc attagttcat agcccatata tggagttccg    5640
cgttacataa cttacggtaa atggcccgcc tggctgaccg cccaacgacc cccgcccatt    5700
gacgtcaata atgacgtatg ttcccatagt aacgccaata gggactttcc attgacgtca    5760
atgggtggac tatttacggt aaactgccca cttggcagta catcaagtgt atcatatgcc    5820
aagtacgccc cctattgacg tcaatgacgg taaatggccc gcctggcatt atgcccagta    5880
catgacctta cgggactttc ctacttggca gtacatctac gtattagtca tcgctattac    5940
catggtgatg cggttttggc agtacaccaa tgggcgtgga tagcggtttg actcacgggg    6000
atttccaagt ctccacccca ttgacgtcaa tgggagtttg ttttggcacc aaaatcaacg    6060
ggactttcca aaatgtcgta caactccgcc ccattgacg caaatgggcg gtaggcgtgt    6120
acggtgggag gtctctgtac tgggtctctc tggttagacc agatctgagc ctgggagctc    6180
tctggctaac tagggaaccc actgcttaag cctcaataaa gcttgccttg agtgcttcaa    6240
gtagtgtgtg cccgtctgtt gtgtgactct ggtaactaga gatccctcag acccttttag    6300
tcagtgtgga aaatctctag cagtggcgcc cgaacaggga cttgaaagcg aaagggaaac    6360
```

| | |
|---|---:|
| cagaggagct ctctcgacgc aggactcggc ttgctgaagc gcgcacggca agaggcgagg | 6420 |
| ggcggcgact ggtgagtacg ccaaaaattt tgactagcgg aggctagaag gagagagatg | 6480 |
| ggtgcgagag cgtcagtatt aagcggggga gaattagatc gcgatgggaa aaaattcggt | 6540 |
| taaggccagg gggaagaaa aaatataaat taaaacatat agtatgggca agcagggagc | 6600 |
| tagaacgatt cgcagttaat cctggcctgt tagaaacatc agaaggctgt agacaaatac | 6660 |
| tgggacagct acaaccatcc cttcagacag gatcagaaga acttagatca ttatataata | 6720 |
| cagtagcaac cctctattgt gtgcatcaaa ggatagagat aaaagacacc aaggaagctt | 6780 |
| tagacaagat agaggaagag caaaacaaaa gtaagaccac cgcacagcaa gcggccgctg | 6840 |
| atcttcagac ctggaggagg agatatgagg gacaattgga gaagtgaatt atataaatat | 6900 |
| aaagtagtaa aaattgaacc attaggagta gcacccacca aggcaaagag aagagtggtg | 6960 |
| cagagagaaa aaagagcagt gggaatagga gctttgttcc ttgggttctt gggagcagca | 7020 |
| ggaagcacta tgggcgcagc gtcaatgacg ctgacggtac aggccagaca attattgtct | 7080 |
| ggtatagtgc agcagcagaa caatttgctg agggctattg aggcgcaaca gcatctgttg | 7140 |
| caactcacag tctggggcat caagcagctc caggcaagaa tcctggctgt ggaaagatac | 7200 |
| ctaaaggatc aacagctcct ggggatttgg ggttgctctg gaaaactcat ttgcaccact | 7260 |
| gctgtgcctt ggaatgctag ttggagtaat aaatctctgg aacagatttg gaatcacacg | 7320 |
| acctggatgg agtgggacag agaaattaac aattacacaa gcttaataca ctccttaatt | 7380 |
| gaagaatcgc aaaaccagca agaaaagaat gaacaagaat tattggaatt agataaatgg | 7440 |
| gcaagtttgt ggaattggtt taacataaca aattggctgt ggtatataaa attattcata | 7500 |
| atgatagtag gaggcttggt aggtttaaga atagtttttg ctgtactttc tatagtgaat | 7560 |
| agagttaggc agggatattc accattatcg tttcagaccc acctcccaac cccgagggga | 7620 |
| cccgacaggc ccgaaggaat agaagaagaa ggtggagaga gagacagaga cagatccatt | 7680 |
| cgattagtga acggatcggc actgcgtgcg ccaattctgc agacaaatgg cagtattcat | 7740 |
| ccacaatttt aaaagaaaag gggggattgg ggggtacagt gcaggggaaa gaatagtaga | 7800 |
| aataatagca acagacatac aaactaaaga attacaaaaa caaattacaa aaattcaaaa | 7860 |
| ttttcgggtt tattacaggg a | 7881 |

<210> SEQ ID NO 17
<211> LENGTH: 1223
<212> TYPE: DNA
<213> ORGANISM: Homo sapiens

<400> SEQUENCE: 17

| | |
|---|---:|
| gtgtcggctc cagatctggc ctccgcgccg ggttttggcg cctcccgcgg gcgcccccct | 60 |
| cctcacggcg agcgctgcca cgtcagacga agggcgcagc gagcgtcctg atccttccgc | 120 |
| ccggacgctc aggacagcgg cccgctgctc ataagactcg gccttagaac cccagtatca | 180 |
| gcagaaggac attttaggac gggacttggg tgactctagg gcactggttt tctttccaga | 240 |
| gagcggaaca ggcgaggaaa agtagtccct tctcggcgat tctgcggagg gatctccgtg | 300 |
| gggcggtgaa cgccgatgat tatataagga gcgccgggt gtggcacagc tagttccgtc | 360 |
| gcagccggga tttgggtcgc ggttcttgtt tgtggatcgc tgtgatcgtc acttggtgag | 420 |
| tagcgggctg ctgggctggc cggggctttc gtgccgccg ggcgctcgg tgggacggaa | 480 |
| gcgtgtggag agaccgccaa gggctgtagt ctgggtccgc gagcaaggtt gccctgaact | 540 |
| gggggttggg gggagcgcac aaaatggcgg ctgttcccga gtcttgaatg gaagacgctt | 600 |

```
gtgaggcggg ctgtgaggtc gttgaaacaa ggtgggggc atggtgggcg gcaagaaccc      660
aaggtcttga ggccttcgct aatgcgggaa agctcttatt cgggtgagat gggctggggc     720
accatctggg gaccctgac gtgaagtttg tcactgactg gagaaactcg ggtttgtcgt      780
ctgttgcggg ggcggcagtt atggcggtgc cgttgggcag tgcacccgta cctttgggag    840
cgcgcgccct cgtcgtgtcg tgacgtcacc cgttctgttg gcttataatg cagggtgggg    900
ccacctgccg gtaggtgtgc ggtaggcttt tctccgtcgc aggacgcagg gttcgggcct    960
agggtaggct ctcctgaatc gacaggcgcc ggacctctgg tgaggggagg gataagtgag   1020
gcgtcagttt ctttggtcgg tttatgtac ctatcttctt aagtagctga agctccggtt    1080
ttgaactatg cgctcggggt tggcgagtgt gttttgtgaa gttttttagg cacctttgga   1140
aatgtaatca tttgggtcaa tatgtaattt tcagtgttag actagtaaat tgtccgctaa   1200
attctggccg tttttggctt ttt                                           1223

<210> SEQ ID NO 18
<211> LENGTH: 1097
<212> TYPE: PRT
<213> ORGANISM: Artificial Sequence
<220> FEATURE:
<223> OTHER INFORMATION: Synthesized Humanized fusion protein with
      sequences from homo sapiens, synthetic green fluorescent protein,
      photinus pyralis, and lentvirus

<400> SEQUENCE: 18

Gly Arg Arg Gln Lys His Lys Glu Arg Pro Gly Ala Ile Leu Ser Ala
1               5                   10                  15

Gly Arg Trp Asn Arg Trp Arg Ala Thr Ala Gly Tyr Glu Glu Ile Arg
            20                  25                  30

Pro Gly Ser Trp Asn Asn Cys Phe Tyr Arg Cys Thr Tyr Arg Gly Gly
        35                  40                  45

His His Leu Arg Val Leu Arg Asn Val Arg Ser Val Gly Arg Ser Tyr
    50                  55                  60

Glu Thr Ile Trp Ala Glu Tyr Lys Ser Gln Asn Arg Arg Met Gln Lys
65              70                  75                  80

Leu Ser Ser Ile Leu Tyr Ala Gly Val Gly Arg Val Ile Tyr Arg Ser
                85                  90                  95

Cys Ser Ala Arg Glu Arg His Leu Thr Ile Ala Gln Gln Tyr Gly
            100                 105                 110

His Phe Ala Ala Tyr Arg Gly Val Arg Phe Gln Lys Gly Val Ala Lys
        115                 120                 125

Asn Phe Glu Arg Ala Lys Lys Ala Pro Asn His Pro Lys Asn Tyr Tyr
    130                 135                 140

His Gly Phe Asn Gly Leu Pro Gly Ile Ser Val Asp Val His Val Arg
145                 150                 155                 160

His Ile Ser Ser Thr Ser Arg Phe Ile Arg Phe Cys Ala Arg Val Leu
                165                 170                 175

Arg Gly Gln Asp Asn Cys Thr Asp His Glu Leu Leu Trp Ile Tyr Trp
            180                 185                 190

Ser Ala Arg Cys Arg Ser Ala Ser Asn Cys Leu Arg Glu Ile Leu Ala
        195                 200                 205

Cys Gln Arg Ser Tyr Phe Trp Gln Ser Asn His Ser Gly Tyr Cys Asp
    210                 215                 220

Phe Lys Cys Cys Ser Ile Pro Ser Arg Phe Trp Asn Val Tyr Tyr Thr
225                 230                 235                 240
```

```
Arg Ile Phe Asp Met Trp Ile Ser Ser Arg Leu Asn Val Ile Arg Arg
                245                 250                 255

Ala Val Ser Glu Glu Pro Ser Gly Leu Gln Asp Ser Lys Cys Ala Ala
            260                 265                 270

Gly Ala Asn Pro Ile Leu Leu Leu Arg Gln Lys His Ser Asp Gln Ile
        275                 280                 285

Arg Phe Ile Phe Thr Arg Asn Cys Phe Trp Arg Ser Pro Leu Gly
    290                 295                 300

Ser Arg Gly Ser Gly Cys Gln Glu Val Pro Ser Ala Arg Tyr Gln Ala
305                 310                 315                 320

Arg Ile Trp Ala His Asp Tyr Ile Ser Tyr Ser Asp Tyr Thr Arg Gly
                325                 330                 335

Gly Thr Gly Arg Gly Arg Ser Cys Ser Ile Phe Ser Glu Gly Cys Gly
            340                 345                 350

Ser Gly Tyr Arg Glu Asn Ala Gly Arg Ser Lys Arg Thr Val Cys
        355                 360                 365

Glu Arg Ser Tyr Asp Tyr Val Arg Leu Cys Lys Gln Ser Gly Ser Asp
    370                 375                 380

Gln Arg Leu Asp Gln Gly Trp Met Ala Thr Phe Trp Arg His Ser Leu
385                 390                 395                 400

Leu Gly Arg Arg Arg Thr Leu Leu His Arg Pro Pro Glu Val Ser Asp
                405                 410                 415

Val Gln Arg Leu Ser Gly Gly Ser Arg Ile Gly Ile His Leu Ala Pro
            420                 425                 430

Thr Pro Gln His Leu Arg Arg Arg Cys Arg Arg Ser Ser Arg Arg Arg
        435                 440                 445

Arg Thr Ser Arg Arg Cys Cys Phe Gly Ala Arg Lys Asp Asp Asp
    450                 455                 460

Gly Lys Arg Asp Arg Gly Leu Arg Arg Gln Ser Ser Asn Asn Arg Glu
465                 470                 475                 480

Lys Val Ala Arg Arg Ser Cys Val Cys Gly Arg Ser Thr Glu Arg Ser
                485                 490                 495

Tyr Arg Lys Thr Arg Arg Lys Lys Asn Gln Arg Asp Pro His Lys Gly
            500                 505                 510

Gln Glu Gly Arg Lys Asp Arg Arg Val Ile Pro Arg Glu Phe Ser Arg
        515                 520                 525

Val Cys Arg Ile Ser Ser Phe His His Gly Leu Leu Arg Gly Arg His
    530                 535                 540

Gln Val His Ala Leu Gln Gly Ala His Gly Gly Leu Arg Glu Arg Pro
545                 550                 555                 560

Arg Val Arg Asp Arg Gly Arg Gly Arg Gly Pro Pro Leu Arg Gly His
                565                 570                 575

Pro Asp Arg Gln Ala Glu Gly Asp Gly Arg Pro Pro Ala Leu Arg
            580                 585                 590

Leu Gly His Pro Val Pro Ser Val Pro Val Arg Leu Gln Gly Leu Arg
        595                 600                 605

Glu Ala Pro Arg Arg His Pro Arg Leu Leu Glu Ala Val Leu Pro Arg
    610                 615                 620

Gly Leu Gln Val Gly Ala Arg Asp Glu Leu Arg Gly Arg Arg Gly
625                 630                 635                 640

Asp Arg Asp Pro Gly Leu Leu Pro Ala Gly Arg Arg Val His Leu Gln
                645                 650                 655
```

```
Gly Glu Ala Ala Arg His Gln Leu Pro Leu Arg Arg Pro Arg Asn Ala
            660                 665                 670

Glu Glu Asp His Gly Leu Gly Gly Leu His Arg Glu Asp Val Pro Arg
            675                 680                 685

Gly Arg Arg Pro Glu Gly Arg Asp Gln Asp Glu Ala Glu Ala Glu Gly
        690                 695                 700

Arg Arg Pro Leu Arg Arg Gly Gln Asp His Leu His Gly Gln Glu
705                 710                 715                 720

Ala Arg Ala Ala Ala Arg Arg Leu Gln Asp Arg His Gln Ala Gly His
                725                 730                 735

His Leu Pro Gln Arg Gly Leu His His Arg Gly Thr Val Arg Ala Arg
            740                 745                 750

Arg Gly Pro Pro Leu His Arg Arg His Arg Gly Pro Gly Ile Arg His
        755                 760                 765

His Ala His Ala Thr Ala Gly Leu Tyr Arg Arg Ser Pro Arg Asp Gly
        770                 775                 780

Glu Asn His His His His Ala Thr Ala Gly Pro Gly Phe Ala Arg
785                 790                 795                 800

Arg Tyr Arg Leu Arg Thr Arg Ala Asp Asp Leu Leu Ala Gly Ala Gly
                805                 810                 815

Gly Phe Arg Asp Asn Arg Glu His Leu His His Thr Thr Pro Pro Arg
            820                 825                 830

Pro Gly Asp Ile Gly Arg Gly Arg Gly Gly Asn Asp Lys Arg Pro
        835                 840                 845

Asp Asn Asn Ala Leu Cys Arg Asp Arg Arg Ser Gly Ser Ser Tyr
850                 855                 860

Arg Gly Gly Gly Trp Glu Leu Thr Cys Pro Ala Pro Gly Pro His His
865                 870                 875                 880

Leu Pro Arg Pro Pro Ser His Arg Leu His Ala Val Leu Pro Gly Arg
                885                 890                 895

Ala Val Pro Tyr Gly Gln His Asp Pro Pro Gly Arg Ala Gly Val Arg
            900                 905                 910

Gly Pro His Pro Ala Asp Leu Ala Arg His Gln His Arg Ala Trp Gly
        915                 920                 925

Pro Ser Gly Gly Gln Thr His Arg Pro Pro Gly Gln Thr Pro Ala Pro
930                 935                 940

Arg Arg Ala Ala Gly Pro Gly Tyr Ala Gly Cys Asp Ser Pro Arg Leu
945                 950                 955                 960

Arg Ala Thr Cys Gln Tyr Gly Ala Val Ser Ala Val Arg Val Val
                965                 970                 975

Ala Gly Gly Leu Gly Thr Ala Phe Gly Asp Gly Arg Ala Ala Pro Gly
            980                 985                 990

Cys Arg Ala Pro Glu Gln Arg Gly Pro Thr Thr Pro Tyr Arg Gly His
        995                 1000                1005

Val Ile Tyr Pro Val Ser Gly Pro Arg Val Asp Gly Pro Gln Arg
        1010                1015                1020

Arg Pro Val Arg Val Cys Leu Gly Leu Gly Arg Leu Gly Gln Thr
        1025                1030                1035

Pro Pro Phe His Ala Arg Leu Tyr Pro Gly Leu Arg Pro Ile Ala
        1040                1045                1050

Arg Arg Leu Pro Gly Arg Pro Ala Ala Thr Tyr Leu Arg Asp Gly
        1055                1060                1065

Pro Asp Pro Arg His His Pro Arg Leu His Thr Asp Asp Met Arg
```

```
            1070              1075              1080
Pro Gly  Ala His Val Cys Pro  Gly Asp Gly Gly  Leu Ile
     1085              1090              1095

<210> SEQ ID NO 19
<211> LENGTH: 2507
<212> TYPE: DNA
<213> ORGANISM: Artificial Sequence
<220> FEATURE:
<223> OTHER INFORMATION: Synthesized nucleotide sequence encoding fusion
      protein with sequences from homo sapiens, photinus pyralis and
      synthetic green fluorescent protein

<400> SEQUENCE: 19
atgccaaaaa cattaagaag ggcccagcgc cattctaccc actcgaagac gggaccgccg     60
gcgagcagct gcacaaagcc atgaagcgct acgccctggt gccggcacc  atcgcctta    120 ccgacgcaca tatcgaggtg acattacct acgccgagta cttcgagatg agcgttcggc     180
tggcagaagc tatgaagcgc tatgggctga atacaaacca tcggatcgtg gtgtgcagcg     240
agaatagctt gcagttcttc atgcccgtgt tgggtgccct gttcatcggt gtggctgtgg     300
ccccagctaa cgacatctac aacgagcgcg agctgctgaa cagcatgggc atcagccagc     360
ccaccgtcgt attcgtgagc aagaaagggc tgcaaaagat cctcaacgtg caaagaagc     420 taccgatcat acaaaagatc atcatcatgg atagcaagac cgactaccag ggcttccaaa     480
gcatgtacac cttcgtgact tcccatttgc cacccggctt caacgagtac gacttcgtgc     540
ccgagagctt cgaccgggac aaaaccatcg ccctgatcat gaacagtagt ggcagtaccg     600
gattgcccaa gggcgtagcc ctaccgcacc gcaccgcttg tgtccgattc agtcatgccc     660
gcgaccccat cttcggcaac cagatcatcc ccgacaccgc tatcctcagc gtggtgccat     720
ttcaccacgg cttcggcatg ttcaccacgc tgggctactt gatctgcggc tttcgggtcg     780
tgctcatgta ccgcttcgag gaggagctat tcttgcgcag cttgcaagac tataagattc     840
aatctgccct gctggtgccc acactattta gcttcttcgc taagagcact ctcatcgaca     900
agtacgacct aagcaacttg cacgagatcg ccagcggcgg ggcgccgctc agcaaggagg     960
taggtgaggc cgtggccaaa cgcttccacc taccaggcat ccgccagggc tacggcctga    1020
cagaaacaac cagcgccatt ctgatcaccc ccgaagggga cgacaagcct ggcgcagtag    1080
gcaaggtggt gcccttcttc gaggctaagg tggtggactt ggacaccggt aagacactgg    1140
gtgtgaacca gcgcggcgag ctgtgcgtcc gtggccccat gatcatgagc ggctacgtta    1200
acaaccccga ggctacaaac gctctcatcg acaaggacgg ctggctgcac agcggcgaca    1260
tcgcctactg ggacgaggac gagcacttct tcatcgtgga ccggctgaag agcctgatca    1320
aatacaaggg ctaccaggta gccccagccg aactggagag catcctgctg caacacccca    1380
acatcttcga cgccggggtc gccggcctgc ccgacgacga tgccggcgag ctgcccgccg    1440
cagtcgtcgt gctggaacac ggtaaaacca tgaccgagaa ggagatcgtg gactatgtgg    1500
ccagccaggt tacaaccgcc aagaagctgc gcggtggtgt tgtgttcgtg gacgaggtgc    1560
ctaaaggact gaccggcaag ttggacgccc gcaagatccg cgagattctc attaaggcca    1620
agaagggcgg caagatcgcc gtgaattctc acggcttccc tcccgaggtg gaggagcagg    1680
ccgccggcac cctgcccatg agctgcgccc aggagagcgg catggataga caccctgctg    1740
cttgcgccag cgccaggatc aacgtcggat cccacggcga tatgacaccc actcgtgcag    1800
gctgcccagg ggcttgccca ggctggtcag ctgggcgatg gcggtctcgt gctgctccac    1860
```

```
gaagccgccg tcctccacgt aggtcttctc caggcggtgc tggatgaagt ggtactcggg   1920
gaagtccttc accacgccct tgctcttcat cagggtgcgc atgtggcagc tgtagaactt   1980
gccgctgttc aggcggtaca ccaggatcac ctggcccacc agcacgccgt cgttcatgta   2040
caccacctcg aagctgggct gcaggccggt gatggtcttc ttcatcacgg ggccgtcgtt   2100
ggggaagttg cggcccttgt actccacgcg gtacacgaac atctcctcga tcaggttgat   2160
gtcgctgcgg atctccacca ggccgccgtc ctcgtagcgc agggtgcgct cgtacacgaa   2220
gccggcgggg aagctctgga tgaagaagtc gctgatgtcc tcggggtact tggtgaaggt   2280
gcggttgccg tactggaagg cggggctcag gatgtcgaag gcgaagggca gggggcgcc    2340 cttggtcacg cggatctgca ccagctggtt gccgaacagg atgttgccct gccgcagcc    2400 ctccatggtg aacacgtggt tgttcaccac gccctccagg ttcaccttga agctcatgat   2460
ctcctgcagg ccggtgttct tcaggatctg cttgctcacc atggtga                2507
```

<210> SEQ ID NO 20
<211> LENGTH: 825
<212> TYPE: PRT
<213> ORGANISM: Artificial Sequence
<220> FEATURE:
<223> OTHER INFORMATION: Synthesized fusion protein with sequences from
      homo sapiens, photnius pyralis and synthetic green fluorescent
      protein

<400> SEQUENCE: 20

```
Ala Lys Asn Ile Lys Lys Gly Pro Ala Pro Phe Tyr Pro Leu Glu Asp
1               5                   10                  15

Gly Thr Ala Gly Glu Gln Leu His Lys Ala Met Lys Arg Tyr Ala Leu
            20                  25                  30

Val Pro Gly Thr Ile Ala Phe Thr Asp Ala His Ile Glu Val Asp Ile
        35                  40                  45

Thr Tyr Ala Glu Tyr Phe Glu Met Ser Val Arg Leu Ala Glu Ala Met
    50                  55                  60

Lys Arg Tyr Gly Leu Asn Thr Asn His Arg Ile Val Val Cys Ser Glu
65                  70                  75                  80

Asn Ser Leu Gln Phe Phe Met Pro Val Leu Gly Ala Leu Phe Ile Gly
                85                  90                  95

Val Ala Val Ala Pro Ala Asn Asp Ile Tyr Asn Glu Arg Glu Leu Leu
            100                 105                 110

Asn Ser Met Gly Ile Ser Gln Pro Thr Val Val Phe Val Ser Lys Lys
        115                 120                 125

Gly Leu Gln Lys Ile Leu Asn Val Gln Lys Lys Leu Pro Ile Ile Gln
    130                 135                 140

Lys Ile Ile Ile Met Asp Ser Lys Thr Asp Tyr Gln Gly Phe Gln Ser
145                 150                 155                 160

Met Tyr Thr Phe Val Thr Ser His Leu Pro Pro Gly Phe Asn Glu Tyr
                165                 170                 175

Asp Phe Val Pro Glu Ser Phe Asp Arg Asp Lys Thr Ile Ala Leu Ile
            180                 185                 190

Met Asn Ser Ser Gly Ser Thr Gly Leu Pro Lys Gly Val Ala Leu Pro
        195                 200                 205

His Arg Thr Ala Cys Val Arg Phe Ser His Ala Arg Asp Pro Ile Phe
    210                 215                 220

Gly Asn Gln Ile Ile Pro Asp Thr Ala Ile Leu Ser Val Val Pro Phe
225                 230                 235                 240
```

```
His His Gly Phe Gly Met Phe Thr Thr Leu Gly Tyr Leu Ile Cys Gly
            245                 250                 255
Phe Arg Val Val Leu Met Tyr Arg Phe Glu Glu Leu Phe Leu Arg
        260                 265                 270
Ser Leu Gln Asp Tyr Lys Ile Gln Ser Ala Leu Leu Val Pro Thr Leu
        275                 280                 285
Phe Ser Phe Ala Lys Ser Thr Leu Ile Asp Lys Tyr Asp Leu Ser
290                 295                 300
Asn Leu His Glu Ile Ala Ser Gly Gly Ala Pro Leu Ser Lys Glu Val
305                 310                 315                 320
Gly Glu Ala Val Ala Lys Arg Phe His Leu Pro Gly Ile Arg Gln Gly
                325                 330                 335
Tyr Gly Leu Thr Glu Thr Thr Ser Ala Ile Leu Ile Thr Pro Glu Gly
            340                 345                 350
Asp Asp Lys Pro Gly Ala Val Gly Lys Val Val Pro Phe Phe Glu Ala
        355                 360                 365
Lys Val Val Asp Leu Asp Thr Gly Lys Thr Leu Gly Val Asn Gln Arg
370                 375                 380
Gly Glu Leu Cys Val Arg Gly Pro Met Ile Met Ser Gly Tyr Val Asn
385                 390                 395                 400
Asn Pro Glu Ala Thr Asn Ala Leu Ile Asp Lys Asp Gly Trp Leu His
                405                 410                 415
Ser Gly Asp Ile Ala Tyr Trp Asp Glu Asp Glu His Phe Phe Ile Val
            420                 425                 430
Asp Arg Leu Lys Ser Leu Ile Lys Tyr Lys Gly Tyr Gln Val Ala Pro
        435                 440                 445
Ala Glu Leu Glu Ser Ile Leu Leu Gln His Pro Asn Ile Phe Asp Ala
    450                 455                 460
Gly Val Ala Gly Leu Pro Asp Asp Asp Ala Gly Glu Leu Pro Ala Ala
465                 470                 475                 480
Val Val Val Leu Glu His Gly Lys Thr Met Thr Glu Lys Glu Ile Val
                485                 490                 495
Asp Tyr Val Ala Ser Gln Val Thr Thr Ala Lys Lys Leu Arg Gly Gly
            500                 505                 510
Val Val Phe Val Asp Glu Val Pro Lys Gly Leu Thr Gly Lys Leu Asp
        515                 520                 525
Ala Arg Lys Ile Arg Glu Ile Leu Ile Lys Ala Lys Lys Gly Gly Lys
    530                 535                 540
Ile Ala Val Asn Ser His Gly Phe Pro Pro Glu Val Glu Glu Gln Ala
545                 550                 555                 560
Ala Gly Thr Leu Pro Met Ser Cys Ala Gln Glu Ser Gly Met Asp Arg
                565                 570                 575
His Pro Ala Ala Cys Ala Ser Ala Arg Ile Asn Val Gly Ser His Gly
            580                 585                 590
Asp Met Thr Pro Thr Arg Ala Gly Cys Pro Gly Ala Cys Pro Gly Trp
        595                 600                 605
Ser Ala Gly Arg Trp Arg Ser Arg Ala Ala Pro Arg Ser Arg Pro
    610                 615                 620
Pro Arg Arg Ser Ser Pro Gly Gly Ala Gly Ser Gly Thr Arg Gly Ser
625                 630                 635                 640
Pro Ser Pro Arg Pro Cys Ser Ser Ser Gly Cys Ala Cys Gly Ser Cys
                645                 650                 655
Arg Thr Cys Arg Cys Ser Gly Gly Thr Pro Gly Ser Pro Gly Pro Pro
```

```
                    660                 665                 670
Ala Arg Arg Arg Ser Cys Thr Pro Pro Arg Ser Trp Ala Ala Gly Arg
            675                 680                 685

Trp Ser Ser Ser Arg Gly Arg Arg Trp Gly Ser Cys Gly Pro Cys
        690                 695                 700

Thr Pro Arg Gly Thr Arg Thr Ser Pro Arg Ser Gly Cys Arg Cys Gly
705                 710                 715                 720

Ser Pro Pro Gly Arg Arg Pro Arg Ser Ala Gly Cys Ala Arg Thr Arg
            725                 730                 735

Ser Arg Arg Gly Ser Ser Gly Arg Ser Arg Cys Pro Arg Gly Thr Trp
            740                 745                 750

Arg Cys Gly Cys Arg Thr Gly Arg Arg Gly Ser Gly Cys Arg Arg Arg
            755                 760                 765

Arg Ala Gly Gly Arg Pro Trp Ser Arg Gly Ser Ala Pro Ala Gly Cys
            770                 775                 780

Arg Thr Gly Cys Cys Pro Cys Arg Ser Pro Pro Trp Thr Arg Gly Cys
785                 790                 795                 800

Ser Pro Arg Pro Pro Gly Ser Pro Ser Ser Pro Ala Gly Arg Cys
            805                 810                 815

Ser Ser Gly Ser Ala Cys Ser Pro Trp
            820                 825

<210> SEQ ID NO 21
<211> LENGTH: 14
<212> TYPE: PRT
<213> ORGANISM: Artificial Sequence
<220> FEATURE:
<223> OTHER INFORMATION: Chemically synthesized linker sequence

<400> SEQUENCE: 21

Leu Glu Asn Ser His Ala Ser Ala Gly Tyr Gln Ala Ser Thr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Chemically synthesized linker sequence

<400> SEQUENCE: 22

Thr Ala Gly Pro Gly Ser Ala Thr
1               5

<210> SEQ ID NO 23
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 23
gaagttggct ggaggtgctc                                            20

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 24
```

```
gctgttggtg gaaggagtgc                                              20

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 25
atcccattgt ctgagatgac c                                            21

<210> SEQ ID NO 26
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 26
gaatccattg tgcaagtcca c                                            21

<210> SEQ ID NO 27
<211> LENGTH: 18
<212> TYPE: DNA
<213> ORGANISM: Artificial Sequence
<220> FEATURE:
<223> OTHER INFORMATION: Chemically synthesized primer sequence

<400> SEQUENCE: 27
acaaagtcgg gagaggag                                                18

<210> SEQ ID NO 28
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 28
atgacgatgg acaagtagcc                                              20

<210> SEQ ID NO 29
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 29
ctcactcggt tctcgatact ggtt                                         24

<210> SEQ ID NO 30
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 30
ggaaggtatt cagccaaacg acca                                         24

<210> SEQ ID NO 31
<211> LENGTH: 19
<212> TYPE: DNA
```

```
<213> ORGANISM: Artificial Sequence
<220> FEATURE:
<223> OTHER INFORMATION: Chemically synthesized primer sequence

<400> SEQUENCE: 31
accccttcat tgacctcaa                                                    19

<210> SEQ ID NO 32
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 32
gcatggactg tggtcatgag t                                                 21

<210> SEQ ID NO 33
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 33
ggcgttctct ttgcaaaggt gttc                                              24

<210> SEQ ID NO 34
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 34
ctcgaaccac atccttctct                                                   20

<210> SEQ ID NO 35
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 35
ggcgttctct ttgcaaaggt gttc                                              24

<210> SEQ ID NO 36
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 36
ctcgaaccac atccttctct                                                   20

<210> SEQ ID NO 37
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 37
cgtacgcaaa ttaaagtcca ga                                                22
```

```
<210> SEQ ID NO 38
<211> LENGTH: 25
<212> TYPE: DNA
<213> ORGANISM: Artificial Sequence
<220> FEATURE:
<223> OTHER INFORMATION: Chemically synthesized primer sequence

<400> SEQUENCE: 38
cagcatccta aacagctcgc agaat                                              25

<210> SEQ ID NO 39
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 39
aagccatgaa cgcagaggag gact                                               24

<210> SEQ ID NO 40
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 40
agctgtccat ggtaccgtaa                                                    20

<210> SEQ ID NO 41
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 41
agaacctgtc acaagctgtg                                                    20

<210> SEQ ID NO 42
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 42
gacagcaagc tgaggatgtc                                                    20

<210> SEQ ID NO 43
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 43
cttcaagcca gaggcctacg                                                    20

<210> SEQ ID NO 44
<211> LENGTH: 20
<212> TYPE: DNA
<213> ORGANISM: Artificial Sequence
<220> FEATURE:
```

```
<223> OTHER INFORMATION: Chemically synthesized primer sequence

<400> SEQUENCE: 44
ccgcctctgt cttcttcagc                                                  20

<210> SEQ ID NO 45
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 45
gtcattgctg aaaccgagaa tg                                               22

<210> SEQ ID NO 46
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 46
gcaaagtact ggatgacacg ct                                               22

<210> SEQ ID NO 47
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 47
gaaccagagg ggagagacag ag                                               22

<210> SEQ ID NO 48
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 48
ccctcagctt gcttttagg ag                                                22

<210> SEQ ID NO 49
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 49
atctactggt ctgcctaaag                                                  20

<210> SEQ ID NO 50
<211> LENGTH: 22
<212> TYPE: DNA
<213> ORGANISM: Artificial Sequence
<220> FEATURE:
<223> OTHER INFORMATION: Chemically synthesized primer sequence

<400> SEQUENCE: 50
cagctcttct tcaaatctat ac                                               22
```

-continued

```
<210> SEQ ID NO 51
<211> LENGTH: 26
<212> TYPE: DNA
<213> ORGANISM: Artificial Sequence
<220> FEATURE:
<223> OTHER INFORMATION: Chemically synthesized primer sequence

<400> SEQUENCE: 51
tgaaggtcgg agtcaacgga tttggt                                        26

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 52
catgtgggcc atgaggtcca ccac                                          24
```